(12) United States Patent
Lin

(10) Patent No.: US 6,723,534 B2
(45) Date of Patent: Apr. 20, 2004

(54) PURIFIED AND ISOLATED PIWI FAMILY GENES AND GENE PRODUCTS AND THERAPEUTIC AND SCREENING METHODS USING SAME

(75) Inventor: Haifan Lin, Durham, NC (US)

(73) Assignee: Duke University, Durham, NC (US)

( * ) Notice: Subject to any disclaimer, the term of this patent is extended or adjusted under 35 U.S.C. 154(b) by 40 days.

(21) Appl. No.: 09/873,737

(22) Filed: Jun. 4, 2001

(65) Prior Publication Data

US 2002/0076797 A1 Jun. 20, 2002

Related U.S. Application Data

(63) Continuation of application No. PCT/US99/28764, filed on Dec. 3, 1999.
(60) Provisional application No. 60/110,901, filed on Dec. 4, 1998.

(51) Int. Cl.$^7$ ............................................. C12P 21/06
(52) U.S. Cl. .................... 435/69.1; 536/23.1; 536/23.5; 435/320.1; 435/325
(58) Field of Search .......................... 536/23.1, 23.5; 435/69.1, 320.1, 325

(56) References Cited

U.S. PATENT DOCUMENTS 5,690,926 A * 11/1997 Hogan ....................... 424/93.1

OTHER PUBLICATIONS

Bork, 2000, Genome Research 10:398–400.*
Brenner, 1999, Trends in Genetics 15: 132.*
Bork et al., 1996, Trends in Genetics 12:425–427.*
Ngo et al., in The Protein Folding Problem and Tertiary Structure Prediction, 1994, Merz et al., (ed.), Birkhauser, Boston, MA, pp. 433 and 492–495.*
European Search Report for 99960653.6–2406–US9928764, Nov. 2003.
Schmidt et al., *A newly identified Minute locus, M(2)32D, encodes the ribosomal protein L9 in Drosophila melanogaster,* Mol. Gen. Genet. 251:381–387 (1996).
Cox et al., *A novel class of evolutionarily conserved genes defined by piwi are essential for stem cell self-renewal,* Genes & Development 12:3715–3727 (1998).

* cited by examiner

*Primary Examiner*—Dave Trong Nguyen
(74) *Attorney, Agent, or Firm*—Jenkins, Wilson & Taylor, P.A.

(57) ABSTRACT

A family of isolated and purified proteins and nucleic acids are disclosed. Particularly, piwi family proteins and cDNAs encoding the same are disclosed. Recombinant host cells, recombinant nucleic acids, recombinant proteins and transgenic animals are also disclosed, along with methods of producing each. Isolated and purified antibodies to piwi family homologs, and methods of producing the same, are also disclosed. piwi family gene products are characterized as having activity in the growth, proliferation and self-renewing division of stem cells, and proliferation of primordial germ cells. Thus, therapeutic, screening, culturing and transgenic methods involving these activities are also disclosed.

14 Claims, 14 Drawing Sheets

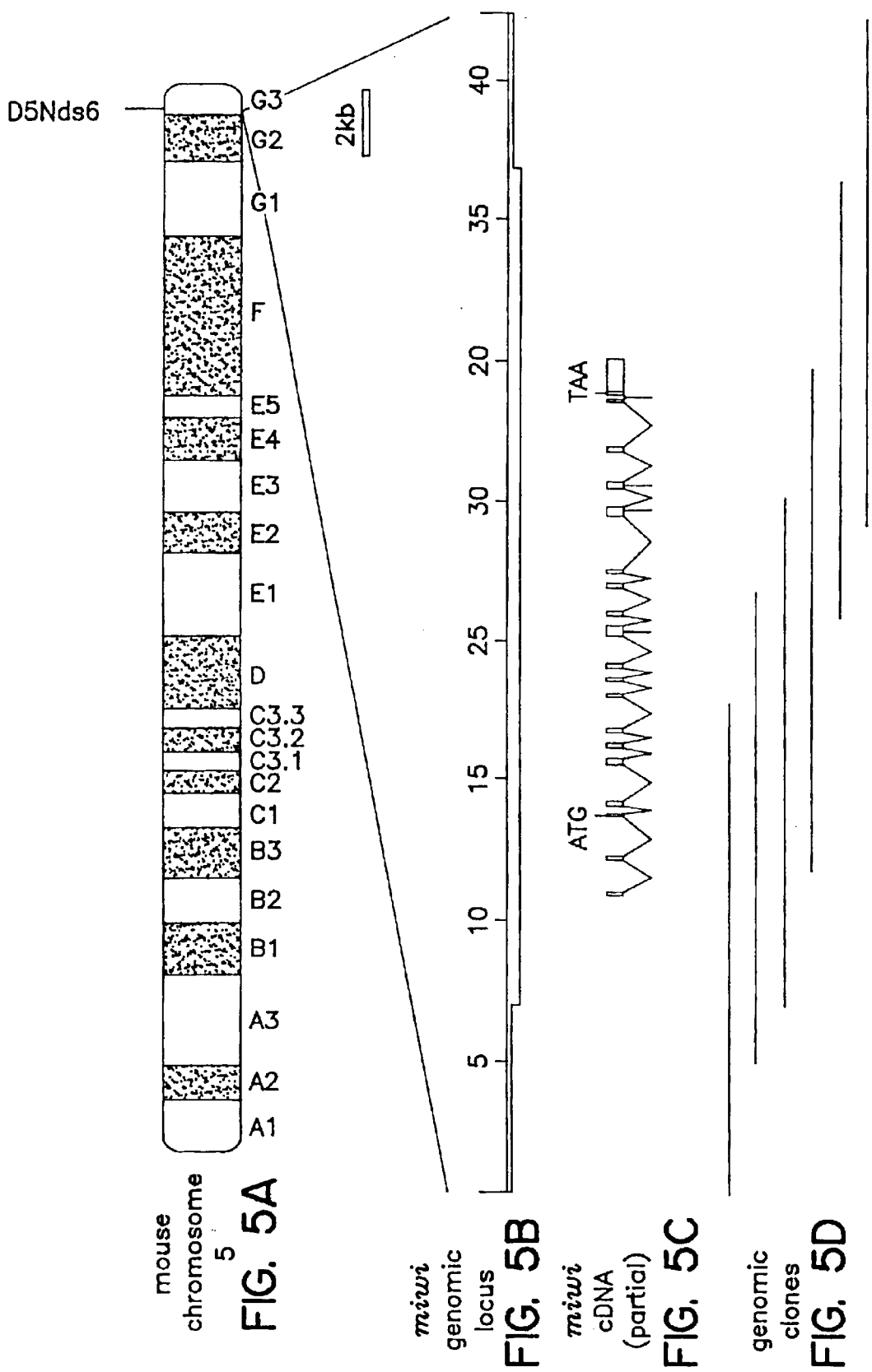

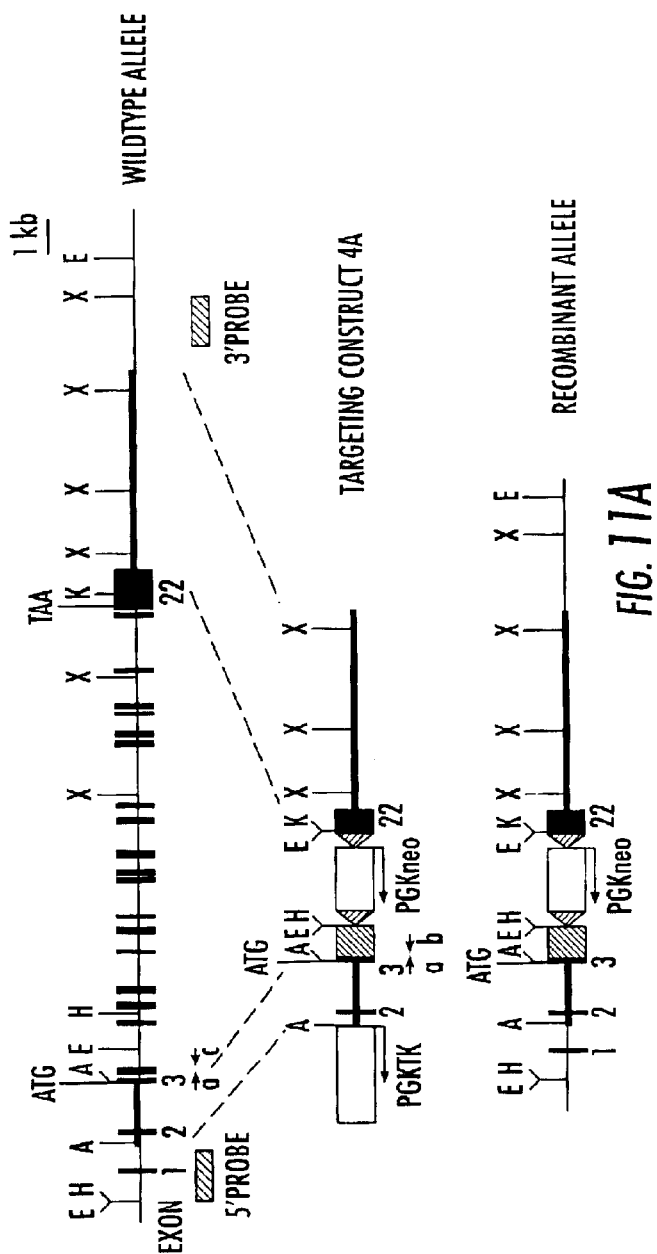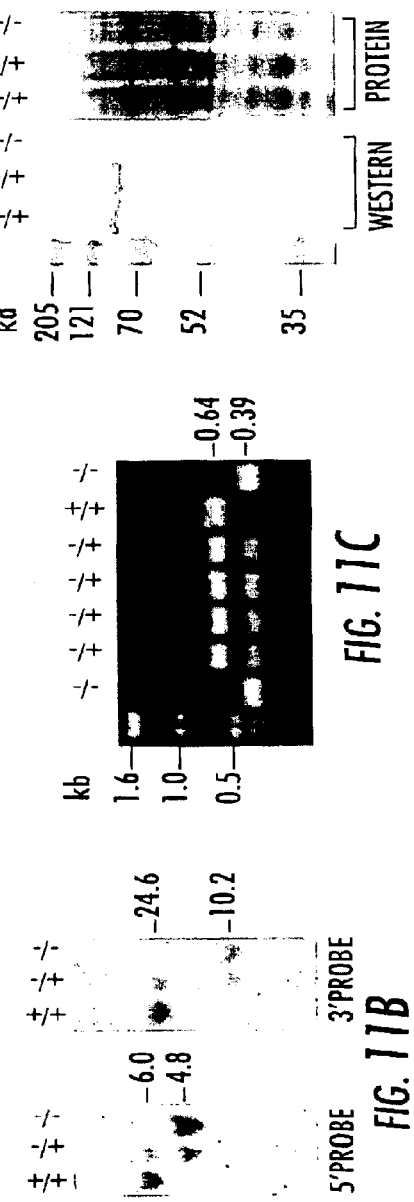
FIG. 11A
FIG. 11B
FIG. 11C
FIG. 11D

PURIFIED AND ISOLATED PIWI FAMILY GENES AND GENE PRODUCTS AND THERAPEUTIC AND SCREENING METHODS USING SAME

PRIORITY APPLICATION INFORMATION

This application is a continuation-in-part of International Application No. PCT/US99/28764, filed Dec. 3, 1999, which claims the benefit of United States Provisional Patent Application 60/110,901, filed Dec. 4, 1998, now abandoned. The disclosure of International Application No. PCT/US99/28764 and United States Provisional Patent Application 60/110,901 are each incorporated herein by reference in their entirety.

GRANT STATEMENT

This work was supported by NIH grant HD 33760. The U.S. Government has certain rights in the invention.

TECHNICAL FIELD

The present invention relates generally to isolated and purified proteins and nucleic acids which modulate stem cell renewal, growth and division and which modulate primordial germ cell proliferation. More particularly, the present invention relates to isolated and purified piwi family proteins and isolated and purified polynucleic acids encoding the same.

The publications and other materials used herein to illuminate the background of the invention, and in particular cases, to provide additional details respecting the practice, are incorporated herein by reference, and for convenience, are referenced by author and year of publication in the following text, and respectively grouped by author in the appended list of references.

TABLE OF ABBREVIATIONS

| | |
|---|---|
| APC | apical polar cell(s) |
| ATCC | American Type Culture Collection |
| bFGF | basic fibroblast growth factor |
| BRL | buffalo rat liver |
| BSA | bovine serum albumin |
| Gb | cystoblast |
| CDR(s) | complementarity determining region(s) |
| COOH | carboxy terminus |
| CyO | a strain of Drosophila |
| DAPI | a DNA specific dye |
| DMEM | Dulbecco's modified Eagle's medium |
| DC | differentiating 16-cell cysts |
| dpc | days post coitum |
| dpp | days post partum |
| DTC | distal tip cell |
| ECL | enhanced chemiluminescent |
| EDTA | ethylenediamine tetraacetate |
| ES | epithetial sheath |
| EST | expressed sequence tags |
| FBS | fetal bovine serum |
| FITC | fluorescein isothiocyanate |
| FC | follicle cell |
| $FRT^{40A}$ | a strain of Drosophila |
| Fu | fusome |
| GC-MS | gas chromatography-mass spectroscopy |
| Ge | germarium(ia) |
| GFP | green fluorescent protein |
| GSC(s) | germline stem cell(s) |
| HAT | cell culture media comprising hypoxanthine, aminopterin, and thymidine |
| hiwi/HIWI | a human homolog of the piwi/PIWI gene and gene product |
| HPLC | high pressure liquid chromatography |
| hsGal4 | a heat shock inducible transgene |

TABLE OF ABBREVIATIONS-continued

| | |
|---|---|
| IS | inner sheath |
| KLH | keyhole limpet hemocyanin |
| MC | mitotically active cysts |
| miwi/MIWI | a murine homolog of the piwi/PIWI gene and gene product |
| MmGFP | mutant GFP with improved stability |
| MPZ | mitotic proliferation zone |
| myc | human oncogene used herein as molecular tag for piwi |
| NH2 | amino terminus |
| ORF | open reading frame |
| PCR | polymerase chain reaction |
| PGC(s) | primordial germ cell(s) |
| piwi/PIWI | a gene and gene product isolated from Drosophila and having stem cell division modulating activity |
| RACE | rapid amplification of cDNA ends |
| RNAi | RNA interference assay |
| SSC(s) | somatic stem cell(s) |
| Sp | spectrosome |
| TFC | terminal filament cells |
| TSX | testis-specific X-linked gene product |
| TUNEL | TdT-mediated dUTP-digoxigenin nick end-labeling |
| UTR | untranslated region |
| VASA | a germline specific marker |
| WT | wild type |

BACKGROUND ART

Stem cells are a very small number of founder cells that play a central role in tissue development and maintenance. In human bodies, stem cells are responsible for generating and/or maintaining approximately 90% of cells in the adult tissues. Over-proliferation of malignant stem cells is the leading cause of cancer while under-proliferation of stem cells or stem-like progenitor cells leads to tissue dystrophy, anemia, immunodeficiency, and male infertility. The crucial role of stem cells has long been attributed to their ability to self-renew and to generate immense number of specialized cells on demand.

The ability of stem cells to self-renew and to produce a large number of differentiated progeny is critical for the development and maintenance of a wide variety of tissues in organisms ranging from insects to mammals (reviewed in Potten, 1997; Lin, 1997; Lin and Schagat, 1997; Morrison et al., 1997). This self-renewing ability is controlled both by extrinsic signaling and by cell-autonomous mechanisms (reviewed in Morrison et al., 1997; Lin and Schagat, 1997). Cell autonomous mechanisms have been elucidated in a few stem cell models such as neuroblasts and germline stem cells in Drosophila (Lin and Schagat, 1997; Deng and Lin, 1997), whereas the role of extrinsic signaling has been elucidated in several systems. For example, the proliferation and differentiation of mammalian stem cells in the hematopoietic, epidermal, and nervous systems depend on extrinsic signals that act on specific receptors on the stem cell surface (Morrison et al., 1997).

In diverse organisms ranging from invertebrates to mammals, the proliferation of germ cells, some of which possess stem cell properties, has been postulated, and, in some cases, shown to be regulated by neighboring non-mitotic somatic cells (Lin, 1997). Particularly, in C. elegans, cell—cell interactions between the somatic distal tip cell (DTC) at the end of each gonadal arm and the underlying mitotic germline nuclei via the lag-2lg/p-1 signaling pathway provides a paradigm for soma-germline interaction (reviewed in Kimble and Simpson, 1997). The glp-1 pathway is required to maintain a population of mitotically active nuclei in the germline.

However, few molecules and/or mechanisms identified in a particular type of stem cells have been shown to be applicable to other stem cell systems. For example, the glp-1 equivalent pathway in Drosophila does not play a role in regulating GSC division and maintenance (Ruohala et al., 1991; Xu et al., 1992).

The self-renewing asymmetric division of GSCs in the Drosophila ovary is known to be controlled both by an intracellular mechanism (Deng and Lin, 1997) and by cell—cell interactions (Lin and Spradling, 1993). The intracellular mechanism involves a cytoplasmic organelle termed the spectrosome that controls the orientation of GSC division (Lin et al., 1994; Deng and Lin, 1997). The cell—cell interaction mechanism involves terminal filament cells, as shown by laser ablation studies (Lin and Spradling, 1993). Recently, dpp has been shown as a key signaling molecule required for GSC division and maintenance (Xie and Spradling, 1998). It is possible that the dpp signal emanates from somatic cells. Alternatively, dpp signal may originate from the germline or even within GSCs, like its mammalian homologs (Zhao et al., 1996).

In mammals, primordial germ cells cultured from the genital ridge have the ability to give rise to pluripotent embryonic stem cells. For example, U.S. Pat. No. 5,690,926 issued Nov. 25, 1997 to Hogan; U.S. Pat. No. 5,670,372 issued Sep. 23, 1997 to Hogan; and U.S. Pat. No. 5,537,357 issued Sep. 26, 1995 to Hogan each disclose pluripotential mammalian embryonic stem cells and methods of making the same. The disclosure of these patents is limited to mammalian embryonic stem cells and particularly to the culturing of murine and other mammalian embryonic stem cells using a combination of growth factors consisting of SCF, FGF and LIF.

Current prior art reports on the culture of avian primordial germ cells (PGCs) have concentrated on efforts to maintain a PGC-phenotype and to stimulate proliferation. See e.g., Chang, I. K. et al., Cell. Biol. Int. 1997 August; 21(8): 495–9; Chang, I. K. et al., Cell. Biol. Int. 1995 February; 19(2): 143–9; Allioli, N. et al., Dev. Biol. 1994 September; 165(1): 30–7 and PCT Publication No. WO 99/06533, published Feb. 11, 1999 (Applicant—University of Massachusetts; Inventors—Ponce de Leon et al.).

As illustrated above, numerous attempts have been devoted to identify genes that control the self-renewing ability of stem cells or the proliferation of primordial germ cells. As a result, a number of growth factors and signaling molecules, such as Steel factor and its c-kit receptor, have been identified to regulate such activity in certain tissues. Despite this progress, there remains a long-felt and continuing need to identify genes that play a role in modulating the growth and self-renewing division of stem cells, particularly GSCs, and that play a role in modulating proliferation of primordial germ cells.

SUMMARY OF THE INVENTION

The present invention contemplates an isolated and purified family of genes and gene products (the piwi family) which plays a role in the growth, proliferation and self-renewing division of stem cells, and proliferation of primordial germ cells. More preferably, a polypeptide of the invention is a recombinant polypeptide. Even more preferably, a polypeptide of the present invention comprises a vertebrate piwi family polypeptide. Even more preferably, a polypeptide of the present invention comprises a mammalian piwi family polypeptide. Even more preferably, a polypeptide of the present invention comprises a human piwi family polypeptide. Even more preferably, a polypeptide of the present invention comprises an amino acid sequence from the amino acid residue sequences of any of SEQ ID NOs:2, 4 and 6.

The present invention also provides an isolated and purified polynucleotide that encodes a polypeptide that plays a role in the growth, proliferation and self-renewing division of stem cells, and proliferation of primordial germ cells. In a preferred embodiment, a polynucleotide of the present invention comprises a DNA molecule from a vertebrate species. Preferred vertebrates comprise mammals, birds orfish. A preferred mammal is a human. More preferably, a polynucleotide of the present invention encodes a polypeptide designated PIWI. Even more preferably, a polynucleotide of the present invention encodes a polypeptide comprising an amino acid residue sequence of any of SEQ ID NOs:2, 4 and 6. Most preferably, an isolated and purified polynucleotide of the invention comprises a nucleotide base sequence of any of SEQ ID NOs:1, 3 and 5.

In another embodiment, the present invention contemplates an antibody immunoreactive with a piwi family polypeptide as described above. SEQ ID NOs:3–6 set forth nucleotide and amino acid sequences from representative vertebrates, human and mouse. Also contemplated by the present invention are antibodies immunoreactive with homologues or biologically equivalent piwi family polynucleotides and polypeptides found in other vertebrates. Preferably, an antibody of the invention is a monoclonal antibody. More preferably, the piwi family polypeptide comprises human PIWI (HIWI). Even more preferably, the piwi polypeptide comprises an amino acid residue sequence of any of SEQ ID NOs:2, 4 and 6.

In another aspect, the present invention contemplates a method of producing an antibody immunoreactive with a piwi family polypeptide as described above, the method comprising the steps of (a) transfecting a recombinant host cell with a polynucleotide that encodes a biologically active piwi family polypeptide; (b) culturing the host cell under conditions sufficient for expression of the polypeptide; (c) recovering the polypeptide; and (d) preparing the antibody to the polypeptide. SEQ ID NOs:3–6 set forth nucleotide and amino acid sequences from representative vertebrates, human and mouse. Preferably, the host cell is transfected with a polynucleotide of any of SEQ ID NOs:1, 3 and 5. Even more preferably, the present invention provides an antibody prepared according to the method described above. Also contemplated by the present invention is the use of homologues or biologically equivalent polynucleotides and polypeptides found in other vertebrates to produce antibodies.

Alternatively, the present invention provides a method of detecting a piwi family polypeptide as described above, wherein the method comprises immunoreacting the polypeptide with an antibody prepared according to the method described above to form an antibody-polypeptide conjugate, and detecting the conjugate.

In yet another embodiment, the present invention contemplates a method of detecting a messenger RNA transcript that encodes a piwi family polypeptide as described above, wherein the method comprises hybridizing the messenger RNA transcript with a polynucleotide sequence that encodes that polypeptide to form a duplex; and detecting the duplex. Alternatively, the present invention provides a method of detecting a DNA molecule that encodes a piwi family polypeptide as described above, wherein the method comprises hybridizing DNA molecules with a polynucleotide that encodes a biologically active piwi family polypeptide to form a duplex; and detecting the duplex.

In another aspect, the present invention contemplates an assay kit for detecting the presence of a piwi family polypeptide in a biological sample, where the kit comprises a first container containing a first antibody capable of immunoreacting with a biologically active piwi polypeptide, with the first antibody. Preferably, the first antibody is present in an amount sufficient to perform at least one assay. Also preferably, an assay kit of the invention further comprises a second container containing a second antibody that immunoreacts with the first antibody. More preferably, the antibodies used in an assay kit of the present invention are monoclonal antibodies. Even more preferably, the first antibody is affixed to a solid support. More preferably still, the first and second antibodies comprise an indicator, and, preferably, the indicator is a radioactive label, a fluorescent label or an enzyme.

In an alternative aspect, the present invention provides an assay kit for detecting the presence, in biological samples, of a piwi family polypeptide, the kits comprising a first container that contains a second polynucleotide identical or complementary to a segment of at least 10 contiguous nucleotide bases of a polynucleotide that encodes a biologically active piwi family polypeptide.

In another embodiment, the present invention contemplates an assay kit for detecting the presence, in a biological sample, of an antibody immunoreactive with a piwi family polypeptide, the kit comprising a first container containing a biologically active piwi family polypeptide that immunoreacts with the antibody, with the polypeptide present in an amount sufficient to perform at least one assay.

In still a further embodiment, this invention pertains to transgenic, therapeutic, screening and culturing methods based upon the self-renewing division of stem cells, and proliferation of primordial germ cells function of piwi family polynucleotides and polypeptides as described herein. Representative therapeutic and culturing methods include administration of a soluble form of the piwi protein and gene therapy approaches using an isolated and purified polynucleotide of the present invention.

Thus, a key aspect of this invention pertains to the discovery of the novel piwi family of proteins and nucleic acids. Preferred nucleic acid and amino acid sequences are described in SEQ ID NOs:1–6.

It is thus another aspect of this invention to provide a purified and isolated piwi family polypeptide having a role in the growth, proliferation and/or self-renewing division of stem cells, and proliferation of primordial germ cells.

The foregoing aspects and embodiments have broad utility given the biological significance of stem cell growth, proliferation and renewal, and primordial germ cell proliferation. By way of example, the foregoing aspects and embodiments are useful in the preparation of screening assays and assay kits that are used to identify compounds that affect or modulate piwi family biological activity, or that are used to detect the presence of the proteins and nucleic acids of this invention in biological samples. Additionally, it is well known that isolated and purified polypeptides have utility as feed additives for livestock and further polynucleotides encoding the polypeptides are thus useful in producing the polypeptides.

Some of the aspects and objects of the invention having been stated hereinabove, other aspects and objects will become evident as the description proceeds, when taken in connection with the accompanying Examples and Drawings as best described hereinbelow.

BRIEF DESCRIPTION OF THE DRAWINGS

FIGS. 5A–5D is a schematic depicting the miwi locus (genomic location and gene structure).

FIG. 5A is a schematic depicting mouse chromosome 5.

FIG. 5B is a schematic depicting the miwi genomic locus.

FIG. 5C is a schematic depicting the location and structure on the miwi cDNA.

FIG. 5D is a schematic depicting the location and structure of miwi genomic clones.

FIGS. 6A–6C depict an alignment of MIWI protein sequence with HIWI, *Drosophila PIWI* and *C. elegans* PRG-1 and PRG-2. Sequences names are shown on the right, and the position of each sequence is shown on the left. Amino acid residues identical among above four genes are boxed in black. The highly conserved C-terminal 104 amino acid residues (including the PIWI box) are underlined.

FIGS. 11A–11D are a summary of the targeting strategy and knockout of the miwi gene.

FIG. 11A is a schematic diagram depicting the genomic organization and targeting of miwi. The GFP reporter (hatched rectangle) and the loxP[PGK-neo] cassette (open rectangle) replace a 15.5 kb ApaI-KpnI genomic region spanning exons 3–22. Exons are represented by filled rectangles (black), and exons 1, 2, 3, and 22 are indicated with the appropriate number designation below the corresponding filled rectangle. The flanking genomic regions used in the targeting vector are shown by thicker lines. The flanking genomic regions used in the targeting vector are shown by thicker lines. ATG, translation start methionine; TAA, translation stop; A, ApaI; E, EcoRI; H, HindIII; K, KpnI; S, SacI; X, XbaI. Shaded rectangles (gray) labeled "5'probe" and "3'probe" indicates the positions probe sequences used for Southern blot analysis presented in FIG. 11B. Arrows labeled "a", "b", and "c" identify the positions of primer sequences used for genotyping analysis presented in FIG. 11C. Scale bar denotes 1-kb.

FIG. 11B presents autoradiographs of two Southern-blots prepared with genomic DNA from wildtype (MIWI$^{+/-}$), heterozygous (MIWI$^{+/-}$) and homozygous (MIWI$^{-/-}$) mice and probed with 5' and 3' probes (indicated in FIG. 11A). For 5' probe analysis, genomic DNA was digested by HindIII; the wildtype allele is 6 kb whereas the targeted allele is 4.8 kb. For 3' probe analysis, genomic DNA was digested by EcoRI; the wildtype allele is 24.6 kb whereas the targeted allele is 10.2 kb.

FIG. 11C is a photograph of a gel showing PCR genotyping analysis. DNA prepared from wildtype, heterozygous miwi$^{+/-}$, and homozygous miwi$^{-/-}$ mice was amplified using primers a, b and c (indicated in FIG. 11A). The wildtype allele yields a 0.64 kb PCR product, whereas the targeted allele yields a 0.39 kb PCR product. Sizes (in kb) of molecular weight markers are indicated at left.

FIG. 11D presents a Western blot and corresponding Coomassie blue-stained gel. The Western blot was prepared using testicular extracts from wildtype, heterozygous miwi$^{+/-}$, and homozygous miwi$^{-/-}$ mice, and the MIWI protein was detected using an anti-MIWI antibody. MIWI protein is absent from miwi$^{-/-}$ mice. The duplicate SDS-PAGE gel stained by Coomassie blue shows equal loading of the testicular extracts in all lanes. Sizes of protein markers (in kd) are indicated at left.

FIG. 12A is a schematic diagram of miwi$^{+/+}$ (miwi$^+$, wild type) and miwi$^{\Delta C}$ alleles. The GFP reporter (hatched rectangle) and the loxP[PGK-neo] cassette (open rectangle) replace the SacI-KpnI genomic region spanning exons 16–22, which encodes the last 245 amino acid residues (including the last 6 residues encoded by exon 16) and 491 base pairs of 3' untranslated region. Exons are represented by filled rectangles, and exons 1, 16, and 22 are indicated with the appropriate number designation below the corresponding filled rectangle. The flanking genomic regions used in the targeting vector are shown by thicker lines. ATG, translation start methionine; TAA translation stop; TAG, translation stop; A, ApaI; E, EcoRI; H, HindIII; K, KpnI; S, SacI; X, XbaI. Scale bar denotes 1-kb.

FIG. 12B is a Western blot (lanes 1–5) and a Coomassie blue-stained duplicate SDS-PAGE gel (lanes 1'–5') of testicular extracts from miwi$^{null}$/miwi$^{null}$ (lanes 1 and 1'), miwi$^{null/+}$ (lanes 2 and 2'), +/+ (lanes 3 and 3'), miwi$^{\Delta C/+}$ (lanes 4 and 4'), and miwi$^{\Delta C}$/miwi$^{\Delta C}$ (lanes 5 and 5') mice. MIWI protein was detected using the MIWI34 anti-MIWI antibody. The truncated MIWI protein is present in homozygous miwi$^{\Delta C}$ mice (lane 5) and retains a molecular weight similar to the wildtype MIWI protein because of the MmGFP fusion. Lanes 1'–5' demonstrate equal protein loading for lanes 1–5.

DETAILED DESCRIPTION OF THE INVENTION

Figure 1:
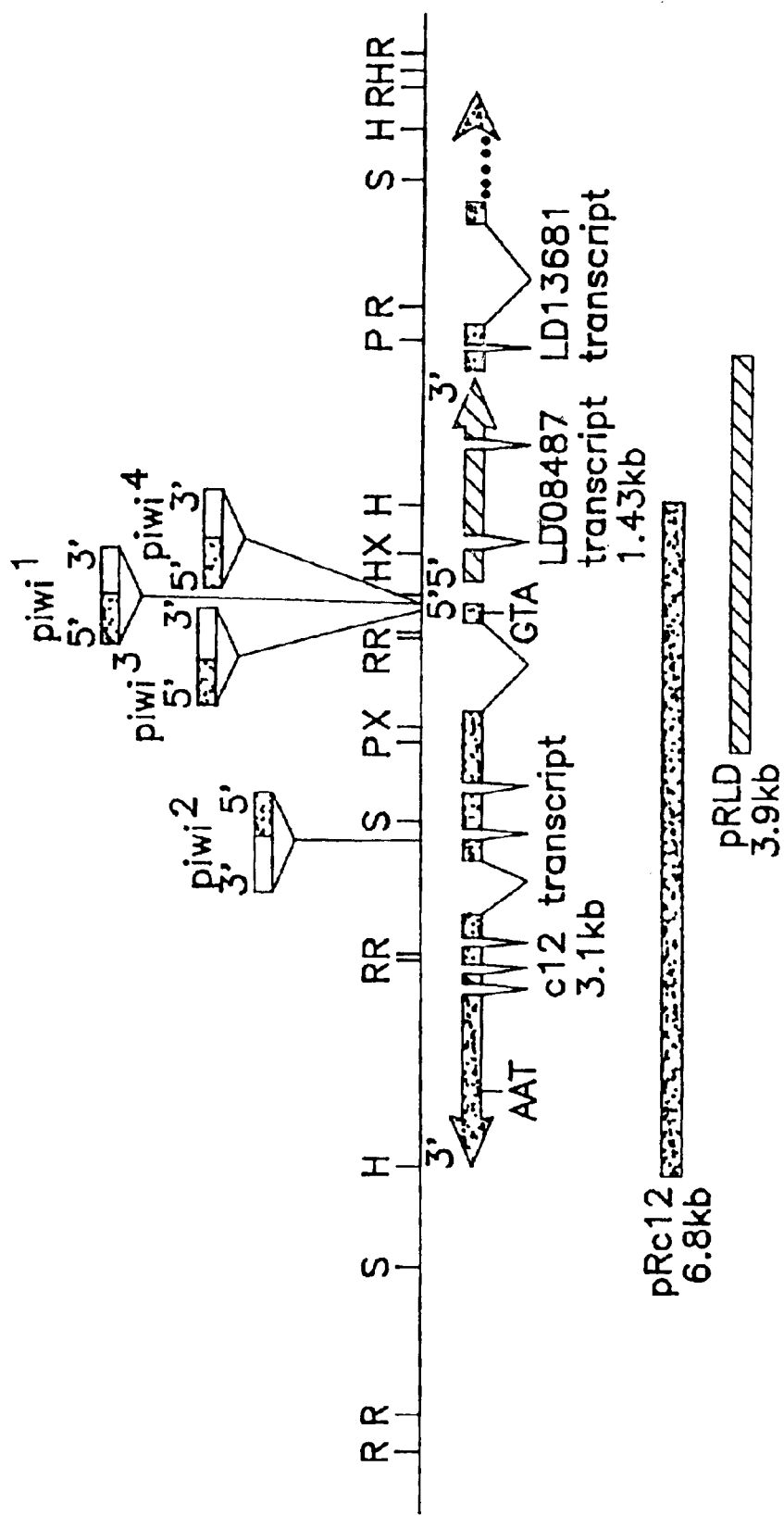
FIG. 1 is a molecular map of the piwi locus. Restriction enzyme map for 15 kb of genomic DNA surrounding the piwi mutations is shown. Three transcripts are represented by thick arrows indicating their relative positions, sizes, splice sites and direction of transcription. The relative insertion sites of the P-element alleles is indicated above the restriction map with orientation of insertion indicated by black (5') and white (3') boxes. The P insertions are not shown according to the scale, with piwi$^2$ insertion partially mapped. Restriction sites: R, EcoRI; H, HindIII; P, PstI; S, SalI; X, XhoI.

The present invention discloses a novel class of genes required for the growth, proliferation and self-renewing division of stem cells, and proliferation of primordial germ cells. The present invention relates to the discovery of a novel class of evolutionarily conserved genes, the piwi family genes, that encode a novel group of basic proteins important for stem cell division, primordial germ cell proliferation and other developmental processes.

The disclosure of the present invention demonstrates that PIWI protein can localize either in the nucleoplasm or cytoplasm and that the dose of the PIWI protein determines both the number and the mitotic rate of germline stem cells, and that the PIWI protein is localized in the germplasm (the cytoplasm of future germ cells) and plays a key role in determining the initial number of germ cells in during embryogenesis. The mouse PIWI protein (i.e., MIWI protein) is also a cytoplasmic factor with very similar functions in germ cell and stem cell determination.

To identify genes essential for stem cell division, germline stem cells in the Drosophila ovary were established as a model by directly identifying these cells and demonstrating their self-renewing asymmetric division pattern. This stem cell model allowed applicant to effectively circumvent difficulties intrinsic to studying mammalian stem cells, such as their rarity, lack of unique morphological markers, hypersensitivity to in vitro manipulation, and inaccessibility to systematic genetic screen. Systematic genetic screens were then conducted to identify mutations that either abolish the self-renewing ability of stem cells or the asymmetry of stem cell division, or both. These screens led to the identification of the *Drosophila piwi* gene that is essential for germline stem cell self-renewal. Subsequent cloning and molecular analysis of the piwi gene and its homologs in C. elegans, the mouse, and human, and the identification of piwi-like genes in Arabidopsis led to the following novel apsects of the present invention.

Definitions and Techniques Affecting Gene Products and Genes

As used in the following detailed description and in the claims, the term "piwi family" refers to a family or group of genes and gene products including, but not limited to, PIWI, HIWI, MIWI, PRG-1 and PRG-2 proteins, and the piwi, hiwi, miwi, prg-1 and prg-2 genes, each of which are further defined herein. The term "piwi family" also includes other members of the piwi family of genes and gene products characterized by biological activity, including but not limited to the biological activities of modulating growth, proliferation and/or self-renewing division of stem cells, and/or proliferation of primordial germ cells.

Preferably, piwi family genes and gene products are isolated from eukaryotic sources. Thus, the term "piwi family" also includes invertebrate homologs. The term "piwi family" further includes vertebrate homologs of piwi family members, including, but not limited to, mammalian, avian and fish homologs. Preferred mammalian homologs of piwi family members include, but are not limited to, murine and human homologs.

The terms "piwi family gene product", "piwi family protein" and "piwi family polypeptide" refer to proteins having amino acid sequences which are substantially identical to the native amino acid sequences in the piwi family and which are biologically active in that they are capable of modulating growth, proliferation and/or self-renewing division of stem cells, and/or proliferation of primordial germ cells, or cross-reacting with anti-piwi family antibodies raised against a piwi family polypeptide.

The terms "piwi family gene product", "piwi family protein" and "piwi family polypeptide" also include analogs of piwi family molecules which exhibit at least some biological activity in common with native piwi family gene products. Furthermore, those skilled in the art of mutagenesis will appreciate that other analogs, as yet undisclosed or undiscovered, may be used to construct piwi family analogs. There is no need for an "piwi family gene product", "piwi family protein" or "piwi family polypeptide" to comprise all, or substantially all of the amino acid sequence of a native piwi family gene product. Shorter or longer sequences are anticipated to be of use in the invention. Thus, the term "piwi family gene product" also includes fusion or recombinant piwi family polypeptides and proteins. Methods of preparing such proteins are described herein in the Examples, among other places.

The terms "piwi family gene", "piwi family gene sequence" and "piwi family gene segment" refer to any DNA sequence that is substantially identical to a polynucleotide sequence encoding a piwi family gene product, piwi family protein or piwi family polypeptide as defined above. The terms also refer to RNA, or antisense sequences, compatible with such DNA sequences. A "piwi family gene", "piwi family gene sequence" and "piwi family gene segment" may also comprise any combination of associated control sequences.

The term "substantially identical", when used to define either a piwi family gene product or piwi family amino acid sequence, or a piwi family gene or piwi family nucleic acid sequence, means that a particular sequence, for example, a mutant sequence, varies from the sequence of a natural piwi family by one or more deletions, substitutions, or additions, the net effect of which is to retain at least some of biological activity of piwi family. Alternatively, DNA analog sequences are "substantially identical" to specific DNA sequences disclosed herein if: (a) the DNA analog sequence is derived from coding regions of the natural piwi family gene; or (b) the DNA analog sequence is capable of hybridization of DNA sequences of (a) under moderately stringent conditions and which encode biologically active piwi family gene product; or (c) the DNA sequences are degenerative as a result of the genetic code to the DNA analog sequences defined in (a) and/or (b). Substantially identical analog proteins will be greater than about 60% identical to the corresponding sequence of the native protein. Sequences having lesser degrees of similarity but comparable biological activity are considered to be equivalents. In determining nucleic acid sequences, all subject nucleic acid sequences capable of encoding substantially similar amino acid sequences are considered to be substantially similar to a reference nucleic acid sequence, regardless of differences in codon sequences.

Percent Similarity

Percent similarity may be determined, for example, by comparing sequence information using the GAP computer program, available from the University of Wisconsin Geneticist Computer Group. The GAP program utilizes the alignment method of Needleman et al. 1970, as revised by Smith et al. 1981. Briefly, the GAP program defines similarity as the number of aligned symbols (i.e. nucleotides or amino acids) which are similar, divided by the total number of symbols in the shorter of the two sequences. The preferred default parameters for the GAP program include: (1) a unitary comparison matrix (containing a value of 1 for identities and 0 for non-identities) of nucleotides and the weighted comparison matrix of Gribskov et al., 1986, as described by Schwartz et al., 1979; (2) a penalty of 3.0 for each gap and an additional 0.01 penalty for each symbol and each gap; and (3) no penalty for end gaps. Other comparison techniques are described in the Examples.

The term "homology" describes a mathematically based comparison of sequence similarities which is used to identify genes or proteins with similar functions or motifs. Accordingly, the term "homology" is synonymous with the term "similarity" and "percent similarity" as defined above.

Thus, the phrases "substantial homology" or "substantial similarity" have similar meanings.

Nucleic Acid Sequences

In certain embodiments, the invention concerns the use of piwi family genes and gene products that include within their respective sequences a sequence which is essentially that of a piwi family gene, or the corresponding protein. The term "a sequence essentially as that of a piwi family gene", means that the sequence substantially corresponds to a portion of a piwi family polypeptide or piwi family gene and has relatively few bases or amino acids (whether DNA or protein) which are not identical to those of a piwi family protein or piwi family gene, (or a biologically functional equivalent of, when referring to proteins). The term "biologically functional equivalent" is well understood in the art and is further defined in detail herein. Accordingly, sequences which have between about 70% and about 80%; or more preferably, between about 81% and about 90%; or even more preferably, between about 91% and about 99%; of amino acids which are identical or functionally equivalent to the amino acids of a piwi family protein or piwi family gene, will be sequences which are "essentially the same".

piwi family gene products and piwi family genes which have functionally equivalent codons are also covered by the invention. The term "functionally equivalent codon" is used herein to refer to codons that encode the same amino acid, such as the six codons for arginine or serine, and also to refer to codons that encode biologically equivalent amino acids (see Table 1). Thus, when referring to the sequence examples presented in SEQ ID NOs:1–6, the substitution of functionally equivalent codons of Table 1 into the sequence examples of SEQ ID NOs:1–6 is envisioned. Thus, applicants are in possession of amino acid and nucleic acids sequences which include such substitutions but which are not set forth herein in their entirety for convenience.

TABLE 1

Functionally Equivalent Codons.

| Amino Acids | | | Codons |
|---|---|---|---|
| Alanine | Ala | A | GCA GCC GCG GCU |
| Cysteine | Cys | C | UGC UGU |
| Aspartic Acid | Asp | D | GAC GAU |
| Glumatic acid | Glu | F | GAA GAG |
| Phenylalanine | Phe | F | UUC UUU |
| Glycine | Gly | G | GGA GGC GGG GGU |
| Histidine | His | H | CAC CAU |
| Isoleucine | Ile | I | AUA AUC AUU |
| Lysine | Lys | K | AAA AAG |
| Leucine | Leu | L | UUA UUG CUA CUC CUG CUU |
| Methionine | Met | M | AUG |
| Asparagine | Asn | N | AAC AAU |
| Proline | Pro | P | CCA CCC CCG CCU |
| Glutamine | Gln | Q | CAA CAG |
| Arginine | Arg | R | AGA AGG CGA CGC CGG CGU |
| Serine | Ser | S | ACG AGU UCA UCC UCG UCU |

TABLE 1-continued

Functionally Equivalent Codons.

| Amino Acids | | | Codons |
|---|---|---|---|
| Threonine | Thr | T | ACA ACC ACG ACU |
| Valine | Val | V | GUA GUC GUG GUU |
| Tryptophan | Trp | W | UGG |
| Tyrosine | Tyr | Y | UAC UAU |

It will also be understood that amino acid and nucleic acid sequences may include additional residues, such as additional N- or C-terminal amino acids or 5' or 3' sequences, and yet still be essentially as set forth in one of the sequences disclosed herein, so long as the sequence meets the criteria set forth above, including the maintenance of biological protein activity where protein expression is concerned. The addition of terminal sequences particularly applies to nucleic acid sequences which may, for example, include various non-coding sequences flanking either of the 5' or 3' portions of the coding region or may include various internal sequences, i.e., introns, which are known to occur within genes.

The present invention also encompasses the use of DNA segments which are complementary, or essentially complementary, to the sequences set forth in the specification. Nucleic acid sequences which are "complementary" are those which are base-pairing according to the standard Watson-Crick complementarity rules. As used herein, the term "complementary sequences" means nucleic acid sequences which are substantially complementary, as may be assessed by the same nucleotide comparison set forth above, or as defined as being capable of hybridizing to the nucleic acid segment in question under relatively stringent conditions such as those described herein. A particular example of a contemplated complementary nucleic acid segment is an antisense oligonucleotide.

Nucleic acid hybridization will be affected by such conditions as salt concentration, temperature, or organic solvents, in addition to the base composition, length of the complementary strands, and the number of nucleotide base mismatches between the hybridizing nucleic acids, as will be readily appreciated by those skilled in the art. Stringent temperature conditions will generally include temperatures in excess of 30° C., typically in excess of 37° C., and preferably in excess of 45° C. Stringent salt conditions will ordinarily be less than 1,000 mM, typically less than 500 mM, and preferably less than 200 mM. However, the combination of parameters is much more important than the measure of any single parameter. (See, e.g., Wetmur & Davidson, 1968). Determining appropriate hybridization conditions to identify and/or isolate sequences containing high levels of homology is well known in the art. (See e.g., Sambrook et al., 1989). For the purposes of specifying conditions of high stringency, preferred conditions are salt concentration of about 200 mM and temperature of about 45° C.

Probe sequences may also hybridize specifically to duplex DNA under certain conditions to form triplex or other higher order DNA complexes. The preparation of such probes and suitable hybridization conditions are well known in the art.

As used herein, the term "DNA segment" refers to a DNA molecule which has been isolated free of total genomic DNA of a particular species. Furthermore, a DNA segment encoding a piwi family polypeptide refers to a DNA segment which contains piwi family coding sequences, yet is isolated away from, or purified free from, total genomic DNA of a source species, such as *Homo sapiens*. Included within the term "DNA segment" are DNA segments and smaller fragments of such segments, and also recombinant vectors, including, for example, plasmids, cosmids, phages, viruses, and the like.

Similarly, a DNA segment comprising an isolated or purified piwi family gene refers to a DNA segment including piwi family coding sequences isolated substantially away from other naturally occurring genes or protein encoding sequences. In this respect, the term "gene" is used for simplicity to refer to a functional protein, polypeptide or peptide encoding unit. As will be understood by those in the art, this functional term includes both genomic sequences and cDNA sequences. "Isolated substantially away from other coding sequences" means that the gene of interest, in this case, the piwi family gene, forms the significant part of the coding region of the DNA segment, and that the DNA segment does not contain large portions of naturally-occurring coding DNA, such as large chromosomal fragments or other functional genes or cDNA coding regions. Of course, this refers to the DNA segment as originally isolated, and does not exclude genes or coding regions later added to the segment by the hand of man.

In particular embodiments, the invention concerns isolated DNA segments and recombinant vectors incorporating DNA sequences which encode a piwi family polypeptide that includes within its amino acid sequence an amino acid sequence selected from any of SEQ ID NOs:2,4 and 6. In other particular embodiments, the invention concerns isolated DNA segments and recombinant vectors incorporating DNA sequences which encode a protein that includes within its amino acid sequence the amino acid sequence of a piwi family polypeptide corresponding to human tissues (referred to herein as HIWI).

It will also be understood that this invention is not limited to the particular nucleic acid and amino acid sequences of any of SEQ ID NOs:1–6. Recombinant vectors and isolated DNA segments may therefore variously include the piwi family polypeptide-encoding region itself, include coding regions bearing selected alterations or modifications in the basic coding region, or include encoded larger polypeptides which nevertheless include piwi family polypeptide-encoding regions or may encode biologically functional equivalent proteins or peptides which have variant amino acid sequences.

In certain embodiments, the invention concerns isolated DNA segments and recombinant vectors which encode a protein or peptide that includes within its amino acid sequence an amino acid sequence essentially as set forth in any of SEQ ID NOs:2, 4 and 6. Naturally, where the DNA segment or vector encodes a full length piwi family gene product, the most preferred nucleic acid sequence is that which is essentially as set forth in any of SEQ ID NOs: 1, 3 and 5 and which encode a protein that exhibits activity in the modulation of growth, proliferation and self-renewing division of stem cells (in for example germline stem cells), and proliferation of primordial germ cells as may be determined by, for example, immunofluorescence assays, as disclosed herein.

The term "a sequence essentially as set forth in any of SEQ ID NOs:2, 4 and 6" means that the sequence substantially corresponds to a portion an amino acid sequence of any of SEQ ID NOs:2, 4 and 6 and has relatively few amino acids which are not identical to, or a biologically functional equivalent of, the amino acids of an amino acid sequence of any of SEQ ID NOs:2, 4 and 6. The term "biologically functional equivalent" is well understood in the art and is further defined in detail herein. Accordingly, sequences, which have between about 70% and about 80%; or more preferably, between about 81% and about 90%; or even more preferably, between about 91% and about 99%; of amino acids which are identical or functionally equivalent to the amino acids of any of SEQ ID NOs:2, 4 and 6, will be sequences which "a sequence essentially as set forth in any of SEQ ID NOs:2, 4 and 6".

In particular embodiments, the invention concerns gene therapy methods that use isolated DNA segments and recombinant vectors incorporating DNA sequences which encode a protein that includes within its amino acid sequence an amino acid sequence of any of SEQ ID NOs:2, 4 and 6, any of SEQ ID NOs:2, 4 and 6 including sequences which are derived from mammalian tissue, among other tissue. In other particular embodiments, the invention concerns isolated DNA sequences and recombinant DNA vectors incorporating DNA sequences which encode a protein that includes within its amino acid sequence the amino acid sequence of the piwi family protein from human tissue (HIWI).

In certain other embodiments, the invention concerns isolated DNA segments and recombinant vectors that include within their sequence a nucleic acid sequence essentially as set forth in any of SEQ ID NOs:1, 3 and 5. The term "a sequence essentially as set forth in any of SEQ ID NOs:1, 3 and 5" are used in the same sense as described above and means that the nucleic acid sequence substantially corresponds to a portion of any of SEQ ID NOs: 1, 3 and 5, respectively, and has relatively few codons which are not identical, or functionally equivalent, to the codons of any of SEQ ID NOs:1, 3 and 5, respectively. Again, DNA segments which encode gene products exhibiting activity in the modulation of growth, proliferation and self-renewing division of stem cells, and proliferation of primordial germ cells or other biological activity of the piwi family gene product will be most preferred. The term "functionally equivalent codon" is used herein to refer to codons that encode the same amino acid, such as the six codons for arginine or serine, and also to refer to codons that encode biologically equivalent amino acids (see Table 1).

The nucleic acid segments of the present invention, regardless of the length of the coding sequence itself, may be combined with other DNA sequences, such as promoters, enhancers, polyadenylation signals, additional restriction enzyme sites, multiple cloning sites, other coding segments, and the like, such that their overall length may vary considerably. It is therefore contemplated that a nucleic acid fragment of almost any length may be employed, with the total length preferably being limited by the ease of preparation and use in the intended recombinant DNA protocol. For example, nucleic acid fragments may be prepared which include a short stretch complementary to a nucleic acid sequence set for in any of SEQ ID NOs:1, 3 and 5 respectively, such as about 10 nucleotides, and which are up to 10,000 or 5,000 base pairs in length, with segments of 3,000 being preferred in certain cases. DNA segments with total lengths of about 1,000, 500, 200, 100 and about 50 base pairs in length are also contemplated to be useful.

The DNA segments of the present invention encompass biologically functional equivalent piwi family proteins and peptides. Such sequences may rise as a consequence of codon redundancy and functional equivalency which are known to occur naturally within nucleic acid sequences and the proteins thus encoded.

Alternatively, functionally equivalent proteins or peptides may be created via the application of recombinant DNA technology, in which changes in the protein structure may be engineered, based on considerations of the properties of the amino acids being exchanged, e.g. Substitution of Ile for Leu at amino acid 13, at amino acid 106 and/or at amino acid 785 for PIWI in SEQ ID NOs:1–2; substitution of Ile for Leu at amino acid 90, at amino acid 383 and/or at amino acid 816 for MIWI in SEQ ID NOs:3–4; and substitution of Ile for Leu at amino acid 76, at amino acid 303 and/or at amino acid 735 for HIWI in SEQ ID NOs:5–6. Changes designed by man may be introduced through the application of site-directed mutagenesis techniques, e.g., to introduce improvements to the antigenicity of the protein or to test piwi family mutants in order to examine activity in the modulation of growth, proliferation and self-renewing division of stem cells, and proliferation of primordial germ cells, or other activity at the molecular level.

If desired, one may also prepare fusion proteins and peptides, e.g., where the piwi family coding region is aligned within the same expression unit with other proteins or peptides having desired functions, such as for purification or immunodetection purposes (e.g., proteins which may be purified by affinity chromatography and enzyme label coding regions, respectively).

Recombinant vectors form important further aspects of the present invention. Particularly useful vectors are contemplated to be those vectors in which the coding portion of the DNA segment is positioned under the control of a promoter. The promoter may be in the form of the promoter which is naturally associated with the piwi family gene, e.g., in mammalian tissues, as may be obtained by isolating the 5' non-coding sequences located upstream of the coding segment or exon, for example, using recombinant cloning and/or PCR technology, in connection with the compositions disclosed herein.

In other embodiments, it is contemplated that certain advantages will be gained by positioning the coding DNA segment under the control of a recombinant, or heterologous, promoter. As used herein, a recombinant or heterologous promoter is intended to refer to a promoter that is not normally associated with a piwi family gene in its natural environment. Such promoters may include promoters isolated from bacterial, viral, eukaryotic, fish, avian or mammalian cells. Naturally, it will be important to employ a promoter that effectively directs the expression of the DNA segment in the cell type chosen for expression. The use of promoter and cell type combinations for protein expression is generally known to those of skill in the art of molecular biology, for example, see Sambrook et al., 1989, specifically incorporated herein by reference. The promoters employed may be constitutive, or inducible, and can be used under the appropriate conditions to direct high level expression of the introduced DNA segment, such as is advantageous in the large-scale production of recombinant proteins or peptides. Appropriate promoter systems contemplated for use in high-level expression include, but are not limited to, the vaccina virus promoter and the baculovirus promoter.

In an alternative embodiment, the present invention provides an expression vector comprising a polynucleotide that encodes a piwi family polypeptide having activity in the modulation of growth, proliferation and self-renewing division of stem cells (including germline and somatic stem cells), cell proliferation (including activity in embryonic development as described in Example 1), proliferation of primordial germ cells, or other biological activity in accordance with the present invention. Also preferably, an expression vector of the present invention comprises a polynucleotide that encodes human piwi family gene product (HIWI). More preferably, an expression vector of the present invention comprises a polynucleotide that encodes a polypeptide comprising an amino acid residue sequence of any of SEQ ID NOs:2, 4 and 6. More preferably, an expression vector of the present invention comprises a polynucleotide comprising the nucleotide base sequence of any of SEQ ID NOs:1, 3 and 5. Even more preferably, an expression vector of the invention comprises a polynucleotide operatively linked to an enhancer-promoter. More preferably still, an expression vector of the invention comprises a polynucleotide operatively linked to a prokaryotic promoter. Alternatively, an expression vector of the present invention comprises a polynucleotide operatively linked to an enhancer-promoter that is a eukaryotic promoter, and the expression vector further comprises a polyadenylation signal that is positioned 3' of the carboxy-terminal amino acid and within a transcriptional unit of the encoded polypeptide.

In yet another embodiment, the present invention provides a recombinant host cell transfected with a polynucleotide that encodes a piwi family polypeptide having activity in the modulation of growth, proliferation and self-renewing division of stem cells (including germline and somatic stem cells), cell proliferation (including activity in embryonic development as described in Example 1), proliferation of primordial germ cells, or other biological activity in accordance with the present invention. SEQ ID NOs:3–6 set forth nucleotide and amino acid sequences from representative vertebrates, human and mouse. Also contemplated by the present invention are homologous or biologically equivalent polynucleotides and piwi family polypeptides found in other vertebrates. Preferably, a recombinant host cell of the present invention is transfected with the polynucleotide that encodes human piwi family polypeptide. More preferably, a recombinant host cell of the present invention is transfected with the polynucleotide sequence of SEQ ID NO:3 (miwi) or SEQ ID NO:5 (hiwi). Even more preferably, a host cell of the invention is a eukaryotic host cell. Still more preferably, a recombinant host cell of the present invention is a vertebrate cell. Preferably, a recombinant host cell of the invention is a mammalian, avian or fish cell.

In another aspect, a recombinant host cell of the present invention is a prokaryotic host cell. Preferably, a recombinant host cell of the invention is a bacterial cell, preferably a strain of Escherichia coli. More preferably, a recombinant host cell comprises a polynucleotide under the transcriptional control of regulatory signals functional in the recombinant host cell, wherein the regulatory signals appropriately control expression of the piwi family polypeptide in a manner to enable all necessary transcriptional and post-transcriptional modification.

In yet another embodiment, the present invention contemplates a method of preparing a piwi family polypeptide comprising transfecting a cell with polynucleotide that encodes a piwi family polypeptide having activity in the modulation of growth, self-renewing division of stem cells (including germline and somatic stem cells), cell proliferation (including activity in embryonic development as described in the Examples), proliferation of primordial germ cells or other biological activity in accordance with the present invention, to produce a transformed host cell; and maintaining the transformed host cell under biological conditions sufficient for expression of the polypeptide. More preferably, the transformed host cell is a eukaryotic cell. More preferably still, the eukaryotic cell is a vertebrate cell. Alternatively, the host cell is a prokaryotic cell. More preferably, the prokaryotic cell is a bacterial cell of *Escherichia coli*. Even more preferably, a polynucleotide transfected into the transformed cell comprises the nucleotide base sequence of any of SEQ ID NOs:1, 3 and 5. SEQ ID NOs:3–6 set forth nucleotide and amino acid sequences for representative vertebrates, mouse and human. Also contemplated by the present invention are homologues or biologically equivalent piwi family polynucleotides and polypeptides found in other vertebrates, particularly warm blooded vertebrates.

As mentioned above, in connection with expression embodiments to prepare recombinant piwi family proteins and peptides, it is contemplated that longer DNA segments will most often be used, with DNA segments encoding the entire piwi family protein, functional domains or cleavage products thereof, being most preferred. However, it will be appreciated that the use of shorter DNA segments to direct the expression of piwi family peptides or epitopic core regions, such as may be used to generate anti-piwi family antibodies, also falls within the scope of the invention.

DNA segments which encode peptide antigens from about 15 to about 50 amino acids in length, or more preferably, from about 15 to about 30 amino acids in length are contemplated to be particularly useful. DNA segments encoding peptides will generally have a minimum coding length in the order of about 45 to about 150, or to about 90 nucleotides. DNA segments encoding full length proteins may have a minimum coding length on the order of about 4,000 nucleotides for a protein in accordance with any of SEQ ID NOs: 2,4 and 6.

Naturally, the present invention also encompasses DNA segments which are complementary, or essentially complementary, to the sequences set forth in any of SEQ ID NOs:1, 3 and 5. The terms "complementary" and "essentially complementary" are defined above. Excepting intronic or flanking regions, and allowing for the degeneracy of the genetic code, sequences which have between about 70% and about 80%; or more preferably, between about 81% and about 90%; or even more preferably, between about 91% and about 99%; of nucleotides which are identical or functionally equivalent (i.e. encoding the same amino acid) of nucleotides of any of SEQ ID NOs:1, 3 and 5, will be sequences which are "a sequence essentially as set forth in any of SEQ ID NOs:1, 3 and 5". Sequences which are essentially the same as those set forth in any of SEQ ID NOs:1, 3 and 5 may also be functionally defined as sequences which are capable of hybridizing to a nucleic acid segment containing the complement of any of SEQ ID NOs:1, 3 and 5 under relatively stringent conditions. Suitable relatively stringent hybridization conditions are described herein and will be well known to those of skill in the art.

Biologically Functional Equivalents

As mentioned above, modification and changes may be made in the structure of the piwi family proteins and peptides described herein and still obtain a molecule having like or otherwise desirable characteristics. For example, certain amino acids may be substituted for other amino acids in a protein structure without appreciable loss of interactive capacity with structures such as, for example, in the nucleus of a cell. Since it is the interactive capacity and nature of a protein that defines that protein's biological functional activity, certain amino acid sequence substitutions can be made in a protein sequence (or, of course, its underlying DNA coding sequence) and nevertheless obtain a protein with like or even countervailing properties (e.g., antagonistic v. agonistic). It is thus contemplated by the inventor that various changes may be made in the sequence of the piwi family proteins and peptides (or underlying DNA) without appreciable loss of their biological utility or activity.

It is also well understood by the skilled artisan that, inherent in the definition of a biologically functional equivalent protein or peptide, is the concept that there is a limit to the number of changes that may be made within a defined portion of the molecule and still result in a molecule with an acceptable level of equivalent biological activity. Biologically functional equivalent peptides are thus defined herein as those peptides in which certain, not most or all, of the amino acids may be substituted. Of course, a plurality of distinct proteins/peptides with different substitutions may easily be made and used in accordance with the invention.

It is also well understood that where certain residues are shown to be particularly important to the biological or structural properties of a protein or peptide, e.g., residues in active sites, such residues may not generally be exchanged. This is the case in the present invention, where if any changes, for example, in the PIWI box of piwi family polypeptides, could result in a loss of an aspect of the utility of the resulting peptide for the present invention.

Amino acid substitutions, such as those which might be employed in modifying the piwi family proteins and peptides described herein, are generally based on the relative similarity of the amino acid side-chain substituents, for example, their hydrophobicity, hydrophilicity, charge, size, and the like. An analysis of the size, shape and type of the amino acid side-chain substituents reveals that arginine, lysine and histidine are all positively charged residues; that alanine, glycine and serine are all a similar size; and that phenylalanine, tryptophan and tyrosine all have a generally similar shape. Therefore, based upon these considerations, arginine, lysine and histidine; alanine, glycine and serine; and phenylalanine, tryptophan and tyrosine; are defined herein as biologically functional equivalents.

In making such changes, the hydropathic index of amino acids may be considered. Each amino acid has been assigned a hydropathic index on the basis of their hydrophobicity and charge characteristics, these are: isoleucine (+4.5); valine (+4.2); leucine (+3.8); phenylalanine (+2.8); cysteine/ cystine (+2.5); methionine (+1.9); alanine (+1.8); glycine (−0.4); threonine (−0.7); serine (−0.8); tryptophan (−0.9); tyrosine (−1.3); proline (−1.6); histidine (−3.2); glutamate (−3.5); glutamine (−3.5); aspartate (−3.5); asparagine (−3.5); lysine (−3.9); and arginine (−4.5).

The importance of the hydropathic amino acid index in conferring interactive biological function on a protein is generally understood in the art (Kyte & Doolittle, 1982, incorporated herein by reference). It is known that certain amino acids may be substituted for other amino acids having a similar hydropathic index or score and still retain a similar biological activity. In making changes based upon the hydropathic index, the substitution of amino acids whose hydropathic indices are within ±2 of the original value is preferred, those which are within ±1 of the original value are particularly preferred, and those within ±0.5 of the original value are even more particularly preferred.

It is also understood in the art that the substitution of like amino acids can be made effectively on the basis of hydrophilicity. U.S. Pat. No. 4,554,101, incorporated herein by reference, states that the greatest local average hydrophilicity of a protein, as governed by the hydrophilicity of its adjacent amino acids, correlates with its immunogenicity and antigenicity, i.e. with a biological property of the protein. It is understood that an amino acid can be substituted for another having a similar hydrophilicity value and still obtain a biologically equivalent protein.

As detailed in U.S. Pat. No. 4,554,101, the following hydrophilicity values have been assigned to amino acid residues: arginine (+3.0); lysine (+3.0); aspartate (+3.0±1); glutamate (+3.0±1); serine (+0.3); asparagine (+0.2); glutamine (+0.2); glycine (0); threonine (−0.4); proline (−0.5±1); alanine (−0.5); histidine (−0.5); cysteine (−1.0); methionine (−1.3); valine (−1.5); leucine (−1.8); isoleucine (−1.8); tyrosine (−2.3); phenylalanine (−2.5); tryptophan (−3.4).

In making changes based upon similar hydrophilicity values, the substitution of amino acids whose hydrophilicity values are within ±2 of the original value is preferred, those which are within ±1 of the original value are particularly preferred, and those within ±0.5 of the original value are even more particularly preferred.

While discussion has focused on functionally equivalent polypeptides arising from amino acid changes, it will be appreciated that these changes may be effected by alteration of the encoding DNA, taking into consideration also that the genetic code is degenerate and that two or more codons may code for the same amino acid.

Sequence Modification Techniques

Modifications to the piwi family proteins and peptides described herein may be carried out using techniques such as site directed mutagenesis. Site-specific mutagenesis is a technique useful in the preparation of individual peptides, or biologically functional equivalent proteins or peptides, through specific mutagenesis of the underlying DNA. The technique further provides a ready ability to prepare and test sequence variants, for example, incorporating one or more of the foregoing considerations, by introducing one or more nucleotide sequence changes into the DNA. Site-specific mutagenesis allows the production of mutants through the use of specific oligonucleotide sequences which encode the DNA sequence of the desired mutation, as well as a sufficient number of adjacent nucleotides, to provide a primer sequence of sufficient size and sequence complexity to form a stable duplex on both sides of the deletion junction being traversed. Typically, a primer of about 17 to 30 nucleotides in length is preferred, with about 5 to 10 residues on both sides of the junction of the sequence being altered.

In general, the technique of site-specific mutagenesis is well known in the art as exemplified by publications (e.g., Adelman et al., 1983). As will be appreciated, the technique typically employs a phage vector which exists in both a single stranded and double stranded form. Typical vectors useful in site-directed mutagenesis include vectors such as the M13 phage (Messing et al., 1981). These phage are readily commercially available and their use is generally well known to those skilled in the art. Double stranded plasmids are also routinely employed in site directed mutagenesis which eliminates the step of transferring the gene of interest from a plasmid to a phage.

In general, site-directed mutagenesis in accordance herewith is performed by first obtaining a single-stranded vector or melting apart the two strands of a double stranded vector which includes within its sequence a DNA sequence which encodes, for example, a human piwi family polypeptide (HIWI). An oligonucleotide primer bearing the desired mutated sequence is prepared, generally synthetically, for example by the method of Crea et al. (1978). This primer is then annealed with the single-stranded vector, and subjected to DNA polymerizing enzymes such as E. coli polymerase I Klenow fragment, in order to complete the synthesis of the mutation-bearing strand. Thus, a heteroduplex is formed wherein one strand encodes the original non-mutated sequence and the second strand bears the desired mutation. This heteroduplex vector is then used to transform appropriate cells, such as E. coli cells, and clones are selected which include recombinant vectors bearing the mutated sequence arrangement.

The preparation of sequence variants of the selected gene using site-directed mutagenesis is provided as a means of producing potentially useful piwi family polypeptide or other species capable of modulating growth, proliferation and self-renewing division of stem cells, and proliferation of primordial germ cells and is not meant to be limiting as there are other ways in which sequence variants of these peptides may be obtained. For example, recombinant vectors encoding the desired genes may be treated with mutagenic agents to obtain sequence variants (see, e.g., a method described by Eichenlaub, 1979) for the mutagenesis of plasmid DNA using hydroxylamine.

Other Structural Equivalents

In addition to the piwi family peptidyl compounds described herein, the inventors also contemplate that other sterically similar compounds may be formulated to mimic the key portions of the peptide structure. Such compounds may be used in the same manner as the peptides of the invention and hence are also functional equivalents. The generation of a structural functional equivalent may be achieved by the techniques of modeling and chemical design known to those of skill in the art. It will be understood that all such sterically similar constructs fall within the scope of the present invention.

Introduction of Gene Products

Where the gene itself is employed to introduce the gene products, a convenient method of introduction will be through the use of a recombinant vector which incorporates the desired gene, together with its associated control sequences. The preparation of recombinant vectors is well known to those of skill in the art and described in many references, such as, for example, Sambrook et al. (1989), specifically incorporated herein by reference.

In vectors, it is understood that the DNA coding sequences to be expressed, in this case those encoding the piwi family gene products, are positioned adjacent to and under the control of a promoter. It is understood in the art that to bring a coding sequence under the control of such a promoter, one generally positions the 5' end of the transcription initiation site of the transcriptional reading frame of the gene product to be expressed between about 1 and about 50 nucleotides "downstream" of (i.e., 3' of) the chosen promoter. One may also desire to incorporate into the transcriptional unit of the vector an appropriate polyadenylation site (e.g., 5'-AATAAA-3'), if one was not contained within the original inserted DNA. Typically, these poly A addition sites are placed about 30 to 2000 nucleotides "downstream" of the coding sequence at a position prior to transcription termination.

While use of the control sequences of the specific gene (i.e., a piwi family promoter for a piwi family gene) will be preferred, there is no reason why other control sequences could not be employed, so long as they are compatible with the genotype of the cell being treated. Thus, one may mention other useful promoters by way of example, including, e.g., an SV40 early promoter, a long terminal repeat promoter from retrovirus, an actin promoter, a heat shock promoter, a metallothionein promoter, and the like.

As is known in the art, a promoter is a region of a DNA molecule typically within about 100 nucleotide pairs in front of (upstream of) the point at which transcription begins (i.e., a transcription start site). That region typically contains several types of DNA sequence elements that are located in similar relative positions in different genes. As used herein, the term "promoter" includes what is referred to in the art as an upstream promoter region, a promoter region or a promoter of a generalized eukaryotic RNA Polymerase II transcription unit.

Another type of discrete transcription regulatory sequence element is an enhancer. An enhancer provides specificity of time, location and expression level for a particular encoding region (e.g., gene). A major function of an enhancer is to increase the level of transcription of a coding sequence in a cell that contains one or more transcription factors that bind to that enhancer. Unlike a promoter, an enhancer can function when located at variable distances from transcription start sites so long as a promoter is present.

As used herein, the phrase "enhancer-promoter" means a composite unit that contains both enhancer and promoter elements. An enhancer-promoter is operatively linked to a coding sequence that encodes at least one gene product. As used herein, the phrase "operatively linked" means that an enhancer-promoter is connected to a coding sequence in such a way that the transcription of that coding sequence is controlled and regulated by that enhancer-promoter. Means for operatively linking an enhancer-promoter to a coding sequence are well known in the art. As is also well known in the art, the precise orientation and location relative to a coding sequence whose transcription is controlled, is dependent interalia upon the specific nature of the enhancer-promoter. Thus, a TATA box minimal promoter is typically located from about 25 to about 30 base pairs upstream of a transcription initiation site and an upstream promoter element is typically located from about 100 to about 200 base pairs upstream of a transcription initiation site. In contrast, an enhancer can be located downstream from the initiation site and can be at a considerable distance from that site.

An enhancer-promoter used in a vector construct of the present invention can be any enhancer-promoter that drives expression in a cell to be transfected. By employing an enhancer-promoter with well-known properties, the level and pattern of gene product expression can be optimized.

For introduction of, for example, the human piwi family gene (hiwi), it is proposed that one will desire to preferably employ a vector construct that will deliver the desired gene to the affected cells. This will, of course, generally require that the construct be delivered to the targeted cells, for example, mammalian, avian or fish germline stem cells. It is proposed that this may be achieved most preferably by introduction of the desired gene through the use of a viral vector to carry the piwi family sequence to efficiently infect the cells. These vectors will preferably be an adenoviral, a retroviral, a vaccinia viral vector or adeno-associated virus. These vectors are preferred because they have been successfully used to deliver desired sequences to cells and tend to have a high infection efficiency. Suitable vector-piwi family gene constructs are adapted for administration as pharmaceutical compositions, as described herein below.

Commonly used viral promoters for expression vectors are derived from polyoma, cytomegalovirus, Adenovirus 2, and Simian Virus 40 (SV40). The early and late promoters of SV40 virus are particularly useful because both are obtained easily from the virus as a fragment which also contains the SV40 viral origin of replication. Smaller or larger SV40 fragments may also be used, provided there is included the approximately 250 bp sequence extending from the Hind III site toward the Bgl I site located in the viral origin of replication. Further, it is also possible, and often desirable, to utilize promoter or control sequences normally associated with the desired gene sequence, provided such control sequences are compatible with the host cell systems.

The origin of replication may be provided either by construction of the vector to include an exogenous origin, such as may be derived from SV40 or other viral (e.g., Polyoma, Adeno, VSV, BPV) source, or may be provided by the host cell chromosomal replication mechanism. If the vector is integrated into the host cell chromosome, the latter is often sufficient.

Where a piwi family gene itself is employed it will be most convenient to simply use a wild type piwi family gene directly. However, it is contemplated that certain regions of a piwi family gene may be employed exclusively without employing an entire wild type piwi family gene. It is proposed that it will ultimately be preferable to employ the smallest region needed to modulate stem cell growth, proliferation and self-renewing division, and/or primordial germ cell proliferation, so that one is not introducing unnecessary DNA into cells which receive a piwi family gene construct. Techniques well known to those of skill in the art, such as the use of restriction enzymes, will allow for the generation of small regions of an exemplary piwi family gene. The ability of these regions to modulate cell signaling can easily be determined by the assays reported in the Examples. In general, techniques for assessing the modulation of stem cell growth, proliferation and self-renewing division, along with primordial germ cell proliferation are known in the art.

Cell Culture Techniques

As disclosed herein, PIWI functions both as a cytoplasmic protein (during embryonic germline development) and as nuclear protein during stem cell division. PIWI has a cell-autonomous function to promote stem cell division in addition to its signaling function in maintaining stem cells. The dose of PIWI gene determines the number of germline stem cells formed in the embryo.

In accordance with the present invention, piwi family genes and gene products can thus be used to expand a primitive cell population in vitro. The term "primitive cell" is adopted herein for convenience to collectively refer to stem cells, primordial germ cells and to other primitive cells having totipotent or pluripotent characteristics, or other characteristics of stem cells and primordial germ cells. The term "stem cell" is meant to have its art-recognized meaning, and to include, but not be limited to, the following examples of stem cells: hematopoietic stem cells, neural stem cells, and germline stem cells. The term "primordial germ cell" is also meant to have its art-recognized meaning. Such expanded primitive cell populations are utilized for therapeutic or genetic engineering purposes in human and mammalian, avian, and fish systems.

The term "sustained" as used herein with respect to primitive cells, and cultures of the same, refers to a cell or cell culture capable of undergoing further cell division, even if the cells are eventually subject to senescence.

A method of culturing primitive cells is thus envisioned in accordance with the present invention. The method comprises providing a culture comprising a primitive cell, and delivering to the provided cell a piwi family gene product, whereby growth of the cell in the culture is accomplished. Preferably, the primitive cell is maintained in culture for a time sufficient to produce a sustained cell culture.

Optionally, the piwi family gene product is delivered to the primitive cell by delivering to the primitive cell an effective amount of a DNA molecule comprising a polynucleotide that encodes a biologically active piwi family polypeptide; and maintaining the primitive cell under conditions sufficient for expression of the polypeptide. Alternatively, the piwi family gene product is delivered to the cell by administration of a biologically active piwi family polypeptide to the culture via the culture media or via a feeder matrix included in the culture.

A preferred embodiment of the method comprises: (a) collecting primitive cells; (b) depositing the primitive cells in contact with a feeder matrix, the feeder matrix comprising a piwi family gene product; and (c) growing the primitive cells on the feeder matrix in the presence of media for a time sufficient to produce a sustained primitive cell culture.

Thus, typically, the cultures of the present invention include a feeder matrix as defined herein. A feeder matrix can either be cells or cell lines cultured for the purpose of obtaining a sustained primitive cell culture. In this case the cell line can be transformed with a piwi family gene product in accordance with techniques disclosed herein so as to produce the piwi family gene product. Alternatively, a feeder matrix can be derived from or provided by the organ or tissue in which the primitive cells are located, e.g., the gonad. Alternatively, the feeder cells comprising the feeder matrix could be substituted with extracellular matrix plus bound growth factors, and particularly including a piwi family gene product.

A feeder matrix as used herein is constructed in accordance with procedures known in the art. As noted above, it is preferred that the feeder matrix be preconditioned. By the term "preconditioned" it is meant that the feeder matrix is cultured in the presence of media for a period of time prior to the depositing of primitive cells in contact with the feeder matrix, e.g. a time sufficient to initiate and establish production of, for example, growth factors or other factors by the feeder matrix, and particularly including a piwi family gene product. Thus, a feeder matrix can be preconditioned by culturing the feeder matrix by itself for one to two days prior to the depositing of primitive cells in contact with the feeder matrix.

Candidate cells for use in the feeder matrix are disclosed in the Examples. Additionally, the feeder matrix can comprise Sertoli cells or fibroblast cells, including mouse fibroblast cells. STO fibroblasts and primary fibroblasts are suitable examples. Also, it is contemplated that feeder matrices comprising cells from other murine species (e.g., rat); other mammalian species (e.g., ungulate, bovine, and porcine species); or avian species (e.g. Gallinacea, chicken, turkey, duck, goose, quail and pheasant) may also be used.

The culturing method of the present invention can optionally comprise establishing a monolayer of feeder cells. Feeder cells may mitotically inactivated using standard techniques. For example, the feeder cells may be exposed to gamma radiation (e.g. 4000 Rads of gamma radiation) or may be treated with Mitomycin C (e.g. 10 µg/ml for 2–3 hours). Procedures for mitotically inactivating cells are also detailed in the information typically sent with cells from the American Type Culture Collection (ATCC), 10801 University Boulevard, Manassas, Va. 20110-2209 (e.g. STO feeder cells are available under ATCC accession number 1503). Monolayers may optionally be cultured to about 80% confluency, preferably to about 90% confluency, and more preferably about 100% confluency. While configuration of the feeder cells as a monolayer is the preferred configuration for the culture, any suitable configuration is contemplated to be within the scope of the present invention. Thus, for example, layers, monolayers, clusters, aggregates or other associations or groupings of feeder cells are contemplated to fall within the scope of the present invention and are particularly contemplated to fall with the meaning of the term "matrix".

Thus, the primitive cells can extend non-uniformly through the feeder cells vertically, horizontally, diagonally, or in any combination thereof, such that cell aggregates are formed. In accordance with the present invention, it is thus contemplated that the cultures can be formed by mixing primitive cells with appropriate feeder cells and inserting the mixture into a suitable culture container, such as a multi-well plate.

The media used in carrying out the present invention may be any suitable media. The media may be a conditioned media or a synthetic media, both of which are known in the art. Conditioned media, and particularly BRL conditioned media, is currently preferred. By way of example, BRL conditioned media is prepared according to art-recognized techniques, such as described by Smith, A. G. and Hooper, M. L., Dev. Biol. 1987 May; 121(1): 1–9. BRL cells are available from ATCC under accession number CRL-1442. The media can be supplemented with a piwi family gene product. The media can also be supplemented with growth factors, including but not limited to leukemia inhibitory factor (LIF), insulin-like growth factor (IGF), fibroblast growth factor (FGF), basic fibroblast growth factor (bFGF), stem cell factor (SCF—also called steel factor or SF), transforming growth factor-$\beta 1$ (TGF-$\beta 1$) and anti-retinoic acid.

Cell cultures of the present invention may be formulated for administration to animals by dissociating the cells (e.g., by mechanical dissociation) and intimately admixing the cells with a pharmaceutically acceptable carrier (e.g., phosphate-buffered saline (PBS) solution). Primitive cells in such formulations may be prepared to carry a heterologous DNA sequence into a subject, preferably a vertebrate subject and more preferably a warm-blooded vertebrate subject, in the manner described in greater detail below.

The primitive cells cultured in accordance with the present invention are useful, among other things, as a tool for the study of embryological development (i.e., by labeling the cells with a marker gene and observing their distribution after injection in vivo) and the production of transgenic animals. They are useful in allowing the application of homologous recombination to the production of transgenic animals.

The primitive cells should also be useful for the production of chimeric animals, including transgenic chimeric animals. It is contemplated that chimeric or transgenic chimeric non-human animals, including particularly chimeric or transgenic chimeric avians (i.e. birds), will be useful for the recovery of heterologous proteins from the animals. In the case of an avian, the protein can be recovered directly from the eggs of such chimeric or transgenic chimeric avians. Such avians can be thus be used for the production and recovery of therapeutic proteins and other polypeptides, including piwi family polypeptides themselves.

The following U.S. Patents pertain to the culturing of stem cells an are used herein to illuminate the background of the invention, and in particular cases, to provide additional details respecting the practice. Each of the following U.S. Patent is incorporated herein by reference in its entirety: U.S. Pat. No. 5,690,926 issued Nov. 25, 1997 to Hogan; U.S. Pat. No. 5,670,372 issued Sep. 23, 1997 to Hogan; U.S. Pat. No. 5,537,357 issued Sep. 26, 1995 to Hogan; U.S. Pat. No. 5,340,740 issued Aug. 23, 1994 to Petitte et al.; U.S. Pat. No. 5,656,479 issued Aug. 12, 1997 to Petitte et al.; and U.S. Pat. No. 5,830,510 issued Nov. 3, 1998 to Petitte et al.

Transgenic Animals

It is also contemplated to be within the scope of the present invention to prepare a transgenic non-human animal which expresses a piwi family gene of the present invention. A preferred transgenic animal is a mouse.

The term "transgene" refers to exogenous genetic material which does not naturally form part of the genetic material of an animal to be genetically altered but can be incorporated into the germ and/or somatic cells of that animal by standard transgenic techniques. The term "heterologous DNA" refers to DNA which has been transferred from one individual animal, species or breed to a different individual animal, species or breed. The term "transgenic" refers to cells, tissues, embryos, fetuses or animals which carry one or more transgenes. The term "chimeric" refers to an embryo, fetus or animal which consists of two or more tissues of different genetic composition.

Techniques for the preparation of transgenic animals are known in the art. Exemplary techniques are described in U.S. Pat. No. 5,489,742 (transgenic rats); U.S. Pat. Nos. 4,736,866, 5,550,316, 5,614,396, 5,625,125 and 5,648,061 (transgenic mice); U.S. Pat. Nos. 5,573,933 (transgenic pigs); 5,162,215 (transgenic avian species) and U.S. Pat. No. 5,741,957 (transgenic bovine species), the entire contents of each of which are herein incorporated by reference.

With respect to a representative method for the preparation of a transgenic mouse, cloned recombinant or synthetic DNA sequences or DNA segments encoding a piwi family gene product are injected into fertilized mouse eggs (e.g. an embryo). The injected eggs are implanted in pseudo pregnant females and are grown to term to provide transgenic mice whose cells express a piwi family gene product. Preferably, the injected sequences are constructed having promoter sequences connected so as to express the desired protein in germline stem cells or other primitive cells of the transgenic mouse.

Fish represent a category of animals of interest for agricultural and ecological reasons. Representative fish species include, but are not limited to, trout, salmon, carp, shark, ray, flounder, sole, tilapia, medaka, goldfish, guppy, molly, platyfish, swordtail, zebrafish, loach, catfish, and the like. Representative methods for the preparation of a transgenic fish have been described by Ozato et al, *Cell Differ.*, 19:237–244 (1986), Inoue et al, *Cell Differ. Dev.*, 29:123–128 (1990), Rokkones et al, *J. Comp. Physiol. B*, 158:751–758 (1989), and Guyomard et al, *Biochimie*, 71:857–863 (1989), describing preparation of transgenic medaka, medaka, salmon and trout, respectively.

The term "avian" as used herein refers to any avian species, including but not limited to Gallinacea sp., chicken, turkey, duck, goose, quail and pheasant. Chicken is currently preferred.

With respect to an exemplary method for the preparation of a transgenic avian species, certain donor cell types have been isolated that retain viability when injected into recipient embryos. See Etches et al., *Poultry Science* 72:882–887 (1993); Etches et al., in *Avian Incubation*, Chapter 22, Butterworth Publishers (1990); Verrinder Gibbins et al., *Fourth World Congress on Genetics Applied to Livestock Production*, Edinburgh, (1990); Petitte et al., *Development* 108, 185–189 (1990)). These studies showed that blastodermal cells derived from Stage X embryos (embryo at oviposition) remained viable when transferred to comparable recipient Stage X embryos.

Thus, the present invention provides a new method of altering the phenotype of an animal, such as a bird, and the animals so produced with the primitive cells cultured in accordance with techniques disclosed herein. The method comprises transfecting primitive cells cultured in accordance with the methods disclosed herein with the DNA sequence in vitro (e.g., by electroporation or transformation with a retroviral vector), and then injecting the transfected primitive cells into an embryo, (e.g. an egg containing an embryonic bird via the yolk sac or onto the chorioallantoic membrane), with the DNA sequence being effective to cause a change in phenotype in the embryonic animal (e.g., a change in protein expression, a change in growth rate, feed efficiency, disease resistance, or a combination of all of these factors). Preferably, the primitive cells are also transfected with a piwi family gene to facilitate production of germ cells in the transgenic or chimeric bird and thereby also facilitate germline transmission of the DNA sequence of interest.

Preferably, in the case of a bird, the egg into which the DNA is introduced is incubated to hatch, and the bird so produced is raised to at least an age at which the change in phenotype is expressed. It is of no deleterious consequence if the transformed embryo and bird is chimeric, so long as a physiological response is achieved in the animal after hatch sufficient to evoke a measurable phenotypic change measured in any suitable way. By way of additional example, protein expression in the chimera, or transgenic offspring thereof produced by germ line transmission of the DNA sequence, may be established through incorporation of an inducible promoter into the introduced DNA sequence coupled with treatment of the chimera, or transgenic offspring thereof, with an agent which induces the promoter.

The mechanism of in ovo injection is not critical, but it is preferred that the method not unduly damage the tissues and organs of the embryo or the extraembryonic membranes surrounding it so that the treatment will not decrease hatch rate. For example, in ovo injections can be carried out by forming a window in a bird egg and then using a micropipette or needle for the injection, such a 50 $\mu$m-diameter micro-pipette or a 50 $\mu$m-diameter needle. If desired, the bird egg can be sealed with a substantially bacteria-impermeable sealing material such as wax or the like to prevent subsequent entry of undesirable bacteria. Suitable sealing material may optionally comprise biologically acceptable antimicrobial compositions.

The DNA sequence introduced with the primitive cells in accordance with the present invention is, in general, a construct comprised of a promoter functional in the cells of the candidate animal and a gene encoding a peptide or protein operably linked to the promoter. Preferably, the protein or peptide is physiologically active and capable of producing a phenotypic change in the animal. In general, the DNA construct may be a linear DNA sequence (introduced into the primitive cells of the invention by electroporation) or a sequence carried by a vector or other suitable carrier for transforming the primitive cells of the invention using various techniques known in the art, such as liposomes, calcium phosphate, electroporation, or DMSO. Vectors, as discussed herein, may be plasmids, viruses (including retroviruses), and phage, whether in native form or derivatives thereof.

The production of cloned genes, recombinant DNA, vectors, transformed host cells, proteins and protein fragments by genetic engineering is well known. See e.g., U.S. Pat. No. 4,761,371 to Bell et al. at Col. 6 line 3 to Col. 9 line 65; U.S. Pat. No. 4,877,729 to Clark et al. at Col. 4 line 38 to Col. 7 line 6; U.S. Pat. No. 4,912,038 to Schilling at Col. 3 line 26 to Col. 14 line 12. Protocols for restriction endonuclease digestion, preparation of vectors, DNA purification and other such procedures are essentially as described in standard cloning manuals. See Sambrook et al., *Molecular Cloning, a Laboratory Manual*, (2d Ed., Cold Spring Harbor Press, N.Y. (1989)).

As disclosed herein, a vector is a replicable DNA construct used herein to either amplify and/or express DNA encoding the gene of interest. A suitable expression vector will have controlling elements capable of expressing the cloned cDNA or genomic DNA placed in the correct orientation when the vector is introduced into the correct host. Such elements typically include but are not limited to a promoter region which interacts specifically with cellular proteins involved in transcription or which may be inducible by administration of an inducing agent, enhancer elements which can stimulate transcription many-fold from linked heterologous promoters, a splice acceptor and/or donor sequence, and termination and polyadenylation signals. Also required is the sequence for a ribosome binding site capable of permitting translation and which is operably linked to the gene to be expressed. Recently, a muscle-specific promoter has been isolated which is positioned upstream of both the skeletal muscle structural gene and the essential proximal promoter element and is operably associated with each. (Mar and Ordahl, *Proc. Natl. Acad. Sci. USA* 85, 6404–6408 (1988)). Vectors comprise plasmids, viruses (e.g. adenovirus, cytomegalovirus), phage, and DNA fragments integratable into the host genome by recombination. The vector may optionally replicate and function independently of the host genome, or may in some instances integrate into the genome itself.

The piwi family genes of the present invention can thus be used to create transgenic animals with increased number of primordial germ cells. Such animals in mammalian, avian, and fish systems should provide an improved platform for germline-mediated gene transfer to create transgenic stocks.

The genetically modified animals could express transgenes of commercial interest, including those having therapeutic or prophylactic value to the animal itself or to its offspring. For example, the transgene of interest can encode a protein or peptide including, but not limited to, growth hormone, thyroid releasing hormone (TRH), Marek's MDX, and immunogenic recombinant antigens such as that for coccidiosis.

Alternatively, the genetically modified animals can be employed in the production of therapeutic agents. For example, genetically modified avian species that can lay eggs containing drugs, proteins and antibodies to ward off illness that have been produced via the insertion the genes that make the proteins into viral and other vectors to get them into the birds. piwi family gene products can also be produced and isolated in this manner.

In accordance with the present invention, piwi family genes can also be inserted into such genetically modified animals to create animals with increased number of primordial germ cells, thereby enhancing the likelihood of germline transmission of the transgene encoding the therapeutic agent due to the increased number of primordial germ cells.

Pharmaceutical Compositions

In a preferred embodiment, the present invention provides pharmaceutical compositions comprising a polypeptide or polynucleotide of the present invention and a physiologically acceptable carrier. More preferably, a pharmaceutical composition comprises a piwi family polypeptide or a polynucleotide that encodes those polypeptides.

A composition of the present invention is typically administered parenterally in dosage unit formulations containing standard, well-known nontoxic physiologically acceptable carriers, adjuvants, and vehicles as desired. The term "parenteral" as used herein includes intravenous, intramuscular, intra-arterial injection, or infusion techniques.

Injectable preparations, for example sterile injectable aqueous or oleaginous suspensions, are formulated according to the known art using suitable dispersing or wetting agents and suspending agents. The sterile injectable preparation can also be a sterile injectable solution or suspension in a nontoxic parenterally acceptable diluent or solvent, for example, as a solution in 1,3-butanediol.

Among the acceptable vehicles and solvents that may be employed are water, Ringer's solution, and isotonic sodium chloride solution. In addition, sterile, fixed oils are conventionally employed as a solvent or suspending medium. For this purpose any bland fixed oil can be employed including synthetic mono- or di-glycerides. In addition, fatty acids such as oleic acid find use in the preparation of injectables.

Preferred carriers include neutral saline solutions buffered with phosphate, lactate, Tris, and the like. Of course, one purifies the vector sufficiently to render it essentially free of undesirable contaminants, such as defective interfering adenovirus particles or endotoxins and other pyrogens such that it does not cause any untoward reactions in the individual receiving the vector construct. A preferred means of purifying the vector involves the use of buoyant density gradients, such as cesium chloride gradient centrifugation.

A transfected cell can also serve as a carrier. By way of example, a liver cell can be removed from an organism, transfected with a polynucleotide of the present invention using methods set forth above and then the transfected cell returned to the organism (e.g. injected intra-vascularly).

Generation of Antibodies

In still another embodiment, the present invention provides an antibody immunoreactive with a polypeptide of the present invention. Preferably, an antibody of the invention is a monoclonal antibody. Means for preparing and characterizing antibodies are well known in the art (See, e.g., *Antibodies A Laboratory Manual*, E. Howell and D. Lane, Cold Spring Harbor Laboratory, 1988).

Briefly, a polyclonal antibody is prepared by immunizing an animal with an immunogen comprising a polypeptide or polynucleotide of the present invention, and collecting antisera from that immunized animal. A wide range of animal species can be used for the production of antisera. Typically an animal used for production of anti-antisera is a rabbit, a mouse, a rat, a hamster or a guinea pig. Because of the relatively large blood volume of rabbits, a rabbit is a preferred choice for production of polyclonal antibodies.

As is well known in the art, a given polypeptide or polynucleotide may vary in its immunogenicity. It is often necessary therefore to couple the immunogen (e.g., a polypeptide or polynucleotide) of the present invention) with a carrier. Exemplary and preferred carriers are keyhole limpet hemocyanin (KLH) and bovine serum albumin (BSA). Other albumins such as ovalbumin, mouse serum albumin or rabbit serum albumin can also be used as carriers.

Means for conjugating a polypeptide or a polynucleotide to a carrier protein are well known in the art and include glutaraldehyde, m-maleimidobencoyl-N-hydroxysuccinimide ester, carbodiimide and bis-biazotized benzidine.

As is also well known in the art, immunogencity to a particular immunogen can be enhanced by the use of non-specific stimulators of the immune response known as adjuvants. Exemplary and preferred adjuvants include complete Freund's adjuvant, incomplete Freund's adjuvants and aluminum hydroxide adjuvant.

The amount of immunogen used of the production of polyclonal antibodies varies, inter alia, upon the nature of the immunogen as well as the animal used for immunization. A variety of routes can be used to administer the immunogen, e.g. subcutaneous, intramuscular, intradermal, intravenous and intraperitoneal. The production of polyclonal antibodies is monitored by sampling blood of the immunized animal at various points following immunization. When a desired level of immunogenicity is obtained, the immunized animal can be bled and the serum isolated and stored.

In another aspect, the present invention contemplates a method of producing an antibody immunoreactive with a piwi family polypeptide, the method comprising the steps of (a) transfecting recombinant host cells with a polynucleotide that encodes that polypeptide; (b) culturing the host cells under conditions sufficient for expression of the polypeptide; (c) recovering the polypeptide; and (d) preparing antibodies to the polypeptide. Preferably, the piwi family polypeptide possess a biological activity in accordance with the present invention. Even more preferably, the present invention provides antibodies prepared according to the method described above.

A monoclonal antibody of the present invention can be readily prepared through use of well-known techniques such as those exemplified in U.S. Pat. No. 4,196,265, herein incorporated by reference. Typically, a technique involves first immunizing a suitable animal with a selected antigen (e.g., a polypeptide or polynucleotide of the present invention) in a manner sufficient to provide an immune response. Rodents such as mice and rats are preferred animals. Spleen cells from the immunized animal are then fused with cells of an immortal myeloma cell. Where the immunized animal is a mouse, a preferred myeloma cell is a murine NS-1 myeloma cell.

The fused spleen/myeloma cells are cultured in a selective medium to select fused spleen/myeloma cells from the parental cells. Fused cells are separated from the mixture of non-fused parental cells, for example, by the addition of agents that block the de novo synthesis of nucleotides in the tissue culture media. Exemplary and preferred agents are aminopterin, methotrexate, and azaserine. Aminopterin and methotrexate block de novo synthesis of both purines and pyrimidines, whereas azaserine blocks only purine synthesis. Where aminopterin or methotrexate is used, the media is supplemented with hypoxanthine and thymidine as a source of nucleotides. Where azaserine is used, the media is supplemented with hypoxanthine.

This culturing provides a population of hybridomas from which specific hybridomas are selected. Typically, selection of hybridomas is performed by culturing the cells by single-clone dilution in microtiter plates, followed by testing the individual clonal supernatants for reactivity with an antigen-polypeptides. The selected clones can then be propagated indefinitely to provide the monoclonal antibody.

By way of specific example, to produce an antibody of the present invention, mice are injected intraperitoneally with between about 1–200 $\mu$g of an antigen comprising a polypeptide of the present invention. B lymphocyte cells are stimulated to grow by injecting the antigen in association with an adjuvant such as complete Freund's adjuvant (a non-specific stimulator of the immune response containing killed *Mycobacterium tuberculosis*). At some time (e.g., at least two weeks) after the first injection, mice are boosted by injection with a second dose of the antigen mixed with incomplete Freund's adjuvant.

A few weeks after the second injection, mice are tail bled and the sera titered by immunoprecipitation against radio-labeled antigen. Preferably, the method of boosting and titering is repeated until a suitable titer is achieved. The spleen of the mouse with the highest titer is removed and the spleen lymphocytes are obtained by homogenizing the spleen with a syringe. Typically, a spleen from an immunized mouse contains approximately $5 \times 10^7$ to $2 \times 10^8$ lymphocytes.

Mutant lymphocyte cells known as myeloma cells are obtained from laboratory animals in which such cells have been induced to grow by a variety of well-known methods. Myeloma cells lack the salvage pathway of nucleotide biosynthesis. Because myeloma cells are tumor cells, they can be propagated indefinitely in tissue culture, and are thus denominated immortal. Numerous cultured cell lines of myeloma cells from mice and rats, such as murine NS-1 myeloma cells, have been established.

Myeloma cells are combined under conditions appropriate to foster fusion with the normal antibody-producing cells from the spleen of the mouse or rat injected with the antigen/polypeptide of the present invention. Fusion conditions include, for example, the presence of polyethylene glycol. The resulting fused cells are hybridoma cells. Like myeloma cells, hybridoma cells grow indefinitely in culture.

Hybridoma cells are separated from unfused myeloma cells by culturing in a selection medium such as HAT media (hypoxanthine, aminopterin, thymidine). Unfused myeloma cells lack the enzymes necessary to synthesize nucleotides from the salvage pathway because they are killed in the presence of aminopterin, methotrexate, or azaserine. Unfused lymphocytes also do not continue to grow in tissue culture. Thus, only cells that have successfully fused (hybridoma cells) can grow in the selection media.

Each of the surviving hybridoma cells produces a single antibody. These cells are then screened for the production of the specific antibody immunoreactive with an antigen/polypeptide of the present invention. Single cell hybridomas are isolated by limiting dilutions of the hybridomas. The hybridomas are serially diluted many times and, after the dilutions are allowed to grow, the supernatant is tested for the presence of the monoclonal antibody. The clones producing that antibody are then cultured in large amounts to produce an antibody of the present invention in convenient quantity.

By use of a monoclonal antibody of the present invention, specific polypeptides and polynucleotide of the invention can be recognized as antigens, and thus identified. Once identified, those polypeptides and polynucleotide can be isolated and purified by techniques such as antibody-affinity chromatography. In antibody-affinity chromatography, a monoclonal antibody is bound to a solid substrate and exposed to a solution containing the desired antigen. The antigen is removed from the solution through an immunospecific reaction with the bound antibody. The polypeptide or polynucleotide is then easily removed from the substrate and purified.

Screening Assays

In yet another aspect, the present invention contemplates a method of screening substances for their ability to affect or modulate the biological activity of piwi family gene products. The present invention also contemplates a method of screening substances for their ability to affect or modulate the biological activity of piwi family gene products to thereby affect or modulate the growth, proliferation and self-renewing division of stem cells, particularly germline stem cells, and proliferation of primordial germ cells. Utilizing the methods and compositions of the present invention, screening assays for the testing of candidate substances can be derived. A candidate substance is a substance which potentially can promote or inhibit the biological activity of a piwi family gene product by binding, or other intermolecular interaction, with the piwi family gene product.

An exemplary method of screening candidate substances for their ability to modulate piwi family biological activity comprises the steps of: (a) establishing replicate test and control samples that comprise a biologically active piwi family polypeptide; (b) administering a candidate substance to test sample but not the control sample; (c) measuring the biological activity of the piwi family polypeptide in the test and the control samples; and (d) determining that the candidate substance modulates piwi family biological activity if the biological activity of the piwi family polypeptide measured for the test sample is greater or less than the biological activity of the piwi family polypeptide measured for the control sample. The biological activities of piwi family that may optionally be examined in connection with a screening assay of the present invention comprise modulating the growth, proliferation and self-renewing division of stem cells, particularly germline stem cells, proliferation of primordial germ cells or other biological activity in accordance with the present invention.

The replicate test and control samples can further comprise a cell that expresses a biologically active piwi family polypeptide. The present invention also contemplates a recombinant cell line suitable for use in the exemplary method. A candidate substance identified according to the screening assay described herein is contemplated to have the ability to modulate piwi family biological activity. Such as candidate compound has utility in the treatment of disorders and conditions associated with the biological activity of piwi family.

In a cell-free system, the method comprises the steps of establishing a control system comprising a piwi family polypeptide and a ligand wherein the piwi family polypeptide is capable of binding to the ligand; establishing a test system comprising the piwi family polypeptide, the ligand, and a candidate compound; measuring the binding affinity of the piwi family polypeptide and the ligand in the control and the test systems; and determining that the candidate compound modulates piwi family activity in a cell-free system if the binding affinity measured for the test system is less than or greater than the binding affinity measured for the control system. An exemplary ligand comprises a monoclonal antibody.

A screening assay of the present invention may also involve determining the ability of a candidate substance to modulate, i.e. inhibit or promote piwi family biological activity and preferably, to thereby modulate the growth, proliferation and self-renewing division of stem cells, particularly germline stem cells, proliferation of primordial germ cells or division of other target cells. Target cells can be either naturally occurring cells known to contain a polypeptide of the present invention or transformed cell produced in accordance with a method of transformation set forth hereinbefore.

As is well known in the art, a screening assay provides a cell under conditions suitable for testing the modulation of piwi family biological activity or of growth, proliferation and self-renewing division of stem cells, particularly germline stem cells, or of proliferation of primordial germ cells. These conditions include but are not limited to pH, temperature, tonicity, the presence of relevant metabolic factors (e.g., metal ions such as for example $Ca^{++}$, growth factor, interleukins, or colony stimulating factors), and relevant modifications to the polypeptide such as glycosylation or prenylation. It is contemplated that a polypeptide of the present invention can be expressed and utilized in a prokaryotic or eukaryotic cell. The host cell can also be fractionated into sub-cellular fractions where the receptor can be found. For example, cells expressing the polypeptide can be fractionated into the nuclei, the endoplasmic reticulum, vesicles, or the membrane surfaces of the cell.

In a preferred embodiment, temperature is from about 20° C. to about 50° C., more preferably from about 30° C. to about 40° C. and, even more preferably about 37° C. Osmolality is preferably from about 5 milliosmols per liter (mosm/L) to about 400 mosm/l and, more preferably from about 200 milliosmols per liter to about 400 mosm/l and, even more preferably from about 290 mosm/L to about 310 mosm/L. The presence of factors can be required for the proper testing of piwi family biological activity modulation in specific cells. Such factors include, for example, the presence and absence (withdrawal) of growth factor, interleukins, or colony stimulating factors. U.S. Pat. Nos. 5,837,479; 5,645,999; 5,786,152; 5,739,278; and 5,352,660 also describe exemplary screening assays, and the entire contents of each are herein incorporated by reference.

In one embodiment, a screening assay is designed to be capable of discriminating candidate substances having selective ability to interact with one or more of the polypeptides of the present invention but which polypeptides are without a substantially overlapping activity with another of those polypeptides identified herein. Exemplary assays including genetic screening assays and molecular biology screens such as a yeast two-hybrid screen which will effectively identify piwi-interacting genes important for piwi-mediated cell growth, proliferation and self-renewing division processes. One version of the yeast two-hybrid system has been described (Chien et al., 1991, *Proc. Natl. Acad. Sci. USA*, 88:9578–9582) and is commercially available from Clontech, Palo Alto, Calif.

Therapeutic Methods

As used herein, the terms "piwi family activity" and "piwi family biological activity" are meant to be synonymous and are meant to refer to any biological activity of a piwi family polypeptide. Exemplary biological activities of piwi family comprise activity in the modulation of growth, proliferation and self-renewing division of stem cells (including germine and somatic stem cells), cell proliferation (including activity in embryonic development as described in the Examples), proliferation of primordial germ cells or other biological activity in accordance with the present invention. The biological activity can be accomplished by endogenous piwi family polypeptides or by piwi family polypeptide administered to a subject. Indeed, an isolated and purified piwi family polypeptide, recombinant piwi family polypeptide, and/or piwi family analog or peptidomimetic, each prepared as described herein, can administered to a subject to impart piwi family biological activity in the subject and to treat a disorder associated with piwi family biological activity in the subject. In such case the imparted piwi family biological activity comprises a piwi family biological activity in accordance with the therapeutic methods of the present invention.

With respect to the therapeutic methods of the present invention, any subject can be treated, including animal and plant subjects. A preferred subject is a vertebrate subject. Preferred examples of vertebrates include fish and warm-blooded vertebrates. A preferred example of a warm-blooded vertebrate is a mammal. A preferred example of a mammal is a human. Additionally, as used herein and in the claims, the term "patient" is contemplated to include both human and animal patients, and thus, veterinary therapeutic uses are contemplated in accordance with the present invention.

Accordingly, the methods of the present invention are particularly contemplated to be useful in the treatment of warm-blooded vertebrates. Therefore, the invention concerns mammals and birds.

Contemplated is the treatment of mammals such as humans, as well as those mammals of importance due to being endangered (such as Siberian tigers), of economical importance (animals raised on farms for consumption by humans) and/or social importance (animals kept as pets or in zoos) to humans, for instance, carnivores other than humans (such as cats and dogs), swine (pigs, hogs, and wild boars), ruminants (such as cattle, oxen, sheep, giraffes, deer, goats, bison, and camels), and horses. Also contemplated is the treatment of birds, including the treatment of those kinds of birds that are endangered, kept in zoos, as well as fowl, and more particularly domesticated fowl, i.e., poultry, such as turkeys, chickens, ducks, geese, guinea fowl, and the like, as they are also of economical importance to humans. Thus, contemplated is the treatment of livestock, including, but not limited to, domesticated swine (pigs and hogs), ruminants, horses, poultry, and the like.

Modulation of piwi Family Biological Activity

In one embodiment, a therapeutic method according to the present invention comprises administering to a subject a substance that inhibits or promotes piwi family biological activity. Such a substance may be identified according to the screening assay set forth above. The method comprises treating a subject suffering from a disorder associated with or mediated by piwi family biological activity by administering to the subject an effective piwi family biological activity-modulating amount of a substance identified according to a screening assay described above. By the term "modulating", it is contemplated that the substance can either promote or inhibit the biological activity of piwi family polypeptides, depending on the disorder to be treated. For example, the administering of antibodies against a chosen PIWI family protein (e.g. HIWI, MIWI, etc.) provides treatment of germline tumor or other developmental or tissue defects caused by piwi family-mediated mechanisms.

Insofar as a piwi family biological activity modulator can take the form of a polypeptide or of an anti-piwi family monoclonal antibody, or fragment thereof, it is to be appreciated that the potency, and therefore an expression of a "therapeutically effective" amount can vary. However, as shown by the present assay methods, one skilled in the art can readily assess the potency of a candidate piwi family biological activity modulator of this invention. A piwi family biological activity modulator can be measured by a variety of means including through the use of a responsive reporter, which drives expression of a reporter gene; interaction of piwi family polypeptides with a monoclonal antibody as described herein; and the like assays.

A preferred piwi family biological activity modulator has the ability to substantially interact with piwi family in solution at modulator concentrations of less than one (1) micro molar ($\mu$M), preferably less than 0.1 $\mu$M, and more preferably less than 0.01 $\mu$M. By "substantially" is meant that at least a 50 percent modulation in piwi family biological activity is observed in the presence of the piwi family biological activity modulator, and a 50% modulation is referred to herein as an IC50 value.

A therapeutically effective amount of a piwi family biological activity modulator of this invention in the form of a monoclonal antibody, or fragment thereof, is typically an amount such that when administered in a physiologically tolerable composition is sufficient to achieve a plasma concentration of from about 0.01 microgram (ug) per milliliter (ml) to about 100 ug/ml, preferably from about 1 ug/ml to about 5 ug/ml, and usually about 5 ug/ml.

A therapeutically effective amount of a piwi family biological activity modulator of this invention in the form of a polypeptide is typically an amount of polypeptide such that when administered in a physiologically tolerable composition is sufficient to achieve a plasma concentration of from about 0.001 microgram ($\mu$g) per milliliter (ml) to about 10 $\mu$g/ml, preferably from about 0.05 $\mu$g/ml to about 1.0 ug/ml.

The monoclonal antibodies or polypeptides of the invention can be administered parenterally by injection or by gradual infusion overtime. Although the tissue to be treated can typically be accessed in the body by systemic administration and therefore most often treated by intravenous administration of therapeutic compositions, other tissues and delivery means are contemplated where there is a likelihood that the tissue targeted contains the target molecule. Thus, monoclonal antibodies or polypeptides of the invention can be administered intravenously, intraperitoneally, intramuscularly, subcutaneously, intra-cavity, transdermally, and can be delivered by peristaltic means.

The therapeutic compositions containing a monoclonal antibody or a polypeptide of this invention are conventionally administered intravenously, as by injection of a unit dose, for example. The term "unit dose" when used in reference to a therapeutic composition of the present invention refers to physically discrete units suitable as unitary dosage for the subject, each unit containing a predetermined quantity of active material calculated to produce the desired therapeutic effect in association with the required diluent; i.e., carrier or vehicle.

The compositions are administered in a manner compatible with the dosage formulation, and in a therapeutically effective amount. The quantity to be administered depends on the subject to be treated, capacity of the subject's system to utilize the active ingredient, and degree of therapeutic effect desired. Precise amounts of active ingredient required to be administered depend on the judgement of the practitioner and are peculiar to each individual. However, suitable dosage ranges for systemic application are disclosed herein and depend on the route of administration. Suitable regimes for administration are also variable, but are typified by an initial administration followed by repeated doses at one or more hour intervals by a subsequent injection or other administration. Alternatively, continuous intravenous infusion sufficient to maintain concentrations in the blood in the ranges specified for in vivo therapies are contemplated. Polypeptide modulators can also be modified as described herein below with respect to biologically active piwi family proteins and protein therapy methods using the same.

Monoclonal Antibodies

The present invention describes, in one embodiment, piwi family modulators in the form of monoclonal antibodies which immunoreact with a piwi family polypeptide and bind the piwi family polypeptide to modulate biological activity as described herein. The invention also describes above cell lines which produce the antibodies, methods for producing the cell lines, and methods for producing the monoclonal antibodies.

The term "antibody or antibody molecule" in the various grammatical forms is used herein as a collective noun that refers to a population of immunoglobulin molecules and/or immunologically active portions of immunoglobulin molecules, i.e., molecules that contain an antibody combining site or paratope. An "antibody combining site" is that structural portion of an antibody molecule comprised of heavy and light chain variable and hypervariable regions that specifically binds antigen.

Exemplary antibodies for use in the present invention are intact immunoglobulin molecules, substantially intact immunoglobulin molecules, single chain immunoglobulins or antibodies, those portions of an immunoglobulin molecule that contain the paratope, including those portions known in the art as Fab, Fab', F(ab')2 and F(v), and also referred to as antibody fragments. Indeed, it is contemplated to be within the scope of the present invention that a monovalent modulator may optionally be is used in the present method. Thus, the terms "modulate", "modulating", and "modulator" are meant to be construed to encompass such promotion.

The phrase "monoclonal antibody" in its various grammatical forms refers to a population of antibody molecules that contain only one species of antibody combining site capable of immunoreacting with a particular epitope. A monoclonal antibody thus typically displays a single binding affinity for any epitope with which it immunoreacts. A monoclonal antibody may therefore contain an antibody molecule having a plurality of antibody combining sites, each immunospecific for a different epitope, e.g., a bispecific monoclonal antibody. Methods of producing a monoclonal antibody, a hybridoma cell, or a hybridoma cell culture are described above.

It is also possible to determine, without undue experimentation, if a monoclonal antibody has the same (i.e., equivalent) specificity (immunoreaction characteristics) as a monoclonal antibody of this invention by ascertaining whether the former prevents the latter from binding to a preselected target molecule. If the monoclonal antibody being tested competes with the monoclonal antibody of the invention, as shown by a decrease in binding by the monoclonal antibody of the invention in standard competition assays for binding to the target molecule when present in the solid phase, then it is likely that the two monoclonal antibodies bind to the same, or a closely related, epitope.

Still another way to determine whether a monoclonal antibody has the specificity of a monoclonal antibody of the invention is to pre-incubate the monoclonal antibody of the invention with the target molecule with which it is normally reactive, and then add the monoclonal antibody being tested to determine if the monoclonal antibody being tested is inhibited in its ability to bind the target molecule. If the monoclonal antibody being tested is inhibited then, in all likelihood, it has the same, or functionally equivalent, epitopic specificity as the monoclonal antibody of the invention.

An additional way to determine whether a monoclonal antibody has the specificity of a monoclonal antibody of the invention is to determine the amino acid residue sequence of the CDR regions of the antibodies in question. "CDRs" (complementarity determining regions) mean the three sub-regions of the light or heavy chain variable regions which have hypervariable sequences and form loop structures that are primarily responsible for making direct contact with antigen. Antibody molecules having identical, or functionally equivalent, amino acid residue sequences in their CDR regions have the same binding specificity. Methods for sequencing polypeptides are well known in the art.

The immunospecificity of an antibody, its target molecule binding capacity, and the attendant affinity the antibody exhibits for the epitope, are defined by the epitope with which the antibody immunoreacts. The epitope specificity is defined at least in part by the amino acid residue sequence of the variable region of the heavy chain of the immunoglobulin that comprises the antibody, and in part by the light chain variable region amino acid residue sequence. Use of the terms "having the binding specificity of" or "having the binding preference of" indicates that equivalent monoclonal antibodies exhibit the same or similar immunoreaction (binding) characteristics and compete for binding to a pre-selected target molecule.

Humanized monoclonal antibodies offer particular advantages over murine monoclonal antibodies, particularly insofar as they can be used therapeutically in humans. Specifically, human antibodies are not cleared from the circulation as rapidly as "foreign" antigens, and do not activate the immune system in the same manner as foreign antigens and foreign antibodies. Methods of preparing "humanized" antibodies are generally well known in the art, and can readily be applied to the antibodies of the present invention. Thus, the invention contemplates, in one embodiment, a monoclonal antibody of this invention that is humanized by grafting to introduce components of the human immune system without substantially interfering with the ability of the antibody to bind antigen.

The use of a molecular cloning approach to generate antibodies, particularly monoclonal antibodies, and more particularly single chain monoclonal antibodies, is also contemplated. The production of single chain antibodies has been described in the art, see e.g., U.S. Pat. No. 5,260,203, the contents of which are herein incorporated by reference. For this, combinatorial immunoglobulin phagemid libraries are prepared from RNA isolated from the spleen of the immunized animal, and phagemids expressing appropriate antibodies are selected by panning on endothelial tissue. The advantages of this approach over conventional hybridoma techniques are that approximately $10^4$ times as many antibodies can be produced and screened in a single round, and that new specificities are generated by H and L chain combination in a single chain, which further increases the chance of finding appropriate antibodies. Thus, an antibody of the present invention, or a "derivative" of an antibody of the present invention pertains to a single polypeptide chain binding molecule which has binding specificity and affinity substantially similar to the binding specificity and affinity of the light and heavy chain aggregate variable region of an antibody described herein.

Other Modulators

Given the disclosure of the piwi family activity in tissues herein, it is also contemplated that as yet undefined chemical compounds may be used to modulate piwi family activity in tissues in accordance with the methods of the present invention. The identification of such compounds is facilitated by the description of screening assays directed to piwi family activity in tissues presented above.

Gene Therapy

In accordance with the present invention, piwi family genes can be used as a tool of gene therapy in humans and mammalian, avian, and fish systems to increase the number of stem cells and to increase proliferation of primordial germ cells in vivo.

For example, over-proliferation of malignant stem cells is the leading cause of cancer while under-proliferation of stem cells or stem-like progenitor cells leads to tissue dystrophy, anemia, immunodeficiency, and male infertility. The crucial role of stem cells has long been attributed to their ability to self-renew and to generate immense number of specialized cells on demand. Thus, piwi family genes can be used for gene therapy in accordance with the present invention. Exemplary gene therapy methods, including liposomal transfection of nucleic acids into host cells, are described in U.S. Pat. Nos. 5,279,833; 5,286,634; 5,399,346; 5,646,008; 5,651,964; 5,641,484; and 5,643,567, the contents of each of which are herein incorporated by reference.

Briefly, piwi family gene therapy directed toward modulation of growth, proliferation and self-renewing division in a target cell is described. Target cells include but are not limited to germline stem cells, primordial germ cells and cancerous ortumorous cells. In one embodiment, a therapeutic method of the present invention contemplates a method for modulating of growth, proliferation or self-renewing division in a cell comprising the steps of: (a) delivering to the cell an effective amount of a DNA molecule comprising a polynucleotide that encodes a piwi family polypeptide that modulates growth, proliferation or self-renewing division; and (b) maintaining the cell under conditions sufficient for expression of said polypeptide.

In a preferred embodiment, the piwi family polypeptide is HIWI or MIWI. Delivery is preferably accomplished by injecting the DNA molecule into the cell. Where the cell is in a subject delivering is preferably administering the DNA molecule into the circulatory system of the subject. In a preferred embodiment, administering comprises the steps of: (a) providing a vehicle that contains the DNA molecule; and (b) administering the vehicle to the subject.

A vehicle is preferably a cell transformed or transfected with the DNA molecule or a transfected cell derived from such a transformed or transfected cell. An exemplary and preferred transformed or transfected cell is a spermatogonial cell or a tumor cell from the tumor being treated. Techniques for transforming or transfecting a cell with a DNA molecule of the present invention are set forth above.

Alternatively, the vehicle is a virus or an antibody that specifically infects or immunoreacts with an antigen of the tumor. Retroviruses used to deliver the constructs to the host target tissues generally are viruses in which the 3'-LTR (linear transfer region) has been inactivated. That is, these are enhancerless 3'-LTR's, often referred to as SIN (self-inactivating viruses) because after productive infection into the host cell, the 3'-LTR is transferred to the 5'-end and both viral LTR's are inactive with respect to transcriptional activity. A use of these viruses well known to those skilled in the art is to clone genes for which the regulatory elements of the cloned gene are inserted in the space between the two LTR's. An advantage of a viral infection system is that it allows for a very high level of infection into the appropriate recipient cell.

Antibodies have been used to target and deliver DNA molecules. An N-terminal modified poly-L-lysine (NPLL)-antibody conjugate readily forms a complex with plasmid DNA. A complex of monoclonal antibodies against a cell surface thrombomodulin conjugated with NPLL was used to target a foreign plasmid DNA to an antigen-expressing mouse lung endothelial cell line and mouse lung. Those targeted endothelial cells expressed the product encoded by that foreign DNA.

It is also envisioned that this embodiment of the present invention can be practiced using alternative viral or phage vectors, including retroviral vectors, adenoviral vectors and vaccinia viruses whose genome has been manipulated in alternative ways so as to render the virus non-pathogenic. Methods for creating such a viral mutation are set forth in detail in U.S. Pat. No. 4,769,331, incorporated herein by reference.

By way of specific example, hiwi, miwi, and their homologs from warm-blooded vertebrates are introduced into isolated spermatogonial cells or other relevant cells. The re-injection of the transgene-carrying cells into the testis or other relevant tissues provides a treatment for male infertility or other relevant diseases in human and animals.

Protein Therapy

In another embodiment, the direct introduction of the piwi family proteins into a diseased tissue is contemplated to provide a therapeutic effect in human and animals. Such a therapeutic method comprises administering to a subject a therapeutic composition which comprises a biologically active piwi family polypeptide of the present invention in amount effective to modulate a piwi-mediated biological activity in the subject.

In one embodiment, a polypeptide for use in such a composition comprises no more than about 100 amino acid residues, preferably no more than about 60 residues, more preferably no more than about 30 residues. Peptides can be linear or cyclic.

A subject polypeptide includes any analog, fragment or chemical derivative of a piwi family polypeptide. Such a polypeptide can be subject to various changes, substitutions, insertions, and deletions where such changes provide for certain advantages in its use. In this regard, an piwi family polypeptide for use in a therapeutic method of the present invention corresponds to, rather than is identical to, the sequence of a native piwi family polypeptide where one or more changes are made and it retains the ability to function as a piwi family polypeptide in one or more of the assays as defined herein. Thus, a polypeptide can be in any of a variety of forms of peptide derivatives, that include amides, conjugates with proteins, cyclized peptides, polymerized peptides, analogs, fragments, chemically modified peptides, and the like derivatives.

The term "analog" includes any polypeptide having an amino acid residue sequence substantially identical to a sequence of an endogenous piwi family polypeptide in which one or more residues have been conservatively substituted with a functionally similar residue and which displays the piwi family biological activity as described herein. Examples of conservative substitutions include the substitution of one non-polar (hydrophobic) residue such as isoleucine, valine, leucine or methionine for another; the substitution of one polar (hydrophilic) residue for another such as between arginine and lysine, between glutamine and asparagine, between glycine and serine; the substitution of one basic residue such as lysine, arginine or histidine for another; or the substitution of one acidic residue, such as aspartic acid or glutamic acid for another. Such substitutions are described in detail above with respect to the isolated and purified piwi family polypeptide of the present invention.

The phrase "conservative substitution" also includes the use of a chemically derivatized residue in place of a non-derivatized residue provided that such polypeptide displays the requisite biological activity.

"Chemical derivative" refers to a subject polypeptide having one or more residues chemically derivatized by reaction of a functional side group. Such derivatized molecules include for example, those molecules in which free amino groups have been derivatized to form amine hydrochlorides, p-toluene sulfonyl groups, carbobenzoxy groups, t-butyloxycarbonyl groups, chloroacetyl groups or formyl groups. Free carboxyl groups may be derivatized to form salts, methyl and ethyl esters or other types of esters or hydrazides. Free hydroxyl groups may be derivatized to form O-acyl or O-alkyl derivatives. The imidazole nitrogen of histidine may be derivatized to form N-imbenzylhistidine. Also included as chemical derivatives are those peptides which contain one or more naturally occurring amino acid derivatives of the twenty standard amino acids. For examples: 4-hydroxyproline may be substituted for proline; 5-hydroxylysine may be substituted for lysine; 3-methylhistidine may be substituted for histidine; homoserine may be substituted for serine; and ornithine may be substituted for lysine. Polypeptides of the present invention also include any polypeptide having one or more additions and/or deletions or residues relative to the sequence of a polypeptide whose sequence is shown herein, so long as the requisite activity is maintained.

The term "fragment" refers to any subject polypeptide having an amino acid residue sequence shorter than that of a polypeptide whose amino acid residue sequence is shown herein.

When a polypeptide of the present invention has a sequence that is not identical to the sequence of a piwi family endogenous polypeptide, it is typically because one or more conservative or non-conservative substitutions have been made, usually no more than about 30 number percent, and preferably no more than 10 number percent of the amino acid residues are substituted. Additional residues may also be added at either terminus of a polypeptide for the purpose of providing a "linker" by which the polypeptides of this invention can be conveniently affixed to a label or solid matrix, or carrier. Labels, solid matrices and carriers that can be used with the polypeptides of this invention are described elsewhere herein.

Amino acid residue linkers are usually at least one residue and can be 40 or more residues, more often 1 to 10 residues, but do not form piwi family polypeptide epitopes. Typical amino acid residues used for linking are tyrosine, cysteine, lysine, glutamic and aspartic acid, or the like. In addition, a subject polypeptide can differ, unless otherwise specified, from the natural sequence of a piwi family polypeptide by the sequence being modified by terminal-NH2 acylation, e.g., acetylation, or thioglycolic acid amidation, by terminal-carboxylamidation, e.g., with ammonia, methylamine, and the like terminal modifications. Terminal modifications are useful, as is well known, to reduce susceptibility by proteinase digestion, and therefore serve to prolong half life of the polypeptides in solutions, particularly biological fluids where proteases may be present. In this regard, polypeptide cyclization is also a useful terminal modification, and is particularly preferred also because of the stable structures formed by cyclization and in view of the biological activities observed for such cyclic peptides as described herein.

Any peptide of the present invention may be used in the form of a pharmaceutically acceptable salt. Suitable acids which are capable of the peptides with the peptides of the present invention include inorganic acids such as trifluoroacetic acid (TFA), hydrochloric acid (HCl), hydrobromic acid, perchloric acid, nitric acid, thiocyanic acid, sulfuric acid, phosphoric acetic acid, propionic acid, glycolic acid, lactic acid, pyruvic acid, oxalic acid, malonic acid, succinic acid, maleic acid, fumaric acid, anthranilic acid, cinnamic acid, naphthalene sulfonic acid, sulfanilic acid or the like. HCl and TFA salts are particularly preferred.

Suitable bases capable of forming salts with the peptides of the present invention include inorganic bases such as sodium hydroxide, ammonium hydroxide, potassium hydroxide and the like; and organic bases such as mono- di- and tri-alkyl and aryl amines (e.g. triethylamine, diisopropyl amine, methyl amine, dimethyl amine and the like), and optionally substituted ethanolamines (e.g. ethanolamine, diethanolamine and the like).

A peptide of the present invention, also referred to herein as a subject polypeptide, can be synthesized by any of the techniques that are known to those skilled in the polypeptide art, including recombinant DNA techniques. Synthetic chemistry techniques, such as a solid-phase Merrifield-type synthesis, are preferred for reasons of purity, antigenic specificity, freedom from undesired side products, ease of production and the like. An excellent summary of the many techniques available can be found in Steward et al., "Solid Phase Peptide Synthesis", W. H. Freeman Co., San Francisco, 1969; Bodanszky, et al., "Peptide Synthesis", John Wiley & Sons, Second Edition, 1976; J. Meienhofer, "Hormonal Proteins and Peptides", Vol. 2, p. 46, Academic Press (New York), 1983; Merrifield, *Adv Enzymol,* 32:221–96, 1969; Fields et al., *Int. J. Peptide Protein Res.,* 35:161–214,1990; and U.S. Pat. No. 4,244,946 for solid phase peptide synthesis, and Schroder et al., "The Peptides", Vol. 1, Academic Press (New York), 1965 for classical solution synthesis, each of which is incorporated herein by reference. Appropriate protective groups usable in such synthesis are described in the above texts and in J. F. W. McOmie, "Protective Groups in Organic Chemistry", Plenum Press, New York, 1973, which is incorporated herein by reference.

In general, the solid-phase synthesis methods contemplated comprise the sequential addition of one or more amino acid residues or suitably protected amino acid residues to a growing peptide chain. Normally, either the amino or carboxyl group of the first amino acid residue is protected by a suitable, selectively removable protecting group. a different, selectively removable protecting group is utilized for amino acids containing a reactive side group such as lysine.

Using a solid phase synthesis as exemplary, the protected or derivatized amino acid is attached to an inert solid support through its unprotected carboxyl or amino group. The protecting group of the amino or carboxyl group is then selectively removed and the next amino acid in the sequence having the complimentary (amino or carboxyl) group suitably protected is admixed and reacted under conditions suitable for forming the amide linkage with the residue already attached to the solid support. The protecting group of the amino or carboxyl group is then removed from this newly added amino acid residue, and the next amino acid (suitably protected) is then added, and so forth. After all the desired amino acids have been linked in the proper sequence, any remaining terminal and side group protecting groups (and solid support) are removed sequentially or concurrently, to afford the final linear polypeptide.

The resultant linear polypeptides prepared for example as described above may be reacted to form their corresponding cyclic peptides. An exemplary method for cyclizing peptides is described by Zimmer et al., *Peptides* 1992, pp. 393–394, ESCOM Science Publishers, B. V., 1993. Typically, tertbutoxycarbonyl protected peptide methyl ester is dissolved in methanol and sodium hydroxide solution are added and the admixture is reacted at 20° C. to hydrolytically remove the methyl ester protecting group. After evaporating the solvent, the tertbutoxycarbonyl protected peptide is extracted with ethyl acetate from acidified aqueous solvent. The tertbutoxycarbonyl protecting group is then removed under mildly acidic conditions in dioxane cosolvent. The unprotected linear peptide with free amino and carboxy termini so obtained is converted to its corresponding cyclic peptide by reacting a dilute solution of the linear peptide, in a mixture of dichloromethane and dimethylformamide, with dicyclohexylcarbodiimide in the presence of 1-hydroxybenzotriazole and N-methylmorpholine. The resultant cyclic peptide is then purified by chromatography.

Antisense Oliqonulceotide Therapy

In another embodiment, the administering of antisense RNA against a chosen piwi family gene (e.g. hiwi, miwi, etc.) provides treatment of germine tumor or other developmental or tissue defects caused by piwi family-mediated mechanisms. In accordance with the present invention such a therapeutic method may alternatively comprise promoting or inhibiting piwi family in a subject by administering an effective amount of a substance that inhibits or promotes expression of a piwi family-encoding nucleic acid segment in the subject. Examples of such a substance, include, for example, an antisense oligonucleotide derived from SEQ ID NOs:1, 3 or 5. Therapeutic methods utilizing antisense oligonucleotides have been described in the art, for example in U.S. Pat. Nos. 5,627,158 and 5,734,033, the contents of each of which are herein incorporated by reference.

Formulation of Therapeutic Compositions

The piwi family biological activity modulating substances, gene therapy vectors, biologically activity piwi family gene products, and substances that inhibit or promote expression of a piwi family-encoding nucleic acid segment described above are adapted for administration as a pharmaceutical compositions as described above. Additional formulation and dose preparation techniques have been described in the art, see for example, those described in U.S. Pat. No. 5,326,902 issued to Seipp et al. on Jul. 5, 1994, U.S. Pat. No. 5,234,933 issued to Marnett et al. on Aug. 10, 1993, and PCT Publication WO 93/25521 of Johnson et al. published Dec. 23, 1993, the entire contents of each of which are herein incorporated by reference.

For the purposes described above, the identified substances may normally be administered systemically or partially, usually by oral or parenteral administration. The doses to be administered are determined depending upon age, body weight, symptom, the desired therapeutic effect, the route of administration, and the duration of the treatment etc. In a human adult, the doses per person per administration are generally between 1 mg and 500 mg, by oral administration, up to several times per day, and between 1 mg and 100 mg, by parenteral administration up to several times per day. Since the doses to be used depend upon various conditions, as mentioned above, there may be a case in which doses are lower than or greater than the ranges specified above.

Solid compositions for oral administration include compressed tablets, pills, dispersible powders, capsules, and granules. In such compositions, one or more of the active substance(s) is or are, admixed with at least one inert diluent (lactose, mannitol, glucose, hydroxypropylcellulose, microcrystalline cellulose, starch, polyvinylpyrrolidone, magnesium metasilicate alminate, etc.). The compositions may also comprise, as is normal practice, additional substances other than inert diluents: e.g. lubricating agents (magnesium stearate, etc.), disintegrating agents (cellulose, calcium glycolate etc.), and assisting agent for dissolving (glutamic acid, aspartic acid, etc.) stabilizing agent (lactose etc.). The tablets or pills may, if desired, be coated with gastric or enteric material (sugar, gelatin, hydroxypropylcellulose or hydroxypropylmethyl cellulose phthalate, etc.). Capsules include soft ones and hard ones.

Liquid compositions for oral administration include pharmaceutically-acceptable emulsions, solutions, suspensions, syrups and elixirs. In such compositions, one or more of the active substance(s) is or are admixed with inert diluent(s) commonly used in the art (purified water, ethanol etc.). Besides inert diluents, such compositions may also comprise adjuvants (wetting agents, suspending agents, etc.), sweetening agents, flavoring agents, perfuming agents and preserving agents.

Other compositions for oral administration include spray compositions which may be prepared by known methods and which comprise one or more of the active substance(s). Spray compositions may comprise additional substances other than inert diluents: e.g. preserving agents (sodium sulfite, etc.), isotonic buffer (sodium chloride, sodium citrate, citric acid, etc.). For preparation of such spray compositions, for example, the method described in U.S. Pat. Nos. 2,868,691 or 3,095,355 may be used.

Injections for parenteral administration include sterile aqueous or non-aqueous solution, suspensions and emulsions. In such compositions, one or more of active substance (s) is or are admixed with at least one inert aqueous diluent(s) (distilled water for injection, physiological salt solution etc.) or inert non-aqueous diluent(s) (propylene glycol, polyethylene glycol, olive oil, ethanol, POLYSOLBATE 80® etc.). Injections may comprise additional other than inert diluents: e.g. preserving agents, wetting agents, emulsifying agents, dispersing agents, stabilizing agents (lactose, etc.), assisting agents such as for dissolving (glutamic acid, aspartic acid, etc.). They may be sterilized, for example, by filtration through a bacteria-retaining filter, by incorporation of sterilizing agents in the compositions or by irradiation. They also be manufactured in the form of sterile solid compositions, for example, by freeze-drying, and which can be dissolved in sterile water or some other sterile diluents for injection immediately before use.

Other compositions for administration include liquids for external use, and endermic linaments (ointment, etc.), suppositories and pessaries which comprise one or more of the active substance(s) and may be prepared by known methods.

Detecting a Polynucleotide or a Polypeptide of the Present Invention

Alternatively, the present invention provides a method of detecting a polypeptide of the present invention, wherein the method comprises immunoreacting the polypeptides with antibodies prepared according to the method described above to form antibody-polypeptide conjugates, and detecting the conjugates.

In yet another embodiment, the present invention contemplates a method of detecting messenger RNA transcripts that encode a polypeptide of the present invention, wherein the method comprises hybridizing the messenger RNA transcripts with polynucleotide sequences that encode the polypeptide to form duplexes; and detecting the duplex. Alternatively, the present invention provides a method of detecting DNA molecules that encode a polypeptide of the present invention, wherein the method comprises hybridizing DNA molecules with a polynucleotide that encodes that polypeptide to form duplexes; and detecting the duplexes.

The detection and screening assays disclosed herein can be used as a prognosis tool. hiwi, miwi and their mammalian homologous genes as well as their protein products can be readily used in clinical setting as a prognostic indicator for screening infertility, germline cancer, or other heritable piwi-related diseases in human and animals.

The detection and screening assays disclosed herein can be also used as a part of a diagnostic method. hiwi, miwi, and their mamalian homologs as well as their proteins can be readily used in clinical practice to diagnose the cause of infertility, testicular cancer, or other heritable piwi-related diseases in human and animals.

Screening Assays for a Polypeptide of the Present Invention

The present invention provides a method of screening a biological sample for the presence of a piwi family polypeptide. Preferably, the piwi family polypeptide possesses a biological activity in accordance with the present invention. A biological sample to be screened can be a biological fluid such as extracellular or intracellular fluid or a cell or tissue extract or homogenate. A biological sample can also be an isolated cell (e.g., in culture) or a collection of cells such as in a tissue sample or histology sample. A tissue sample can be suspended in a liquid medium or fixed onto a solid support such as a microscope slide.

In accordance with a screening assay method, a biological sample is exposed to an antibody immunoreactive with the polypeptide whose presence is being assayed. Typically, exposure is accomplished by forming an admixture in a liquid medium that contains both the antibody and the candidate polypeptide. Either the antibody or the sample with the polypeptide can be affixed to a solid support (e.g., a column or a microtiter plate).

The biological sample is exposed to the antibody under biological reaction conditions and for a period of time sufficient for antibody-polypeptide conjugate formation. Biological reaction conditions include ionic composition and concentration, temperature, pH and the like.

Ionic composition and concentration can range from that of distilled water to a 2 molal solution of NaCl. Preferably, osmolality is from about 100 mosmols/l to about 400 mosmols/l and, more preferably from about 200 mosmols/l to about 300 mosmols/l. Temperature preferably is from about 4° C. to about 100° C., more preferably from about 15° C. to about 50° C. and, even more preferably from about 25° C. to about 40° C. pH is preferably from about a value of 4.0 to a value of about 9.0, more preferably from about a value of 6.5 to a value of about 8.5 and, even more preferably from about a value of 7.0 to a value of about 7.5. The only limit on biological reaction conditions is that the conditions selected allow for antibody-polypeptide conjugate formation and that the conditions do not adversely affect either the antibody or the polypeptide.

Exposure time will vary interalia with the biological conditions used, the concentration of antibody and polypeptide and the nature of the sample (e.g., fluid or tissue sample). Means for determining exposure time are well known to one of ordinary skill in the art. Typically, where the sample is fluid and the concentration of polypeptide in that sample is about $10^{-10}$M, exposure time is from about 10 minutes to about 200 minutes.

The presence of polypeptide in the sample is detected by detecting the formation and presence of antibody-polypeptide conjugates. Means for detecting such antibody-antigen (e.g., receptor polypeptide) conjugates or complexes are well known in the art and include such procedures as centrifugation, affinity chromatography and the like, binding of a secondary antibody to the antibody-candidate receptor complex.

In one embodiment, detection is accomplished by detecting an indicator affixed to the antibody. Exemplary and well known such indicators include radioactive labels (e.g., $^{32}$P, $^{125}$I, $^{14}$C), a second antibody or an enzyme such as horse radish peroxidase. Means for affixing indicators to antibodies are well known in the art. Commercial kits are available.

Screening Assay for Anti-Polypeptide Antibody

In another aspect, the present invention provides a method of screening a biological sample for the presence of antibodies immunoreactive with a piwi family polypeptide. Preferably the piwi family polypeptide has a biological activity in accordance with the present invention. In accordance with such a method, a biological sample is exposed to a piwi family polypeptide under biological conditions and for a period of time sufficient for antibody-polypeptide conjugate formation and the formed conjugates are detected.

Screening Assay for Polynucleotide That Encodes a piwi Family Polypeptide of the Present Invention A DNA molecule and, particularly a probe molecule, can be used for hybridizing as an oligonucleotide probe to a DNA source suspected of encoding a piwi family polypeptide of the present invention. Preferably the piwi family polypeptide possesses a biological activity in accordance with the present invention. The probing is usually accomplished by hybridizing the oligonucleotide to a DNA source suspected of possessing a piwi family gene. In some cases, the probes constitute only a single probe, and in others, the probes constitute a collection of probes based on a certain amino acid sequence or sequences of the polypeptide and account in their diversity for the redundancy inherent in the genetic code.

A suitable source of DNA for probing in this manner is capable of expressing a polypeptide of the present invention and can be a genomic library of a cell line of interest. Alternatively, a source of DNA can include total DNA from the cell line of interest. Once the hybridization method of the invention has identified a candidate DNA segment, one confirms that a positive clone has been obtained by further hybridization, restriction enzyme mapping, sequencing and/or expression and testing.

Alternatively, such DNA molecules can be used in a number of techniques including their use as: (1) diagnostic tools to detect normal and abnormal DNA sequences in DNA derived from patient's cells; (2) reagents for detecting and isolating other members of the polypeptide family and related polypeptides from a DNA library potentially containing such sequences; (3) primers for hybridizing to related sequences for the purpose of amplifying those sequences; (4) primers for altering native piwi family DNA sequences; as well as other techniques which rely on the similarity of the DNA sequences to those of the DNA segments herein disclosed.

As set forth above, in certain aspects, DNA sequence information provided by the invention allows for the preparation of relatively short DNA (or RNA) sequences (e.g., probes) that specifically hybridize to encoding sequences of a selected piwi family gene. In these aspects, nucleic acid probes of an appropriate length are prepared based on a consideration of the encoding sequence for a polypeptide of this invention. The ability of such nucleic acid probes to specifically hybridize to other encoding sequences lend them particular utility in a variety of embodiments. Most importantly, the probes can be used in a variety of assays for detecting the presence of complementary sequences in a given sample. However, other uses are envisioned, including the use of the sequence information for the preparation of mutant species primers, or primers for use in preparing other genetic constructions.

To provide certain of the advantages in accordance with the invention, a preferred nucleic acid sequence employed for hybridization studies or assays includes probe sequences that are complementary to at least a 14 to 40 or so long nucleotide stretch of a nucleic acid sequence of the present invention, such as a sequence shown in any of SEQ ID NOs:1, 3 and 5. A size of at least 14 nucleotides in length helps to ensure that the fragment is of sufficient length to form a duplex molecule that is both stable and selective. Molecules having complementary sequences over stretches greater than 14 bases in length are generally preferred, though, to increase stability and selectivity of the hybrid, and thereby improve the quality and degree of specific hybrid molecules obtained. One will generally prefer to design nucleic acid molecules having gene-complementary stretches of 14 to 20 nucleotides, or even longer where desired. Such fragments can be readily prepared by, for example, directly synthesizing the fragment by chemical means, by application of nucleic acid reproduction technology, such as the PCR technology of U.S. Pat. No. 4,683,202, herein incorporated by reference, or by introducing selected sequences into recombinant vectors for recombinant production.

Accordingly, a nucleotide sequence of the present invention can be used for its ability to selectively form duplex molecules with complementary stretches of the gene. Depending on the application envisioned, one employs varying conditions of hybridization to achieve varying degrees of selectivity of the probe toward the target sequence. For applications requiring a high degree of selectivity, one typically employs relatively stringent conditions to form the hybrids. For example, one selects relatively low salt and/or high temperature conditions, such as provided by 0.02M-0.15M NaCl at temperatures of 50° C. to 70° C. Such conditions are particularly selective, and tolerate little, if any, mismatch between the probe and the template or target strand.

Of course, for some applications, for example, where one desires to prepare mutants employing a mutant primer strand hybridized to an underlying template or where one seeks to isolate polypeptide coding sequences from related species, functional equivalents, or the like, less stringent hybridization conditions are typically needed to allow formation of the heteroduplex. Under such circumstances, one employs conditions such as 0.15M-0.9M salt, at temperatures ranging from 20° C. to 55° C. Cross-hybridizing species can thereby be readily identified as positively hybridizing signals with respect to control hybridizations. In any case, it is generally appreciated that conditions can be rendered more stringent by the addition of increasing amounts of formamide, which serves to destabilize the hybrid duplex in the same manner as increased temperature. Thus, hybridization conditions can be readily manipulated, and thus will generally be a method of choice depending on the desired results.

In certain embodiments, it is advantageous to employ a nucleic acid sequence of the present invention in combination with an appropriate means, such as a label, for determining hybridization. A wide variety of appropriate indicator means are known in the art, including radioactive, enzymatic or other ligands, such as avidin/biotin, which are capable of giving a detectable signal. In preferred embodiments, one likely employs an enzyme tag such a urease, alkaline phosphatase or peroxidase, instead of radioactive or other environmentally undesirable reagents. In the case of enzyme tags, calorimetric indicator substrates are known which can be employed to provide a means visible to the human eye or spectrophotometrically, to identify specific hybridization with complementary nucleic acid-containing samples.

In general, it is envisioned that the hybridization probes described herein are useful both as reagents in solution hybridization as well as in embodiments employing a solid phase. In embodiments involving a solid phase, the sample containing test DNA (or RNA) is adsorbed or otherwise affixed to a selected matrix or surface. This fixed, single-stranded nucleic acid is then subjected to specific hybridization with selected probes under desired conditions. The selected conditions depend interalia on the particular circumstances based on the particular criteria required (depending, for example, on the G+C contents, type of target nucleic acid, source of nucleic acid, size of hybridization probe, etc.). Following washing of the hybridized surface so as to remove nonspecifically bound probe molecules, specific hybridization is detected, or even quantified, by means of the label.

Assay Kits

In another aspect, the present invention contemplates assay kits for detecting the presence of a polypeptide of the present invention in biological samples, where the kits comprise a first container containing a first antibody capable of immunoreacting with the polypeptide, with the first antibody present in an amount sufficient to perform at least one assay. Preferably, the assay kits of the invention further comprise a second container containing a second antibody that immunoreacts with the first antibody. More preferably, the antibodies used in the assay kits of the present invention are monoclonal antibodies. Even more preferably, the first antibody is affixed to a solid support. More preferably still, the first and second antibodies comprise an indicator, and, preferably, the indicator is a radioactive label or an enzyme.

The present invention also contemplates a kit for screening agents. Such a kit can contain a polypeptide of the present invention. The kit can contain reagents for detecting an interaction between an agent and a receptor of the present invention. The provided reagent can be radiolabeled. The kit can contain a known radiolabelled agent capable of binding or interacting with a receptor of the present invention.

In an alternative aspect, the present invention provides assay kits for detecting the presence, in biological samples, of a polynucleotide that encodes a polypeptide of the present invention, the kits comprising a first container that contains a second polynucleotide identical or complementary to a segment of at least 10 contiguous nucleotide bases of, as a preferred example, SEQ ID NOs:1, 3 and 5.

In another embodiment, the present invention contemplates assay kits for detecting the presence, in a biological sample, of antibodies immunoreactive with a polypeptide of the present invention, the kits comprising a first container containing a piwi family polypeptide, that immunoreacts with the antibodies, with the polypeptide present in an amount sufficient to perform at least one assay. Preferably, the piwi family polypeptide has a biological activity in accordance with the present invention. The reagents of the kit can be provided as a liquid solution, attached to a solid support or as a dried powder. Preferably, when the reagent is provided in a liquid solution, the liquid solution is an aqueous solution. Preferably, when the reagent provided is attached to a solid support, the solid support can be chromatograph media ora microscope slide. When the reagent provided is a dry powder, the powder can be reconstituted by the addition of a suitable solvent. The solvent can be provided.

EXAMPLES

The following examples have been included to illustrate preferred modes of the invention. Certain aspects of the following examples are described in terms of techniques and procedures found or contemplated by the present inventors to work well in the practice of the invention. These examples are exemplified through the use of standard laboratory practices of the inventors. In light of the present disclosure and the general level of skill in the art, those of skill will appreciate that the following examples are intended to be exemplary only and that numerous changes, modifications and alterations can be employed without departing from the spirit and scope of the invention.

In exploring stem cell renewal mechanisms in the germline, the piwi gene is disclosed herein to be essential for GSC maintenance in Drosophila. The role of the piwi gene is characterized herein by recessive mutations that cause failure in GSC maintenance in both females and males. piwi mutant gonads contain a normal number of GSCs at the onset of gametogenesis. However, mutant adult gonads are devoid of GSCs and contain only a very small number of gametes that is approximately equal to or less than the wild-type number of GSCs. These observations reveal that piwi is essential for GSC maintenance in both males and females.

Summary of Observations in Examples

The purification and isolation of cDNAs representing piwi family genes from human, mouse, and Drosophila are disclosed in the Examples, along with the primary sequence of the PIWI proteins in human, mouse and Drosophila as deduced from the isolated cDNA sequences.

Further, the identification of piwi homologous genes, prg-1 and prg-2, and their role in germline self-renewal in *C. elegans* is described in the Examples. The identification of two piwi family-like genes in Arabidopsis, Zwille and argonaute(ago), that are required for meristem cell divisions is also described.

A highly conserved protein signature motif of 43-amino acid residues, the PIWI box, that exists in piwi family genes from human, mouse, Drosophila, *C. elegans*, and Arabidopsis, as well as in a broader class of novel genes is also described in the Examples.

The demonstration that the PIWI and MIWI proteins are nuclear proteins is also disclosed.

The essential function of piwi for Drosophila germline stem cell growth, proliferation and self-renewal and also for early embryonic development is also disclosed.

The specific expression pattern of miwi and hiwi in the adult murine and human testis, respectively, but not in the adult murine or human ovary which do not contain germline stem cells is also demonstrated in the Examples. miwi is further shown to be expressed in germline stem cells (and specifically not in somatic cells) of the mouse testis.

The essential role of piwi family genes in mammalian spermatogenesis is also disclosed. A null mutation of miwi, wherein most of the miwi sequence is deleted, results in male infertility with specific defects during early stages of spermatogenesis. A mutation that specifically deletes miwi sequences encoding the PIWI box show abnormalities indistinguishable from those of the null mutant, demonstrating the essentiality of the PIWI box for piwi gene functions.

Also disclosed is a demonstration that miwi contributes to the long term self-renewing ability of hematopoietic stem cells.

Thus, as disclosed herein, the function of piwi family genes in regulating proliferation of germ cells and other stem cells is conserved among human, mouse, Drosophila, *C. elegans*, and Arabidopsis.

Example 1

Isolation and Purification of piwi

The cloning and characterization of the *Drosophila piwi* gene is disclosed in this Example. Germline stem cells (GSCs) serve as the source for gametogenesis in diverse organisms. The piwigene product is required for the asymmetric division of GSC to produce and maintain a daughter GSC but is not essential for the further differentiation of the committed daughter cell. Genetic mosaic and RNA in situ analyses indicate that piwi expression in adjacent somatic cells regulates GSC division.

piwi encodes a highly basic novel protein well conserved during evolution. This Example also describes the isolation of piwi family homologs in *C. elegans* and human. This Example further describes the identification of Arabidopsis piwi family-like genes known to be required for meristem cell maintenance. Decreasing *C. elegans* piwi expression reduces the proliferation of GSC-equivalent cells. Thus, piwi represents a novel class of genes required for GSC division in diverse organisms.

Drosophila has been used in the art as a model for studying mechanisms that are conserved among diverse developmental systems. As show herein, this is also the case for the study of stem cells. In Drosophila, stem cells exist in the germline at the apical tip of the ovariole, the functional unit of the ovary. In the ovariole, germline stem cells (GSCs) are located in a specialized structure called the germarium, as first proposed by Brown and King (1962, 1964). The existence of GSCs was strongly supported by germline clonal analysis (Schüpbach et al., 1978; Wieschaus and Szabad, 1979) and directly verified by laser ablation (Lin and Spradling, 1993). In each germarium, 2–3 GSCs contact the somatic basal terminal filament cells. GSCs undergo oriented asymmetric divisions to produce a daughter stem cell which remains associated with the terminal filament and a differentiated daughter, the cystoblast, that becomes displaced one cell away from the terminal filament (Lin and Spradling, 1997; Deng and Lin, 1997). The germline cyst then becomes enveloped by follicle cells produced by somatic stem cells (Margolis and Spradling, 1995) to form an egg chamber, which buds off the germarium, joins pre-existing egg chambers in a linear array to form an ovariole, and eventually develops into a mature egg (reviewed in King, 1970; Spradling, 1993). This assembly-line organization, with each egg chamber representing a differentiated stem cell product whose position along the ovariole corresponds to its birth order, provides a unique opportunity to study stem cell division.

To investigate the nature of the piwi-mediated mechanism, this Example reports that piwi mediates a somatic signaling mechanism essential for the division and maintenance of GSCs in Drosophila. Moreover, piwi encodes a novel basic protein well conserved in *C. elegans* and humans, and also conserved in Arabidopsis, where two piwi family-like genes are known to be required for meristem cell maintenance. It is also demonstrated that the *C. elegans* piwi family homolog is also required for germline proliferation and maintenance. Thus, piwi family genes represent essential stem cell genes existing in diverse organisms.

Drosophila strains and culture. All strains were grown at 25° C. on yeast-containing molasses/agar medium. The piwi$^1$, piwi$^3$ and piwi$^4$ mutations are single PZ insertional mutations reported by Lin and Spradling (1997) while the piwi$^2$ mutation is a single P-ry$^{11}$ transposable insertion. Oregon R (Ore-R) serves as the wildtype strain for all experiments.

Phenotypic analysis of piwi mutants. Piwi mutations were balanced over CyO-y$^+$ and introduced into the y/y genetic background. The homozygous and heterozygous larvae were separated at the late third instar stage by scoring mouth hooks and denticle belts for y. They were then dissected to obtain the ovary immediately or were aged at 25° C. to desired pupal stages before dissection. Dissected ovaries were analyzed by immunofluorescence microscopy for defects in ovary differentiation and GSC division.

Immunocytochemistry and immunofluorescence microscopy. Wild type and mutant ovaries from larval, pupal, or adult stages were dissected, fixed and stained as described by Lin et al. (1994). For immunofluorescence staining, anti-VASA antibodies (Hay et al., 1990) were used to specifically mark germ cells at 1:2000 dilution. Anti-a-spectrin antibodies (Byers et al., 1987) were used to outline somatic cells and to mark spectrosomes and fusomes (Lin and Spradling, 1995) at 1:200 dilution. The monoclonal anti-MYC epitope antibody 1–9E10.2 was described by Evan et al. (1985) and was used at 1:2 dilution. All the fluorescence-conjugated secondary antibodies were from Jackson ImmunoResearch Laboratory Inc., Westgrove, Pa., and were used at 1:200 dilution.

Immunofluorescently labeled samples were also counterstained with the DNA specific dye DAPI as described in Lin and Spradling (1993). The immunologically labeled samples were examined using Nomarski and epifluorescence microscopy under a Zeiss AXIOPLAN® microscope (Zeiss, Oberkochen, Germany) equipped with a STAR-1™ cooled CCD camera (Photometrics, Tucson, Ariz.). Selected samples were further analyzed by confocal microscopy using a Zeiss LSM410™ confocal microscope mounted on an AXIOVERT® 100. Images from the Zeiss AXIOPLAN® were collected using IP Lab software and confocal images were processed using the LSM410 software. All images were processed using the Adobe Photoshop™ program (Adobe Systems, Inc., San Jose, Calif.).

Figure 2:
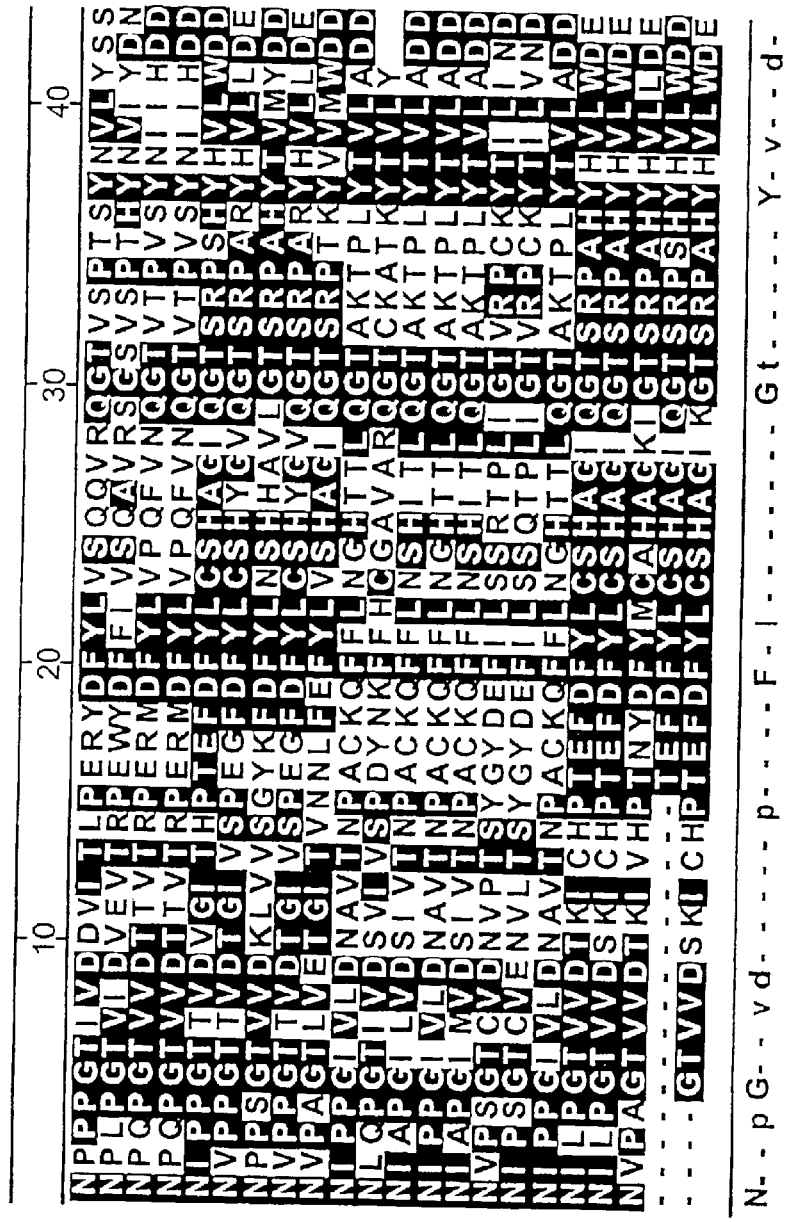
FIG. 2 depicts alignment of predicted PIWI protein sequence with its homologs in the piwi box domain in 22 different proteins. The alignments were generated using Block Maker™ analysis (Henikoff et al., 1995) against amino acids 740–782 of the predicted piwi sequence. The amino acid sequences were deduced from genomic DNA sequences for *C. elegans* (Ce G) or from cDNA (EST) sequences (E) for Rattus sp. (Rs) and *Oryza sativa* (Os). GenBank accession numbers and cosmid designations (Ce) are indicated for each sequence. Residues identical to the consensus are highlighted. Shown below the alignments, residues which are absolutely conserved are shown as capital letters and residues which are 80% or more conserved are shown as lower case letters while dashes indicate their spacing.

Cloning of piwi and mapping of its mutations. piwi maps to the left arm of the second chromosome within polytene band 32C, as defined by insertions of single transposable elements (Lin and Spradling, 1997). DNA fragments flanking the piwi$^1$, piwi$^3$, and piwi$^4$ insertions were recovered by a plasmid rescue method (Wilson et al., 1989). Genomic DNA in the rescued plasmid was used to isolate additional genomic clones from a λ genomic DNA library (Maniatis et al., 1978) to constitute a 36 kb region of overlapping walk clones (FIG. 2). The insertion sites for piwi$^1$, piwi$^3$, and piwi$^4$ were first mapped by Southern blots of EcoRI digested walk clones, and then precisely determined by DNA sequencing. The site of the piwi$^2$ insertion was determined by sequencing its flanking DNA fragments isolated by inverse PCR of piwi$^2$ genomic DNA using primers specific to the P-element termini (Ochman et al., 1990).

Genomic DNA fragments derived from the piwi locus were used to probe Northern blots of poly (A)+ RNA from wild-type male and female flies. Three non-overlapping transcripts, α (1.1 kb), β (0.64 kb), and c12 (3.1 kb) were identified in the region and only c12 was interrupted by piwi mutations. 9.36 kb of genomic DNA that encompasses the c12 transcription unit was sequenced either using a Sequenase kit (U.S. Biochemical) or an ABI 377 Prism DNA Sequencer (Perkin-Elmer, Applied Biosystems Inc). All sequence data was analyzed using the DNASTAR software package (DNASTAR, Madison, Wis.). Two additional transcripts, LD08487 (1.43 kb) and LD1 3681, were identified on the right side of the P-insertions by BLAST analysis (Altschul, et al., 1990) of genomic sequence.

Two overlapping cDNA clones which together represent the 3.1 kb full length c12 mRNA and the LD08487 cDNA were sequenced. Comparison between the genomic and the cDNA sequences precisely determined the intron-exon organization of these two transcription units. The LD13681 transcription unit were also mapped by partial sequencing. Standard molecular biology techniques were carried out according to Sambrook et al. (1989).

Transgenic rescue. The 6.8 kb HindIII/EcoRV (pRc12; piwi) and 3.9 kb PstI (PRLD; LD08487) genomic fragments were subcloned into the P element transformation vector pCaSpeR4 (Pirrotta, 1988). Transgenic flies were produced according to Spradling and Rubin (1982), using w; Δ2–3 Sb e/TM6 e (Robertson et al., 1988) embryos as recipients. Transgenes were then seperated from the Δ2–3 transposase and introduced into the homozygous piwi$^1$ background for fertility tests by genetic crosses. Six independent pRc12 inserts and eight independent pRLD inserts were recovered. Rescue crosses were carried out at 25° C.

Northern blot analysis and piwi cDNA isolation. Poly (A)+ mRNA isolation, Northern blot preparation, and $^{32}$P-labeled probe preparation by random-hexamer extension were according to Sambrook et al. (1989). For FIG. 2B, the probe was made from a 5.4 kb HindIII genomic fragment encompassing the piwi transcription unit. The same probe was used to isolate a 2.1 kb partial cDNA from the pNB40 third instar library of Brown and Kafatos, 1989. Using the sites within the polylinker (HindIII at 5' end and NotI at 3' end), the 2.1 kb cDNA was subcloned into pBlueScript KS(+) (Stratagene), resulting in a construct denoted pDC1. A primer, pDC1 5'REV, 5'-ACGATAAGTTCTGTTAT-3' (SEQ ID NO:1 1) was designed downstream of the 5' end of pDC1 and was used in combination with library specific primers to screen the Tulle Hazelrigg ovarian cDNA library (Friedman et al., 1990). A partially overlapping 500 bp PCR product was isolated, cloned into the pGEM-T vector (Promega, Madison, Wis.), and used to probe the same library. An overlapping 1 kb cDNA clone was isolated and subcloned into the SalI site of pDC1 to produce a full length 3.1 kb piwi cDNA construct denoted pDC2.

Characterization of piwi homologs from C. elegans and Homo sapiens. The BLAST algorithm (Altschul et al., 1990) was used to search the non-redundant databases at the National Center for Biotechnology Information (NCBI) at the National Library of Medicine. The Prosite Protein Motif Database (DNAStar, Madison, Wis.) was also searched to identify domains shared between piwi and other known proteins. The PIWI ORF was used to query the SWISS-Prot database by BLAST for homologous proteins. Significantly, the search identified two C. elegans predicted proteins of unknown function. Expressed sequence tags (ESTs) corresponding to these two gene products were then identified as D2030.6 (prg-1; GenBank accession No. Z73906) and C01G5.2 (prg-2; GenBank accession NoU50068) from GenBank. Dr. Yuji Kohara (National Institute of Genetics, Japan) kindly provided λ ZAPII phagemid clones corresponding to prg-1 and prg-2.

The piwi cDNA was further used to query the NCBI dbEST database and identified an EST, zw68h01.r1, isolated from a human testes cDNA library, GenBank accession number AA430311. This 0.9 kb EST clone was sequenced and used to screen an oligo-(dT) primed human testis cDNA library (Clontech, Palo Alto, Calif.). A 2.3 kb cDNA clone corresponding to hiwi was isolated and sequenced.

Whole-mount tissue in situ hybridization. Ovarian whole-mount tissue in situ hybridization was performed as described in Yue and Spradling (1992) with DIG-labeled (Genius Kit, Boerhinger Mannheim) full length piwi cDNA from pDC2 as a probe. For detecting RNA in surface cells, ovaries were digested 5 minutes with 50 μg/ml proteinase K. Under this condition, only terminal filament cells and anterior sheath cells, but not any other surface cells, were stained with the piwi cDNA probe. The pBST control probe did not show any significant signal. For detecting RNA in inner germarial cells, the digestion was 7–10 minutes. Under this condition, the piwi probe revealed a hybridization pattern as shown in Results, the pBST control probe did not show any significant signal, while the positive control oskar probe showed specific staining in presumptive oocytes (Ephrussi et al., 1991). Staging of egg chambers is according to King (1970).

Genetic clonal analyses and germarial transplantation. The piwi$^1$ and piwi$^2$ germline clones were generated with the FLP-DFS technique as described in Chou and Perrimon (1996). y, w P[hsFLP]$^{12}$; P[ovo$^{D1}$]$^{2L}$, FRT$^{40A}$/CyO males were crossed to w; piwi$^1$, FRT$^{40A}$/CyO virgin females to produce y,w P[hsFLP]$^{12}$; P[ovo$^{D1}$]$^{2L}$, FRT$^{40A}$/piwi$^1$, FRT$^{40A}$ progeny. Identical crosses were performed with w; piwi$^2$, FRT$^{40A}$/CyO virgin females. The genotype of the flies were verified both by Southern analysis for the presence of piwi P insertion and the FRT as well as by sterility tests by backcrossing to the original piwi allele. Crosses were carried out for two days to produce transheterozygous progeny. After 2 days, adults were transferred to fresh vials. Larvae were heat shocked on days 3 and 4 for one hour in a 37° C. water bath to induce mitotic recombination. The heat-shocked females with germline clones were crossed to Ore-R males for fertility tests and their ovarian phenotype examined by immunofluorescence microscopy.

To generate somatic clones of piwi$^1$ and piwi$^2$ the above described piwi$^1$, FRT$^{40A}$/CyO and piwi$^2$, FRT$^{40A}$/CyO strains were crossed to w; P[hsFLP]$^{9F}$; P[w$^+$; hs-NM], FRT$^{40A}$/CyO males as described in Xu and Rubin (1993). Females of the genotype w, P[hsFLP]$^{9F}$; P[w$^+$; hs-NM], FRT$^{40A}$/piwi, FRT$^{40A}$ were crossed to Ore-R males for fertility tests. Clonal induction was carried out as described above except that females of the appropriate genotype were subjected to an additional 20-minute heat shock at 37° C. 90 minutes prior to dissection to induce the expression of the myc tag. Germarial transplantation was carried out as described by Lin and Spradling (1993).

RNA-mediated interference (RNAi). Templates for in vitro transcription were cloned into pBluescript KS (+) and transcribed using either T7 or T3 RNA polymerases according to the manufacturer's protocol (Megascript T7 and T3 kits, Ambion). prg-1 cDNA served as the experimental RNA for injection while pBluescript KS(+) RNA was used as a negative control. RNA integrity was determined by gel electrophoresis; concentration was determined by a combination of UV spectrophotometry and ethidium bromide staining. Injections used an equimolar mixture of uncapped sense and antisense RNA at a concentration of 10 mg/ml. Gonadal injections of wild type N2 Bristol hermaphrodites was done as described in Mello and Fire (1995).

After recovery and transfer to standard solid media, injected animals were transferred to fresh culture plates at 24 hours intervals to facilitate the identification of phenotypic differences. Germlines of progeny produced between 6 and 48 hours after injection were examined for gamete differentiation either by DAPI staining or fertility. For DAPI analysis, adult hermaphrodites displaying RNAi induced phenotypes were fixed overnight in Carnoy's solution (60% ethanol; 30% acetic acid; 10% chloroform; Sulston and Hodgkin, 1988). The mitotic index is defined as the ratio between the number of prophase, metaphase, anaphase, and telophase nuclei and the total number of nuclei in the MPZ.

Piwi mutations eliminate the growth, proliferation and self-renewing division of germline stem cells. piwi$^1$ mutant ovaries contain a normal number of mispositioned GSCs at the onset of oogenesis at the late third instar larval stage, which, however, leads to an equal or somewhat smaller number of gametes in the adult gonads that no longer contain GSCs (Lin and Spradling, 1997). This failure of germline maintenance could be due to: (1) the differentiation of GSCs without growth, proliferation and self-renewing divisions; (2) a defect in the asymmetry of GSC division, producing aberrant germ cells that eventually degenerate; and/or (3) a secondary defect influenced by abnormal ovary differentiation.

To examine whether the failure of germline maintenance is indeed a secondary defect due to abnormal ovary development, the ovarian morphology of piwi$^2$ and piwi$^3$ mutants which also fail to maintain GSCs was examined. The examination relied on Nomarski optics as well as markers that specifically identify germ cells, somatic cells, and spectrosomes/fusomes, germline specific organelles that indicate individual stages of germ cell development (Lin et al., 1994; Lin and Spradling, 1995). These mutant ovaries show normal morphology at the third instar larval stage. Their germline cells are normal in number and are correctly positioned along the medial plane of the ovary. Moreover, the expected number of terminal filaments are forming, so that at the pupal stage, the ovary differentiates normally, partitioning GSCs and their daughter cells correctly into individual germaria and ovarioles. GSCs are able to divide several times to provide a normal complement of germ cells to the germarium. Yet, GSCs subsequently fail to continue self-renewing divisions, and the existing germline cysts often degenerate during the late pupal stage so that the adult ovarioles contain germlineless germaria and fewer egg chambers than expected. These observations indicate that the failure of GSC maintenance in piwi mutants is not a secondary defect due to abnormal ovary development.

To examine whether the failure of GSC maintenance is due to differentiation without self-renewing divisions or due to aberrant divisions followed by degeneration, the ovarian development of the piwi[1] mutant was examined more closely. The piwi[1] third instar larval ovaries contain a normal number of 50–70 presumed GSCs that are mis-positioned. However, these GSCs still seem to, and indeed must have, partitioned during subsequent pupal development, since the number of ovarioles formed in most adult ovaries is within the normal range (13±3 in mutant vs. 15±3 in wildtype). Hence, the effect of piwi[1] on GSC mis-positioning is not essential for oogenesis.

The main oogenic defect of the piwi[1] mutant is the differentiation of GSCs without self-renewing divisions immediately following the initiation of oogenesis. At this stage in wildtype ovaries, GSCs in 16–23 newly formed germaria have initiated asymmetric divisions to generate multiple developing germline cysts. However, in mutant ovaries, GSCs and their immediate differentiated daughters, cystoblasts, are undetectable, as indicated by the absence of spectrosome-containing germ cells. Instead, most ovaries contain differentiated germline cysts whose number approximately equals that of GSCs. These cysts are much larger in size and contain 2- to multi-cell stage fusomes, indicating their differentiating state. By the adult stage, most ovarioles contain only two normal or abnormal egg chambers derived from these cysts, but no other germline cells. This defect contrasts the development of wildtype ovaries, in which ovarioles contain a fully developed germarium and a stage 1 egg chamber by the 48-hour pupal stage, and have produced multiple egg chambers by adult stage. This observation indicates that the mutant GSCs have differentiated into germline cysts without self-renewing divisions. The abnormal fusome morphology often seen in cysts suggest that they contain more or less than the normal number of 16 cells, which indeed was seen in adult egg chambers.

Thus, piwi is required for the self-renewing division of GSCs during oogenesis in Drosophila. Confocal images showing third instar larval ovaries from wild-type, piwi[2], and piwi[1] mutant flies, respectively, were prepared and stained with a germline specific marker VASA in green and spectrin in red to mark somatic cells and spectrosomes/fusomes. GSCs were positioned medially along the anterio-posterior axis in the wild-type and piwi[2] ovary; however, GSCs are mispositioned in the piwi[1] mutant ovary. Spectrosomes (Sp) appear as red dots in germ cells. A 50 μm measurement bar was used in the analysis of the confocal images.

Confocal images of 24-hour pupal ovaries from wild-type and piwi[1] mutant flies, respectively, were prepared, with wild type stained solely for VASA while piwi[1] mutant was stained for both VASA in green and spectrin in red. At this stage, the wild-type ovary has partitioned into individual germaria (Ge), which contain GSCs and early germline cysts. In piwi[1] mutant ovaries germ cells still appear to have been partitioned, although the partition is distorted by the highly differentiated large germline cysts containing elaborate fusomes (Fu). The number of cysts did not exceed the number of GSCs.

Confocal images of 48-hour pupal ovaries from wild-type, piwi[2] and piwi[1] mutant flies, respectively, were prepared and stained with VASA in green and spectrin in red. By this stage, in both wild-type and piwi[2] mutant ovaries, germaria have fully developed and stage 1 egg chambers (S1) have budded off the germarium in synchrony due to continued GSC division. However, in piwi[1] mutant ovaries, the number of germline cysts remained unchanged, despite their continued differentiation.

A confocal image of a 72-hour pupal ovary from piwi[2] mutant flies was prepared and stained with VASA in green and spectrin stained in red. At this stage, GSCs fail to self-renew and some existing germline cysts start to degenerate. DAPI images of 0–1 day old adult ovarioles from wild-type, piwi[2] and piwi[1] mutant flies, respectively, were also prepared. Both piwi[1] (L) and piwi[2] (H) mutant ovarioles typically contain two normal or abnormal egg chambers connected to a germlineless germaria (Ge). In contrast, wild-type ovarioles contain a long string of developing egg chambers produced continuously by the germarium. piwi[3] phenotype is indistinguishable from that of piwi[2].

Molecular cloning of Drosophila piwi. To study the molecular nature of the piwi-mediated mechanism, a 15 kb genomic region flanking the piwi insertions was cloned. Candidate transcripts in the region were identified, and a 6.8 kb genomic fragment (pRc12) containing a 3.1 kb transcript interrupted by piwi mutations (transcript c12) was able to rescue the piwi phenotype completely (FIG. 1). An overlapping 3.9 kb genomic fragment (pRLD) containing a 1.43 kb transcript immediately adjacent to the piwi mutations fails to rescue the piwi phenotype (FIG. 1). Therefore, the c12 transcript is the piwi mRNA.

Drosophila PIWI represents a novel class of conserved proteins. To study the structure of the piwi gene, two overlapping cDNA clones which together represent the 3.1 kb full length c12 mRNA were isolated and sequenced. The c12 cDNA sequence contains a large open reading frame (ORF) starting at +84 bp and encoding a protein of 843 amino acid residues with a predicted molecular weight of 97.2 kD (SEQ ID NOs:1 and 2). Multiple stop codons in all three frames are present upstream of the putative start codon. Downstream of the ORF is a 432 bp 3' untranslated region (UTR) followed by a 55-bp poly(A) tail not encoded in the genomic sequence. Thus, piwi RNA is present in piwi[1]/CyO adult males and females. Northern blots including female and male lanes containing approximately 10 and 1.5 mg of polyA+ RNA, respectively, were prepared. They were exposed for 3.5 and 12 hours, respectively, and a band was observed at 3.1 kb in each lane.

The PIWI protein is a highly basic (pI 9.6) novel protein with no obvious similarity to other known proteins or functional motifs in the databases. It is characterized by alternating basic and acidic regions and is particularly basic over the C-terminal 100 amino acid residues. Hydropathy analysis indicates that the PIWI protein contains no significant local hydrophobic regions that could be potential signal peptide ortransmembrane domains. PSORT analysis (Nakai and Kanehisa, 1992) predicts nuclear localization of the PIWI protein. The protein has 21 conserved protein kinase C phosphorylation sites, 14 casein kinase 2 phosphorylation sites, and 4 tyrosine phosphorylation sites, indicating its potential as a phosphorylation target.

To determine whether the PIWI protein is conserved during evolution, applicant searched for its homologous sequences at the protein level and identified two ORFs of unknown function from *C. elegans* and an expressed sequence tag (EST, AA43031 1) from a human testis CDNA library. Applicant isolated and sequenced cDNAs for the two *C. elegans* genes, herein named prg-1 and prg-2 (prg for piwi-related gene) to verify their homology to *Drosophila piwi*. The prg-1 and prg-2 genes share 40.1% and 38.5% amino acid identity to piwi, respectively, over their entire length. In the C-terminal 104 amino acid region, the homology increases to 55.8% and 56.7%, respectively. Moreover, prg-1 and prg-2 are 90% identical to each other over their full length and 98% identical at the C-terminus. This high degree of homology suggests that prg-1 and prg-2 may represent a gene duplication event. The two clones differ primarily in that prg-1 is 60 amino acids longer at the N-terminus than prg-2. Using ACeDB (Thierry-Mieg and Durbin, 1992), prg-1 was mapped to chromosome I between unc-15 and gld-1 in cosmid D2030 and prg-2 was mapped to chromosome IV, between unc-44 and smg-7 on cosmid C01G5.

To isolate human piwi homologs, the human EST (0.9 kb) clone was sequenced and used to screen a human testis cDNA library. A resulting 2.3 kb partial cDNA, herein named hiwi (for human pwi), shows 47.1% identical amino acid sequence to the *Drosophila piwi* over its full length, with 58.7% identity at the C-terminus. No piwi-related sequences were found from bacteria or yeast genomes whose entire sequences are known. This is consistent with the stem cell-related function of piwi and indicative of piwi family-like genes specific for multicellular organisms.

In addition to the above piwi family homologs, a large number of putative and known proteins were identified from various animals and plants which share significant homology with piwi solely at their respective C-termini. This indicates that the piwi family is a large novel gene family. Within this family are 13 additional putative *C. elegans* proteins and three *A. thaliana* proteins, two of which are required for meristem cell divisions (Moussian, et al., 1998; Bohmert, et al., 1998). Particularly, between piwi and the three Arabidopsis genes, ZWILLE (ZLL) argonaute (ago), and argonaute-like (Moussian et al., 1998; Bohmert et al., 1998), an overall homology of approximately 20% amino acid identity was observed. The homology increases to 32% to 52% identity in four regions, 30–100 amino acid residues each, located throughout the length of the PIWI protein, including the highly conserved C-terminal region. Given the role of ZLL and ago in meristem cell division (Moussian et al., 1998; Bohmert et al., 1998), this homology may have important implications for a conserved stem cell mechanism.

PIWI, PRG-1, PRG-2, and HIWI differ from ZLL and AGO proteins, and especially from the 13 additional putative *C. elegans* proteins, predominantly at the N-terminus, suggesting that this region may be involved in piwi-specific function. The C-terminal conservation suggests that this region of PIWI may contain a novel functional domain that plays an important role for the general activity of these proteins in diverse biochemical processes, with the N-terminus rendering the specificity of the activity.

To examine the C-terminal region of homology more closely, the sequences were aligned using Block Maker™, which reveals characteristic regions of protein families (Henikoff et al., 1995) (FIG. 2). Block Maker™ analysis identified a 43 amino acid domain conserved among all 22 proteins, within which five residues are absolutely conserved with defined spacing. Eight more residues are also conserved with defined spacing among all known genes across the phyla except for several *C. elegans* ORFs with unknown function. This region is referred to herein as the PIWI box and represents a novel conserved functional motif. PIWI, that is the piwi family of gene products, thus represents a novel class of evolutionarily conserved proteins with conserved functionality, as described herein below.

*Drosophila piwi* mRNA is present in both the germline and soma during oogenesis. To investigate in which cells piwi is expressed to regulate GSC division, the expression pattern of piwi during oogenesis was examined by in situ hybridization of whole mount Drosophila ovaries with DIG-labeled DNA probes prepared from the piwi cDNA clone. piwi mRNA is detected specifically in the somatic terminal filament cells apical to GSCs in the germarium and anterior sheath cells as well as in the germline. In the germline, it is first abundantly expressed in region 2 of the germarium where 16-cell germline cysts are formed, persists at a lower level through stages 1–6 of oogenesis, is at its lowest level between stage 7–9, becomes strongly expressed again at stage 10, and eventually accumulates in early embryos (for staging, see King, 1970). Given that removing sheath cells does not affect oogenesis whereas the terminal filament cells play a role in regulating GSC division (Lin and Spradling, 1993), it is likely that the somatic expression in the terminal filament is responsible for piwi function in regulating GSC division.

Thus, piwi mRNA expression in Drosophila ovaries was characterized. A complete Ore-R ovariole was studied and showed germline piwi expression in region II of the germarium (GeII) and in early stage egg chambers up to stage 10 (S10) was studied. In the germarium, the piwi RNA was also detected in the terminal filament cells (TF) and epithelial sheath cells (ES) apical to GSCs. piwi RNA was also observed to be uniformly present in early embryos. The aforementioned structures were reviewed on slides, and the slides included bars denoting 50 μm, 10 μm and 50 μm for ovariole, germarium and early embryos, respectively, to facilitate review.

Piwi expression in apical somatic cells regulates GSC division while its expression in the germline provides a maternal component for embryogenesis. To examine the roles of somatic and germline piwi expression, genetic clonal analyses on piwi$^1$ and piwi$^2$ mutations was conducted. First, the germline requirement of piwi was tested by germline clonal analysis using the FLP-DFS technique (Chou and Perrimon, 1996). The ovo$^{D1}$ dominant mutation blocks oogenesis at the very beginning stage in a cell-autonomous manner, so that piwi$^+$ ovo$^{D1}$ females contain germ cells that never differentiate beyond the germarium. In this ovo$^{D1}$ background, applicant generated germline cells homozygous for either the piwi$^1$ or piwi$^2$ mutation by applying a heatshock treatment at the second and early third instar larval stage. The resulting adult females developed some completely normal ovarioles in which germline cells at all stages of oogenesis were observed, and mature eggs were continuously being produced (see Table 3).

This result demonstrates that removing the piwi$^+$ ovo$^{D1}$ chromosome from the germline allows oogenesis, including GSC division, to occur normally. Thus, the requirement of piwi for GSC division does not reside in the germline but in somatic cells.

Eggs produced from homozygous piwi[1] or piwi[2] GSC clones are arrested in embryogenesis, not rescuable by the paternal piwi[+] gene (see Table 3). Approximately 30% of the arrested embryos show severe mitotic defects during cleavage stage. The remaining embryos show various morphological defects during late embryogenesis, including a high frequency of severe deformation of the head region. These defects demonstrate that piwi expression in the germline provides an essential maternal contribution for embryogenesis.

To determine whether piwi is required in somatic cells outside the ovary for GSC maintenance, wildtype germaria were transplanted into the abdominal cavity of homozygous piwi[2] and wildtype females, which produced 17±0 egg chambers (n=13) after 7 days of incubation in the host. Parallel transplantation into wildtype host yielded 16±2 egg chambers (n=5), indicating that the wildtype germaria continued oogenesis at a normal rate in the piwi[2] females. Hence, piwi is not required in extra-ovarian cells for GSC maintenance.

To determine in which group of ovarian somatic cells piwi is required for GSC maintenance, applicant used a similar FRT-mediated technique for somatic clonal analysis of piwi[1] and piwi[2], marking the piwi[+] chromosome with a transgenic myc tag so that homozygous piwi somatic cells are identified by their lack of myc epitope expression (Xu and Rubin, 1993). By inducing mitotic recombination at the second and third instar larval stages, piwi[−] somatic clones were generated throughout ovarioles, with some egg chambers completely covered by piwi mutant follicle cells. These egg chambers develop normally, indicating that piwi function is not required in follicle cells for egg chamber development. Since follicle cells are derived from their precursor cells in region II of the germarium (Margolis and Spradling, 1995), this suggests that piwi is not required in somatic cells from germarial region II on for GSC division and ovarian development. These results, together with the piwi expression pattern in situ, suggest that piwi is required in somatic cells in the anterior-most tip of the germarium to regulate GSC division.

Thus, piwi function is dispensable in the germline and differentiated follicle cells for GSC division. A pair of ovaries containing ovarioles with homozygous piwi[−] germline clones and ovarioles with piwi[+] ovo[D1] germline stained for DAPI to mark DNA and for VASA to mark germ cells for observation via confocal microscopy. The piwi[+] ovo[D1] germline cells were arrested at the beginning of oogenesis in the germarium due to the ovo[D1] mutation. By contrast, in ovarioles in the left ovary containing piwi[−] germline clones, GSCs divided normally, giving rise to a progression of morphologically wild-type egg chambers which eventually develop into mature eggs. This indicates that piwi is not required in the germline for GSC division and subsequent steps of oogenesis. To facilitate confocal microscopy, bars denoting 100 μm were employed in each slide.

Confocal microscopy was also employed to show that piwi[−] clones in differentiated follicle cells do not effect normal GSC division and egg chamber development. Egg chambers were stained with DAPI and a monoclonal anti-MYC antibody. Absence of MYC staining was indicative of homozygous piwi-clones. Induction of somatic clones around an entire early stage egg chamber had no effect on GSC division and oogenesis. Similarly, removing piwi function from some follicle cells of later stage egg chambers also had no effect on oogenesis. Therefore, piwi function is dispensable in differentiated follicle cells for oogenesis including GSC division. To facilitate confocal microscopy, bars denoting 50 μm were employed in each slide.

piwi-like genes in C. elegans are also required for germline self-renewal. The high degree of sequence homology between piwi and its homologs in other organisms suggests a potential functional conservation. This hypothesis was tested in C. elegans. Guo and Kemphues (1995) have shown that the injection of specific antisense RNA into the germline syncytium of C. elegans eliminates maternal and zygotic gene activity, producing a gene-specific loss-of-function effect that may persist through several generations. This technique, as refined by Fire et al. (1998) and termed RNA-mediated interference (RNAi), was used to assess the function of prg-1 and prg-2. Given the extremely high homology between prg-1 and prg-2, an anti-prg-1 RNA was used for injection to interfere with the function of both genes. The F1 progeny of the injected worms were designated as prg-RNAi worms for simplicity.

In wild-type C. elegans, two germline precursor cells, Z2 and Z3, give rise to approximately 2000 germ cells in the adult hermaphrodite. Germline proliferation occurs throughout most of larval development (L1–L4) and continues in the adult. This proliferation and maintenance of the germine requires signals from the DTC at the tip of each gonadal arm. During gonadal development, DTC migration results in the formation of two U-shaped gonadal arms by the L4 stage. Germline proliferation is limited to the distal end of each arm, forming a mitotic proliferation zone (MPZ) which serves as the GSC equivalent in C. elegans. Moving proximally, near the U turn of the gonad, germ cells enter meiotic prophase and then further differentiate into gametes at the proximal half of each arm, producing sperm in L4 and then oocytes in young adults.

The phenotype of prg-RNAi worms was examined both by quantitating their fertility and by assessing their gonadal and germline development via DAPI staining and Nomarski optics. As controls for RNA injection, worms were injected with BlueScript plasmid RNA sequences.

Figure 3:
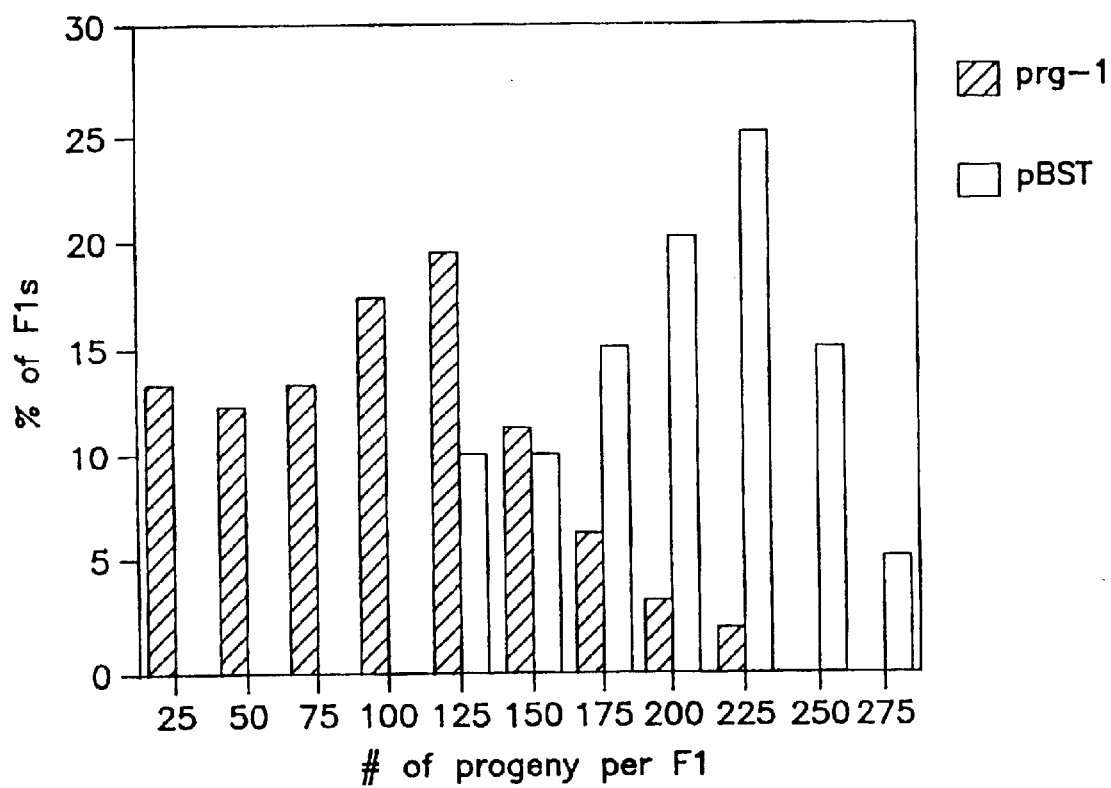
FIG. 3 is a graph showing that prg-RNAi significantly reduces germline proliferation in *C. elegans* and that reducing prg activity affects fertility. The graph indicates the number of progeny produced by a single F1 worm from an RNAi prg-1 or pBST injected mother vs. the percentage of F1 animals which produced that given number of progeny. Comparison of prg-RNAi (striped bars) with PBST RNAi (solid bars) animals reveals two distinctive distributions.

The prg-RNAi worms show three major aspects of germline defects. First, as indicated by the distribution of the number of progeny per F1 animal (FIG. 3), the fertility difference between the prg-RNAi and control worms is highly significant (t value=7.93, p<0.0001). On average, prg-RNAi worms produced 92±53 progeny (n=99), with 75.5% of prg-RNAi worms giving rise to fewer than 125 progeny. By contrast, control RNAi animals on average produced 191±40 progeny (n=20), with 90% of these animals giving rise to greater than 125 progeny. The significant reduction of the fertility, as well as other defects described below, may still only reflect a partial loss of prg-1 and prg-2 function, since the RNAi technique is known to phenocopy partial rather than complete loss-of-function mutants (Kuwabara, 1996).

Second, DAPI staining reveals a dramatic shortening of MPZ in prg-RNAi worms. On average, adult prg-RNAi worms exhibited a 50% reduction in the number of mitotic nuclei as compared to control animals. Associated with the reduction of the mitotic zone is a gonadal shortening. 57% of prg-RNAi worms (n=287) exhibited a moderate to severe shortening. In the most severe case, the gonadal arm never made the U-turn. The number of sperm produced in these worms is greatly reduced as well. By contrast, only 7% of the BlueScript-RNA-injected control animals (n=548) exhibited a mild gonadal shortening. The above observed gonadal defects in prg-RNAi worms indicate that prg-1 and prg-2 are essential for germine proliferation and maintenance. Since the gonadal shortening may be due to a defect in DTC migration, it is also possible that prg-1 and prg-2 play a role in proper gonadogenesis.

Thus, reducing prg activity results in reductions in both the MPZ and the mitotic index. Variable defects in both the size of the MPZ and the mitotic index were observed by DAPI staining and preparation of photomicrographs of same. The MPZ in each micrograph was denoted in white brackets. In moderate to severely defective animals, a 50% reduction in the number of mitotic nuclei and a concomitant five-fold reduction in the mitotic index were typically observed. A measurement bar was included in the wildtype photomicrograph and denoted 100 μm for all panels.

In addition to the MPZ shortening, the mitotic index in the remaining mitotic zone is further reduced by 5.5 fold from $(7.1\pm2.2)\%$ (n=1,339 nuclei, $n_s$=10 worms) in the control RNAi injected worms to $(1.3\pm0.8)\%$ (n=1,409 nuclei, $n_s$=10 worms) in prg-RNAi worms with mildly to moderately shortened gonads. This indicates the important role of prg-1 and prg-2 in maintaining the mitotic ability of the germline stem cell nuclei.

Drosophila piwi is required for the self-renewing divisions of stem cells in the germline. The above experimentation demonstrates that piwi provides for female and male GSC maintenance predominantly by promoting the self-renewing division of GSCs. In a germarium, it normally takes at least 10 hours for a GSC division to occur and 5 days for a cystoblast to develop into a stage one egg chamber (King, 1970; Lin and Spradling, 1993). Necrosis and apoptosis during oogenesis are also easily detectable. Thus, examination of the piwi mutant phenotype at 24-hour intervals immediately prior to the onset of oogenesis is sufficient to monitor every major event in germine proliferation, differentiation, or cell death. Under these conditions, GSC divisions would have been detected as an increased number of germline cysts, whereas cell death process would have been easily detected by looking for pycnotic nuclei and necrotic bodies via DAPI staining and Nomarski optics (Lin and Spradling, 1993; Forbes et al., 1996a, b; Lin and Spradling, 1997). Numerous cases of GSC divisions and cell death in the germline during Drosophila oogenesis have been detected using these criteria (Lin and Spradling, 1993; Forbes et al., 1996a, b; Lin and Spradling, 1997).

Despite their high sensitivity, the techniques followed in this Example, even though more systematic, did not detect either GSC division or cell death in piwi mutants. Instead, immediately following the onset of oogenesis, only differentiating cysts were detected in piwi[1] mutant ovaries, with the cyst number generally corresponding to the number of GSCs. Although this does not rule out the possibility that infrequent GSC divisions or cell death might have been missed, which might account for the smaller-than-expected number of gametes sometimes observed in adult piwi mutants, these factors do not weaken the conclusion that the predominant defect of piwi mutants is the differentiation of GSCs without accompanying self-renewing division.

A number of elegant studies have identified genes that regulate germline proliferation. In mammalian systems, mechanisms mediated by paracrine factors such as the Steel factor (the ligand of the c-Kit receptor tyrosine kinase), leukemia inhibitory factor (LIF), and basic fibroblast growth factor (bFGF), control the proliferation and survival of primordial germ cells, i.e., the precursors of GSCs (reviewed in Lin, 1997). In C. elegans, the LAG-2/GLP-1 pathway is essential for the self-renewal of a stem-cell equivalent population of germline nuclei in the gonad (reviewed in Kimble and Simpson, 1997). In the Drosophila ovary and testis, the BAM-mediated mechanism is involved in the further development of the differentiated GSC daughter (McKearin and Ohlstein, 1995); the dpp pathway plays a similar role in testis (Matunis et al. 1997). More recently, this pathway has been shown to be essential for GSC division and maintenance in the ovary (Xie and Spradling, 1998). Among these discoveries, piwi is the first gene known to mediate a somatic signaling mechanism to regulate the division and maintenance of GSCs in Drosophila. It therefore provides an important entry point for studying the somatic control of stem cell division in the germline.

The piwi gene family and the conservation of a stem cell self-renewinq mechanism. The identification of prg-1 and prg-2 in C. elegans and hiwi in human suggest that piwi represents a novel class of evolutionarily conserved genes (described herein as the "piwi family") with potentially important functions in GSC self-renewal. Among this class of genes, the significantly higher homology between piwi and hiwi as compared to that between piwi and prg-1/prg-2 suggests that hiwi function is closer to piwi. Consistent with this, GSC division and gametogenesis in humans are much more similar to that in Drosophila than that in C. elegans whose gonads contain syncytial mitotic germline nuclei which divide symmetrically and are capable of self-renewing only as a population. The RNAi experiments described herein, which likely interfered with the activity of both prg-1 and prg-2 due to their extremely high homology, caused germline depletion similar to that in piwi mutants. This suggests that the piwi-mediated mechanism in germline self-renewal is conserved even in this evolutionarily distant organism without stereotypic GSCs.

The conservation of the piwi-mediated mechanism appears to extend to the plant kingdom as well. A level of homology between PIWI and ZLL and AGO was observed. Intriguingly, ZLL is essential for maintaining stem cells of the shoot meristem in an undifferentiated state during the transition from embryo-specific development to repetitive organ formation through the self-perpetuating shoot meristem divisions (Moussian et al., 1998). AGO also plays an important role in maintaining normal apical shoot meristem function (Bohmert et al., 1998). Thus, the homology between piwi and ZLL and ago further suggests the existence of a family of novel genes essential for stem cell division in diverse organisms.

The conserved piwi mechanism may mediate cell—cell interactions. In Drosophila, genetic mosaic and piwi expression analyses together suggest that piwi function is required in the apical non-mitotic somatic cells to control GSC division. Similarly, in A. thaliana, it is thought that ZLL is required to maintain the undifferentiated state of shoot meristem stem cells by relaying positional information, possibly by mediating cell—cell interactions within the center of the shoot meristem (Moussian et al., 1998).

Stem cells are characterized by two common properties that extend across diverse species: the capacity for self-renewal and the ability to give rise to numerous progeny that are fated for further differentiation (for review see Lin, 1997; Morrison et al., 1997). Although significant progress has been made in identifying genes important for stem cell function, no common molecular mechanism shared by diverse stem cell types in diverse organisms has been characterized with respect to those two basic stem cell properties. The piwi gene family represents the first class of such genes. The analysis of the piwi gene family, therefore, provides an important first step towards the elucidation of molecular mechanisms underlying stem cell divisions.

The analyses of this Example were extended to homologs in C. elegans, an isolated human homolog (hiwi), and identified two piwi-like genes in Arabidopsis which are known to maintain meristem cells. This work reveals a new class of genes that play an essential role in stem cell division in multicellular organisms ranging from invertebrates to humans and plants.

TABLE 2 piwi[1] rescue results by pRc12 and pRLD[a,b]

| | piwi[1]/piwi[1] | piwi[1]/CyO | pRC12; piwi[1]/piwi[1] | pRLD; piwi[1]/piwi[1] |
|---|---|---|---|---|
| females | 0 (136) | 100 (45) | 100 (39) | 0 (81) |
| males | 0 (119) | 97.8 (47) | 88.4 (43) | 0 (64) |

[a]The percentage of fertile flies for each genotype and sex are indicated. The number of individuals tested for fertility (n) is in parentheses.
[b]Data are pooled from 6 and 4 independent insertion lines on the X and 3rd chromosomes for pRLD and pRc12, respectively. Not included are two other pRc12 rescue lines which showed sex-specific restoration of fertility, presumably due to position effects stemming from the insertion site.

TABLE 3 piwi function in GSC division is soma-dependent, while its function in embryogenesis is germline dependent*

| | FLP/FRT ovo$^{D1}$-induced germline clones % embryos laid/female | Heat-shock hatched | N | Avg. # eggs |
|---|---|---|---|---|
| (a) | piwi[1], FRT/ovo$^{D1}$, FRT × Oregon$^R$ males + | 37 | 50.4 | 0 |
| (b) | piwi[2], FRT/ovo$^{D1}$, FRT × Oregon$^R$ males + | 26 | 66.7 | 0 |
| (c) | piwi[1], FRT/ovo$^{D1}$, FRT × Oregon$^R$ males − | 44 | 0 | na |
| (d) | piwi[2], FRT/ovo$^{D1}$, FRT × Oregon$^R$ males − | 26 | 0 | na |
| (e) | ovo$^{D1}$, FRT/CyO × Oregon$^R$ males + | 20 | 0 | na |
| (f) | ovo$^{D1}$, FRT/CyO × Oregon$^R$ males − | 10 | 0 | na |

*In all tester and control crosses, a number (N) of newly eclosed females were allowed to lay eggs at 25° C. for 2 days.
In both piwi[1] and piwi[2] testers, germline develops beyond that of ovo$^{D1}$ mutant ovarioles only following heat shock, giving rise to numerous eggs. This indicates the generation of piwi-germline clones and the dispensability of piwi function in the germline for normal GSC division. However, none of the eggs develop beyond embryogenesis, indicating the germline piwi expression is required as a maternal component for embryogenesis. The ovo$^{D1}$, FRT control females lay no eggs either with or without heat-shock.
na = not applicable.

Example 2

Molecular Cloning and Expression Analysis of Hiwi, A Human Homolog of the *Drosophila Piwi* Gene Essential for Germline Stem Cell Division and Embryogenesis piwi is a novel gene first identified in Drosophila and was demonstrated to be essential for germline stem cell development in Example 1. In this Example the cloning of a 3.47 kb human piwi homolog that includes the whole open reading frame through cDNA library screening and 5' RACE is described. Sequence analysis showed high identity of HIWI to *Drosophila PIWI*, especially in the C-terminal domain of the protein. Chromosome mapping showed located hiwi to Chromosome 12q 24. 33, approximately 130 kb from the AFM 295 ye5 marker. Northern blot analysis revealed that hiwi is only expressed in the testis among human adult tissues. The sequence and expression homology between human and *Drosophila piwi* genes suggested that piwi is conserved during evolution and plays an important role during early stages of spermatogenesis in human.

Human spermatogenesis followed a precise and coordinated manner in the seminiferous epithelium of testis (reviewed in Bellve, 1979; Thomas et al., 1989; Hoog, 1995). During this period the germ cells undergo a series of stage-specific morphological transitions, beginning with the proliferation and renewal of spermatogonia, followed by meiosis of spermatocytes, and finished by differentiation of spermatids during spermiogenesis (Oakberg, 1956a; Nebel et al., 1961; Bellve et al., 1977; Russel et al., 1990). Closing to the basal membrane, type A spermatogonia are stem cells (Bartmanska and Clermont, 1983; De Rooij, 1988), undergoing a series of mitoses to give rise to more type A cells or produce type B spermatogonia which passes through a mitotic division to differentiate into spermatocytes.

Spermatocytes need to undergo a final round of DNA replication before entering meiosis. During meiosis, the synaptonemal complex and the recombination nodule become associated with chromosomes, which was thought to be important for two basic tasks in meiosis, the reduction of ploidy level and generation of new combinations of genes (reviewed in von Wettstein et al., 1984). The most radical morphological changes occured during spermiogenesis (Oakberg, 1956b). Based on acrosome formation and nuclear condensation, the round spermid differentiated into mature spermatozoa which released into the lumen indicating the end of the spermatogenesis (reviewed in Bellve and O'Brien, 1983).

The proliferation and differentiation of germ cells in the seminiferous tubule has been demonstrated to be associated with adjacent somatic cells, the Sertoli cells (reviewed in Russel and Griswold, 1993; Griswold, 1995; Bitgood et al., 1996; de Miguel et al., 1997). The tubule of human testis is composed of germ cells in all stages of spermatogenesis. From basal membrane to lumen are cells ranging from stem cell to differentiated cell state and from proliferation to differentiation stage. Particular cell at particular developmental stage is associated with others at given sites in the tubule, the least mature stem cells are located furthest outside, while the most mature spermatozoa are located inside the seminiferous epithelium. The specific tubule organization and cellular association thus provide a good model system to study germ cell development.

Genes expressed in male germ cells had been identified in high mammals (Kramer and Erickson, 1982; Gold et al., 1983; Thomas et al., 1989; Wolgemuth and Watrin, 1991; Hoog, 1995). Some of these genes were expressed exclusively during spermatogenesis (reviewed in Willison and Ashworth, 1987; Erickson, 1990; Sandlow et al., 1997; van Roijen et al., 1998), while others were expressed only in the later stages of spermatogenesis (Shankar et al., 1998; Zhu and Naz, 1998). Hower, very few genes had been demonstrated that was expressed specifically in the early stage of spermatogenesis, in the stem cells (Menke et al., 1997).

To study the mechanisms of piwi family function in germline stem cells in various organisms during evolution and especially its role in human beings, molecular cloning and expression analysis of human piwi family homolog was performed.

5'-RACE. A 2.3 kb partial human piwi family cDNA clone was first isolated from adult human testis cDNA library through library screening. To obtain the 5' end of this gene, a cDNA synthesis primer and a gene specific primer has been designed. Adult human testis Poly A+ RNA was purchased from Clontech, Palo Alto, Calif. First-strand cDNA was obtained by using the above cDNA synthesis primer and AMV reverse transcriptase (Clontech, Palo Alto, Calif.). Second-strand synthesis CDNA synthesis was performed with second-strand enzymes bought from Clontech, Palo Alto, Calif. subsequently. Using the above gene specific primer and an adaptor primer obtained from Clontech, Palo Alto, Calif., an 1.4 kb fragment has been obtained through 5'-RACE PCR by using MarathonTM cDNA Amplification Kit (Clontech, Palo Alto, Calif.) and has been cloned into a pGEM-T Easy vector (Promega, Madison, Wis.) subsequently.

Construction of a full length human piwi homolog and its sequence analysis. The fully-length hiwi cDNA was generated in a modified pGEM-T Easy vector (Promega, Madison, Wis.) by partial digestion of above two overlapping cDNA fragments with SacI and subsequent ligation with $T_4$ DNA ligase (Gibco). The full length human piwi family homolog was sequenced fully on both strands using an ABI 377 Prism™ DNA Sequencer (Perkin-Elmer, Applied Biosystems) and analyzed using the DNAStar™ sequence analysis package (DNASTAR, Madison, Wis.). Homologous comparison between hiwi and its homologs was carried out using the Megalign™ program from the DNAStar™ package.

Chromosome mapping. Radiation Hybrid mapping against Stanford G3 Human Hamster panel was used for chromosome mapping for hiwi.

Northern Blot Analysis. A 0.9 kb EST fragment used for Northern blot analysis was purchased from ATCC (American Type Culture Collection) and was subcloned into a pBlueScript KS(+) vector (Stratagene) with EcoRI and HindIII. The 3.47 kb plasmid DNA obtained from 5'RACE was used to make sense and antisense RNA probes for in situ hybridization. The above plasmid DNA were linearized with appropriate restriction enzymes. Using these linearized template DNA, sense and antisense RNA probes for Northern blot analysis and in situ hybridization were transcribed from the T7 and SP6 promoters with appropriate T7 and SP6 RNA polymerase (Gibco), following the protocols suggested by manufacturers. Probes used for Northern blot analysis were labeled by $^{32}$P-UTP (Amersham).

Premade Northern blot of high-quality poly A+ RNA from different human tissues (Human Multiple Tissue Nothern Blot II) was purchased from Clontech, Palo Alto, Calif. Human β-actin cDNA probe (Clontech, Palo Alto, Calif.) was used as a positive control. ExpressHyb™ Hybridization Solution (Clontech, Palo Alto, Calif.) was used as hybridization buffer for Northern analysis. The hybridization for both sample blot and positive control was performed under 68° C. for 2 hours followed by 2 washes in 2×SSC, 0.05% SDS for 50 minutes at room temperature, and another 2 washes in 0.1×SSC, 0.1% SDS for 40 minutes at 50° C. The sample blot was exposed at −80° C. for 10 hours while the positive control was exposed for 2 hours at the same temperature.

Figure 4:
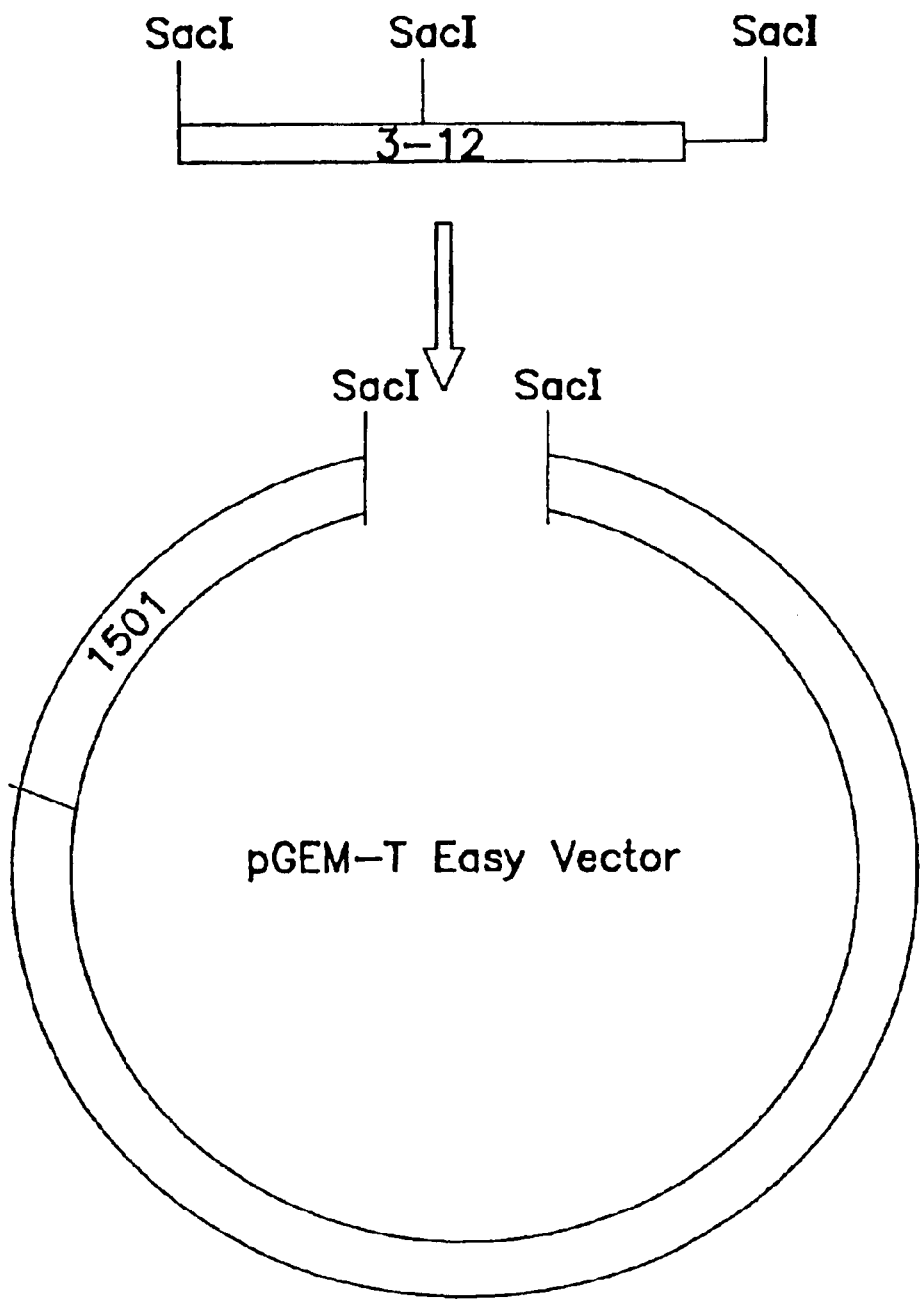
FIG. 4 depicts the construction of full length hiwi cDNA clone. The 2.3 kb cDNA fragment obtained from library screening (herein named 3–12) was subcloned into a pBluescript® KS$^+$ plasmid vector, the 3–12 insert is shown as an open box, the polycloning site on the vector is shown as a dark line. The 1.4 kb cDNA fragment obtained from 5'RACE (herein named 1501) was subcloned into a pGEM-T Easy™ vector. The 1501 in pGEM-T Easy™ vector was digested with SacI to construct a vector for subsequent ligation. The 3–12 in pBluescript® KS$^+$ vector was partially digested with SacI to obtain the insert. This partially digested 3–12 insert DNA was used to do ligation with 1501 in pGEM-T easy vector to construct a full length hiwi cDNA clone.
Figure 7:
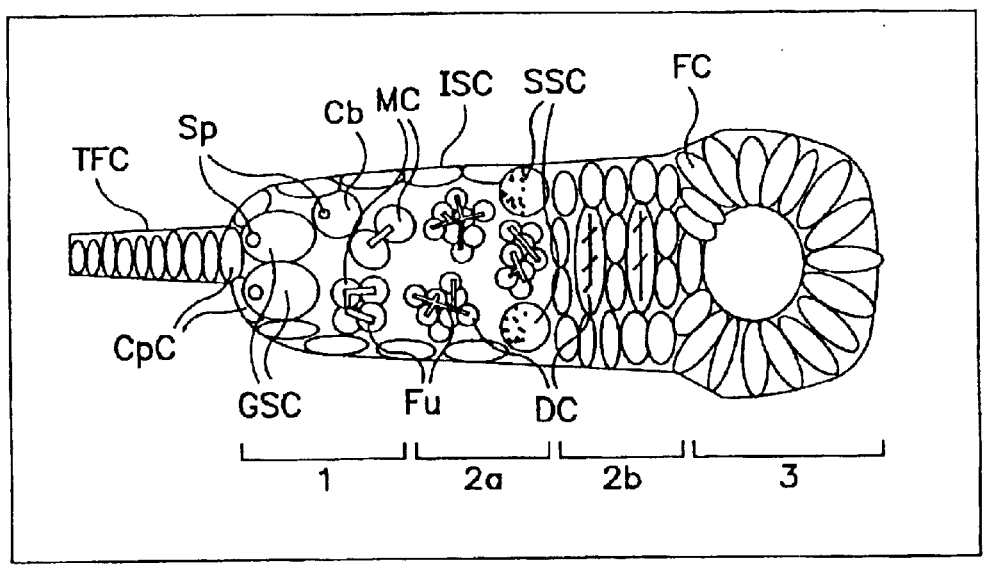
FIG. 7 is a schematic diagram of a Drosophila germarium. The schematized germarium is oriented with the apical end toward the left. The numbers below the germarium in the brackets denote distinct regions within the germarium. Germarial region 1 extends from the apical terminal filament cells (TFC, including cap cells, CpC) to the zone of mitotically active cysts. Germarial regions 2a and 2b include differentiating 16-cell cysts. Two somatic stem cells (SSC) are located at the border between regions 2a and 2b. Germarial region 3 contains a newly formed egg chamber that is preparing to bud off from the germarium and contribute to the developing string of egg chambers that comprise the rest of the ovariole. Abbreviations: GSC, germline stem cell; Sp, spectrosome; ISC, inner sheath cell; Cb, cystoblast; Fu, fusome; MC, mitotically active cysts; DC, differentiating 16-cell cysts; FC, follicle cell.
Figure 8:
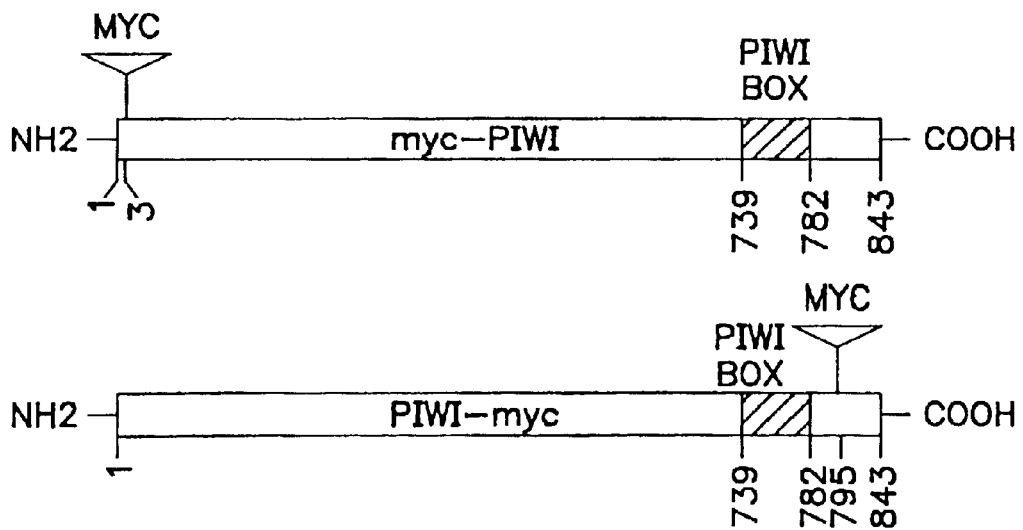
FIG. 8 is a schematic diagram of the myc-PIWI and PIWI-myc constructs. The myc-piwi transgene encodes a 97.5 kDa protein. In the myc-PIWI construct, the myc epitope is inserted after the third amino acid residue of PIWI. In the PIWI-myc construct, the epitope is inserted 13 amino acids downstream of the highly conserved PIWI box (hatched), 48 residues away from the C-terminus. Abbreviations: NH2, the amino terminus; COOH, the carboxy terminus.
Figure 9:
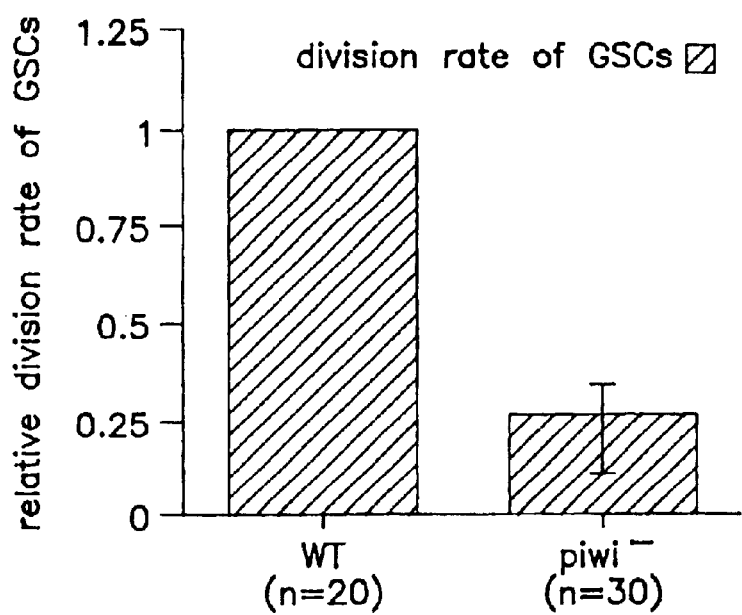
FIG. 9 is a graph displaying the relative division rates of wild-type and piwi⁻ GSCs and demonstrating that PIWI acts cell-autonomously in GSCs to promote their division. The number of germaria counted is given in parentheses.

Cloning of full-length human piwi cDNA clone. An isolated 2.3 kb partial human piwi cDNA clone from a human testis library by library screening is described in Example 1. To obtain the 5' end of this gene, by using a gene-specific primer, a 1.4 kb cDNA fragment containing overlapping sequence was obtained through 5'RACE and subcloned. To obtain a full length human piwi family clone, the above overlapping cDNA clones were partially digested. Fragments of the correct sizes were subsequently ligated and subcloned into a pGEM-T Easy vector (FIG. 4) to generate the 3472 bp full-length human piwi family (hiwi) that includes an open reading frame (ORF) encoding a protein of 861 amino acids, with a predicted molecular weight of 94.71 kDa (FIG. 7 and FIG. 8). The ORF starts at 167 bp and stops at 2749 bp. Upstream of the start codon is a 166 bp 5'untranslated region (5'UTR). Downstream of the stop codon is a 723 bp 3'untranslated region (3'UTR).

Protein sequence analysis showed that HIWI is 36.6% identical to *Drosophila PIWI* at amino acid level over its full length and 58.7% identical at the C terminal 104 amino acid residues. HIWI also shares 33.4% and 33.1% identity with two *C. elegans* PIWI family homologs PRG-1 and PRG-2 over its full length while the percentage increased to 57.7% and 58.7% at the C-terminals, suggesting piwi family genes and gene products are conserved during evolution. In addition, the higher degree of sequence homology between the C terminals suggests a conserved role of the C-terminal domain of PIWI in protein function.

Chromosomal mapping of hiwi. By using Radiation Hybrid mapping method against the Stanford G3 panel, human piwi was mapped to chromosome 12q 24.33, approximately 130 kb from the AFM 295 ye5 marker.

Tissue distribution of hiwi in adult human. Northern blot analysis were performed to study the tissue distribution of hiwi in adult human tissues. A variety of human tissues were examined, including spleen, thymus, prostate, testis, ovary, small intestine, colon and peripheral blood leukocyte. Among them, two transcripts were detected in testis: a more abundant 3.6 kb band and a less abundant band of 8.1 kb. No expression was found in other analyzed tissues, consistent with the known functions of hiwi in GSC division.

An autoradiograph of Northern blot analysis of hiwi mRNA in adult human and mouse tissues was thus prepared. The expression of hiwi mRNA in different tissues: spleen; thymus; prostate; testis; ovary; small intestine; colon; peripheral blood leukocyte. Two hiwi transcripts of 3.6 kb and 8.1 kb are visible in testis. Human β-actin cDNA probe was used as a positive control for the Northern blot with above tissues.

The specific expression of hiwi in the testis is contemplated to modulate the mechanism of some human genetic diseases related to testis malignancy and/or infertility. hiwi and other mammalian piwi family genes play an important role in germline stem cell division and other stem cell-related processes and are thus contemplated to be useful in the therapeutic methods, the screening methods, and the diagnostic and prognostic methods of the present invention set forth herein.

Example 3 miwi, a Murine Homolog of piwi, Encodes a Cytoplamsic Protein Essential for Spermatogenesis This Example shows cloning, expression analysis, and functional analysis of a mammalian member of the family, miwi, that is essential for spermatogenesis. miwi shares significant homology with other piwi family members, especially in the C-terminal PIWI box region. It encodes a cytoplasmic protein that is specifically expressed in spermatocytes of the adult testis. Consistent with its expression pattern, miwi-null mice are viable and female fertile, but completely male sterile. Histological and molecular marker analyses suggest that spermatogonial differentiation appears to be delayed, apoptosis increases drastically in spermatogenic cells at all stages, and spermatogenesis is arrested by the round spermatid stage, blocking spermiogenesis. These analyses reveal novel functions of a piwi family gene in mammalian spermatogenesis. Moreover, deletion of the C-terminal PIWI box region of MIWI leads to spermatogenic defects indistinguishable from the complete MIWI deletion, suggesting that this highly conserved region is essential for the function of PIWI family proteins.

Materials and Methods miwi cloning and Northern analysis. Multiple cDNAs representing 3.5 kb of the 3' end of miwi mRNA were isolated from mouse testis cDNA libraries obtained from Clontech Laboratories, Inc. (Palo Alto, Calif.) and from Dr. Quangquan Zhao using a human EST clone zw68h01.r1, a hiwi cDNA, (Cox et al., 1998) as an initial probe. To retrieve cDNA sequence of the entire ORF, 5'RACE was performed using the MARATHON™ cDNA Amplification Kit (Clontech Laboratories, Inc. of Palo Alto, Calif.) with 5'-TGCACTGCCAGGTCCTTCATCAC-3' (SEQ ID NO:12) as the reverse transcription primer and 5'-GGCCAGTCATTTTCCAGTCAGCTCAGGTG-3' (SEQ ID NO:13) as the miwi-specific PCR primer. Together, these miwi cDNAs cover 4.06 kb miwi mRNA sequence, including the complete ORF and 3'-UTR. Since the 4.7 kb miwi transcript is at least 20-fold more abundant than the 6.5 kb transcript, these cDNAs likely represent the 4.7 kb transcript. To obtain a miwi genomic sequence, a miwi probe was used to isolate clones comprising 42 kb of genomic DNA from a lambda library provided by Dr. J. Rossant via Dr. J. Klingensmith. 29.2 kb of genomic DNA was subcloned into the pBlueScript KS (+) vector (Stratagene of La Jolla, Calif.) and sequenced. The alignment of this genomic region to miwi cDNA reveals the intron/exon structures. Northern analysis was conducted using a 2.0 kb miwi cDNA as a probe and blots purchased from Clontech (Palo Alto, Calif.) (2 $\mu$g poly(A)$^+$ RNA/lane).

Mapping the miwi locus. The miwi locus was located by PCR-based meiotic mapping against the European Collaborative Interspecific Backcross (EUCIB) panel. A primer pair from the 3' UTR region of the miwi cDNA was used to amplify the corresponding region in 50 EUCIB backcrosses. The PCR products were heat-denatured and separated by nondenaturing gel electrophoresis to detect motility shift caused by single stranded conformation polymorphism. Non-polymorphic and polymorphic samples were scored as 1 and 2, respectively. The scores were then submitted to the EUCIB on-line database to obtain the mapping data.

Antibody generation. Two miwi cDNA fragments corresponding to amino acid residues 239–524 (MIWI34) and 532–862 (MIWI56) were cloned into the pGEM®-EX vector (Promega of Madison, Wis.) for bacterial overexpression of the peptides. Inclusion bodies containing the overexpressed peptides (>80% purity) were purified from the bacteria and dissolved in solubilization buffer (7M urea). The solubilized inclusion bodies were used to immunize rabbits, performed by Cocalico Biologicals, Inc. (Reamstown, Pa.). Antisera R132 and R133 were generated using MIWI34 as an antigen, while antisera R134 and R135 were generated using MIWI56 as an antigen. Antibodies were affinity purified by immuno-blotting (Harlow and Lane, 1988). All of the four antibodies recognize the same protein on western blots. Antisera R133 was used for all the experiments described herein, and is referred to as "anti-MIWI antibody".

RNA in situ hybridization. Digoxygenin-rUTP-labeled sense and antisense RNAs were translated from a 1.9 kb miwi cDNA fragment corresponding to amino acids 137–767 and subsequently used as probes for in situ hybridization on 8 $\mu$m testis cryosections. Hybridization was carried out at 60° C. overnight in a buffer (pH6.5) containing 50% formamide, 1.3×SSC, 5 mM EDTA, 0.5% CHAPS, 0.2% TWEEN-20™, 50 $\mu$g/ml yeast RNA, 100 $\mu$g/ml heparin, and 0.1–1 $\mu$g/ml sense or antisense RNA probe. After post-hybridization washes, sections were probed with alkaline phosphatase-conjugated anti-dioxigenin antibody (1:1000, Roche Molecular Biochemicals of Basel, Switzerland) at room temperature for 1 hour. The enzymatic reaction was carried out using FAST RED™ compound (Roche Molecular Biochemicals of Basel, Switzerland) as a substrate according to the manufacturer's instruction.

Western blotting and immuno-microscopy. For Western blotting, dissected mouse tissues were homogenized in 3–5 volumes of sample buffer (5% 2-mercaptoethanol, 3% SDS, 10% glycerol, 62.5 mM Tris-HCl pH6.8), boiled for 5 minutes, and separated by 10% SDS-PAGE (50 $\mu$g/lane). Proteins were transferred to a GENESCREEN™ filter (Genetix of Hampshire, United Kingdom), probed with 1:10 dilution of purified anti-MIWI antibody, and detected by anti-rabbit IgG antibodies conjugated with alkaline phosphatase or horseradish peroxidase. Immunohistochemical staining was performed on testis cryosections following the protocol of Anderson et al (1999). Anti-MIWI antibodies, anti-TSX antibody (Cunningham et al., 1998), and anti-laminin antibody (Sigma Co. of St. Louis, Mo.) were used at 1:1, 1:1000, and 1:30 dilutions, respectively. The rat monoclonal antibodies BC7 and TRA54 (gifts from Dr. Y. Nishimune) were used at a dilution of 1:500, and monoclonal antibody EE2 (also a gift from Dr. Y. Nishimune) was used at a dilution of 1:200. All secondary antibodies were purchased from Jackson ImmunoResearch Laboratory (West Grove, Pa.) and used at 1:100 dilution. DAPI (1 $\mu$g/ml) was used to label nuclei in some samples.

Construction of miwi$^{null}$ and miwi$^{\Delta C/\Delta C}$ mice. To generate the miwi$^{null}$ allele, the replacement targeting vector KO-4A was constructed in the pPNTloxPneo vector (Shalaby et al., 1995) using a 2.0 kb ApaI fragment and a 7.0 kb KpnI-NotI fragment for the 5' and 3' flanking homologous regions, respectively (FIG. 11A). 25 $\mu$g of NotI-linearized KO-4A DNA was used for electroporation of 1×10$^7$ R1 embryonic stem cells. 142 clones which survived the double selections were screened by PCR using primers 5'-ATGGGGTCTTTTCTTGCTCA-3' (SEQ ID NO:14) and 5'-TGCCCATTAACATCACCATC-3' (SEQ ID NO:15). The positive clones were verified by Southern analysis using 3' and 5' external probes (FIG. 11B). Three recombinant embryonic stem cell clones (A9, E4, and G10) were injected into host blastocysts following standard protocols (Hogan et al., 1994). One injected clone, A9, showed germline transmission of the mutant allele. The male chimera was crossed with C57BL/6J (JAX). Genomic DNA from the agouti F1 pups was analyzed by PCR for the presence of the mutant allele using the following 3 primers (FIG. 11C): Primer a: 5'-TGATTTGGGGACTTATTTTAGAGC-3' (SEQ ID NO:16), primer b: 5'-ACTTACCTTGTGACTTGGATGTG-3' (SEQ ID NO:17), and primer c: 5'-TTGAAAAGCATTGAACACCATMG-3' (SEQ ID NO:18). Homozygous mutant mice were obtained by crossing heterozygous males to either heterozygous females or homozygous mutant females. A miwi$^{null}$ mouse colony is maintained in a mixed genetic background of 129 and C57BL/6.

Figure 12A:
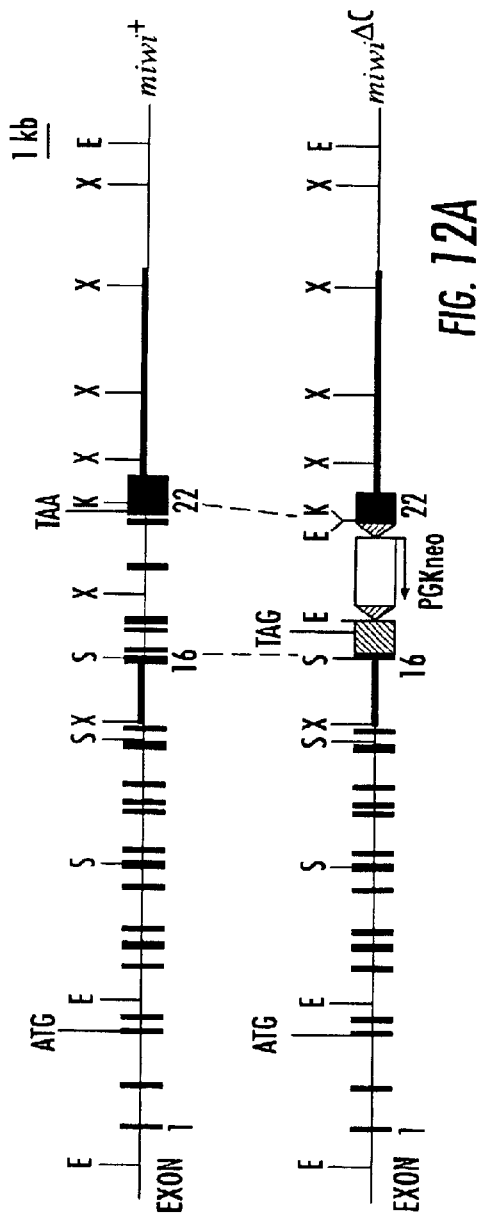
FIGS. 12A–12B present the targeting strategy and knockout of the sequence encoding the C-terminal region of MIWI.
Figure 12B:
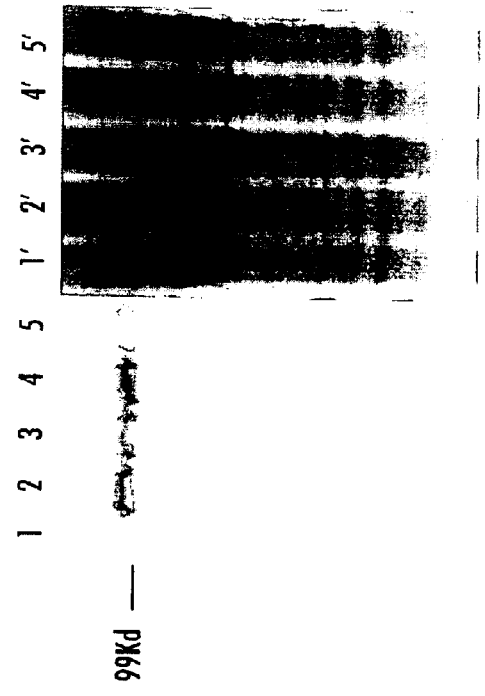
Figure 13:
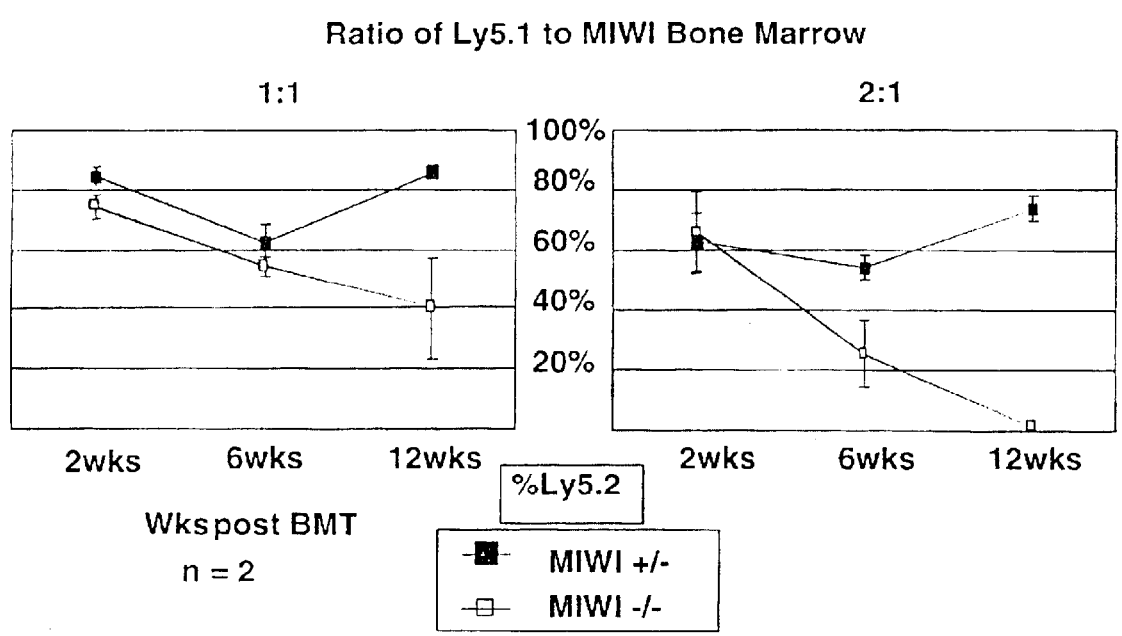
FIG. 13 presents graphs depicting the percentage of hematopoietic cells derived bone marrow surviving at the 2, 4, or 6 weeks following bone marrow transplantation (Wks post BMT) into irradiated ly5.1 mice. The left graph, labeled above as "1:1" shows the results of transplantation experiments wherein a 1:1 ratio of miwi$^{+/-}$ and miwi$^{-/-}$ (marked by ly5.2) was used. The right graph, labeled above as "2:1" shows the results of transplantation experiments wherein a 2:1 ration of miwi$^{+/-}$ and miwi$^{-/-}$ (marked by ly5.2) were used. (■), hematopoietic cells derived from bone marrow of miwi$^{+/-}$ mice; (□), hematopoietic cells derived from bone marrow of miw$^{-/-}$ mice.

To generate the miwi$^{\Delta C}$ allele, the replacement targeting vector KO-5B was also constructed in the pPNTloxPneo vector (Shalaby et al., 1995) using a 1.9 kb XbaI-SalI fragment and a 7.0 kb KpnI-NotI fragment for the 5' and 3' flanking homologous regions, respectively (FIG. 12A). 25pg of NotI-linearized KO-5B DNA was used for electroporation of 1×10$^7$ R1 embryonic stem cells. 130 clones that survived the double selections were screened by PCR using primers 5'-GATMCCACCGCCCTGCCTTTCAC-3' (SEQ ID NO:19) and 5'-TGCCCATTAACATCACCATC-3' (SEQ ID NO:20). The positive clones were verified by Southern analysis using a 3.6 kb Sac I genomic fragment spanning exons 9–14 as the 5' external probe and the same 3' external probe as for the KO-4A construct (FIG. 12B). Three recombinant embryonic stem cell clones (A1, C10, and D2) were injected into host blastocysts following standard protocols (Hogan et al., 1994). Two injected clones, C10 and D2, showed germline transmission of the mutant allele. The male chimera was crossed with C57BL/6J (JAX). Genomic DNA from the agouti F1 pups was analyzed by PCR for the presence of the mutant allele using the same method as for KO-4A. Homozygous mutant mice were obtained by crossing heterozygous males to either heterozygous females or homozygous mutant females. A miwi$^{\Delta C}$ mouse colony is maintained in a mixed 129 and C57BL/6 background as for miwi$^{null}$.

Histology and cell proliferation/apoptosis assays. Male mice were injected intraperitoneally with 50 µg/g BrdU (bromodeoxyuridine) (Roche Molecular Biochemicals of Basel, Switzerland) 8 hours before being sacrificed (6 hours for 2 week- and 4 week-old animals). Testes were dissected, weighed, fixed in either Bouin (Sigma of St. Louis, Mo.) or 4% paraformaldehyde overnight at 4° C., and cut into 8 µm cryo- or paraffin sections. Hematoxylin/eosin staining and periodic acid-Shiff/hematoxylin staining were performed for histological analysis of paraffin sections. RNA in situ hybridization and immunohistochemical staining were generally performed on cryosections, and alternatively on paraffin sections. Incorporated BrdU signal was detected using a 1:3.5 dilution of mouse anti-BrdU mAb (Becton, Dickinson, and Company of Franklin Cakes, N.J.) and a FITC-conjugated goat anti-mouse secondary antibody. Apoptosis was analyzed by TUNEL labeling (TdT-mediated dUTP-digoxigenin end-labeling) using the APOTAG® kit (Intergen of Purchase, New York).

Results

Molecular cloning and mapping of miwi. To investigate the function of piwi family genes in mammalian development, a 4.06 kb miwi cDNA containing a 191 bp 5' untranslated region (UTR) was isolated. A cDNA containing 2.59 kb open reading frame (ORF), and a 1.17 kb 3' UTR followed by a poly(A) tail was also isolated. The ORF is preceded by multiple in-frame stop codons, indicating its completeness. To characterize the miwi gene structure, about 40 kb of genomic DNA from the miwi locus was isolated. The miwi cDNA corresponds to a 19.2 kb genomic region, encoded by 22 exons, with the ORF starting in the third exon and ending in the 22nd exon (FIG. 5). The previously defined PIWI box is encoded by exons 20 and 21 (Cox et al., 1998). A representative miwi cDNA is set forth as SEQ ID NO:3, and a representative MIWI protein is set forth as SEQ ID NO:4.

To locate the miwi locus in the mouse genome, single strand polymorphic mapping was performed against the European Collaborative Interspecific Backcross panels. The mapping data indicated that miwi is located on chromosome 5 near the D5nds6 marker with a Iod score of 9.8.

The miwi ORF predicts that the MIWI protein contains 862 amino acid residues (FIG. 6), with a relative molecular mass ($M_r$) of 98,600 and an isoelectric point of 9.46. Except for a 100–200 amino acid stretch at the N-terminus, MIWI shares significant homology over its entire length with other PIWI family proteins, such as MILI from mice (GenBank GI No. 7416113; 42% identity), HIWI (Cox et al., 1998; 94% identity) and HILI (GenBank GI No. 8922370; 46% identity) from humans, PIWI (Cox et al., 1998; 37% identity) and AUBERGINE (Wilson et al., 1996; Schmidt et al., 1999; 38% identity) from Drosophila, PRG-1 and PRG-2 from C. elegans (Cox et al., 1998; 34% and 33% identity), and PAP from Paramecium (GenBank GI No. 6630673; 28% identity, respectively). Interestingly, all these proteins are either involved in the development of the germline or its equivalent. The homology at the C-terminal PIWI Box region is particularly high (FIG. 6), suggesting the potential importance of this region for the MIWI protein function.

miwi is specifically expressed in the germine during spermatoqenesis.

To explore the role of miwi in development, miwi expression was assessed in major adult organs and in embryos of various stages by Northern blot analysis. A Northern blot was prepared using adult mouse tissues, including heart, brain, spleen, lung, liver, muscle, kidney, and testis, and hybridized using a miwi probe. miwiencodes a4.7 kb abundant transcript and a 6.5 kb present at low levels, both of which are specifically expressed in the adult testis, but are not detectable in other adult organs. Hybridization with a β-actin probe was performed as a loading control. A Northern blot was also prepared using staged embryos at 7, 11, 15, and 17 days post coitum (dpc) and hybridized using a miwi probe. miwi transcript was not detected in embryos at any of the stages examined. The adult- and testis-specific expression of miwi was further confirmed by in situ hybridization, by examining the expression of the miwi-GFP knock-in chimeric gene, and by Western blot analysis (described herein below).

A Northern blot was also prepared using staged embryos at 7, 11, 15, and 17 days post coitum (dpc) and hybridized using a miwi probe. miwi transcript was not detected in embryos at any of the stages examined.

miwi RNA expression was further examined in testis using tissue sections multiply labeled to detect miwi RNA and the laminin antigen found on seminiferous tubules. miwi RNA and laminin were distinguished by use of alternate fluorescent labels. In the testis, miwi RNA is not detectable at 1, 3, 6, and 9 days post partum (dpp), but is first detected in cells in the center of the seminiferous tubules at 12 dpp, a stage when zygotene spermatocytes first appear. When the tubule lumen becomes conspicuous at 14 dpp, miwi RNA is restricted to the lumenal side of the seminiferous epithelium where developing spermatocytes reside. In fully developed adult testes, miwi RNA is detected in a small number of germ cells at the basal layer of the tubule, and is abundantly present in primary spermatocytes that are one-cell layer away from the basement membrane.

The germline-specific expression of miwi was confirmed by counter-staining testis sections with the anti-TSX (testis-specific X-linked gene product) antibody, a Sertoli cell marker (Cunningham et al., 1998). The miwi-expressing cells do not express TSX, suggesting that they are not Sertoli cells. At all postnatal stages, miwi RNA expression is only detectable in a subset of seminiferous tubules, indicating that miwi expression is dependent on seminiferous tubule cycle.

MIWI is a cytoplasmic protein. To further characterize miwi function, anti-MIWI antibodies were generated that recognize an about 100 kD antigen of expected MIWI protein size. For detection of MIWI protein in adult tissues, a Western blot was prepared using adult dissected mouse tissues, including bone marrow, brain, heart, kidney, liver, lung, ovary, spleen, testis, and thymus. 50 µg of protein were loaded in each lane, and the blot was probed using an anti-MIWI antibody. The MIWI antigen is detectable only in the testis, where it is expressed specifically in the germline in a pattern similar to the miwi RNA expression pattern. Moreover, this antigen is eliminated in miwi$^{null}$ testes, as indicated by Western blotting and by immunofluorescence microscopy analyses (as described herein below). These data indicate that the antigen detected by the anti-MIWI antibody is the MIWI protein.

To further evaluate the distribution of MIWI protein in testis, immunostaining experiments were performed to simultaneously detect MIWI protein and laminin, and further stained using DAPI. The MIWI and laminin labels were detected using different fluorophores such that MIWI, laminin, and DAPI were each distinguishable when viewed using a fluorescence microscope.

MIWI is a cytoplasmic protein that is first detectable at 14 dpp, soon after the first appearance of zygotene stage spermatocytes. In the adult testis, MIWI is detected in primary spermatocytes 1–2 cell layers away from the basal lamina. The level of MIWI protein is sharply reduced in secondary spermatocytes and round spermatids, and is not detectable in elongating spermatids or mature sperm. In addition, MIWI is not detectable in somatic cells such as Sertoli cells or interstitial cells outside the tubules. This expression pattern suggests that MIWI can play a cell autonomous role in spermatocyte development and/or spermatid differentiation.

Spermatogenesis in miwi$^{null}$ mice is arrested at the onset of spermiogenesis. To investigate the function of MIWI in vivo, miwi-deficient mice were generated by homologous recombination that replaced the genomic region corresponding to almost the entire MIWI ORF with a MmGFP ORF (Zernicka-Goetz et al., 1997) (FIG. 11A). The resulting recombinant allele contains a fusion ORF that encodes the first nine amino acid residues of MIWI, followed by a PPRQ linker (SEQ ID NO:21) and the MmGFP peptide. This genotype was confirmed by genomic Southern analysis (FIG. 11B) and PCR genotyping analysis (FIG. 11C). In these homozygous miwi-deficient mice, no native MIWI protein was detected in the testis by Western blot analysis (FIG. 11D) or by immunofluorescence microscopy. Thus, this allele was designated miwi$^{null}$.

The miwi$^{null}$ mice, also referred to as miwi$^{-/-}$ mice, develop to apparently normal adults. Interbreeding of heterozygotes miwi$^{+/-}$ adults yielded the Mendelian ratio (71:139:63) of wild type miwi$^{+/+}$, heterozygous miwi$^{+/-}$, and homozygous miwi$^{-/-}$ offsprings. In addition, crossing heterozygous miwi$^{+/-}$ males to homozygous miwi$^{-/-}$ females also yielded the predicted 1:1 ratio of heterozygous miwi$^{+/-}$ to homozygous miwi$^{-/-}$ offspring (83:75). These results indicate that there is no lethality caused by the miwi$^{null}$ mutation. Furthermore, miwi$^{null}$ mice are female fertile but completely male sterile. Testes from adult miwi$^{-/-}$ males (8–24 weeks old, n=28) are on average 29% smaller by weight than wild type or miwi$^{+/-}$ testes (n=28). Moreover, no sperm is found in the epidydimus of miwi$^{-/-}$ mice.

To evaluate spermatogenesis in miwi$^{-/-}$ mice, testis sections were procured from miwi$^{+/-}$ and miwi$^{-/-}$ mice, and stained with hematoxylin/eosin to reveal cellular morphology and enable the identification of cell types including spermatogonia, spermatocytes, round spermatids, and elongated spermatids. Histological examination of miwi$^{-/-}$ testes revealed that spermatogenesis is arrested at the round spermatid stage. Spermatids fail to initiate cellular elongation or nuclear condensation (step 8 of spermiogenesis). In some tubules, even round spermatids are absent.

Testis sections were also immunostained to detect cyclin D3, an antigen strongly expressed in elongated spermatids (Zhang et al., 1999). In contrast to abundant staining in miwi$^{+/-}$ testes, cyclin D3 was not detected in miwi$^{-/-}$ testes.

To further characterize the miwi$^{-/-}$ phenotype, testis sections were labeled with an antibody that specifically binds the TRA54 antigen, which labels a round organelle in pachytene spermatocytes and the acrosome in spermatids before step 12 of spermiogenesis (Pereira et al., 1998). In testes derived from miwi$^{-/-}$ mice, TRA54 staining was delocalized or absent, indicating abnormal or absent acrosomes. Periodic acid-Schiff's staining of testis sections was also performed, and did not detect any acrosomes in miwi$^{-/-}$ round spermatids.

Collectively, the histological and immunostaining observations of testis development in miwi$^{-/-}$ mice indicate that miwi is required during the initial stages of spermiogenesis.

miwi$^{null}$ mice show early spermatogenic defects. Prior to arrest at the round spermatid stage, miwi$^{-/-}$ mice show earlier spermatogenetic defects. Degenerating germ cells with pycnotic nuclei were frequently observed in regions corresponding to spermatocytes and spermatids. TUNEL labeling (TdT-mediated dUTP-digoxigenin nick end-labeling) revealed that miwi$^{-/-}$ testes contain a drastically increased number of apoptotic cells from the basal layer to the lumenal layer of the seminiferous epithelium, when compared to the number of apoptotic cells in a same testes region derived from a miwi$^{+/-}$ mouse. TUNEL labeling was observed in testis sections also labeled to detect laminin to outline the seminiferous tubules and with DAPI, to facilitate determination of the position and identity of dying cells. The results suggest that miwi is required for the survival and development of spermatogonia, spermatocytes, and round spermatids.

A related observation is that antibody EE2, which recognizes the spermatogonia and early spermatocytes at the basal layer (Koshimizu et al. 1995; up to zygotene stage), frequently marks two layers of germ cells in miwi$^{-/-}$ testes. Testis sections were viewed when multiply labeled to detect the EE2 antigen, laminin, and nuclei. The EE2 and laminin staining protocols employed different fluorophores such that each label was distinguishable from the other, and further distinguishable from the nuclear dye DAPI.

To distinguish whether expansion of the germ cell layer was due to overproliferation or delayed differentiation of spermatogonia and/or early spermatocytes, the proliferation of germ cells was examined using a BrdU (bromodeoxyuridine) incorporation assay. miwi$^{+/-}$ and miwi$^{-/-}$ testes were observed to incorporate BrdU to a similarextent, indicating a similar frequency of cell division. Hence, the miwi deficiency appears to cause delayed differentiation rather than overproliferation.

To further distinguish whether a differentiation delay occurs in spermatogonia or in spermatocytes, anti-BC7 was used to label spermatocytes from leptotene to early pachytene stages (Koshimizu et al., 1993). Testis sections were viewed when multiply labeled to detect the BC7 antigen, laminin, and nuclei. The BC7 and laminin staining protocols employed different fluorophores such that each label was distinguishable from the other, and further distinguishable from the nuclear dye, DAPI. miwi$^{+/-}$ and miwi$^{-/-}$ testes showed a similar pattern of BC7 staining, suggesting that the delay occurs at the spermatogonial stage. Thus, miwi deficiency appears to cause a delay in spermatogonial differentiation.

To examine when these defects first occur during postnatal development in miwi$^{-/-}$ animals, testis histology was examined at various postnatal stages. Histological review was facilitated by staining of testis sections with haemotoxylin/eosin. Although there was no detectable difference between miwi$^{+/-}$ and miwi$^{-/-}$ testes from 2-week old mice, the spermatogenic defects described above were evident in 4-week old miwi$^{-/-}$ testes. This time point coincides with the first appearance of elongated spermatids in wild type and heterozygous testes. These observations suggest that in miwi$^{-/-}$ testes spermatid arrest occurs during the first wave of spermatogenesis while defects in spermatogonia and spermatocytes are manifested in a more gradual fashion.

Figure 6A:
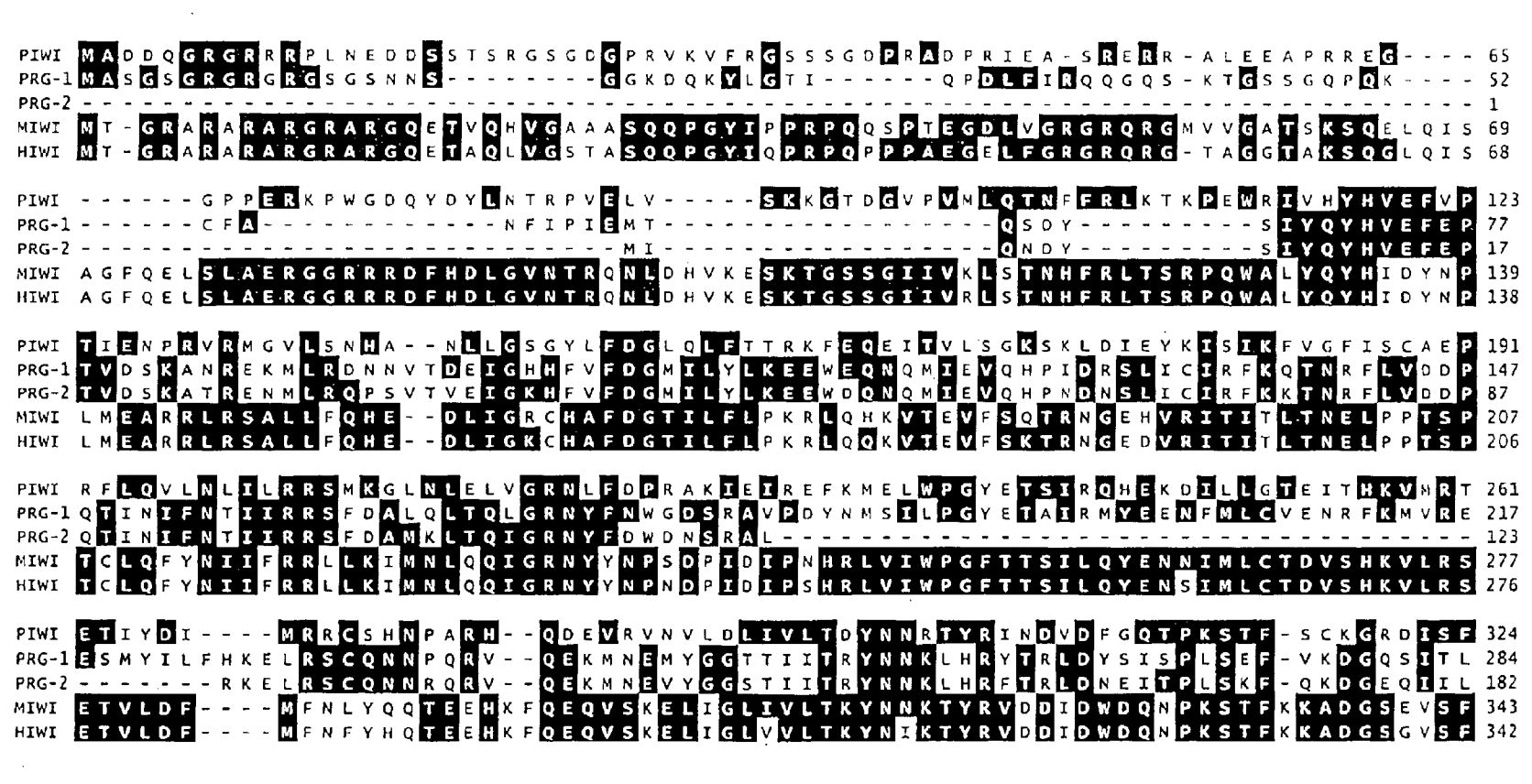
Figure 6B:
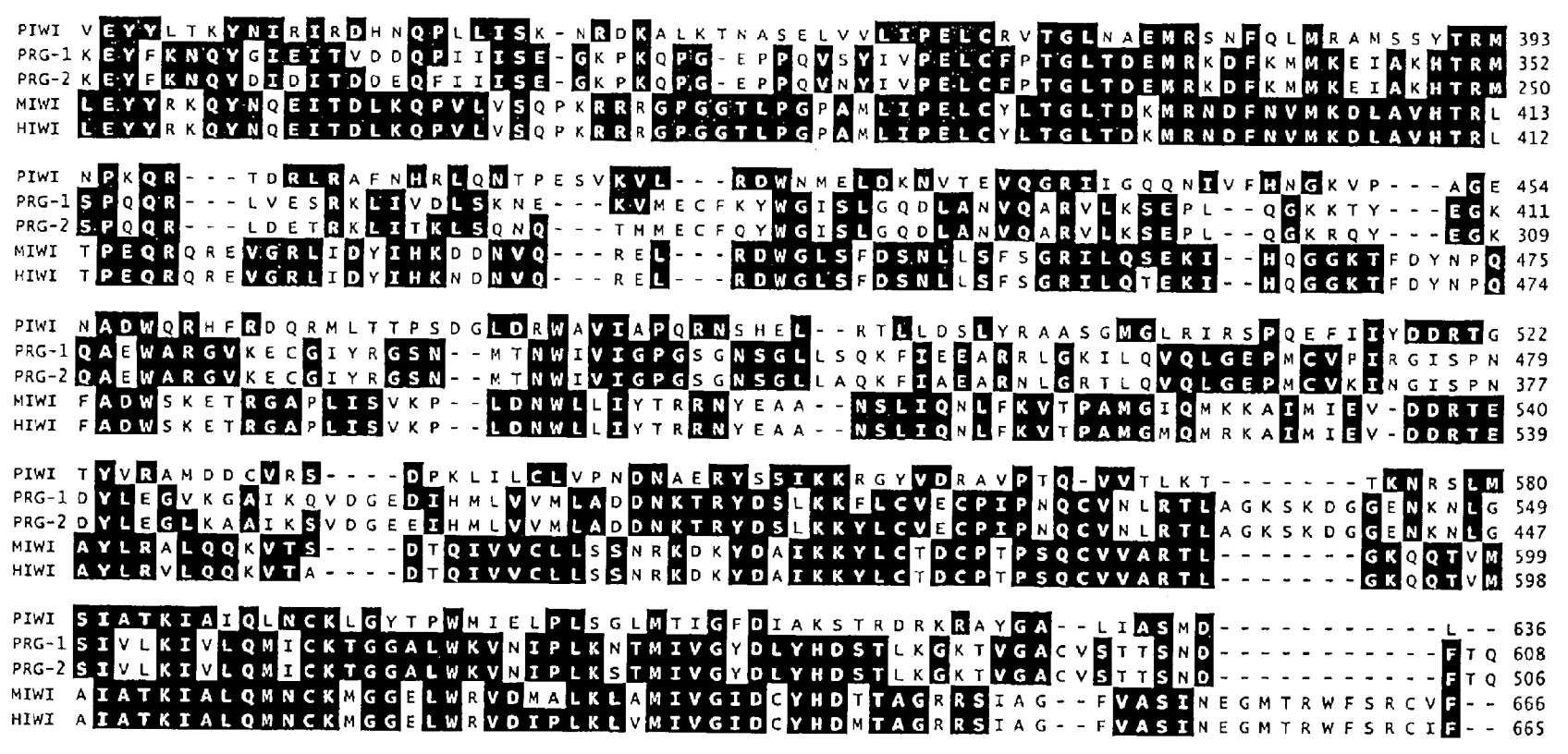
Figure 6C:
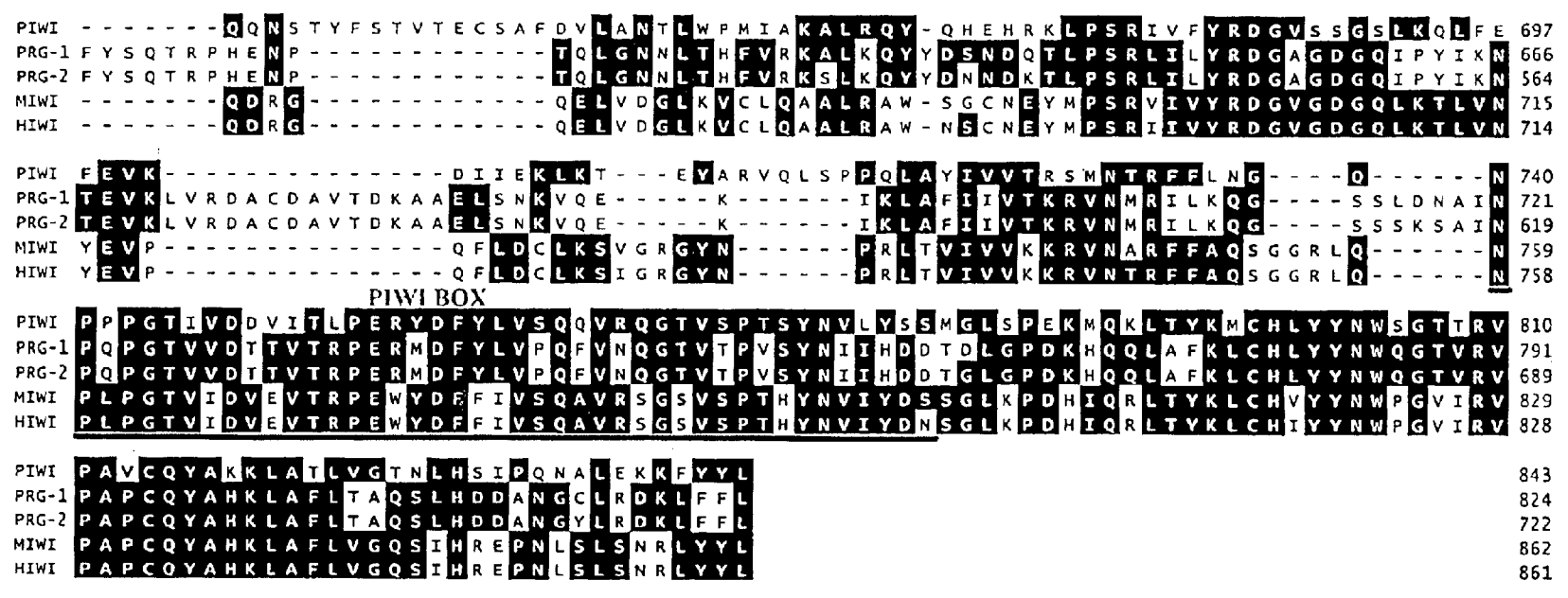

Deleting the C-terminal PIWI box region of MIWI causes miwi$^{null}$-like defects. The piwi family genes are highly conserved in the C-terminal PIWI box-coding region (Cox et al., 1998) (FIG. 6). The essential role of miwi in spermatogenesis provides an opportunity to test whether the PIWI box-coding region is important for MIWI function. miwi-deficient mice were generated in which the C-terminal 245 amino acid residues of MIWI are replaced by a 239 amino acid residue MmGFP-coding sequence (FIG. 12A). The resulting recombinant miwi$^{\Delta C}$ allele contains a fusion ORF that encodes the first 617 amino acid residues of MIWI fused to the 239 residue MmGFP peptide, generating a $M_r$ 97,600 hybrid protein that is essentially the same size as the MIWI protein ($M_r$ 98,600). This genotype was confirmed by genomic Southern and PCR genotyping analyses. Indeed, the hybrid protein is present in homozygous miwi$^{\Delta C}$ mice, suggesting that substituting the C-terminal 245 residues of MIWI with a MmGFP peptide of similar length does not significantly affect the stability of the protein (FIG. 12B).

Homozygous miwi$^{\Delta C}$ mice show phenotype that are indistinguishable from that of homozygous miwi$^{null}$ mice. First, the miwi$^{\Delta C}$ mice develop normally to adulthood at expected Mendelian ratios. Intercrosses between miwi$^{\Delta C/+}$ mice produced the expected Mendelian ratios of progeny genotypes, i.e, 17 miwi$^{+/+}$, 46 miwi$^{\Delta C/+}$, and 23 miwi$^{\Delta C/\Delta C}$ mice. Second, miwi$^{\Delta C/\Delta C}$ mice were female fertile but completely male sterile. Third, histological examination of testes derived from miwi$^{\Delta C/\Delta C}$ revealed that spermatogenesis is also arrested at the round spermatid stage, before step 8 of spermiogenesis. No spermatid was ever detected to undergo cellular elongation or nuclear condensation. In some tubules, even round spermatids are absent. Fourth, prior to arrest at the round spermatid stage, miwi$^{\Delta C/\Delta C}$ mice showed earlier spermatogenic defects indistinguishable from those observed in miwi$^{null}$ animals, as assessed by histological analysis at three weeks. Degenerating germ cells with pycnotic nuclei were frequently observed in regions corresponding to spermatocytes and spermatids. Lastly, the early spermatogenic defects were first detectable in miwi$^{\Delta C/\Delta C}$ at 21 dpp. Similarly, miwi$^{null}$ mice show spermatogenic defects by 28 dpp, but are not observed at 14 dpp. The apparently identical phenotypes of miwi$^{null}$ and miwi$^{\Delta C/\Delta C}$ mice suggest that the C-terminal PIWI box-containing region is essential for MIWI function.

Discussion

Although a number of genes are known to be involved in spermatogenesis, only a few such genes are known to have testis-specific expression or function. As disclosed herein, miwi is essential for spermatogenesis, and miwi is expressed specifically in the testicular germline. The phenotype of miwi null mutant mice reveals the involvement of miwi in both early and late stages of spermatogenesis, while the germline-specific expression of miwi further suggests that MIWI functions cell-autonomously during mammalian spermatogenesis. Since miwi is a member of the piwi gene family, the disclosure herein reveals, for the first time, the novel function of this gene family in mammalian systems.

The role of MIWI as a cell-autonomous molecule essential for spermiogenesis. Mammalian spermatogenesis is controlled by both inter- and intracellular mechanisms. The intercellular mechanism includes BMP8a and b (bone morphogenetic proteins 8a and 8b) signaling, which is required for the initiation and maintenance of spermatogenesis, with their downstream factor MADR1 (MAD-related protein 1) expressed in the germline (Zhao et al., 1996; Zhao and Hogan, 1997; Zhao et al., 1998). In addition, DHH (desert hedge hog) signal from Sertoli cells is required for various stages of spermatogenesis apparently via regulating the formation of adult-type Leydig cells and the normal development of peritubular cells and seminiferous tubules (Bitgood et al., 1996; Clark et al., 2000). Moreover, STEEL (stem cell factor) signaling from Sertoli to the c-KIT receptor (receptor tyrosine kinase) on the surface of germ cells is required for spermatogonial differentiation (Yoshinaga et al., 1991; Ohta et al., 2000).

By contrast, germline-specific expression of miwi suggests that MIWI acts cell-autonomously in spermatogenesis. This mode of action is shared by cell cycle regulators such as cyclin A1 and HSP-70.2 (heat shock protein of 70.2 kD) (Dix et al., 1996; Zhu et al., 1997; Liu et al., 1998), DNA repair and recombination genes such as MLH1 (MutL homolog 1), MSH5 (muscle segment homeobox 5), ATM (ataxia telangiectasia mutated), SCP3 (synaptonemal complex protein 3) (Baker et al., 1996; Barlow et al., 1996; Edelmann et al., 1996; Elson et al., 1996; Xu et al., 1996; de Vries et al., 1999; Edelmann et al., 1999; Yuan et al., 2000), transcription factors such as A-MYB (MYB-related protein A) and EGR4 (early growth response protein 4) (Toscani et al., 1997; Tourtellotte et al., 2000), and RNA binding proteins such as DAZLA (deleted in azoospermia-like) and VASA (Ruggiu et al., 1997; Tanaka et al., 2000). However, targeted disruptions of these additional genes block spermatogenesis at the spermatocyte stage rather than the round spermatid stage, as observed in miwi$^{-/-}$.

The miwi phenotype is similar to the effect of premature translation of protamine-1 in round spermatids (Lee et al., 1995). However, no protamine is detected in miwi$^{null}$ mice, indicating that the premature accumulation of protamines is not the cause of the spermatogenic arrest in these mice.

A molecule whose deficiency causes miwi$^{null}$-like arrest at the round spermatid stage is CREM (cAMP responsive element modulator), a transcription factor proposed to be a master switch for spermiogenesis (Blendy et al., 1996; Nantel et al., 1996; Zhou et al., 1996; Sassone-Corsi 2000). CREM is essential for the expression of spermiogenic factors such as protamines, transition proteins (TNPs), calspermine, mitochondrial capsule selenoprotein and angiotensin-converting enzyme. The phenotypic similarity between miwi and CREM mutants suggests that miwi could be involved in initiating spermiogenesis as well. This "master switch" phenotype differs from that of other spermiogenic factors, such as TNP1 (transition protein 1) involved in histone displacement and chromatin condensation (Yu et al., 2000), the RNA binding protein TARBP2 (TAR (HIV) binding protein 2) that regulates protamine translation (Zhong et al., 1999), HR6B ubiquitin-conjugating enzyme involved in DNA repair (Roset et al., 1996), or casein kinase required for nuclear condensation and acrosome development (Xu et al., 1999). Loss of TNP1, TARBP2, HR6B, or casein kinase function causes limited abnormalities at the elongated spermatid stage, but spermiogenesis is nevertheless completed at observable frequencies. The definitive arrest of spermatogenesis at the onset of spermiogenesis in miwi mutants suggests that MIWI is essential for the initiation of the entire spermiogenic program.

The role of MIWI in early spermatogenesis. In addition to its essential role in spermiogenesis, miwi appears to be involved in earlier stages of spermatogenesis, even as early as the germine stem cell stage. An earlier role is suggested by the delay of spermatogonial differentiation and elevated apoptosis in spermatogenic cells in miwi mutant testes, as well as by abundant miwi expression in spermatocytes.

Molecular activity of MIWI. All PIWI family proteins share a highly conserved C-terminal region that is enriched with highly basic and highly charged residues (Cox et al., 1998). As disclosed herein, replacement of the C-terminal region by an unrelated peptide sequence of similar size (i.e. the GFP sequence) appears to completely abolish the MIWI activity in various stages of spermatogenesis, resulting in a miwi$^{null}$-like phenotype. These results provide the first evidence that this region is crucial for the function of a PIWI family protein.

In summary, miwi is essential for germline stem cell division and other stem cell-related processes. Thus, miwi and other mammalian piwi family genes are useful in the therapeutic methods, screening methods, and diagnostic and prognostic methods of the present invention set forth herein.

Example 4

PIWI Family Proteins are Nuclear Proteins Whose Level Determines the Number of Stem Cells in the Germline Two immunofluorescence micrographs were prepared and showed germline cells (marked in green) in the Drosophila germarium in the background of normal and elevated level of PIWI. The ectopically elevated expression of piwi causes an increase in the number of stem cells and/or their immediate daughter cells (cystoblasts) from normally 2–3 to approximately 15, with 7 of which were shown in the focal plan of micrograph of elevated PIWI levels. Stem cells were marked by the spectrosome (Sp), an organelle specific to these cells. The differentiating germine cyst contains fusome (F), an organelle specific to mitotic stage of cyst development. Thus, over-expression of piwi increases the number of germline stem cells/cystoblasts.

Immunofluorescence micrographs of detection of a myc-tagged PIWI protein (with and without myc as a control) in Drosophila ovariole, Drosophila terminal filament, basal cells and GSC in Drosophila germarium, apical polar cells (APC) in Drosophila egg chambers, and hub cells in Drosophila testis were also prepared. These micrographs showed that PIWI is a nuclear protein present in both the germline and in somatic cells at different stages of oogenesis and spermatogenesis. myc-PIWI was shown to completely rescue the defects caused by loss of piwi function, thus demonstrating a therapeutic method of the present invention. PIWI is demonstrated to be a nuclear protein at certain development stages. MIWI and HIWI proteins are thus also contemplated to be nuclear proteins at certain development stages.

Additionally, as disclosed below, the PIWI protein can localize either in the nucleoplasm or cytoplasm, the dose of the PIWI protein determines both the number and the mitotic rate of germline stem cells, and the PIWI protein is localized in the germplasm (the cytoplasm of future germ cells) and plays a key role in determining the initial number of germ cells in during embryogenesis. The mouse PIWI protein (i.e., MIWI protein) has also been observed in the cytoplasm via antibody screening and is thus also envisioned to be a cytoplasmic factor with very similar functions in germ cell and stem cell determination. Thus, the HIWI protein is thus also envisioned to be a cytoplasmic protein at certain development stages.

Example 5 piwi Encodes a Nucleoplasmic Factor Whose Activity Modulates the Number and Division Rate of Germline Stem Cells As disclosed above, piwi represents the first class of genes known to be required for stem cell self-renewal in diverse organisms. In the Drosophila ovary, piwi is required in somatic signaling cells to maintain germline stem cells. In this Example it is shown that that piwi encodes a novel nucleoplasmic protein present in both somatic and germline cells, with the highly conserved C-terminal region essential for its function. Removing PIWI protein from single germline stem cells significantly decreases the rate of their division. This is indicative of a second role for PIWI as a cell-autonomous promoter of germline stem cell division. Consistent with its dual function, over-expression of piwi in somatic cells causes an increase both in the number of germline stem cells and the rate of their division. Thus, PIWI is a key regulator of stem cell division—its somatic expression modulates the number of germline stem cells and the rate of their division while its germline expression also contributes to promote stem cell division in a cell-autonomous manner.

Materials and Methods

Drosophila strains and culture. All Drosophila strains were grown at 25° C. on yeast-containing molasses/agar medium. The following fly strains were used in this study: piwi$^1$ and piwi$^2$ mutant chromosomes, generated in different genetic screens (Lin and Spradling, 1997), were dominantly marked with Irregular facets (If) (Lindsley and Zimm, 1992); ep(2)1024 is an EP element insertion (Rorth, 1996; Rorth et al., 1998) in the piwi 5' UTR; piwi$^1$FRT40A/CyO and piwi$^2$FRT40A/CyO; hsFlp; +FRT40A/CyO (Xu and Rubin, 1993); hsFlp; armadillo-lacZ FRT40A (armlacZ FRT40A, Lecuit and Cohen, 1997); hsGal4 (Brand and Perrimon, 1993) are as described herein above.

Generation of mutant germline stem cell clones. piwi mutant GSC clones were generated by Flp-mediated recombination as described by Xu and Rubin (1993). To generate wild-type and mutant GSC clones for analyses, piwi$^+$ FRT40A/CyO, piwi$^1$FRT40A/CyO and piwi$^2$FRT40A/CyO males were mated to w hsFlp1; armlacZ FRT40A virgin females, respectively, to produce w hsFlp1/+; piwi* FRT40A/armlacZ FRT40A progeny, where * denotes the wildtype or mutant alleles. The parental adults were transferred to fresh vials after 2 days. Larvae from the original vials were heat-shocked once daily for 1 hour in a 37° C. water bath on days 3 and 4 to induce mitotic recombination immediately prior to the onset of oogenesis at the late third instar stage as described herein above. After eclosion, adult w hsFlp1/+; piwi* FRT40A/armlacZ FRT40A females were transferred to fresh food at room temperature and ovaries were removed 1 week, 2 weeks, and 3 weeks after the last heat shock treatment and processed for anti-lacZ antibody staining to look for lacZ-negative clones.

Heat-shock induced PIWI overexpression. To construct a piwi-overexpressing stock, ep(2)1024/CyO virgin females were crossed to males homozygous for a hsGal4 transgene on chromosome 3. Females carrying both the ep(2)1024 chromosome and the hsGal4 transgene were heat shocked at 37° C. for 1 hour each time with an interval of 12 hours for 3–4 days. At the end of the heat shock regime, ovaries were dissected and processed for antibody staining.

To analyze the functionality of the PIWI protein produced by hsGal4-induced overexpression of ep(2)1024, ep(2)1024/

CyO; hsGal4/hsGal4 virgin females were crossed to piwi[1]If/CyO; +/+males to produce the ep(2)1024/piwi[1]If; hsGal4/+ transheterozygous progeny. After 2 days, parental adults were transferred to fresh vials. Larvae were heat shocked daily for 1 hour at 37° C. starting at day 3 and continued to 3 days after eclosion. The transheterozygous progeny were subsequently dissected and processed for antibody staining. The transheterozygous progeny which were not subjected to the heat shock regime served as controls.

Immunofluorescence microscopy and BrdU labeling. Ovaries and testes were dissected, fixed and stained as described by Lin et al. (1994). For immunofluorescence staining the following antisera were used: polyclonal anti-Vasa antibody (1:2000; Hay et al., (1990)), monoclonal anti-Hts antibody 1B1 (1:1; Zaccai and Lipshitz, (1996)), polyclonal anti-a-spectrin antibody (1:200; Byer et al., (1987)), monoclonal anti-myc epitope antibody 1–9E10.2 (1:50; Evan et al., 1985), monoclonal anti-BamC antibody (1:1000; McKearin and Ohlstein, 1995), polyclonal anti-β-galactosidase antibody (1:600; Cappel, Costa Mesa, Calif.), monoclonal anti-BrdU antibody (1:50; Becton-Dickinson, Franklin Lakes, N.J.). All the fluorescence-conjugated secondary antibodies were from Jackson Immunoresearch Laboratory (Westgrove, Pa.) and were used at 1:200 dilution.

Immuno-fluorescently labeled samples were also counter-stained with DAPI as described previously (Lin and Spradling, 1993). Micrographs were taken using either a Zeiss AXIOPLAN® microscope or a Zeiss LSM410™ confocal microscope (Zeiss, Oberkochen, Germany) as described herein above. BrdU labeling was performed essentially as described in Gonczy and DiNardo (1996). Briefly, on day 3 of the heat shock regime, ep(2)1024; hsGAL4 females were transferred to an Eppendorf tube that was held horizontally and contained 100 μl of 100 mM BrdU in grape juice. The flies were fed (pulse) with BrdU for 1 hour at room temperature. After the pulse, flies were returned to fresh vials without BrdU for 12 hours at room temperature (chase). These females were subsequently dissected and fixed for immunofluorescence labeling with anti-BrdU and anti-α-spectrin antibodies.

Construction of transgenes encoding N- and C-terminal-tagged PIWI proteins. Synthetic oligonucleotides (Gibco BRL) encoding a myc-epitope were cloned into unique sites at the N- and C-terminus of the piwi ORF in a 6.8 kb piwi genomic construct (pRc12) that fully rescues the piwi activity (Examples 1–4 above and Cox et al., 1998) as follows: For the N-terminal myc insertion, the following primers were used: Bcl/myc: 5'-GAT CAT ATG GAG CAA AAG CTT ATT AGC GAG GAA GAT CTG AAT-3' (SEQ ID NO:7) and Bcl/antisense myc: 5'-GAT CAT TCA GAT CTT CCT CGC TAA TAA GCT TTT GCT CCA TAT-3' (SEQ ID NO:8). The primers were annealed according to the manufacturer's recommendations and cloned into a unique BclI recognition site in a Bluescript clone containing piwi genomic DNA.

The resulting recombinant myc-piwi gene was cloned into pCasper 4 (Pirrotta, 1988) to produce the plasmid pPMB1–6 in which the myc sequence is inserted between PIWI amino acid residues 3 and 4. For the C-terminal myc insertion, the following primers were used: Nhe/myc: 5'-CTA GCA TAT GAG CAA AAG CTT ATT AGC GAG GAA GAT CTG AAT AAG-3' (SEQ ID NO:9) and Nhe/antisense myc: 5'-CTA GCT TAT TCA GAT CTT CCT CGC TAA TAA GCT TTT GCT CAT ATG-3' (SEQ ID NO:10). Primers were annealed as described above and cloned into a unique NheI recognition site in a Bluescript clone containing part of piwi genomic DNA. The recombinant insert was cloned into pCasper 4 (Pirrotta, 1988) to produce the plasmid pPMN in which myc is inserted between PIWI amino acid residues 795 and 796. The insertions were confirmed by DNA sequencing.

P-element mediated germline transformation. Transgenic flies were produced according to Spradling and Rubin, 1982, using w; 2–3 Sb e/TM6 e (Robertson et al., 1988) embryos as recipients. Eight independent pPMB 1–6 lines and twelve independent pPMN lines were recovered. The myc-tagged transgenes were then separated from the 2–3 transposase and introduced into the homozygous piwi background forfertilitytests by genetic crosses. Rescue crosses were carried out at 25° C. Each transgene was further tested for Myc expression by whole-mount immunofluorescence.

Immunoblotting analysis and in vitro translation. To prepare total protein extracts from pPMB 1–6 transgenic flies, ovaries were dissected in 1×EBR (130 mM NaCl; 5 mM KCl; 2 mM $CaCl_2$; 10 mM Hepes pH 6.9) and homogenized in 1×sample buffer (5% 2-mercaptoethanol, 3% SDS, 10% glycerol, 62.5 mM TrisCl pH 6.8, 0.1% bromophenol blue). Protein samples were boiled 5 minutes at 95° C. and then loaded on 10% SDS-PAGE gels. After electrophoresis, gels were electro-transferred to Genescreen (NEN Research Products, DuPont, Wilmington, Del.) in a TRANS-BLOT® apparatus (Bio-Rad Laboratories, Inc., Hercules, Calif.). Blots were blocked for 1 hour in Blotto (5% non-fat dry milk in 1×PBS) and primary antibodies were subsequently diluted in Blotto followed by an incubation overnight at 4° C. The monoclonal 9E10 anti-myc antibody (Evan et al., (1985)) was used at a dilution of 1:50. HRP-conjugated anti-mouse IgG secondary antibody (Jackson Immunoresearch Laboratory, Westgrove, Pa.) was used at 1:4000. Blots were washed and processed for detection using enhanced chemi-luminescent (ECL) reagents as recommended by the manufacturer (Amersham, Buckinghamshire, England). In vitro translation analysis was performed on the plasmid pDC2 to produce $^{35}$S-labeled PIWI protein according to the manufacturer's recommendations (Promega, Madison, Wis.). The translation products were separated on a 10% SDS-PAGE gel and images were collected by exposing the gel to X-ray film.

Quantitation of germline stem cell division rate. Relative division rate of piwi GSCs was determined as follows: The number of marked piwi⁻ cysts in 30 germaria was counted to obtain the average number of the piwi⁻ cysts per germarium. This number is then divided by the average number of marked wild-type cysts per germarium as obtained from counting 20 germaria. The relative division rate of GSCs in the piwi-overexpressing germaria and that in the wild-type and un-induced ep(2)1024 control germaria was determined by counting the frequency of telophase spectrosomes contacting the cap cells in the 2–3 GSCs in the most apical region of the germarium.

Results

PIWI is a nuclear protein present in both the soma and germline in both sexes. Examples 1–4 above demonstrate that piwi encodes a 97.2 kDa novel protein required for the self-renewing division of GSCs in both males and females. To elucidate further the function of piwi in regulating GSC division, the expression and subcellular behavior of the PIWI protein was studied in vivo. The PIWI protein was tagged by inserting a sequence encoding a myc epitope (Evan et al., (1985)) into the piwi gene, at the 5' end of the piwi open reading frame (FIG. 2). The p[5'-myc-piwi]

transgene (denoted as myc-piwi) was introduced into Drosophila via P-element mediated germline transformation (Spradling and Rubin, (1982)). myc-piwi fully restores the fertility and gametogenesis of piwi¹ mutant males and females (Table 4). Thus, the myc-PIWI protein confers wild-type PIWI function. In contrast, a p[piwi-3'-myc] transgene (denoted as piwi-myc) with the myc sequence inserted in the highly conserved C-terminal region (FIG. 7) fails to rescue any piwi mutant phenotype (Table 4). The PIWI-myc protein was not detectable either by Western blotting analysis or by immunostaining of the transgenic ovaries (Table 4), indicating that this region is essential at least for the stability of the PIWI protein.

TABLE 4

Rescue of the piwi¹ phenotype and myc expression by myc-PIWI and PIWI-myc¹

| | # of independent transgenic lines | Staining for myc | rescue of piwi¹ fertility² | | | | | |
|---|---|---|---|---|---|---|---|---|
| | | | female | | | male | | |
| | | | piwi¹ | myc;piwi¹ | piwi¹/CyO | piwi¹ | myc;piwi¹ | piwi¹/CyO |
| myc-PIWI | 8 | 100% (8) | 0 | 34.9 ± 6.8 | 30.9 ± 8.7 | 0 | 49.8 ± 6.7 | 49.8 ± 0.6 |
| PIWI-myc | 12 | 0% (7) | 0 | 0 | 30.9 ± 8.7 | 0 | 0 | 49.8 ± 0.6 |

1- The number of independent transformant lines tested for myc staining and for fertility is indicated in parentheses.
2- The fertility rescue is measured by counting the number of F1 adult eclosed from the tester or control parents. The data presented in the table is a summarized from three independent transgenic lines of myc-PIWI and two independent transgenic lines of PIWI-myc. piwi¹ denotes homozygous piwi¹, myc;piwi¹ denotes either myc-piwi;piwi¹/piwi¹ or piwi-myc; piwi¹/piwi¹ transgenic lines. Homozygous piwi¹ females not only show zero fertility as indicated, but also fail to lay eggs. The small number of eggs produced by these females are retained in the ovary and eventually undergo atrophy.

The expression of myc-PIWI was confirmed by immunoblot analysis using a monoclonal anti-myc antibody as a probe, which reveals a single 97.5 kDa band in the ovarian extract of myc-piwiflies. This agrees well with both the 97.2 kDa predicted size of PIWI and the 97.1 kDa observed size of PIWI when a full-length piwi cDNA was translated in vitro. Furthermore, eight independent myc-piwi transgenic lines share the identical subcellular localization pattern throughout gametogenesis. Thus, the myc-PIWI protein reflects the function and distribution of endogenous PIWI.

The expression and localization pattern of myc-PIWI during gametogenesis was also examined by immunofluorescence microscopy. Whole mount ovaries and testes isolated from wild-type flies carrying a myc-piwi transgene were stained with the anti-myc antibody to visualize myc-PIWI; this antibody did not detect any signal above the background in ovaries and testes from siblings without myc-piwi. The samples were also stained with anti-VASA antibody to highlight germ cells and DAPI to label nuclear DNA. In the third instar larval ovary, where GSCs begin their asymmetric divisions, myc-PIWI was found in the nucleus of all germ cells of the ovary. In addition, myc-PIWI was also present in the nuclei of the forming terminal filament cells. In adult ovaries, myc-PIWI is present in the nuclei of both the somatic and germline cells, as predicted by piwi RNA in situ analyses described in Examples 1–4. Specifically, in the germarium, myc-PIWI is expressed in all the somatic cells, including the main terminal filament cells, the cap cells and the inner sheath cells, consistent with the genetic clonal analyses presented herein above which indicated that piwi is required in these cells to maintain GSCs. PIWI is also expressed in somatic stem cells and the follicle cells in the germarium.

In the germline, myc-PIWI shows a dynamic nuclear expression pattern: it is present abundantly in GSCs, but is down-regulated in cystoblasts and developing cysts. In 16-cell cysts in regions 2 and 3, the myc-PIWI regains its high level expression, and remains so in nurse cells and oocytes in post-germarial egg chambers throughout oogenesis. This expression is consistent with the clonal and RNA in situ analyses presented herein above which indicate that PIWI is also loaded in eggs as a maternal component essential for embryogenesis. In all post-germarial egg chambers, myc-PIWI is also specifically expressed in the anterior polar follicle cells. The consistent nuclear localization of myc-PIWI in various types of somatic and germline cells during oogenesis indicates that PIWI is a nuclear protein.

Therefore, PIWI is a nuclear protein present in the soma and germline of both sexes. In the third instar larval ovaries, PIWI is present in the nucleus of all germline cells (GSC) as well as in forming terminal filament cells (TFC) as revealed by myc-PIWI in red and by VASA, a germline-specific marker, in green. PIWI is expressed in a dynamic pattern in the adult germarium (Ge), while being weakly expressed in main terminal filament cells and strongly expressed in cap cells (CpC). In the soma, PIWI is strongly expressed in the cap cells, inner sheath cells (ISC), somatic stem cells (SSC), and follicle cells (FC). In the germline, PIWI is expressed in germine stem cells (GSC) and is downregulated in cystoblasts (Cb) and early mitotic cysts. PIWI regains its high level expression in differentiating 16-cell cysts (DC) in regions 2b and 3.

In post-germarial egg chambers, PIWI is expressed strongly in all nurse cell nuclei (NCN) as well as in the nucleus (germinal vesicle, GV) of the developing oocyte. In the somatic follicle cell layer around each egg chamber, PIWI is expressed in anterior polar follicle cells (APC). The sharp down regulation of PIWI in cystoblast is also evident in the germarium, in which the three PIWI-bright small nuclei at the germarial apex are cap cell nuclei. The two larger nuclei in the next layer are GSC nuclei. Other small PIWI-bright nuclei in region 1 are inner sheath nuclei. The PIWI-negative region starts with a cystoblast positioned in the third layer.

In the third instar larval testis, PIWI, is present in the nuclei of both somatic and germline cells. In the soma, PIWI is expressed in the nuclei of hub cells (Hub) apical to GSCs and in cyst progenitor cells (CPC). In the germline, PIWI is present in the nuclei of GSCs and their immediate daughters. The apical region of the adult testis shows the same apical-distal organization as the third instar larval testis. PIWI expression pattern in the adult testis is identical to that in the third instar larval testis. PIWI is expressed in hub cells, GSC, and CPC. Ovaries from sibling females which do not carry the myc-piwi transgene show no specific staining with the anti-Myc antibody.

PIWI is also expressed as a nuclear protein during spermatogenesis. In the third instar larval testes which contain mostly premeiotic germ cells, myc-PIWI is localized to the nuclei of apical somatic cells, including the hub cells, which are the testicular equivalent of terminal filament cells. myc-PIWI is also present in somatic stem cells and their progeny, the cyst progenitor. At the apical germline, PIWI is present in the nuclei of GSCs and their immediate daughter cells. In newly formed 16-cell cysts of primary spermatocytes somewhat away from the apex, the myc-PIWI staining is sharply reduced in the germline. The staining is only present in the cyst progenitor cells, which are equivalent to follicle cells in the ovary. Once the developing cyst enters the spermatocyte growth phase, myc-PIWI expression is completely undetectable. This pattern of expression is maintained in the adult testis which displays the same apical-distal organization but now contains more differentiated post-meiotic germ cells in the basal region of the testis. Given the role of piwi in testicular germline stem cell maintenance described herein above, the nuclear localization of PIWI in the testis is envisioned to be of functional importance.

PIWI is localized in the nucleoplasm. To further investigate the role of PIWI in the nucleus, the subnuclear localization of the myc-PIWI protein was examined. In interphase GSCs, myc-PIWI is present in subnuclear areas where DNA staining is the weakest. The myc-PIWI staining appears as numerous bright foci in DNA-deficient areas that are sometimes connected into a network, complementing the DNA staining pattern. The DNA-bright area is completely devoid of myc-PIWI. In interphase cap cells, myc-PIWI shows a similar staining pattern. This staining pattern suggests that, in interphase somatic and germline nuclei, myc-PIWI is not associated with the chromatin or the nuclear envelope, but is localized in the nucleoplasm.

The nucleoplasmic localization of myc-PIWI is even more evident during GSC division. At metaphase, myc-PIWI is not associated with mitotic chromosomes or the nuclear envelope area, but becomes scattered throughout the cytoplasm, forming concentrated foci at the cell cortex. The localization pattern remains so throughout anaphase. This dynamic localization pattern of myc-PIWI verifies that PIWI is not associated with chromosomes or the nuclear envelope, but is a nucleoplasmic factor that is dispersed into the cytoplasm during mitosis.

The myc-PIWI protein also shows clear nucleoplasmic localization in the nuclei of nurse cells, oocytes, and follicle cells in developing egg chambers. In nurse cell nuclei, myc-PIWI is accumulated in subnuclear areas devoid of DNA staining, complementing the DNA localization pattern. This complementary relationship is most clearly illustrated in the oocyte nucleus (germinal vesicle), in which chromatin forms a discrete subnuclear structure called the karyosome that occupies a spherical area in the nucleus (King, 1970). The myc-PIWI staining is not detectable in the karyosome, but is conspicuously present in the nucleoplasm that surrounds the karyosome. In follicle cells, myc-PIWI is also localized in the nucleoplasm in a punctate fashion. Thus, PIWI is a nucleoplasmic factor in all types of ovarian cells.

Therefore, PIWI is localized in the nucleoplasm. In the interphase germline stem cell nucleus, myc-PIWI mostly accumulates as bright foci in DNA-deficient areas within the nucleus. DNA-bright spots were observed to be are completely devoid of myc-PIWI. This complementary staining pattern is also observed in cap cells (CpC).

In metaphase and anaphase germline stem cells, the myc-PIWI staining is dispersed throughout the cytoplasm, forming numerous foci at the cortical region of the cell. In a stage 4 egg chamber (for staging, see King, 1970), myc-PIWI is accumulated in regions of nurse cell nuclei (NCN) and follicle cell nuclei (FCN) devoid of DNA staining. In the germinal vesicle (GV), the myc-PIWI staining is absent from the karyosome (K) but present in the nucleoplasm that surrounds it. The oocyte region of a stage 6 egg chamber showing the complementary myc-PIWI and DNA staining in the germinal vesicle (GV) and follicle cell nuclei (FCN). A magnified view of a nurse cell nuclei (NCN) in a stage 6 egg chamber, showing the largely non-overlapping staining pattern of myc-PIWI and DNA.

PIWI is cell-autonomously required in germline stem cells to promote their division. The above-presented clonal analyses indicated that piwi functions in the apical somatic cells of the germarium to regulate GSC maintenance. However, as PIWI is also present in the nuclei of GSCs, the function of PIWI in GSCs was evaluated by removing PIWI from a single stem cell using the FLP/FRT-mediated clonal technique (Xu and Rubin, 1993). piwi$^1$ and piwi$^2$ mutations were used for generating piwi$^-$ deficient clones because they are both strong mutations, as described in Examples 1–4. The piwi$^-$ stem cell clones were induced in piwi FRT/armlacZ FRT transheterozygous flies.

The armlacZ transgene (Lecuit and Cohen, 1997) is expressed in all somatic and germline cells in the germarium. piwi deficient clones created by a mitotic recombination no longer contain the armlacZ gene and can thus be identified by the absence of the lacZ protein. The control lacZ-negative piwi$^+$ germline clones were induced in piwi$^+$ FRT/armlacZ FRT transheterozygous flies for comparison. Since it takes four days for a cystoblast to develop into an egg chamber that buds off the germarium (Margolis and Spradling, (1995)), among piwi-deficient clones, only GSC clones can persist over more than five days (FIG. 5B). If no piwi$^-$ GSC is observed five days after induced mitotic recombination, this would clearly indicate the failure of piwi$^-$ stem cells to maintain themselves.

Because recombination events can only occur in mitotically active cells yet all somatic signaling cells are postmitotic, this approach allows the analysis of the cell-autonomous function of piwi in single GSCs without the complication of generating mutant clones in the signaling cells. However, even if any somatic clones are induced, they can be readily identified. Furthermore, by marking individual mutant and wild-type GSCs, the relative division rate and maintenance ability of each stem cell can be determined by counting the number of its cyst progeny within the germarium (also see Xie and Spradling, 1998). Finally, the cell-autonomous function of piwi in the germline can be assessed at all stages of oogenesis by examining the development of the individually marked piwi$^-$ germline cysts and egg chambers.

Mitotic recombination was induced immediately prior to oogenesis and looked for piwi$^-$ GSC clones one week, two weeks, and three weeks following oogenesis. piwi$^-$ GSCs were present even three weeks following oogenesis, consistent with the above-presented observation that PIWI in GSCs is not required for their maintenance.

The number of marked piwi$^-$ and piwi$^+$ germline cysts was then examined in tester and control germaria to compare the division rate between the piwi⁻ and piwi⁺ GSCs within the germarium. For accurate comparison, germaria that contain only two GSCs, one marked and one unmarked, were always examined. In wild-type control germaria, marked wild-type stem cells gave rise to approximately 50% of the cysts present within the germarium. This indicated that the lacZ-marked and unmarked wild-type stem cells divide at the same rate (FIG. 5). However, in tester germaria, the number of the marked piwi⁻ germline cysts is consistently only 25% of marked wild-type cysts (FIG. 5). This analysis reveals that piwi⁻ GSCs divided four-fold slower than wild-type GSCs. Thus, in addition to its somatic function, PIWI acts cell-autonomously in the stem cells to facilitate their division.

The piwi⁻ cysts and postgermarial piwi⁻ egg chambers were examined by DAPI staining and by Nomarski microscopy for potential developmental defects. They usually developed normally, suggesting that piwi does not play a cell-autonomous role in germline cyst development and subsequent stages of oogenesis.

Therefore, PIWI acts cell-autonomously in GSCs to promote their division. Germaria were labeled with anti-LacZ antibody for piwi⁺ cells and anti-1B1 antibody for spectrosomes and fusomes. Marked stem cells and cysts developed from piwi⁻ germline stem cells (GSCs) are recognized by the absence of lacZ expression. In a piwi⁻ lacZFRT/piwi⁺ lacZ⁺ FRT germarium in the absence of heat shock, no piwi⁻ lacZFRT/piwi⁻ lacZFRT clones were induced. GSCs are distinguished by the presence of the spectrosome (Sp) in direct contact with the terminal filament cells (TFC).

A piwi⁻ lacZFRT/piwi⁺ lacZ⁺ FRT germarium was stained one week after heat shock, and showed a wild-type GSC and a mutant GSC, as well as three piwi⁻ cysts derived from the mutant stem cell. The entire ovariole is enveloped by the epithetial sheath (ES), which is different from the inner sheath cells (IS). The graph of FIG. 5 displays the relative division rates of wild-type and piwi⁻ GSCs. The number of germaria counted is given in parentheses. Only germaria containing one marked and one unmarked GSC were examined.

Overexpression of PIWI increases the number of germline stem cells. Examples 1–4 above establish that the somatic expression of PIWI is essential for GSC maintenance. This somatic induction can be achieved via a threshold mechanism, in which a certain level of somatic PIWI activity is required to establish or maintain the stem cell identity, but a higher level of somatic PIWI expression will not increase the number of GSCs. Alternatively, the PIWI-mediated somatic induction could act via a dosage-dependent mechanism, in which the somatic level of PIWI dictates the number of GSCs.

To test these possibilities, PIWI was overexpressed in the somatic cells of the adult ovary via heat shock induction using hsp70-Gal4 (hsGal4) and ep(2)1024, an EP element inserted in the 5' UTR of the piwi locus. EP is a modified P element carrying an $UAS_t$ promoter oriented to transcribe the flanking genomic sequence upon the activation of the yeast Gal4 protein (Rorth, (1996)). Specifically, ep(2)1024 in the 5'UTR of piwi is oriented in the same direction of piwi transcription so that it can produce a piwi mRNA containing the complete PIWI open reading frame. The $UAS_t$ promoter is active in the soma but not in the germline (Rorth, 1998), and its somatic specificity was confirmed by examining the ovarian expression of the $UAS_t$-GFP reporter gene under experimental conditions. Because endogenous PIWI is expressed in all somatic cells in the germarium, by constructing a Drosophila strain that contains hsGal4 and ep(2) 1024, it was possible to over-express, but not ectopically express, piwi specifically in the somatic cells by heat shock induction.

To verify that ep(2)1024 can express a functional PIWI protein, ep(2)1024 was overexpressed by heat shocking hsGal4 in an ep(2)1024/piwi¹ mutant background. Because ep(2)1024 is a strong loss-of-function mutation of piwi, ep(2)1024/piwi¹; hsGal4 females and males in the absence of heat shock display typical piwi phenotype. In contrast, the same mutants, after receiving daily heat shock treatment from the second instar larvae to three days after eclosion, produced significantly restored fertility in both ep(2)1024/ piwi¹ females and males. The morphology of both the ovaioles and testes in the heatshocked mutants are indistinguishable from their wild-type siblings. In addition, the fertility of the rescued mutants is comparable to their wild-type siblings. Heatshock starting at the pupal stage does not rescue the fertility. Therefore, ep(2)1024 can produce a functional PIWI protein capable of rescuing the piwi mutant phenotype when expressed in somatic cells.

ep(2)1024 was then used to overexpress PIWI in wild-type adult females, and its effects on GSCs were analyzed. The females were heat-shocked at a 12-hour interval for three days and then dissected. The ovaries were stained with anti-VASA antibody (Hay et al., (1990)) to highlight germ cells and anti-1B1 antibody (Zaccai and Lipshitz, (1996)) to outline somatic cells as well as to label spectrosomes and fusomes that mark individual stages of germline development in the germarium (Lin and Spradling, (1995)). Wild-type germaria typically have 2–3 spectrosome-containing cells, with one often being a cystoblast that is not associated with the terminal filament. This is also the case for uninduced ep(2)1024/+ germaria. Interestingly, the number of the spectrosome-containing germ cells increased to an average of 7.5 cells per ep(2)1024/+ germarium following heat shock induction. In the most extreme case, up to 15 spectrosome-containing cells were observed in a single germarium. This increase is not due to the expression of hsGal4 alone, since ovaries from hsGal4 females subjected to the same heat shock regime were indistinguishable from wild-type. Thus, overexpression of PIWI in the soma leads to a 3–4 fold increase in the number of GSCs and/or cystoblasts.

Thus, the observation that EP(2)1024 expression rescues the piwi¹ mutant phenotype was shown via DAPI staining of the gonads from ep(2) 1024/piwi¹; hsGAL4 females and males either without or with heat shock. In the absence of the heat shock, the ovaries and testes display the typical piwi¹ mutant phenotype. Following hsGal4-induced over-expression of the ep(2)1024 in the soma, significant rescue of the mutant phenotype was observed in both females and males. Specifically, in females, germline stem cells are maintained and a string of developing egg chambers was observed. Similarly, in males, germline stem cells were also rescued, and spermatogenesis was fully restored.

To distinguish whether the spectrosome-containing cells are stem cells or cystoblasts, the germaria were stained with anti-cytoplasmic BAM (BAM-C) antibody, since BAM-C is only expressed in cystoblasts and early mitotic cysts but not in GSCs (McKearin and Ohlstein, (1995)). In piwi-overexpressed germaria, BAM-C staining is strongly present in early cysts. However, BAM-C staining is conspicuously absent from all the spectrosome-containing cells. This observation suggests that the ectopically induced spectrosome-containing cells are GSC-like cells.

The observation that somatic PIWI over-expression increases the number of germline stem cells was supported a confocal z-series analysis (10 μm stacks) of wild-type germarium immunofluorescently labeled with anti-1B1 antibody. At the apical tip of region 1 in direct contact with the terminal filament, two germline stem cells containing spectrosomes (Sp) were observed. Posterior to germline stem cells, developing germline cysts containing branched fusomes (Fu) were observed. A germarium from a ep(2)1024; hsGal4 female was observed to display many germline stem-like cells following 4 days of heat shock treatment, with 12 shown in this focal plan as indicated by spectrosomes (Sp; stained with anti-1B1 antibody) and the absence of the BAM-C protein. The stem-like cells were evenly distributed between regions 1 and 2a. The BAM-C protein was only present in a cyst containing a branched fusome in region 2a.

A germarium containing ectopic stem-like cells was stained with anti-BrdU and anti-a-spectrin antibodies following BrdU incorporation as described above in the Materials and Methods. Some mitotically active germline cells which have incorporated BrdU in their nuclei were observed. A fusome-containing germline cyst (Fu) was present in region 1 but not in contact with somatic cells. A germarium from an ep(2)1024; hsGal4 female subjected to 4 days of heat shock treatments followed by 4–5 days of culture at room temperature was also stained. The stainings indicated anti-VASA and anti-1B1 antibody signals, respectively. This germarium, like a typical wild-type germarium, contained two germline stem cells contacting the apical somatic cells and a cystoblast that is one cell away from the terminal filament. In addition, the number of fusome-containing cysts (Fu) have increased to a normal level.

Figure 10:
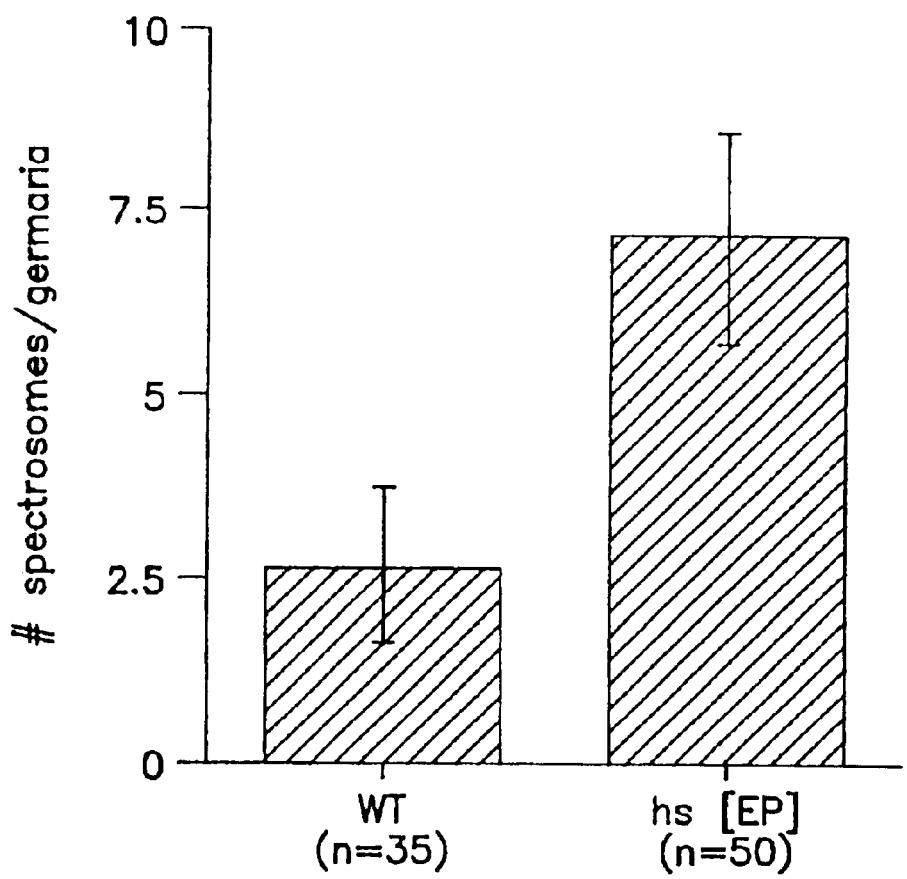
FIG. 10 is a graph displaying a comparison of the number of spectrosomes present per wild-type germarium versus per piwi-overexpressed germarium and demonstrating that somatic PIWI over-expression increases the number of germline stem cells. The number of germaria examined (n) is in parentheses.

FIG. 10 depicts a graphical comparison of the number of spectrosomes present per wild-type germarium versus perpiwi-overexpressed germarium. The number of germaria examined (n) is in parentheses. All germaria are oriented with anterior toward the left.

The ectopic GSC-like cells appear to be functional GSCs. First, they incorporate BrdU, an indicator of DNA replication, at a level similar to the wild-type GSCs. This suggests that they are not arrested in the cell cycle. Second, these GSC-like cells can all differentiate within four days following the withdrawal of heat shock; leaving the germaria with only 2–3 GSCs at their normal locale. No signs of cell death, such as pycnotic nuclei or apoptotic bodies, were detected by DAPI staining and Nomarski optics. This suggests that the GSC-like cells are capable of oogenesis. Thus, the dependence of GSC number on the PIWI level reveals that piwi-mediated somatic signaling controls the number of GSCs via a dosage dependent mechanism.

The ectopically induced GSCs show an even distribution pattern along the germarial axis. In wild-type germaria, spectrosome-containing cells are exclusively located in the apical area of region 1, either in direct contact with or one-cell away from the terminal filament (for stem cells and cystoblasts, respectively). However, following PIWI overexpression, spectrosome-containing cells were evenly expanded along the somatic germarial wall to both regions 1 and 2a. All the spectrosome-containing cells are in apparent contact with the somatic cells; there is no apparent gradient of the stem-like cell distribution towards the terminal filament. In wild-type germaria, inner sheath cells express as much PIWI as cap cells, and much more than the main terminal filament cells, yet there are no GSCs located near them in posterior region 1 or region 2a. Therefore, the appearance of the ectopic stem-like cells in the entire regions 1 and 2a following piwi-overexpression suggests that a very high level of PIWI in the inner sheath cells expands the stem cell domain to region 2.

Over-expression of PIWI increases the rate of germline stem cell division. Since over-expression of piwi in somatic cells increases the number of GSCs, yet loss of piwi function from the soma and germline in piwi mutants abolishes stem cell division and thus their maintenance, one might expect that over-expression of piwi in the soma may also increase the rate of GSC division. To address this possibility, the mitotic index of GSCs in piwi-overexpressed females was directly quantified. GSC division is unique in that it has an unusually long telophase-to-interphase period characterized by the presence of a dumb bell-shaped telophase spectrosome spanning the two daughter cells. Deng and Lin, (1997); de Cuevas and Spradling, (1998). The morphologically distinctive telophase spectrosome provides an easy marker for the accurate measurement of the telophase/early interphase index, which is a direct quantitation of the frequency of GSC division.

To avoid a bias in quantifying the division frequency due to the presence of an increased number of GSC-like cells in piwi-overexpressed germaria, the 2–3 anterior-most GSCs that contact the terminal filament were quantified, and the same number of stem cells in the wild-type and uninduced ep(2)1024 controls were quantified. In the wild-type and uninduced ep(2)1024 controls, 20–25% of germaria contained a single GSC with a telophase spectrosome; only 2–3% of germaria contained two GSCs with telophase spectrosomes. These frequencies are increased to 31% and 13% in piwi-overexpressed germaria. Moreover, 3% of the piwi-overexpressed germaria contain three GSCs with a telophase spectrosome, a situation that was not observed in the control germaria. These results indicate that in addition to an increase in the number of stem cells, piwi overexpression also increases the rate of GSC division. Because the GSCs under examination are located in their normal niche, the increase in their mitotic frequency should be mostly, if not all, due to the increased PIWI expression in the terminal filament.

Four micrographic panels of anti-1B1 images of germaria containing 0, 1, 2, and 3 telophase spectrosome-containing germline stem cells were prepared and examined. The frequency of observing such germaria in the wild-type control, the uninduced ep(2)1024 control, and the piwi-overexpressed germaria is presented in Table 5. The number of germaria counted for each genotype (n) is given in parentheses.

TABLE 5

| | Percentage (%) of GSC in Telophase | | |
|---|---|---|---|
| Telophase GSCs | W.T. (n = 100) | EP (−) HS (n = 100) | EP (+) HS (n = 100) |
| 0 | 73 | 77 | 53 |
| 1 | 25 | 20 | 31 |
| 2 | 2 | 3 | 13 |
| 3 | 0 | 0 | 0 |

Discussion

Stem cells are characterized by two common properties: the capacity for self-renewal and the ability to propagate numerous progeny fated for further differentiation (for review, see Morrison et al., 1997; Lin, 1997). The unique self-renewing division of stem cells is controlled by both intracellular and extrinsic signaling mechanisms (Knoblich, 1997; Lin, 1997). Example 5 shows that piwi encodes a novel nucleoplasmic protein present in both somatic and germline cells of both sexes. Moreover, the single stem cell clonal analyses and piwi overexpression experiments establish the important function of piwi in both the intracellular and the cell—cell signaling mechanisms. Example 5 thus reveals a novel nuclear factor whose activity modulates the number of GSCs and the rate of their division.

The role of PIWI as a nucleoplasmic factor in somatic signaling. The immunofluorescence analysis of the fully functional myc-PIWI protein reveals that PIWI is a nucleoplasmic protein. Consistent with RNA in situ analyses, PIWI is present in both the soma and the germline during oogenesis. In Example 5 the cell-autonomous function of PIWI as a mitotic promoter in GSCs is revealed. PIWI is localized in the nucleoplasm in both the apical somatic cells and GSCs. Hence, the nucleoplasm is the likely site of PIWI function, and in accordance with one aspect of the present invention, PIWI is the first nucleoplasmic factor known to play a key role in controlling GSC division.

As a nucleoplasmic factor in the apical somatic cells, PIWI is expressed in three types of post-mitotic cells that form a somatic cap surrounding GSCs and their immediate daughter cells: the main terminal filament cells, the cap cells, and the inner sheath cells. Among these cell types, the main terminal filament cells express a very low level of PIWI while cap cells and inner sheath cells express a very high level of PIWI. Since cap cells are in direct contact with GSCs, it is envisioned that PIWI expression in cap cells plays a role in somatic signaling.

Since PIWI is a nucleoplasmic protein, it is unlikely a somatic signal itself, but rather an essential component of the somatic signaling machinery responsible for producing the signal. Given its nucleoplasmic localization, PIWI might be involved in post-transcriptional mRNA processing in the nucleus or in nuclear functions indirectly related to gene expression. In either case, the somatic activity of PIWI acts via a dosage dependent mechanism to control the number of GSCs in the germline. Therefore, piwi can help to define a stem cell niche in the germarium for GSC maintenance, with the size of the niche corresponding to the level of PIWI activity.

A number of genes, including fs(1)Yb (King and Lin, 1999) and dpp (Xie and Spradling, 1998), have recently been shown to play roles in the cell—cell signaling mechanism in maintaining GSCs. Among these genes, dpp is the only known signaling molecule. DPP over-expression dramatically expands the number of GSCs and prevents their differentiation, leading to tumorous germaria filled with undifferentiated GSC-like cells (Xie and Spradling, 1998). This overexpression phenotype, in sharp contrast to that of piwi, suggests that DPP is not the downstream signal of the piwi-mediated mechanism, even though it may be one of the signals. fs(1)Yb, on the other hand, shares a very similar loss-of-function phenotype with piwi. These two genes are more likely to be involved in the same somatic signaling pathway.

The role of PIWI as a nucleoplasmic factor in germline stem cells. PIWI is expressed dynamically in the germline of the germarium. In region 1, PIWI is present in the nucleus of GSCs at a high level but is sharply down regulated in cystoblasts and early mitotic cysts. This expression pattern correlates well with the mitosis-promoting function of PIWI in GSCs as revealed by single stem cell clonal analysis. The differential distribution of proteins between the stem cell and the cystoblast has also been observed for several other factors known to be important for GSC division or differentiation. For example, PUM is required for GSC mainte-nance (Lin and Spradling, 1997; Forbes and Lehmann, 1998) and is accumulated at a high level in GSCs but a low level in the cystoblasts (Forbes and Lehmann, 1998; Parisi and Lin, 1999). On the other hand, NOS and BAM-C are required for cystoblast development and are localized either preferentially or exclusively in the cystoblast.

All of these molecules, except for BAM-C, are known to play important roles in other developmental processes (Cox et al., 1998; Parisi and Lin, 1999). For example, the germline expression of PIWI during oogenesis also provides PIWI as a maternal component essential for embryogenesis (Cox et al., 1998). Therefore, the asymmetric fates between GSCs and cystoblasts might not be determined by unique "stem cell factors" or "cystoblast factors". It, instead, may be created by unique combinations of various regulatory molecules that are repeatedly used throughout development.

This pleiotropic function of stem cell genes is also manifested within the stem cell mechanisms, in which piwi is involved in both somatic signaling and in cell-autonomous mitotic functions. piwi thus acts in two distinct cell types and in two different mechanisms. Although applicant does not desire to be bound by any particular mechanism of action, it is contemplated that the PIWI protein directly or indirectly mediates gene expression in the nucleus either at the transcriptional or post-transcriptional level. The different piwi target genes or their products in different cell types then lead to the distinctively different cellular function of piwi.

Example 6

PIWI is a Pole Plasm Component Required for Pole Cell Formation, Migration and Transcriptional Quiescence This Example shows that PIWI is also a maternally deposited polar granule component that plays a key role in pole cell formation, migration, and transcriptional quiescence. However, unlike most other genes known to be required for pole cell formation, piwi is specifically required for pole cell formation with no effect on abdominal patterning. PIWI is dynamically expressed during germ plasm assembly and pole cell formation. The protein is first expressed in polar granules at the posterior end of the embryo and is subsequently expressed in the nuclei of all primordial germ cells throughout embryogenesis. Furthermore, the piwi gene product directs germ plasm assembly and controls the number of pole cells formed at the posterior pole of the Drosophila embryo. These results indicate that piwi has many of the properties of a germ cell-specific determinant.

Materials and Methods

Drosophila strains and culture. All strains were grown at 25° C. on yeast-containing molasses/agar medium. The following fly strains were used in this study: w; piwi$^1$, FRT$^{40A}$/CyO and w; piwi$^2$, FRT$^{40A}$/CyO (as disclosed in Examples 1–4) were used to generate maternal clones; y, w P[hsFLP]$^{12}$; P[ovo$^{D1}$]$^{2L}$, FRT$^{40A}$/CyO (Chou and Perrimon, 1996); P[myc-PIWI] insertions on the second and X chromosomes were used to increase the piwi copy number as well as to visualize PIWI protein expression; 4×oskar flies bear two wild-type copies of oskar on the third chromosome and two transgenic rescue copies of oskaron the second chromosome (Ephrussi and Lehmann, 1992. OregonR (Ore-R) serves as the wild-type control in all experiments.

Immunohistochemistry. Ovaries were dissected, fixed and stained as described in Lin et al., 1994. Embryos were collected, fixed and stained according procedure described by Patel et al. (1989). For immunofluorescence staining the following antisera were used: polyclonal anti-VASA antibody (1:2000; Hay et al., 1990); monoclonal anti-MYC epitope antibody (1:50; Evan et al., 1985); monoclonal anti-SXL antibody (1:500; Bopp et a/., 1991). All the fluorescence-conjugated secondary antibodies were from Jackson Immunoresearch Laboratory, Westgrove, Pa. and were used at 1:200 dilution. Immunofluorescently labeled samples were also counterstained with DAPI as described previously (Lin and Spradling, 1993). Micrographs were taken using either a Zeiss AXIOPLAN® microscope or a Zeiss LSM410™ confocal microscope (Zeiss, Oberkochen, Germany) as described herein above.

Maternal clones. To generate embryos maternally depleted for piwi the following fly strains were crossed: y, w P[hsFLP]$^{12}$; P[ovo$^{D1}$]$^{2L}$, FRT$^{40A}$/CyO males were crossed to w; piwi$^{1}$, FRT$^{40A}$/CyO virgin females to produce y, w P[hSFLP]$^{12}$; P[ovo$^{D1}$]$^{2L}$, FRT$^{40A}$/piwi$^{1}$, FRT$^{40A}$ progeny. Identical crosses were performed with w; piwi$^{2}$, FRT$^{40A}$/CyO virgin females. Crosses were carried out for two days to produce transheterozygous progeny. After 2 days, adults were transferred to fresh vials. Larvae were heat shocked on days 3 and 4 for one hour in a 37° C. water bath to induce mitotic recombination. The heat-shocked females with germline clones were crossed to Ore-R males or to piwi$^{2}$ mutant males. Embryos collected from these females were subsequently analyzed by immunofluorescence microscopy. Due to the presence of a copy of the ovo$^{D1}$ gene in these females, only piwi$^{-}$ germline clones can give rise to a mature egg.

Pole cell formation is dosage-dependent for piwi. Single copy embryos are from piwi$^{1}$/CyO females and two copy embryos for both piwi and oskar are from Ore-R females. For the four-copy piwi embryos, a P[myc-PIWI] rescue transgene was homozygoused on a wild-type second chromosome; two such lines were examined for their effects on embryonic development. For the four-copy osk embryos, an osk rescue transgene was homozygoused on the second chromosome of an otherwise wild-type fly as described by Ephrussi and Lehmann, 1992. For the six-copy piwi embryos, P[myc-PIWI] transgenes on the X chromosome and second chromosome were homozygoused to generate four transgenic copies in addition to the two wild-type copies on the second chromosome. For maternally depleted embryos, germline clones were produced as described above. Embryos from females carrying germline clones were collected and analyzed to examine the role of piwi in germline development. For pole cell counts, all embryos were stained with anti-VASA antibody and the pole cells of 50 embryos of each maternal genotype, described above, were counted in triplicate for each embryo. The pole cell count reflects the initial number of pole cells present shortly after budding at the posterior pole and prior to any amplification or migration. Embryo staging was performed as described in Zalokar and Erk (1976) according to the number of nuclei present.

Results

PIWI encodes a polar granule component with a dynamic behavior during pole cell formation. As disclosed above, piwi is maternally required for embryogenesis. To examine piwi function in embryogenesis, PIWI protein expression in embryos was analyzed using a myc-tagged piwi transgene. Embryos were collected from females carrying a P[myc-PIWI] transgene and subsequently stained these embryos with antibodies against MYC to visualize P[myc-PIWI] protein expression and VASA, a polar granule component and pole cell-specific marker. Embryos were counterstained with DAPI to visualize nuclei and allow a stage-specific analysis of PIWI expression during embryogenesis (Zalokar and Erk, 1976).

PIWI is first expressed in a crescent at the posterior pole of the embryo during mitotic cycles 1–7, where it is co-localized with VASA during these cycles, including localization to polar granules of which VASA is a component. Thus, piwi encodes a polar granule component. During mitotic cycles 8–10, PIWI is dynamically expressed in the forming pole cells. At this stage in embryogenesis, nuclei have migrated from the center of the embryo and some of them enter the posterior pole plasm. These posterior nuclei become the first to cellularize as they bud off from the embryo to form pole cells. At the onset of pole cell formation, during mitotic cycles 8 and 9, PIWI is expressed cytoplasmically in an overlapping pattern with VASA in polar buds. However, at mitotic cycle 10 when pole cell formation and budding is complete PIWI completely translocates to the nucleus of all pole cells. PIWI is also zygotically expressed in somatic cells at the stage. PIWI remains nuclear in pole cells throughout germ cell migration and finally gonad coalescence.

Maternal PIWI is required for pole cell formation. To analyze the potential requirement of piwi in embryogenesis embryos maternally depleted for piwi were generated. Females with piwi$^{1}$ germline stem cell clones were crossed to wild-type males and embryos from these females were collected. To assay germline formation and development, germ cells were visualized by staining with an anti-VASA antibody. In the absence of maternal piwi product, a dramatic reduction in the number of pole cells formed was observed. Maternally depleted piwi embryos contain on average 7.5±5 pole cells at mitotic cycle 10, the pole cell formation stage, in contrast to the 24±5 pole cells formed in wild-type embryos at the same stage. These results indicate that maternal piwi is required for pole cell formation as a wild-type paternal copy of piwi$^{+}$ is insufficient to rescue the pole cell formation defect.

Following pole cell formation there are typically one to two amplificatory mitoses in the pole cell population such that 30–40 pole cells are present prior to germ cell migration. There is no additional amplification of the pole cell population once germ cell migration has commenced (Williamson and Lehmann, 1996). To determine whether piwi is required for the amplification of the pole cell population, embryos lacking maternal piwi for the number of pole cells present before germ cell migration and after gonad coalescence were examined. There is no amplification of germ cells in the absence of maternal piwi; rather, a small decrease in the average number of germ cells present at gonad coalescence was observed. Prior to germ cell migration piwi$^{-}$ embryos contained 7.5±5 germ cells, however at germline coalescence the average number of germ cells dropped to 4.5±3 germ cells. Thus, in addition to its requirement for pole cell formation, maternally deposited piwi also plays a role pole cell amplification and survival.

The maternal effect of piwi on pole cell formation is similar to that observed with the posterior group genes which are also required for pole plasm assembly and pole cell formation. To examine whether maternally depleted piwi embryos have any abdominal defects, Nomarski optics were used to examine the segmentation pattern of these embryos. There is no readily apparent defect in abdominal patterning. Thus, in contrast to the posterior group genes, piwi does not appear to be required for proper abdominal patterning of the embryo.

Maternal PIWI is required for pole cell migration. To analyze the effect of removing maternal piwi function on germ cell migration, embryos from females bearing piwi mutant germline stem cell clones were collected and stained for the germ cell specific marker VASA. In addition to its role for proper pole cell formation and proliferation, piwi activity also plays a role in successful germ cell migration. During pole cell migration in wild-type embryos, germ cells exit the posterior midgut and then actively migrate through the endoderm along its basal surface until making contact with the overlying mesodermal cells (Warrior, 1994). At late stage 10 to early stage 11 (for staging, see Zalokar and Erk, 1976), germ cells transfer from the endoderm into the mesoderm where they will associate with somatic gonadal precursor cells which give rise to the gonadal mesoderm. Finally, at stage 14 of embryogenesis, germ cells coalesce with somatic gonadal precursors in parasegment 10 to establish the primordial gonad.

However, in embryos lacking maternal PIWI, defects in germ cell migration are seen from stage 10 onwards which marks the active phase of germ cell migration. As germ cells exit from the posterior midgut pocket, they fail to undergo directional migration over the surface of the endoderm. Rather, they are found migrating in a random fashion to many different sites within the embryo. In some cases highly aberrant germ cell migration into the anterior end of the embryo was observed. The random patterns of germ cell migration in these mutant embryos indicates a requirement for maternal PIWI in germ cell guidance. In addition to the defect in germ cell migration, defects in overall pole cell morphology were observed. In contrast to wild-type pole cells, pole cells maternally depleted of piwi are of variable size and shape and display unusual blebbing and aberrant pseudopodia. This indicates that maternal piwi also plays a role in proper pole cell morphology which might be essential for proper pole cell migration.

Previously, it has been demonstrated that signals produced by surrounding somatic tissues act to guide germ cells by both attractive and repulsive forces (Jaglarz and Howard, 1994; 1995; Zhang et al., 1997; Van Doren et al., 1998). However, few genes have been identified that control germ cell migration and are expressed in germ cells themselves. The expression of piwi in pole cells during migration suggests that piwi function is cell-autonomous. This is similar to nanos and pgc-1 both of which are expressed in germ cells and are required for normal germ cell migration (Forbes and Lehmann, 1998; Kobayashi et al., 1996). These data indicate that germ cell migration is controlled by both instructive signaling mechanisms as well as by cell-autonomous mechanisms within migrating germ cells.

Maternal PIWI plays a role in the transcriptional quiescence of pole cells. Transcriptional repression in germ cells has been implicated as a key mechanism in the establishment and maintenance of the germ cell fate (for review, see Seydoux and Strome, 1999). In Drosophila, zygotic transcription in the soma is detectable as early as one hour after egg laying (AEL; Pritchard and Schubiger, 1996). In the germline, however, general RNA synthesis is not detected until 3.5 hours AEL at embryonic stage 8 (Zalokar, 1976) and poly (A) containing mRNA transcripts are not observed in early germ cell nuclei (Lamb and Laird, 1976). Few genes have been shown to be specifically transcribed in pole cells and among the known genes, vasa is the earliest gene at embryonic stage 9–10 (Hay et al., 1988b). Transcription of all other genes to be expressed in pole cells is not observed until the primordial gonad reinitiates proliferation at embryonic stage 16–18 (Mevel-Ninio et al., 1995). Transcription is reinitiated in pole cells just before they migrate through the midgut epithelium approximately 3.5 hours AEL (Zalokar, 1976).

To analyze the potential role of piwi in the regulation of transcriptional quiescence in early germ cells, embryos maternally depleted of piwi were double-labeled with VASA, a germ cell specific marker, and SXL, a somatic sex-specific marker which is normally absent in pole cells. Ectopic expression of SXL protein in pole cells prior to embryonic stage 9 was observed. This indicates that the mechanism which normally maintains transcriptional quiescence in pole cells is dependent on proper piwi function.

piwi Dose Determines the Initial Number of Pole Cells. Given the critical role of piwi in pole cell formation and development, the role of piwi in germ plasm assembly was further evaluated by examining the relationship between piwi gene dosage and the number of pole cells formed, which is also a reflection of the amount of pole plasm formed at the posterior end of the egg. The piwi copy number was increased in females from one to four and collected embryos from these females to examine the number of pole cells formed. In identically staged samples, embryos with one or two copies of the piwi gene contained on average 24±5 pole cells. However, a two-fold increase in piwi gene dosage over wild-type levels yields embryos containing on average 50±7 pole cells at the same developmental stage. This phenotype is strikingly similar to the phenotype displayed when oskar gene dosage is increased from one to four copies (Ephrussi and Lehmann, 1992). Like oskar, a two-fold increase in piwi gene dosage leads to an increase in both the amounts of known pole plasm components, such as VASA, at the posterior pole of the embryo and the number of pole cells formed. However, in contrast to oskar, increasing piwi gene dosage does not cause defects in abdominal patterning or polarity (Ephrussi and Lehmann, 1992). In support of the apparent linear effect of piwi gene dosage on the number of pole cells formed, we found that a three-fold increase in piwi gene dosage results in embryos containing on average 66±7.5 pole cells, representing a three-fold increase over the number of pole cells in wild-type embryos at the same developmental stage.

Discussion piwi plays a role in embryonic germline determination. piwi encodes a polar granule component which is maternally required for pole cell formation. However, unlike other posterior group genes which are also required for abdominal patterning, piwi is specifically involved in pole cell formation. This Example indicates that, unlike the posterior group genes, piwi does not appear to be required for the proper localization of the abdominal determinant, nanos.

At the molecular level, germ plasm assembly occurs in a stepwise ordered fashion. The presence of the VASA protein in the small population of pole cells formed in embryos lacking maternal piwi indicates that piwi must act downstream of vasa and therefore oskar in pole cell formation (for review, see Rongo and Lehmann, 1996). In this hierarchy of gene activity, oskar is required for the localization of vasa and tudor to the pole plasm. In addition, all three gene products are polar granule components which like piwi are required for pole cell formation. However, piwi has a role in pole cell formation which is downstream of the requirements for germ plasm assembly. This requirement is very similar to that reported for other putative germ cell determinants including, germ cell-less (gcl) (Jongens et al., 1992), polar-granule component-1 (pgc-1) (Nakamura et al., 1996), and mtlr RNA (Kobayashi et al., 1993). All of these genes act downstream of tud and are required for pole cell formation, but not for abdominal segmentation. These results suggest piwi can act as a maternally deposited germ cell determinant downstream of tud as well.

Maternal PIWI level determines the initial number of pole cells. A direct relationship was observed between the dosage of the piwi gene and the concentration of other pole plasm components, such as VASA, at the posterior pole of the embryo. This phenotype is highly similar to that observed when oskar copy number is increased in embryos (Ephrussi and Lehmann, 1992). For both piwi and oskar, an increase in gene copy number leads to an accumulation of pole plasm components which is independent of the dosage of other component genes. Therefore, both piwi and oskar can modulate the number of pole cells formed through a gene dosage effect via regulating the amount of pole plasm. Pole cell formation involves a hierarchy of gene expression. It has been proposed that oskar acts as a limiting factor for all aspects of pole plasm function (Ephrussi and Lehmann, 1992). The highly similar phenotypes observed in embryos carrying four copies of either piwi or oskar, suggest that osk is not the only limiting factor for germ cell formation and that piwi might be a downstream target of oskar in determining pole cell formation. The presence of VASA protein in germ cells of embryos maternally depleted for piwi also suggests that piwi is required downstream of oskar for pole cell formation (Ephrussi and Lehmann, 1992).

As disclosed herein, piwi is a member of a large class of evolutionarily conserved genes. Intriguingly, piwi is related to aubergine, a Drosophila gene required to promote oskar translation (Wilson et al., 1996). piwi, however, is not likely to promote oskartranslation since piwi-depleted embryos do not show osk-like defects. Alternatively, piwi may act downstream of oskar, but in a completely oskar-independent fashion.

Previous analyses have revealed that pole plasm assembly is a two-step process beginning in oogenesis. The first step is the localization of oskar mRNA to the posterior pole of the oocyte. The second step is the recruitment of vasa and tudor by oskar. Both vasa and tudor are required for pole plasm assembly. Downstream of tudor there is a bifurcation of the hierarchy leading to germ cell determination and the proper localization of the abdominal determinant nanos, respectively. In the germ cell determination branch are potential germ cell determinants which are required for pole plasm assembly and pole cell formation, but are not required for abdominal patterning. The data presented in the Examples suggests that piwi is likely to act downstream of oskar in the germ cell determination branch as a germ cell determinant.

piwi's potential role as a germ cell determinant can be further addressed by ectopically expressing the piwi mRNA at the anterior end of the embryo to examine whether it can induce pole cell formation. This approach has used in identifying molecules crucial to germ cell determination (Ephrussi and Lehmann, 1992; Jongens et al., 1994).

Maternal PIWI is required for migration and transcriptional quiescence of germ cells. In addition to initial pole cell formation, piwi activity is required for successful germ cell migration. Maternal PIWI is nuclearly localized to all pole cells as they form and remains nuclear throughout germ cell migration and primordial gonad formation. In the absence of maternal PIWI, germ cells migrate in a highly randomized fashion with few germ cells actually reaching the gonadal mesoderm. Recent studies have identified several genes which regulate germ cell migration (Moore et al., 1998; Zhang et al., 1996), however, unlike piwi, all of these genes appear to be required in the soma and none of these mutants result in such randomized migration of germ cells as that observed in piwi mutant germ cells. In addition to piwi, maternal NOS has also been shown to act cell-autonomously in germ cells to facilitate their migration (Forbes and Lehmann, 1998). Somatic signaling has been shown to exert both attractive and repulsive forces on germ cells in order to guide their migration (Zhang et al., 1996; Van Doren et al., 1998a). The aberrant germ cell migration observed in embryos lacking maternal PIWI could result from a failure to respond to these somatic guidance cues perhaps due to the absence of specific receptors for the cues on the surface of germ cells. In any case, these results indicate that soma-germline signaling is essential for proper germ cell migration and that maternally supplied products, such as PIWI and NOS, are required for successful germ cell migration.

The small decrease in the average number of germ cells after migration was initiated in piwi-depleted embryos indicates that maternal PIWI also plays a role in germ cell survival. Both in vitro and in vivo studies suggest that the mammalian stem cell genes White (W) and Steel (Sl) also function in the survival of primordial germ cells (Gomperts et al., 1994). Sl mutants are sterile due to poor germ cell survival and improper migration (Witte, 1990). Therefore, PIWI and SL play a similar role in the proliferation and migration of primordial germ cells. However, the SL function is zygotically required, just as nos and ovo in Drosophila. piwi is the first clearly demonstrated case where a maternally provided product functions in the survival of pole cells during embryogenesis.

This Example further reveal that maternal PIWI is required for transcriptional repression in early germ cells. Transcriptional repression has been implicated as an essential mechanism in the establishment and maintenance of the germ cell fate (for review, see Seydoux and Strome, 1999). Previous studies indicate that the repression of RNAP II activity in early germ cells may be part of an evolutionarily conserved mechanism that distinguishes the germline from the soma during early embryogenesis (Seydoux and Dunn, 1997). Germ cells in both Drosophila melanogaster and C. elegans have been shown to lack a specific phosphoepitope of RNAP II until germ cells associate with the gut primordium during gastrulation (Seydoux and Dunn, 1997). The phosphorylation of RNAP II is a prerequisite for its transcriptional activity. Thus, the absence of the phosphoepitope suggests that RNAP II activity is inhibited in early embryonic germ cells (Seydoux and Dunn, 1997; Van Doren et al., 1998).

While applicant does not wish to be bound by a particular mechanism of action, piwi could function to repress transcription in early germ cells by regulating the expression of this specific phosphoepitope of RNAP II. In C. elegans, the pie-1 gene product has been shown to function in transcriptional repression of the germ cell lineage (Mello et al., 1992). In Drosophila, piwi represents the first gene implicated in regulating transcriptional quiescence in germ cells. Prior to zygotic gene expression in the Drosophila embryo, germ cells undergo a wide range of morphological and cellular behaviors including precocious cellularization, translational regulation (Dalby and Glover, 1993), germ cell-specific cell cycle regulation (Sonnenblick, 1941) as well as the development of a migratory cellular morphology (Jaglarz and Howard, 1995).

Therefore, the germ plasm, which is maternally provided, must contain a combination of factors which controls these processes in early germ cells. Maternally provided factors in the germ plasm must function to repress germ cell gene expression as well as to activate specific gene expression in primordial germ cells at the appropriate time. Thus, the mechanisms for timing the onset of zygotic gene expression in the germline should be maternally provided as cell-autonomous factors to germ cells. PIWI is envisioned to represent such a factor to maintain transcriptional quiescence until the appropriate developmental timepoint. The loss of transcriptional repression in germ cells lacking maternal PIWI could result in the loss of normal germ cell properties due to differentiation, which could account for the defective pole cell migration.

PIWI as a factor for maintaining totipotentcy in germ cells. Primordial germ cells are the only population of cells in the organism that retain totipotent potential. Based on studies of genes such as pie-1, transcriptional repression has emerged as a key mechanism that prevents germ cells from expressing genes that would cause them to enter other lineages and differentiate (Mello et al., 1992; for review, see Seydoux and Strome, 1999). piwi is essential for the maintenance and proliferation of germline stem cells in both males and females. Germline stem cells, like primordial germ cells, should be pluripotent; the maintenance of their identity is vital for the propagation of the species. Furthermore, PIWI is specifically expressed in all pole cell nuclei and is required for proper germ cell formation and transcriptional repression. Particularly, piwi gene dosage is directly related to the number of pole cells formed. These data, taken together, suggest that piwi has many of the essential properties required for establishing and maintaining pluripotentcy during germine development.

Example 7 miwi Contributes to the Long Term Self-Renewing Ability of Hematopoietic Stem Cells To test for the role of miwi in long term self-renewing ability of hematopoietic stem cells (HSCs), miwi$^{+/-}$ (marked by ly5.1) and miwi$^{-/-}$ (marked by 5.2) bone marrow cells were co-transplanted into irradiated ly5.1 mice at ratios of 1:1 and 2:1, respectively. The percentage of hematopoietic cells was assayed at 2, 6, and 12 weeks following bone marrow transplantation. In both co-transplantation experiments, the percentage of hematopoietic cells derived from miwi$^{-/-}$ bone marrow steadily decreased over the course of the assay (FIG. 14). Particularly, in the co-transplantation experiment using a 2:1 ratio of miwi$^{+/-}$ to miwi$^{-/-}$, miwi$^{-/-}$ hematopoietic cells were completely depleted by 12 weeks following co-transplantation. These results suggest that miwi contributes to the long-term self-renewing ability of HSCs.

References

Adelman et al. (1983) *DNA* 2:183.
Allioli, N. et al., *Dev. Biol.* 1994 September; 165(1): 30–7
Altschul et al. (1990) *J. Mol. Biol.* 215:403–410.
Anderson, R. et al. *Development* 126:1655–1664.
Ausubel et al. (1992) *Current Protocols in Molecular Biology*, (J. Wylie & Sons, N.Y.)
Baker et al., (1996) *Nat. Genet.* 13:336–342.
Barker, D. D., et al. (1992) *Genes Dev.,* 6:2312–2326.
Barlow et. al., (1996) *Cell*, 86:159–171.
Bartmanska and Clermont (1983) *Cell Tiss. Kinet.* 16:135–143.
Bellve et al. (1977) *J. Cell Biol.* 74:68–85.
Bellve and O'Brien (1983) *The Mammalian Spermatozoon: Structure and Temporal Assembly, in Mechanisms and Control of Animal Fertilization* (Hartman, J. F. ed.), pp. 55–137, Academic Press, New York.
Bellve, A. R. (1979) *The Molecular Biology of Mammalian Spermatogenesis, in Oxford Review of Reproductive Biology* (eds), pp 159–261, Oxford University Clarendon Press, Oxford.
Benfey, P. N., (1999) *Curr. Biol.* 9:171–172.
Bitgood et al., (1996) *Curr. Biol.* 6:298–304.
Blendy et al., (1996) *Nature*, 380:162–165.
Bodanszky, et al., "Peptide Synthesis", John Wiley & Sons, Second Edition, 1976.
Bohmert, K., et al. (1998) *Embo J.* 17:170–180.
Brand, A. H., and Perrimon, N. (1993) *Development* 118:401–415.
Brown, E. H., and King, R. C. (1962) *Growth* 26:53–70.
Brown and Kafatos (1988) *J. Mol. Biol.* 203:425–437.
Brown, E. H., and King, R. C. (1964) *Growth* 28:41–81.
Byers et al. (1987) *J. Cell Biol.* 105:2103–2110.
Catalanotto et al., (2000) *Nature,* 404:245.
Chang, I. K. et al., *Cell. Biol. Int.* 1997 August; 21(8): 495–9.
Chang, I. K. et al., *Cell. Biol. Int.* 1995 February; 19(2): 143–9.
Chien et al. (1991) *Proc. Natl. Acad. Sci. USA* 88:9578–9582.
Chou and Perrimon (1996) *Genet.* 144:1673–1679.
Clark et al., (2000) *Biol. Reprod.,* 63:1825–1838.
Cox, D. N., et al., (1998) *Genes Dev.* 12:3715–3727.
Crea et al. (1978) *Proc. Natl. Acad. Sci. U.S.A,* 75:5765.
Cunningham et al., (1998) *Dev. Biol.,* 204:345–360.
de Miguel et al. (1997) *Virchows Arch.* 431(2):131–8.
de Rooij D. G. (1988) *J. Cell Sci. Suppl.* 10:181–194.
de Cuevas, M. and Spradling, A. C. (1998) *Development,* 125:2781–2789.
Deng and Lin (1997) *Dev. Biol.* 189:79–94.
De Vries et al., (1999) *Genes Dev.,* 13:523–531.
Dix et al., (1996) *Proc. Natl. Acad. Sci. USA,* 93:3264–3268.
Edelman et al., (1996) *Cell,* 85:1125–1134.
Edelman et al., (1999) *Nat. Genet.,* 21:123–127.
Eichenlaub et al. (1979) *J. Bacteriol* 138:559–566.
Elson et al., (1996) *Proc. Natl. Acad. Sci. USA,* 93:13084–13089.
Ephrussi et al. (1991) Cell 66:37–50.
Erickson, R. P. (1990) Trends Genet. 6:264–269.
Etches et al., in *Avian Incubation*, Chapter 22, Butterworth Publishers (1990)
Etches et al., *Poultry Science* 72:882–887 (1993);
Evan, G. I., et al. (1985) *Mol. Cell. Biol.* 5:3610–3616.
Fields et al., *Int. J. Peptide Protein Res.,* 35:161–214, 1990
Fire et al. (1998) *Nature* 391:806–811.
Forbes et al. (1996a) *Development* 122:1125–1135.
Forbes and Spradling (1996b), *Development* 122:3283–3294
Forbes and Lehmann (1998) *Development* 125:679–690.
Friedman et al. (1990) *Screening Lambda Gt11 Libraries, in PCR Protocols: A Guide to Methods and Applications* (Innis et al. eds.), pp.253–260, Academic Press, San Diego, Calif.
Fuller, M. (1993). *Spermatogenesis. In Drosophila Development.* (eds. M. Bate and A. Martinez Arias), pp. 71–148. Cold Spring Harbor Press, Cold Spring Harbor, N.Y.
Gillmor et al. (1997) *Nature Struct. Biol.* 4:1003–1009.
Gold et al. (1983) *J. Exp. Zool.* 225:123–134.
Gonczy, P. and DiNardo, S. (1996) *Development* 122:2437–2447.
Green et al. (1989) *J. Invest. Dermatol.* 93:486–491.

Griswold, M. D. (1995) *Biol. Reprod.* 52:211–216.
Griswold, (1998) *Sem. Cell Dev. Biol.,* 9:451–457.
Guo and Kemphues (1995) *Cell* 81:611–620.
Guyomard et al., (1989) *Biochimie,* 71:857–863.
Harlow et al., (1988) *Antibodies: A Laboratory Manual,* Cold Spring Harbor Laboratory Press, Cold Spring Harbor, N.Y.
Hay et al. (1990) *Development* 109:425–433.
Henikoff et al. (1995) *Gene* 163:17–26.
Hogan et al., (1994) *Manipulating the Mouse Embryo: A Laboratory Manual,* Cold Spring Harbor Laboratory Press, Cold Spring Harbor, N.Y.
Hoog, C. (1995) *Int. J. Dev. Biol.* 39:719–726.
Howell et al. (1988) *Antibodies A Laboratory Manual, (Cold Spring Harbor Laboratory).*
Inoue et al., *Cell Differ. Dev.,* 29:123–128 (1990).
Keski-Oja et al., *J. Cell Biochem.* 33:95 (1987).
Ketterling et al. (1993) *Am J Hum Genet.* 52(1):152–66.
Kimble and Simpson (1997) *Ann. Rev. Cell Dev. Biol.* 13:333–361.
King, F. J., and Lin, H. (1999) *Development* 126:1833–1844.
King, R. C. (1970) *Ovarian Development in Drosophila melanogaster* Academic Press, New York.
Knoblich, J. A. (1997) *Curr. Opin. Cell Biol.* 9:833–841.
Koesters et al., (1999) *Genomics,* 61:210–218.
Koshimizu et al., (1995) *Mol. Reprod. Dev.,* 40:221–227.
Koshimizu et al., (1993) *Biol. Reprod.,* 49:875–884.
Kramer and Erickson (1982), *J. Reprod. Fertil.* 64:139–144.
Kuwabara, P. E. (1996) *Genet.* 144:597–607.
Kyte et al. (1982) *J. Mol. Biol.* 157:105.
Lecuit, T., and Cohen, S. M. (1997) *Nature* 388;139–145.
Lee, S. J. (1990) *Mol. Cell. Biol.* 3239–3242.
Lee et al., (1995) *Proc. Natl. Acad. Sci. USA,* 92:12451–12455.
Lin, H. (1997) *Annu. Rev. Genet.* 31:455–491.
Lin and Schagat (1997) *Trends Genet.* 13:33–39.
Lin, H. and Schagat, T. (1997) *Trends Genet.* 13:33–39.
Lin and Spradling (1997) *Development* 124:2463–2476.
Lin and Spradling (1995) *Dev. Genetics* 16:6–12.
Lin et al. (1994) *Development* 120:947–956.
Lin, H. (1998) *Curr. Opin. Cell Biol.* 10:687–693.
Lin and Spradling (1993) *Dev. Biol.* 159:140–152.
Lindsley, D. L. and Zimm, G. G. (1992). The genome of *Drosophila melanogaster.* Academic Press Inc., New York, N.Y.
Liu et al., (1997) *Development,* 124:2463–2476.
Liu et al., (1998) *Nat. Genet.,* 20:377–380.
Lord and Dexter (1988) *J. Cell Sci. Suppl.* 10.
Mahowald and Kambysellis (1980) *Oogenesis, in Genetics and Biology of Drosophila,* pp 141–224. Academic Press, London.
Maniatis et al. (1978) *Cell* 15:687–701.
Mar and Ordahl, *Proc. Natl. Acad. Sci. USA* 85:6404–6408 (1988)
Margolis and Spradling (1995) *Development* 121:3797–3807.
Margolis, J. and Spradling, A. C. (1995) *Development* 121:3797–3807.
Matunis et al. (1997) *Development* 124:4383–4391.
McKearin and Ohlstein (1995) *Development* 121:2937–2947.
McKearin, D. and Spradling, A. C. (1990) *Genes Dev.* 4:2242–2251.
McOmie, *Protective Groups in Organic Chemistry,* Plenum Press, New York, (1973)
Meienhofer, *Hormonal Proteins and Peptides,* Vol. 2, p.46, Academic Press, New York, (1983)

Mello and Fire (1995), *Methods Cell Biol.* 48:451–482.
Menke et al. (1997) *Am J Hum Genet.* 60:237–241.
Merrifield (1969) *Adv Enzymol* 32:221–96.
Messing et al. (1981) *Third Cleveland Symposium on Macromolecules and Recombinant DNA,* Editor A. Walton, (Elsevier, Amsterdam).
Morrison et al. (1997) *Cell* 88:287–298.
Morrison, S. J., et al. (1997). *Cell,* 88:287–298.
Moussian et al. (1998) *EMBO J.* 17:1799–1809.
Munier et al. (1998) FEBS lett. 4: 434(3): 289–94.
Murata, Y. and Wharton, R. P. (1995) *Cell* 80: 747–756.
Nakai and Kanehisa (1992) *Genomics* 14:897–911.
Nantel et al., (1996) *Nature,* 380:159–162.
Nebel et al. (1961) *Science* 134:832–833.
Needleman et al. (1970) *J. Mol. Biol.* 48:443.
Oakberg (1956) *Am. J. Anat.* 99:507–516.
Oakberg (1956) *Am. J. Anat.* 99:391–409.
Ochman et al. (1990) *Amplification of flanking sequences by Inverse PCR, in PCR protocols: a Guide to Methods and Applications* (Innis et al., eds.), pp. 219–227. Academic Press, San Diego, Calif.
Ohta et al., (2000) *Development,* 127:2125–2131.
Ozato et al, *Cell Differ.,* 19:237–244 (1986).
Parisi, M. J. and Lin, H. (1998) *Cell Res.* 8:15–21.
Parisi, M. J. and Lin, H. (1999) *Genetics,* 153:235–250.
Pereira et al., (1998) *Int. J. Androl.,* 21:34–40.
Petitte et al., *Development* 108:185–189 (1990)
Pirrotta (1988) *Vectors for P-element transformation in Drosophila, in Vectors. A Survey of Molecular Cloning Vectors and Their Uses.* (Rodriguez and Denhardt, eds.), pp.437–456. Butterworths, London, England.
Potten, C. S. (1997). *Stem cells.* Academic Press, London, England.
Ravnik and Wolgemuth (1996) *Dev Biol.* 173:69–78.
Robertson, H. M., et al. (1988) *Genetics* 118:461–470.
Roest et al., (1996) *Cell,* 86:799–810.
Rokkones et al., *J. Comp. Physiol. B,* 158:751–758 (1989).
Rorth, P. (1998). *Mech. Dev.* 78:113–118.
Rorth, P. et al., (1998) *Development* 125:1049–1057.
Rorth, P. (1996) *Proc. Natl. Acad. Sci. USA* 93:12418–12422.
Ruggiu et al., (1997) *Nature,* 389:73–77.
Ruohola et al. (1991) *Cell* 66:433–449.
Russel and Griswold, (eds.) (1993) *The Sertoli Cell,* Cache River Press, Clearwater.
Russel et al. (1990). *Histological and Histopathological Evaluation of the Testis,* Cache River Press, Clearwater.
Sambrook et al. (1989) *Molecular Cloning: A Laboratory Manual* (Cold Spring Harbor Laboratory Press, Cold Spring Harbor, N.Y.).
Sandlow et al. (1997) *Urology* 49(3), 494–500.
Sassone-Corsi, (2000) *Mol. Reprod. Dev.,* 56:228–229.
Schmidt et al., (1999) *Genetics,* 151:749–760.
Schroder et al., "The Peptides", Vol.1, Academic Press (New York) (1965).
Schupbach, T., et al. (1978) *Willhelm Roux Arch.* 184: 41–56.
Shalaby et al., (1995) *Nature,* 376:62–66.
Shankar et al. (1998) *Biochem Biophys Res Commun.* 13: 243(2): 561–5.
Shimmin et al. (1993) *Nature* 22, 362(6422): 745–7.
Smith, A. G. and Hooper, M. L., *Dev. Biol.* 1987 May; 121(1): 1–9
Smith et al., *Adv. Appl. Math.* 2:482 (1981).
Spradling and Rubin (1982) *Science* 218:341–347.
Spradling A. (1993) *Developmental Genetics of Oogenesis, in Drosophila Development,* (Bate and Martinez-Arias eds.), pp. 1–70, Cold Spring Harbor, N.Y.

Steward et al. (1969) *Solid Phase Peptide Synthesis*, W. H. Freeman Co., San Francisco.
Sulston and Hodgkin (1988) *Methods, in The Nematode Caenorhabditis elegans*, (ed. W. B. Wood), pp. 598–600. Cold Spring Harbor Press, Cold Spring Harbor, N.Y.
Tabara et al., (1999) *Cell,* 99:123–132.
Tanaka et al., (2000) *Genes Dev.,* 14:841–853.
Thierry-Mieg and Durbin (1992) *Cahiers IMABIO* 5:15–24.
Thomas et al. (1989) *Biol. Reprod.* 41:729–739.
Toscani et al., (1997) *Nature,* 386:713–717.
Tourtellotte et al., (2000) *Mol. Cell. Biol.,* 20:5361–5268.
U.S. Pat. No. 2,868,691
U.S. Pat. No. 3,095,355
U.S. Pat. No. 4,196,265
U.S. Pat. No. 4,244,946
U.S. Pat. No. 4,554,101
U.S. Pat. No. 4,683,202
U.S. Pat. No. 4,686,283
U.S. Pat. No. 4,761,371
U.S. Pat. No. 4,877,729
U.S. Pat. No. 4,912,038
U.S. Pat. No. 4,736,866
U.S. Pat. No. 4,769,331
U.S. Pat. No. 5,120,535
U.S. Pat. No. 5,162,215
U.S. Pat. No. 5,234,933
U.S. Pat. No. 5,279,833
U.S. Pat. No. 5,286,634
U.S. Pat. No. 5,326,902
U.S. Pat. No. 5,352,660
U.S. Pat. No. 5,399,346
U.S. Pat. No. 5,436,288
U.S. Pat. No. 5,489,742
U.S. Pat. No. 5,550,316
U.S. Pat. No. 5,573,933
U.S. Pat. No. 5,580,979
U.S. Pat. No. 5,583,103
U.S. Pat. No. 5,589,375
U.S. Pat. No. 5,614,396
U.S. Pat. No. 5,624,816
U.S. Pat. No. 5,625,125
U.S. Pat. No. 5,627,158
U.S. Pat. No. 5,641,484
U.S. Pat. No. 5,643,567
U.S. Pat. No. 5,645,999
U.S. Pat. No. 5,646,008
U.S. Pat. No. 5,648,061
U.S. Pat. No. 5,651,964
U.S. Pat. No. 5,693,488
U.S. Pat. No. 5,723,593
U.S. Pat. No. 5,734,033
U.S. Pat. No. 5,739,278
U.S. Pat. No. 5,741,957
U.S. Pat. No. 5,753,687
U.S. Pat. No. 5,770,609
U.S. Pat. No. 5,776,902
U.S. Pat. No. 5,780,436
U.S. Pat. No. 5,786,152
U.S. Pat. No. 5,837,479
van Roijen et al. (1998) *Hum Reprod.* 13(6): 1559–66.
Vanfleteren et al. (1994) *Mol. Phylogenet. Evol.* 3:92–101.
Verrinder Gibbins et al., *Fourth World Congress on Genetics Applied to Livestock Production*, Edinburgh, (1990);
Von Wettstein et al. (1984) *Annu. Rev. Genet.* 18: 331–413.
Wetmur & Davidson (1968) *J. Mol. Biol.* 31:349–370.
Wieschaus and Szabad (1979) *Dev. Biol.* 68:29–46.
Willison and Ashworth (1987) *Trends Genet.* 3: 351–355.
Wilson et al. (1989) *Genes Dev.* 3:1301–1313.
Wilson et al., (1996) *Development,* 122:631–1639.
WO 93/25521
WO 96/40276
WO 99/06533
Wolgemuth and Watrin (1991) *Mamm Genome* 1:283–288.
Xie and Spradling (1998) *Cell* 94:251–260.
Xu and Rubin (1993) *Development* 117:1223–37.
Xu et al. (1992) *Development* 115:913–922.
Xu et al., (1996) *Genes Dev.,* 10:2411–2422.
Xu et al., (1999) *Nat. Genet.,* 23:118–121.
Yoshinaga et al., (1991) *Development,* 113:689–699.
Yu et al., (2000) *Proc. Natl. Acad. Sci. USA,* 97:4683–4688.
Yuan et al., (2000) *Mol. Cell,* 5:73–83.
Yue and Spradling (1992) *Genes Dev.* 6:2443–2454.
Zaccai, M. and Lipshitz, H. D. (1996). *Zygote* 4:159–166.
Zhang et al., (1999) *Endocrinology,* 140:2790–2800.
Zhao et al. (1996) *Genes Dev.* 10:1657–1669.
Zhao et al., (1997) *Mech. Dev.,* 61:63–73
Zhao et al., (1998) *Development,* 125:1103–1112.
Zhong et al., (1999) *Nat. Genet.,* 22:171–174.
Zhou et al., (1996) *Proc. Natl. Acad. Sci. USA,* 93:12262–12266.
Zhu et al., (1997) *Development,* 124:3007–3014.
Zhu and Naz (1998) *Biochem Biophys Res Commun.* 10:249(1):56–60.
Zimmer et al., *Peptides* 1992, pp.393–394, ESCOM Science Publishers, B. V. 1993.
Zou et al., (1998) *Gene,* 211:187–194.

It will be understood that various details of the invention may be changed without departing from the scope of the invention. Furthermore, the foregoing description is for the purpose of illustration only, and not for the purpose of limitation—the invention being defined by the claims.

What is claimed is:

1. An isolated and purified polynucleic acid encoding a biologically active piwi family polypeptide comprising an amino acid sequence as set forth in any of SEQ ID NOs: 2, 4 and 6.

2. The polynucleic acid of claim 1, further comprising a piwi family-encoding polynucleic acid sequence as set forth in any of SEQ ID NOs: 3 and 5.

3. An isolated and purified polynucleic acid encoding a biologically active piwi family polypeptide, wherein the polynucleic acid is at least about 75% identical to a sequence as set forth in any of SEQ ID NOS: 1, 3, and 5, and wherein the polypeptide comprises the PIWI box.

4. The polynucleic acid of claim 3, wherein the encoded polypeptide comprises a vertebrate piwi family polypeptide.

5. The polynucleic acid of claim 3, wherein the encoded polypeptide comprises a mammalian piwi family polypeptide.

6. The polynucleic acid of claim 3, wherein the encoded polypeptide comprises a human piwi family polypeptide.

7. The polynucleic acid of claim 3, further defined as a DNA segment.

8. A recombinant vector comprising the polynucleic acid of claim 3.

9. The recombinant vector of claim 8, wherein the vector is a recombinant expression vector.

10. The recombinant vector of claim 8 further defined as cony rising at least a 1,000 nucleotide long contiguous stretch of a polynucleic and sequence as essentially set forth in any of SEQ ID NOs:1, 3 and 5.

11. A recombinant host cell comprising the recombinant vector of claim 8.

12. The recombinant host cell of claim 11, wherein the host cell is a procaryotic cell.

13. The recombinant host cell of claim 11, wherein the host cell is a eukaryotic cell.

14. A method of preparing a piwi family polypeptide, comprising: transforming a cell with the polynucleic acid of claim 3 to produce a piwi family under conditions suitable for the expression of said polypeptide.

* * * * *

SEQUENCE LISTING

<160> NUMBER OF SEQ ID NOS: 21

<210> SEQ ID NO 1
<211> LENGTH: 3047
<212> TYPE: DNA
<213> ORGANISM: Drosophila sp.
<220> FEATURE:
<221> NAME/KEY: CDS
<222> LOCATION: (84)..(2612)
<221> NAME/KEY: misc_feature
<222> LOCATION: (120)

```
<223> OTHER INFORMATION: n=a or c, Xaa=Leu or Ile
<221> NAME/KEY: misc_feature
<222> LOCATION: (399)
<223> OTHER INFORMATION: n=a or t, Xaa=Leu or Ile
<221> NAME/KEY: misc_feature
<222> LOCATION: (2436)
<223> OTHER INFORMATION: n=a or c, Xaa=Leu or Ile

<400> SEQUENCE: 1
ctgagtccaa agcgtcgttt tcaaagtact ctttcagttt ccattgtgaa gttttaagtg      60
atcgcgagtg ccaaaaagta aca atg gct gat gat cag gga cgt gga cgc agg     113
                         Met Ala Asp Asp Gln Gly Arg Gly Arg Arg
                           1               5                  10 cgt cca ntt aac gaa gat gat tcc tct act tcc cga ggt agt ggt gat       161
Arg Pro Xaa Asn Glu Asp Asp Ser Ser Thr Ser Arg Gly Ser Gly Asp
            15                  20                  25 ggg ccg cgg gtg aaa gta ttc aga gga tct tca tca ggt gac ccg aga       209
Gly Pro Arg Val Lys Val Phe Arg Gly Ser Ser Ser Gly Asp Pro Arg
        30                  35                  40 gcg gat cct cgt ata gag gct tca aga gag aga aga gct ctc gag gaa       257
Ala Asp Pro Arg Ile Glu Ala Ser Arg Glu Arg Arg Ala Leu Glu Glu
    45                  50                  55 gct ccc agg cgt gaa ggt ggc ccg cca gag cga aag ccg tgg ggt gac       305
Ala Pro Arg Arg Glu Gly Gly Pro Pro Glu Arg Lys Pro Trp Gly Asp
60                  65                  70 caa tat gat tac ctg aat acc cgt ccg gtt gag ctg gta tcc aag aag       353
Gln Tyr Asp Tyr Leu Asn Thr Arg Pro Val Glu Leu Val Ser Lys Lys
        75                  80                  85                  90 gga acc gat ggc gtc ccg gtc atg ctg cag acg aac ttt ttt cga nta       401
Gly Thr Asp Gly Val Pro Val Met Leu Gln Thr Asn Phe Phe Arg Xaa
                95                 100                 105 aaa acc aag ccg gaa tgg cgg atc gtt cat tat cac gtg gag ttt gtg       449
Lys Thr Lys Pro Glu Trp Arg Ile Val His Tyr His Val Glu Phe Val
            110                 115                 120 ccg acc atc gag aat cct cgt gtc cgt atg gga gtt ttg tcc aat cat       497
Pro Thr Ile Glu Asn Pro Arg Val Arg Met Gly Val Leu Ser Asn His
        125                 130                 135 gct aac ctt ctg gga tca ggc tat cta ttc gac gga ctg caa ctg ttc       545
Ala Asn Leu Leu Gly Ser Gly Tyr Leu Phe Asp Gly Leu Gln Leu Phe
    140                 145                 150 acc acc agg aaa ttc gag cag gaa atc acg gtg ctc agc gga aag tcg       593
Thr Thr Arg Lys Phe Glu Gln Glu Ile Thr Val Leu Ser Gly Lys Ser
155                 160                 165                 170 aag ctg gac att gaa tac aag ata tcc ata aag ttc gtt gga ttc ata       641
Lys Leu Asp Ile Glu Tyr Lys Ile Ser Ile Lys Phe Val Gly Phe Ile
                175                 180                 185 tcg tgt gct gag ccc cgc ttt ttg caa gtc tta aat cta ata ttg cgc       689
Ser Cys Ala Glu Pro Arg Phe Leu Gln Val Leu Asn Leu Ile Leu Arg
            190                 195                 200 cgc tcg atg aag ggc cta aat ttg gaa tta gtt ggc cgt aat ctc ttt       737
Arg Ser Met Lys Gly Leu Asn Leu Glu Leu Val Gly Arg Asn Leu Phe
        205                 210                 215 gat ccc cga gct aag atc gaa ata agg gag ttc aaa atg gag cta tgg       785
Asp Pro Arg Ala Lys Ile Glu Ile Arg Glu Phe Lys Met Glu Leu Trp
    220                 225                 230 ccg ggc tat gag aca tcg att cgt cag cac gaa aaa gat att tta ttg       833
Pro Gly Tyr Glu Thr Ser Ile Arg Gln His Glu Lys Asp Ile Leu Leu
235                 240                 245                 250 ggc acc gaa ata act cac aaa gtt atg cgc acc gag acg atc tac gac       881
Gly Thr Glu Ile Thr His Lys Val Met Arg Thr Glu Thr Ile Tyr Asp
                255                 260                 265
```

```
ata atg cga cgt tgc tca cac aat ccg gct cgt cat cag gac gaa gta      929
Ile Met Arg Arg Cys Ser His Asn Pro Ala Arg His Gln Asp Glu Val
        270                 275                 280 cgg gta aat gtt ttg gac ttg att gtc ctt acg gat tac aat aac aga      977
Arg Val Asn Val Leu Asp Leu Ile Val Leu Thr Asp Tyr Asn Asn Arg
            285                 290                 295 act tat cgt atc aat gat gtc gac ttt gga caa act ccg aaa tca aca     1025
Thr Tyr Arg Ile Asn Asp Val Asp Phe Gly Gln Thr Pro Lys Ser Thr
        300                 305                 310 ttc agt tgc aag ggt aga gat atc agt ttc gtg gaa tac tat ctc act     1073
Phe Ser Cys Lys Gly Arg Asp Ile Ser Phe Val Glu Tyr Tyr Leu Thr
315                 320                 325                 330 aaa tat aat ata cgc att cgc gac cac aat cag ccg ctg ctg att tcc     1121
Lys Tyr Asn Ile Arg Ile Arg Asp His Asn Gln Pro Leu Leu Ile Ser
            335                 340                 345 aaa aat agg gac aag gct cta aaa act aac gct agc gaa tta gtg gta     1169
Lys Asn Arg Asp Lys Ala Leu Lys Thr Asn Ala Ser Glu Leu Val Val
        350                 355                 360 cta att cct gag ctc tgc cga gtg act ggg ctc aat gcc gag atg cgc     1217
Leu Ile Pro Glu Leu Cys Arg Val Thr Gly Leu Asn Ala Glu Met Arg
            365                 370                 375 tca aac ttt cag ctt atg cgt gcc atg agc agt tat acg cga atg aac     1265
Ser Asn Phe Gln Leu Met Arg Ala Met Ser Ser Tyr Thr Arg Met Asn
380                 385                 390 ccc aaa caa cgc act gat cga ttg cgc gct ttt aac cac cgt tta caa     1313
Pro Lys Gln Arg Thr Asp Arg Leu Arg Ala Phe Asn His Arg Leu Gln
395                 400                 405                 410 aac act cca gaa agt gtg aag gtc ttg aga gac tgg aac atg gaa ctg     1361
Asn Thr Pro Glu Ser Val Lys Val Leu Arg Asp Trp Asn Met Glu Leu
            415                 420                 425 gac aag aac gtc aca gaa gta caa ggc cgg ata att gga cag cag aac     1409
Asp Lys Asn Val Thr Glu Val Gln Gly Arg Ile Ile Gly Gln Gln Asn
        430                 435                 440 atc gtg ttt cat aat gga aag gtt cct gct gga gaa aac gct gat tgg     1457
Ile Val Phe His Asn Gly Lys Val Pro Ala Gly Glu Asn Ala Asp Trp
            445                 450                 455 caa agg cac ttc aga gac caa agg atg ctt acc act ccg agc gat ggc     1505
Gln Arg His Phe Arg Asp Gln Arg Met Leu Thr Thr Pro Ser Asp Gly
        460                 465                 470 ctc gat cgt tgg gct gtc atc gcg ccg caa agg aat tcc cat gaa ctc     1553
Leu Asp Arg Trp Ala Val Ile Ala Pro Gln Arg Asn Ser His Glu Leu
475                 480                 485                 490 cga act cta ctt gac tct ttg tat aga gca gct agt gga atg ggt ctt     1601
Arg Thr Leu Leu Asp Ser Leu Tyr Arg Ala Ala Ser Gly Met Gly Leu
            495                 500                 505 aga att cga agc ccc cag gaa ttc ata att tat gat gat cgc act gga     1649
Arg Ile Arg Ser Pro Gln Glu Phe Ile Ile Tyr Asp Asp Arg Thr Gly
        510                 515                 520 act tat gtg aga gca atg gat gat tgt gtg cgc tca gat ccc aaa ctt     1697
Thr Tyr Val Arg Ala Met Asp Asp Cys Val Arg Ser Asp Pro Lys Leu
        525                 530                 535 ata tta tgc ctc gta ccc aat gat aac gcc gaa aga tac tca tca atc     1745
Ile Leu Cys Leu Val Pro Asn Asp Asn Ala Glu Arg Tyr Ser Ser Ile
        540                 545                 550 aaa aag aga gga tac gtt gac agg gcg gtg cca act caa gtt gtg acc     1793
Lys Lys Arg Gly Tyr Val Asp Arg Ala Val Pro Thr Gln Val Val Thr
555                 560                 565                 570 ctt aaa acg acc aag aac cgt agc ctt atg agc att gcc acc aaa ata     1841
Leu Lys Thr Thr Lys Asn Arg Ser Leu Met Ser Ile Ala Thr Lys Ile
```

```
                        575                 580                 585
gca atc caa ctg aat tgc aag ttg gga tat aca ccc tgg atg atc gaa    1889
Ala Ile Gln Leu Asn Cys Lys Leu Gly Tyr Thr Pro Trp Met Ile Glu
            590                 595                 600 cta ccc ttg tcc gga ctg atg aca att ggc ttt gac att gcg aag agc    1937
Leu Pro Leu Ser Gly Leu Met Thr Ile Gly Phe Asp Ile Ala Lys Ser
        605                 610                 615 aca cga gat cgg aag agg gcc tac gga gca ttg att gcc tca atg gat    1985
Thr Arg Asp Arg Lys Arg Ala Tyr Gly Ala Leu Ile Ala Ser Met Asp
    620                 625                 630 cta cag caa aac tcc acg tac ttc agc aca gtc acg gag tgc agc gcc    2033
Leu Gln Gln Asn Ser Thr Tyr Phe Ser Thr Val Thr Glu Cys Ser Ala
635                 640                 645                 650 ttt gat gtg ctc gct aac acc ctt tgg ccg atg ata gca aag gcc ctg    2081
Phe Asp Val Leu Ala Asn Thr Leu Trp Pro Met Ile Ala Lys Ala Leu
            655                 660                 665 cgc caa tat caa cat gag cat agg aag ctg cca tct cga atc gta ttt    2129
Arg Gln Tyr Gln His Glu His Arg Lys Leu Pro Ser Arg Ile Val Phe
        670                 675                 680 tat cga gac ggt gtg agc tcc ggc tct cta aag cag ctt ttt gaa ttt    2177
Tyr Arg Asp Gly Val Ser Ser Gly Ser Leu Lys Gln Leu Phe Glu Phe
    685                 690                 695 gaa gtc aag gac atc att gag aag ttg aaa act gaa tac gcc cgc gtc    2225
Glu Val Lys Asp Ile Ile Glu Lys Leu Lys Thr Glu Tyr Ala Arg Val
700                 705                 710 cag cta agc cca ccg caa tta gct tat att gtg gta acc aga tcc atg    2273
Gln Leu Ser Pro Pro Gln Leu Ala Tyr Ile Val Val Thr Arg Ser Met
715                 720                 725                 730 aac acg cgc ttc ttc ctc aac gga caa aat cct ccg cct ggt act ata    2321
Asn Thr Arg Phe Phe Leu Asn Gly Gln Asn Pro Pro Pro Gly Thr Ile
            735                 740                 745 gtt gat gac gtt ata act ctg ccc gag aga tac gac ttt tat ctg gtc    2369
Val Asp Asp Val Ile Thr Leu Pro Glu Arg Tyr Asp Phe Tyr Leu Val
        750                 755                 760 tcg caa caa gtt cgt cag ggt aca gtg tcg ccg acc agc tac aat gtt    2417
Ser Gln Gln Val Arg Gln Gly Thr Val Ser Pro Thr Ser Tyr Asn Val
    765                 770                 775 ctt tat agc agc atg ggt ntc tca ccg gag aaa atg caa aaa ctt acg    2465
Leu Tyr Ser Ser Met Gly Xaa Ser Pro Glu Lys Met Gln Lys Leu Thr
780                 785                 790 tac aag atg tgc cac ttg tac tac aat tgg tcg ggc acc aca cga gtg    2513
Tyr Lys Met Cys His Leu Tyr Tyr Asn Trp Ser Gly Thr Thr Arg Val
795                 800                 805                 810 cca gca gtt tgc cag tac gct aag aag cta gct acc ctc gtg ggt acg    2561
Pro Ala Val Cys Gln Tyr Ala Lys Lys Leu Ala Thr Leu Val Gly Thr
            815                 820                 825 aac ttg cac tct att ccg caa aac gcg ctc gaa aag aag ttt tat tat    2609
Asn Leu His Ser Ile Pro Gln Asn Ala Leu Glu Lys Lys Phe Tyr Tyr
        830                 835                 840 cta taattggata taatttagaa tggagtatta atccttacta agaggccata         2662
Leu tatgaaacta gcccagacat ttatactttt tcaatacttc cttacttttg ctaagcactt    2722
cagcatttat gactaaatat tttgtatttg aaatgcatta ctgctctttt ttcaaacaaa    2782
agcaaaattg aggattaaga ttctggtatt taagcataag accagaggaa attcccaaac    2842
aaacatttaa agtatctcat caagacatgt tcattaattt ggaatataat tactttattt    2902
tttattgtat attttagttt atgtaaagaa aaattacata catccatgtt tgcttactta    2962
```

-continued

```
accacacatt catggctgct tatattcgtg aaaaaaaaaa aaaaaaaaaa aaaaaaaaaa      3022
aaaaaaaaaa aaaaaaaaaa aaaaa                                           3047
```

```
<210> SEQ ID NO 2
<211> LENGTH: 843
<212> TYPE: PRT
<213> ORGANISM: Drosophila sp.
<220> FEATURE:
<221> NAME/KEY: misc_feature
<222> LOCATION: (13)
<223> OTHER INFORMATION: Xaa=Leu or Ile
<221> NAME/KEY: misc_feature
<222> LOCATION: (106)
<223> OTHER INFORMATION: Xaa=Leu or Ile
<221> NAME/KEY: misc_feature
<222> LOCATION: (785)
<223> OTHER INFORMATION: Xaa=Leu or Ile

<400> SEQUENCE: 2

Met Ala Asp Asp Gln Gly Arg Gly Arg Arg Pro Xaa Asn Glu Asp
 1               5                  10                  15

Asp Ser Ser Thr Ser Arg Gly Ser Gly Asp Gly Pro Arg Val Lys Val
                20                  25                  30

Phe Arg Gly Ser Ser Ser Gly Asp Pro Arg Ala Asp Pro Arg Ile Glu
                35                  40                  45

Ala Ser Arg Glu Arg Arg Ala Leu Glu Glu Ala Pro Arg Arg Glu Gly
        50                  55                  60

Gly Pro Pro Glu Arg Lys Pro Trp Gly Asp Gln Tyr Asp Tyr Leu Asn
 65                  70                  75                  80

Thr Arg Pro Val Glu Leu Val Ser Lys Lys Gly Thr Asp Gly Val Pro
                85                  90                  95

Val Met Leu Gln Thr Asn Phe Arg Xaa Lys Thr Lys Pro Glu Trp
            100                 105                 110

Arg Ile Val His Tyr His Val Glu Phe Val Pro Thr Ile Glu Asn Pro
            115                 120                 125

Arg Val Arg Met Gly Val Leu Ser Asn His Ala Asn Leu Leu Gly Ser
        130                 135                 140

Gly Tyr Leu Phe Asp Gly Leu Gln Leu Phe Thr Thr Arg Lys Phe Glu
145                 150                 155                 160

Gln Glu Ile Thr Val Leu Ser Gly Lys Ser Lys Leu Asp Ile Glu Tyr
                165                 170                 175

Lys Ile Ser Ile Lys Phe Val Gly Phe Ile Ser Cys Ala Glu Pro Arg
            180                 185                 190

Phe Leu Gln Val Leu Asn Leu Ile Leu Arg Arg Ser Met Lys Gly Leu
        195                 200                 205

Asn Leu Glu Leu Val Gly Arg Asn Leu Phe Asp Pro Arg Ala Lys Ile
    210                 215                 220

Glu Ile Arg Glu Phe Lys Met Glu Leu Trp Pro Gly Tyr Glu Thr Ser
225                 230                 235                 240

Ile Arg Gln His Glu Lys Asp Ile Leu Leu Gly Thr Glu Ile Thr His
                245                 250                 255

Lys Val Met Arg Thr Glu Thr Ile Tyr Asp Ile Met Arg Arg Cys Ser
            260                 265                 270

His Asn Pro Ala Arg His Gln Asp Glu Val Arg Val Asn Val Leu Asp
        275                 280                 285

Leu Ile Val Leu Thr Asp Tyr Asn Asn Arg Thr Tyr Arg Ile Asn Asp
    290                 295                 300
```

-continued

```
Val Asp Phe Gly Gln Thr Pro Lys Ser Thr Phe Ser Cys Lys Gly Arg
305                 310                 315                 320

Asp Ile Ser Phe Val Glu Tyr Tyr Leu Thr Lys Tyr Asn Ile Arg Ile
                325                 330                 335

Arg Asp His Asn Gln Pro Leu Leu Ile Ser Lys Asn Arg Asp Lys Ala
            340                 345                 350

Leu Lys Thr Asn Ala Ser Glu Leu Val Val Leu Ile Pro Glu Leu Cys
        355                 360                 365

Arg Val Thr Gly Leu Asn Ala Glu Met Arg Ser Asn Phe Gln Leu Met
    370                 375                 380

Arg Ala Met Ser Ser Tyr Thr Arg Met Asn Pro Lys Gln Arg Thr Asp
385                 390                 395                 400

Arg Leu Arg Ala Phe Asn His Arg Leu Gln Asn Thr Pro Glu Ser Val
                405                 410                 415

Lys Val Leu Arg Asp Trp Asn Met Glu Leu Asp Lys Asn Val Thr Glu
            420                 425                 430

Val Gln Gly Arg Ile Ile Gly Gln Gln Asn Ile Val Phe His Asn Gly
        435                 440                 445

Lys Val Pro Ala Gly Glu Asn Ala Asp Trp Gln Arg His Phe Arg Asp
    450                 455                 460

Gln Arg Met Leu Thr Thr Pro Ser Asp Gly Leu Asp Arg Trp Ala Val
465                 470                 475                 480

Ile Ala Pro Gln Arg Asn Ser His Glu Leu Arg Thr Leu Leu Asp Ser
                485                 490                 495

Leu Tyr Arg Ala Ala Ser Gly Met Gly Leu Arg Ile Arg Ser Pro Gln
            500                 505                 510

Glu Phe Ile Ile Tyr Asp Asp Arg Thr Gly Thr Tyr Val Arg Ala Met
        515                 520                 525

Asp Asp Cys Val Arg Ser Asp Pro Lys Leu Ile Leu Cys Leu Val Pro
530                 535                 540

Asn Asp Asn Ala Glu Arg Tyr Ser Ser Ile Lys Lys Arg Gly Tyr Val
545                 550                 555                 560

Asp Arg Ala Val Pro Thr Gln Val Val Thr Leu Lys Thr Thr Lys Asn
                565                 570                 575

Arg Ser Leu Met Ser Ile Ala Thr Lys Ile Ala Ile Gln Leu Asn Cys
            580                 585                 590

Lys Leu Gly Tyr Thr Pro Trp Met Ile Glu Leu Pro Leu Ser Gly Leu
        595                 600                 605

Met Thr Ile Gly Phe Asp Ile Ala Lys Ser Thr Arg Asp Arg Lys Arg
    610                 615                 620

Ala Tyr Gly Ala Leu Ile Ala Ser Met Asp Leu Gln Gln Asn Ser Thr
625                 630                 635                 640

Tyr Phe Ser Thr Val Thr Glu Cys Ser Ala Phe Asp Val Leu Ala Asn
                645                 650                 655

Thr Leu Trp Pro Met Ile Ala Lys Ala Leu Arg Gln Tyr Gln His Glu
            660                 665                 670

His Arg Lys Leu Pro Ser Arg Ile Val Phe Tyr Arg Asp Gly Val Ser
        675                 680                 685

Ser Gly Ser Leu Lys Gln Leu Phe Glu Phe Glu Val Lys Asp Ile Ile
    690                 695                 700

Glu Lys Leu Lys Thr Glu Tyr Ala Arg Val Gln Leu Ser Pro Pro Gln
705                 710                 715                 720

Leu Ala Tyr Ile Val Val Thr Arg Ser Met Asn Thr Arg Phe Phe Leu
```

-continued

```
                    725                 730                 735
Asn Gly Gln Asn Pro Pro Gly Thr Ile Val Asp Asp Val Ile Thr
                740                 745                 750
Leu Pro Glu Arg Tyr Asp Phe Tyr Leu Val Ser Gln Gln Val Arg Gln
                755                 760                 765
Gly Thr Val Ser Pro Thr Ser Tyr Asn Val Leu Tyr Ser Ser Met Gly
            770                 775                 780
Xaa Ser Pro Glu Lys Met Gln Lys Leu Thr Tyr Lys Met Cys His Leu
785                 790                 795                 800
Tyr Tyr Asn Trp Ser Gly Thr Arg Val Pro Ala Val Cys Gln Tyr
                805                 810                 815
Ala Lys Lys Leu Ala Thr Leu Val Gly Thr Asn Leu His Ser Ile Pro
                820                 825                 830
Gln Asn Ala Leu Glu Lys Lys Phe Tyr Tyr Leu
            835                 840
```

<210> SEQ ID NO 3
<211> LENGTH: 4064
<212> TYPE: DNA
<213> ORGANISM: Mus sp.
<220> FEATURE:
<221> NAME/KEY: CDS
<222> LOCATION: (191)..(2776)
<221> NAME/KEY: misc_feature
<222> LOCATION: (458)
<223> OTHER INFORMATION: n=a or c, Xaa=Leu or Ile
<221> NAME/KEY: misc_feature
<222> LOCATION: (836)
<223> OTHER INFORMATION: n=a or c, Xaa=Leu or Ile
<221> NAME/KEY: misc_feature
<222> LOCATION: (1337)
<223> OTHER INFORMATION: n=a or c, Xaa=Leu or Ile
<221> NAME/KEY: misc_feature
<222> LOCATION: (2636)
<223> OTHER INFORMATION: n=a or c, Xaa=Leu or Ile

<400> SEQUENCE: 3

```
agaagcctgc tacagggggt ggcgtgagga gcctcaagga ctgcggacct aagcgtgcta      60
agcacggggc caggatagga ctggacgctg ctggaccacg acgatcaggg agtgaccccc     120
accagcatcc agcctgcggc agttgtagga ctggaaggag gccaagctga acacctgagc     180
tgactggaaa atg act ggc cga gcc cga gct cgg gcc cgc ggc agg gca        229
            Met Thr Gly Arg Ala Arg Ala Arg Ala Arg Gly Arg Ala
              1               5                  10 cga ggt cag gag acg gtg cag cat gtt ggg gct gct gcg agc cag caa       277
Arg Gly Gln Glu Thr Val Gln His Val Gly Ala Ala Ala Ser Gln Gln
     15                  20                  25 cct ggg tac atc cca ccg aga cct caa cag tcc ccc aca gag ggg gac       325
Pro Gly Tyr Ile Pro Pro Arg Pro Gln Gln Ser Pro Thr Glu Gly Asp
 30                  35                  40                  45 ttg gtt ggc cga gga cga cag agg ggg atg gta gtc gga gcc aca tcc       373
Leu Val Gly Arg Gly Arg Gln Arg Gly Met Val Val Gly Ala Thr Ser
             50                  55                  60 aag tca caa gaa ctg cag atc tca gct ggg ttt cag gag ctg tca ctg       421
Lys Ser Gln Glu Leu Gln Ile Ser Ala Gly Phe Gln Glu Leu Ser Leu
         65                  70                  75 gca gag aga gga ggg cgt cgc cga gac ttc cat gac ntt ggt gtg aac       469
Ala Glu Arg Gly Gly Arg Arg Arg Asp Phe His Asp Xaa Gly Val Asn
     80                  85                  90 acc aga cag aac ctt gac cat gtc aaa gag tca aag aca ggc tcc tct       517
Thr Arg Gln Asn Leu Asp His Val Lys Glu Ser Lys Thr Gly Ser Ser
 95                 100                 105
```

-continued

```
ggc atc att gtg aag ctg agc acc aac cac ttc cgg ctg acc tcg cgc        565
Gly Ile Ile Val Lys Leu Ser Thr Asn His Phe Arg Leu Thr Ser Arg
110             115                 120                 125 cca cag tgg gcc ctg tat cag tac cac atc gac tac aat ccc ctg atg        613
Pro Gln Trp Ala Leu Tyr Gln Tyr His Ile Asp Tyr Asn Pro Leu Met
                130                 135                 140 gag gcc cga agg ctt cgc tcc gca ctg ctc ttc cag cat gaa gac ctc        661
Glu Ala Arg Arg Leu Arg Ser Ala Leu Leu Phe Gln His Glu Asp Leu
            145                 150                 155 att gga agg tgt cat gct ttc gat ggg aca ata ttg ttt tta cct aag        709
Ile Gly Arg Cys His Ala Phe Asp Gly Thr Ile Leu Phe Leu Pro Lys
        160                 165                 170 aga cta cag cac aag gtc aca gaa gta ttc agt cag act cgg aat ggg        757
Arg Leu Gln His Lys Val Thr Glu Val Phe Ser Gln Thr Arg Asn Gly
    175                 180                 185 gaa cac gtg agg atc acc atc acc ctg acc aac gag ctg ccg ccc acc        805
Glu His Val Arg Ile Thr Ile Thr Leu Thr Asn Glu Leu Pro Pro Thr
190                 195                 200                 205 tcg ccc acc tgc ctg cag ttc tat aac atc ntc ttc agg agg ctc ttg        853
Ser Pro Thr Cys Leu Gln Phe Tyr Asn Ile Xaa Phe Arg Arg Leu Leu
                210                 215                 220 aaa atc atg aat ttg caa caa att gga cgg aat tat tac aat cca agt        901
Lys Ile Met Asn Leu Gln Gln Ile Gly Arg Asn Tyr Tyr Asn Pro Ser
            225                 230                 235 gac ccg att gat att cca aac cac agg ttg gtg atc tgg ccc ggc ttc        949
Asp Pro Ile Asp Ile Pro Asn His Arg Leu Val Ile Trp Pro Gly Phe
        240                 245                 250 acc acc tcc atc ctt cag tat gag aac aac atc atg ctc tgc aca gac        997
Thr Thr Ser Ile Leu Gln Tyr Glu Asn Asn Ile Met Leu Cys Thr Asp
    255                 260                 265 gtc agc cac aag gtg ctc cgc agc gag act gtc cta gac ttc atg ttc       1045
Val Ser His Lys Val Leu Arg Ser Glu Thr Val Leu Asp Phe Met Phe
270                 275                 280                 285 aat cta tac cag cag aca gag gag cac aag ttc cag gag caa gtg tcg       1093
Asn Leu Tyr Gln Gln Thr Glu Glu His Lys Phe Gln Glu Gln Val Ser
                290                 295                 300 aag gag ctc ata ggc ctc atc gtt ctc acc aag tac aat aac aag acc       1141
Lys Glu Leu Ile Gly Leu Ile Val Leu Thr Lys Tyr Asn Asn Lys Thr
            305                 310                 315 tac cgg gtg gat gac att gac tgg gac cag aat cca aag agc acc ttc       1189
Tyr Arg Val Asp Asp Ile Asp Trp Asp Gln Asn Pro Lys Ser Thr Phe
        320                 325                 330 aag aag gcg gat ggc tcg gag gtc agc ttc ctg gag tac tac agg aag       1237
Lys Lys Ala Asp Gly Ser Glu Val Ser Phe Leu Glu Tyr Tyr Arg Lys
    335                 340                 345 caa tac aac cag gag atc acg gac ctg aag cag ccg gtg ctg gtg agc       1285
Gln Tyr Asn Gln Glu Ile Thr Asp Leu Lys Gln Pro Val Leu Val Ser
350                 355                 360                 365 caa ccc aag cgg agg aga ggc ccc ggc ggc acc ctg cct ggc cca gct       1333
Gln Pro Lys Arg Arg Arg Gly Pro Gly Gly Thr Leu Pro Gly Pro Ala
                370                 375                 380 atg ntc atc cct gaa ctc tgc tat ctc aca ggc ctg act gat aaa atg       1381
Met Xaa Ile Pro Glu Leu Cys Tyr Leu Thr Gly Leu Thr Asp Lys Met
            385                 390                 395 cgc aat gat ttc aat gtg atg aag gac ctg gca gtg cac acg cgg ctg       1429
Arg Asn Asp Phe Asn Val Met Lys Asp Leu Ala Val His Thr Arg Leu
        400                 405                 410 acc cct gag cag cgg cag cgg gag gtg ggc cgc ctc atc gac tac atc       1477
Thr Pro Glu Gln Arg Gln Arg Glu Val Gly Arg Leu Ile Asp Tyr Ile
```

```
                    415                 420                 425
cac aag gat gac aat gtg cag aga gag ctt cga gac tgg ggc ctg agc    1525
His Lys Asp Asp Asn Val Gln Arg Glu Leu Arg Asp Trp Gly Leu Ser
430                 435                 440                 445 ttc gac tca aac ttg ctg tcc ttc tct gga aga atc tta caa tct gag    1573
Phe Asp Ser Asn Leu Leu Ser Phe Ser Gly Arg Ile Leu Gln Ser Glu
                450                 455                 460 aag atc cac cag ggc gga aag acg ttt gat tac aac cca caa ttt gca    1621
Lys Ile His Gln Gly Gly Lys Thr Phe Asp Tyr Asn Pro Gln Phe Ala
            465                 470                 475 gac tgg tcc aaa gaa aca aga ggc gcg ccg ctg atc agc gtg aag cca    1669
Asp Trp Ser Lys Glu Thr Arg Gly Ala Pro Leu Ile Ser Val Lys Pro
        480                 485                 490 ttg gat aac tgg ctg ctg atc tat acc cgc agg aat tat gaa gca gcc    1717
Leu Asp Asn Trp Leu Leu Ile Tyr Thr Arg Arg Asn Tyr Glu Ala Ala
    495                 500                 505 aac tca ctg ata cag aac ctg ttc aaa gtg act cca gcc atg ggc atc    1765
Asn Ser Leu Ile Gln Asn Leu Phe Lys Val Thr Pro Ala Met Gly Ile
510                 515                 520                 525 cag atg aaa aag gca atc atg atc gag gtg gat gac aga aca gaa gct    1813
Gln Met Lys Lys Ala Ile Met Ile Glu Val Asp Asp Arg Thr Glu Ala
                530                 535                 540 tat ctg aga gcc ttg cag cag aag gtg acg tca gac act cag ata gtt    1861
Tyr Leu Arg Ala Leu Gln Gln Lys Val Thr Ser Asp Thr Gln Ile Val
            545                 550                 555 gtc tgt ctc ttg tca agt aat cgg aag gac aaa tat gat gcc atc aag    1909
Val Cys Leu Leu Ser Ser Asn Arg Lys Asp Lys Tyr Asp Ala Ile Lys
        560                 565                 570 aag tac ttg tgt aca gac tgc ccc acc cca agt cag tgt gtg gtg gcc    1957
Lys Tyr Leu Cys Thr Asp Cys Pro Thr Pro Ser Gln Cys Val Val Ala
575                 580                 585 cgg acc ctg ggc aag cag caa aca gtc atg gcc att gcc acc aag atc    2005
Arg Thr Leu Gly Lys Gln Gln Thr Val Met Ala Ile Ala Thr Lys Ile
590                 595                 600                 605 gcc ctg cag atg aac tgc aag atg gga ggc gag ctc tgg cgg gtg gac    2053
Ala Leu Gln Met Asn Cys Lys Met Gly Gly Glu Leu Trp Arg Val Asp
                610                 615                 620 atg gcc ctg aaa ctg gca atg atc gtg ggc atc gac tgt tac cat gac    2101
Met Ala Leu Lys Leu Ala Met Ile Val Gly Ile Asp Cys Tyr His Asp
            625                 630                 635 acc aca gct ggg cgg agg tcc atc gca gga ttc gtc gcc agc atc aat    2149
Thr Thr Ala Gly Arg Arg Ser Ile Ala Gly Phe Val Ala Ser Ile Asn
        640                 645                 650 gaa ggg atg acc cgc tgg ttc tcc cgc tgc gtc ttt cag gac cgc ggg    2197
Glu Gly Met Thr Arg Trp Phe Ser Arg Cys Val Phe Gln Asp Arg Gly
    655                 660                 665 cag gag ctg gtg gat ggt ctc aag gtg tgc ttg caa gct gct ctg agg    2245
Gln Glu Leu Val Asp Gly Leu Lys Val Cys Leu Gln Ala Ala Leu Arg
670                 675                 680                 685 gct tgg agt ggc tgc aat gaa tac atg ccc agc cgt gtc atc gtg tac    2293
Ala Trp Ser Gly Cys Asn Glu Tyr Met Pro Ser Arg Val Ile Val Tyr
                690                 695                 700 cga gac ggt gtg ggg gac ggg cag ctg aag acc ctg gtc aat tat gag    2341
Arg Asp Gly Val Gly Asp Gly Gln Leu Lys Thr Leu Val Asn Tyr Glu
            705                 710                 715 gtc cca cag ttc cta gat tgc ctc aag tca gtc ggg aga ggt tac aac    2389
Val Pro Gln Phe Leu Asp Cys Leu Lys Ser Val Gly Arg Gly Tyr Asn
        720                 725                 730 cca aga ctg act gta atc gtg gtg aag aag cgt gtc aat gcc agg ttt    2437
```

```
Pro Arg Leu Thr Val Ile Val Val Lys Lys Arg Val Asn Ala Arg Phe
    735                 740                 745 ttt gct cag tct ggg gga aga ctt cag aac cct ctt cca ggg aca gtc    2485
Phe Ala Gln Ser Gly Gly Arg Leu Gln Asn Pro Leu Pro Gly Thr Val
750                 755                 760                 765 atc gat gtg gaa gtc acc aga cca gag tgg tat gac ttt ttc atc gtg    2533
Ile Asp Val Glu Val Thr Arg Pro Glu Trp Tyr Asp Phe Phe Ile Val
                770                 775                 780 agc cag gca gtg aga agc ggg agt gtg tcc aca cac tac aat gtc        2581
Ser Gln Ala Val Arg Ser Gly Ser Val Ser Pro Thr His Tyr Asn Val
            785                 790                 795 atc tat gac agc agt ggc ctg aag ccc gac cac atc cag cgg ctg aca    2629
Ile Tyr Asp Ser Ser Gly Leu Lys Pro Asp His Ile Gln Arg Leu Thr
        800                 805                 810 tac aag ntc tgc cac gtg tac tat aat tgg cct gga gtc atc cga gtc    2677
Tyr Lys Xaa Cys His Val Tyr Tyr Asn Trp Pro Gly Val Ile Arg Val
    815                 820                 825 cct gca cct tgc cag tat gca cac aag ctg gcc ttc ctc gtg ggc cag    2725
Pro Ala Pro Cys Gln Tyr Ala His Lys Leu Ala Phe Leu Val Gly Gln
830                 835                 840                 845 agc atc cac aga gag cca aac ctc tcc ctg tcc aac cgc ctc tac tac    2773
Ser Ile His Arg Glu Pro Asn Leu Ser Leu Ser Asn Arg Leu Tyr Tyr
                850                 855                 860 ctc taaccagcag cgagggccgg catgctggtt tccttcagag ctctgcccaa         2826
Leu tccttcagtt ctatttttca taggatgagg ttctagcggg atgttggggg tagggggttgg  2886 gggccgctgt tttgttttgt tttgttttta gttgttggtg tgtagcggct atagagttaa  2946
ctaaggctta tgtttgcttt gtttctcatg gtgtgttgtg acagtttgct tggcagagtg  3006
gtggcaaggg ccgtggtacc acagatagac tttcctaaag cagccgtgtt ggcaggttct  3066
tggaggtgct cctgggagca cctcctattg tacgctgctc tctctctctc tctctctctc  3126
tctctctctc tctctctctc tctctctctc tgcatgtttg aatttaaaag aggaaaggac  3186
acaaggcaag aatgcccaga gcatcctaga tgggtgctat atgggactct gacacctcag  3246
gttcttaaag ataaaaaggc cagaggtacc tttctgtaat tcttttaaga gttaggtcat  3306
aaggaatgaa aagagttact tttctccctc catgaaagtg ttttttaaga ctgacaaggc  3366
cggtggtgga gtgagtgttg ttgttttgtt tcgcaatttt cttaccaagt gaaattactg  3426
accataattt tatttaatag ttttttagttt ttgaaagcct gtgttttctt tgcttttaaa  3486
ctacaggcga ccactctggg ataggattcc actcccaaaa gtaatgtgtt gggtgtggtg  3546
gcacacgcct gtgatctcag gactcaggag gtgaagccag gggaacccca agttcccggt  3606
cagcctaggc tacatagtga gactttgtct taacaaacag aaaaaaagaa aaagaaagaa  3666
aaaaaaaaga aagaaaaaaa aaraaagaaa aatggagcag tatgagttat gggtgccagt  3726
ttctgcagga gactttggga gtaagagctg cctctgttcc taagaggctg caaggctgcg  3786 gctgggggggc cagttcaggt gccaggtgag gtacggccac atctatttgc ctggctcttt  3846
gacaaagaga gcagcttaga gtggctagag tgtgatgagt tttacacaat ggcgatgtgt  3906
gtgtgtgccc ctggcacagc tcaataaagt ttctgtctca ctttaaaaaa aaaaaaaaa   3966 aaaaaaaaaa aaaaaaaaa aaaaaaaaaa aaaaaaaaaa aaaaaaaaaa aaaaaaaaaa   4026
aaaaaaaaaa aaaaaaaaa aaaaaaaaaa aaaaaaa                            4064
```

<210> SEQ ID NO 4
<211> LENGTH: 862

-continued

```
<212> TYPE: PRT
<213> ORGANISM: Mus sp.
<220> FEATURE:
<221> NAME/KEY: misc_feature
<222> LOCATION: (90)
<223> OTHER INFORMATION: Xaa=Leu or Ile
<221> NAME/KEY: misc_feature
<222> LOCATION: (216)
<223> OTHER INFORMATION: Xaa=Leu or Ile
<221> NAME/KEY: misc_feature
<222> LOCATION: (383)
<223> OTHER INFORMATION: Xaa=Leu or Ile
<221> NAME/KEY: misc_feature
<222> LOCATION: (816)
<223> OTHER INFORMATION: Xaa=Leu or Ile

<400> SEQUENCE: 4

Met Thr Gly Arg Ala Arg Ala Arg Ala Arg Gly Arg Ala Arg Gly Gln
 1               5                  10                  15

Glu Thr Val Gln His Val Gly Ala Ala Ala Ser Gln Gln Pro Gly Tyr
            20                  25                  30

Ile Pro Pro Arg Pro Gln Gln Ser Pro Thr Glu Gly Asp Leu Val Gly
        35                  40                  45

Arg Gly Arg Gln Arg Gly Met Val Val Gly Ala Thr Ser Lys Ser Gln
    50                  55                  60

Glu Leu Gln Ile Ser Ala Gly Phe Gln Glu Leu Ser Leu Ala Glu Arg
 65                  70                  75                  80

Gly Gly Arg Arg Arg Asp Phe His Asp Xaa Gly Val Asn Thr Arg Gln
                85                  90                  95

Asn Leu Asp His Val Lys Glu Ser Lys Thr Gly Ser Ser Gly Ile Ile
            100                 105                 110

Val Lys Leu Ser Thr Asn His Phe Arg Leu Thr Ser Arg Pro Gln Trp
        115                 120                 125

Ala Leu Tyr Gln Tyr His Ile Asp Tyr Asn Pro Leu Met Glu Ala Arg
    130                 135                 140

Arg Leu Arg Ser Ala Leu Leu Phe Gln His Glu Asp Leu Ile Gly Arg
145                 150                 155                 160

Cys His Ala Phe Asp Gly Thr Ile Leu Phe Leu Pro Lys Arg Leu Gln
                165                 170                 175

His Lys Val Thr Glu Val Phe Ser Gln Thr Arg Asn Gly Glu His Val
            180                 185                 190

Arg Ile Thr Ile Thr Leu Thr Asn Glu Leu Pro Pro Thr Ser Pro Thr
        195                 200                 205

Cys Leu Gln Phe Tyr Asn Ile Xaa Phe Arg Arg Leu Leu Lys Ile Met
    210                 215                 220

Asn Leu Gln Gln Ile Gly Arg Asn Tyr Tyr Asn Pro Ser Asp Pro Ile
225                 230                 235                 240

Asp Ile Pro Asn His Arg Leu Val Ile Trp Pro Gly Phe Thr Thr Ser
                245                 250                 255

Ile Leu Gln Tyr Glu Asn Asn Ile Met Leu Cys Thr Asp Val Ser His
            260                 265                 270

Lys Val Leu Arg Ser Glu Thr Val Leu Asp Phe Met Phe Asn Leu Tyr
        275                 280                 285

Gln Gln Thr Glu Glu His Lys Phe Gln Glu Gln Val Ser Lys Glu Leu
    290                 295                 300

Ile Gly Leu Ile Val Leu Thr Lys Tyr Asn Asn Lys Thr Tyr Arg Val
305                 310                 315                 320

Asp Asp Ile Asp Trp Asp Gln Asn Pro Lys Ser Thr Phe Lys Lys Ala
```

```
                325                 330                 335
Asp Gly Ser Glu Val Ser Phe Leu Glu Tyr Tyr Arg Lys Gln Tyr Asn
                340                 345                 350
Gln Glu Ile Thr Asp Leu Lys Gln Pro Val Leu Val Ser Gln Pro Lys
                355                 360                 365
Arg Arg Arg Gly Pro Gly Thr Leu Pro Gly Pro Ala Met Xaa Ile
            370                 375                 380
Pro Glu Leu Cys Tyr Leu Thr Gly Leu Thr Asp Lys Met Arg Asn Asp
385                 390                 395                 400
Phe Asn Val Met Lys Asp Leu Ala Val His Thr Arg Leu Thr Pro Glu
                405                 410                 415
Gln Arg Gln Arg Glu Val Gly Arg Leu Ile Asp Tyr Ile His Lys Asp
                420                 425                 430
Asp Asn Val Gln Arg Glu Leu Arg Asp Trp Gly Leu Ser Phe Asp Ser
                435                 440                 445
Asn Leu Leu Ser Phe Ser Gly Arg Ile Leu Gln Ser Glu Lys Ile His
        450                 455                 460
Gln Gly Gly Lys Thr Phe Asp Tyr Asn Pro Gln Phe Ala Asp Trp Ser
465                 470                 475                 480
Lys Glu Thr Arg Gly Ala Pro Leu Ile Ser Val Lys Pro Leu Asp Asn
                485                 490                 495
Trp Leu Leu Ile Tyr Thr Arg Arg Asn Tyr Glu Ala Ala Asn Ser Leu
                500                 505                 510
Ile Gln Asn Leu Phe Lys Val Thr Pro Ala Met Gly Ile Gln Met Lys
        515                 520                 525
Lys Ala Ile Met Ile Glu Val Asp Asp Arg Thr Glu Ala Tyr Leu Arg
530                 535                 540
Ala Leu Gln Gln Lys Val Thr Ser Asp Thr Gln Ile Val Val Cys Leu
545                 550                 555                 560
Leu Ser Ser Asn Arg Lys Asp Lys Tyr Asp Ala Ile Lys Lys Tyr Leu
                565                 570                 575
Cys Thr Asp Cys Pro Thr Pro Ser Gln Cys Val Val Ala Arg Thr Leu
                580                 585                 590
Gly Lys Gln Gln Thr Val Met Ala Ile Ala Thr Lys Ile Ala Leu Gln
        595                 600                 605
Met Asn Cys Lys Met Gly Gly Glu Leu Trp Arg Val Asp Met Ala Leu
                610                 615                 620
Lys Leu Ala Met Ile Val Gly Ile Asp Cys Tyr His Asp Thr Thr Ala
625                 630                 635                 640
Gly Arg Arg Ser Ile Ala Gly Phe Val Ala Ser Ile Asn Glu Gly Met
                645                 650                 655
Thr Arg Trp Phe Ser Arg Cys Val Phe Gln Asp Arg Gly Gln Glu Leu
                660                 665                 670
Val Asp Gly Leu Lys Val Cys Leu Gln Ala Ala Leu Arg Ala Trp Ser
                675                 680                 685
Gly Cys Asn Glu Tyr Met Pro Ser Arg Val Ile Val Tyr Arg Asp Gly
                690                 695                 700
Val Gly Asp Gly Gln Leu Lys Thr Leu Val Asn Tyr Glu Val Pro Gln
705                 710                 715                 720
Phe Leu Asp Cys Leu Lys Ser Val Gly Arg Gly Tyr Asn Pro Arg Leu
                725                 730                 735
Thr Val Ile Val Val Lys Lys Arg Val Asn Ala Arg Phe Phe Ala Gln
                740                 745                 750
```

```
Ser Gly Gly Arg Leu Gln Asn Pro Leu Pro Gly Thr Val Ile Asp Val
        755                 760                 765

Glu Val Thr Arg Pro Glu Trp Tyr Asp Phe Phe Ile Val Ser Gln Ala
    770                 775                 780

Val Arg Ser Gly Ser Val Ser Pro Thr His Tyr Asn Val Ile Tyr Asp
785                 790                 795                 800

Ser Ser Gly Leu Lys Pro Asp His Ile Gln Arg Leu Thr Tyr Lys Xaa
                805                 810                 815

Cys His Val Tyr Tyr Asn Trp Pro Gly Val Ile Arg Val Pro Ala Pro
                820                 825                 830

Cys Gln Tyr Ala His Lys Leu Ala Phe Leu Val Gly Gln Ser Ile His
                835                 840                 845

Arg Glu Pro Asn Leu Ser Leu Ser Asn Arg Leu Tyr Tyr Leu
                850                 855                 860

<210> SEQ ID NO 5
<211> LENGTH: 3472
<212> TYPE: DNA
<213> ORGANISM: Homo sapiens
<220> FEATURE:
<221> NAME/KEY: CDS
<222> LOCATION: (167)..(2749)
<221> NAME/KEY: misc_feature
<222> LOCATION: (392)
<223> OTHER INFORMATION: n=t or a, Xaa=Leu or Ile
<221> NAME/KEY: misc_feature
<222> LOCATION: (1073)
<223> OTHER INFORMATION: n=c or a, Xaa=Leu or Ile
<221> NAME/KEY: misc_feature
<222> LOCATION: (2369)
<223> OTHER INFORMATION: n=c or a, Xaa=Leu or Ile

<400> SEQUENCE: 5
gggcgaattg ggcccgacgt cgcatgctcc cggccgccat ggcggccgcg ggaattcgat     60
tccatcctaa tacgactcac tatagggctc gagcggccgc ccgggcaggt ctgaggtgca    120
aggaccagga ctagggcgag ggcagcggtc caagaaatag aaaaca atg act ggg       175
                                                 Met Thr Gly
                                                   1 aga gcc cga gcc aga gcc aga gga agg gcc cgc ggt cag gag aca gcg     223
Arg Ala Arg Ala Arg Ala Arg Gly Arg Ala Arg Gly Gln Glu Thr Ala
  5                  10                  15 cag ctg gtg ggc tcc act gcc agt cag caa cct ggt tat att cag cct     271
Gln Leu Val Gly Ser Thr Ala Ser Gln Gln Pro Gly Tyr Ile Gln Pro
 20                  25                  30                  35 agg cct cag ccg cca cca gca gag ggg gaa tta ttt ggc cgt gga cgg     319
Arg Pro Gln Pro Pro Pro Ala Glu Gly Glu Leu Phe Gly Arg Gly Arg
                 40                  45                  50 cag aga gga aca gca gga gga aca gcc aag tca caa gga ctc cag ata     367
Gln Arg Gly Thr Ala Gly Gly Thr Ala Lys Ser Gln Gly Leu Gln Ile
         55                  60                  65 tct gct gga ttt cag gag tta tcg nta gca gag aga gga ggt cgt cgt     415
Ser Ala Gly Phe Gln Glu Leu Ser Xaa Ala Glu Arg Gly Gly Arg Arg
     70                  75                  80 aga gat ttt cat gat ctt ggt gtg aat aca agg cag aac cta gac cat     463
Arg Asp Phe His Asp Leu Gly Val Asn Thr Arg Gln Asn Leu Asp His
 85                  90                  95 gtt aaa gaa tca aaa aca ggt tct tca ggc att ata gta agg tta agc     511
Val Lys Glu Ser Lys Thr Gly Ser Ser Gly Ile Ile Val Arg Leu Ser
100                 105                 110                 115 act aac cat ttc cgg ctg aca tcc cgt ccc cag tgg gcc tta tat cag    559
```

```
                Thr Asn His Phe Arg Leu Thr Ser Arg Pro Gln Trp Ala Leu Tyr Gln
                            120                 125                 130 tat cac att gac tat aac cca ctg atg gaa gcc aga aga ctc cgt tca              607
Tyr His Ile Asp Tyr Asn Pro Leu Met Glu Ala Arg Arg Leu Arg Ser
            135                 140                 145 gct ctt ctt ttt caa cac gaa gat cta att gga aag tgt cat gct ttt              655
Ala Leu Leu Phe Gln His Glu Asp Leu Ile Gly Lys Cys His Ala Phe
            150                 155                 160 gat gga acg ata tta ttt tta cct aaa aga cta cag caa aag gtt act              703
Asp Gly Thr Ile Leu Phe Leu Pro Lys Arg Leu Gln Gln Lys Val Thr
165                 170                 175 gaa gtt ttt agt aag acc cgg aat gga gag gat gtg agg ata acg atc              751
Glu Val Phe Ser Lys Thr Arg Asn Gly Glu Asp Val Arg Ile Thr Ile
180                 185                 190                 195 act tta aca aat gaa ctt cca cct aca tca cca act tgt ttg cag ttc              799
Thr Leu Thr Asn Glu Leu Pro Pro Thr Ser Pro Thr Cys Leu Gln Phe
            200                 205                 210 tat aat att att ttc agg agg ctt ttg aaa atc atg aat ttg caa caa              847
Tyr Asn Ile Ile Phe Arg Arg Leu Leu Lys Ile Met Asn Leu Gln Gln
            215                 220                 225 att gga cga aat tat tat aac cca aat gac cca att gat att cca agt              895
Ile Gly Arg Asn Tyr Tyr Asn Pro Asn Asp Pro Ile Asp Ile Pro Ser
            230                 235                 240 cac agg ttg gtg att tgg cct ggc ttc act act tcc atc ctt cag tat              943
His Arg Leu Val Ile Trp Pro Gly Phe Thr Thr Ser Ile Leu Gln Tyr
            245                 250                 255 gaa aac agc atc atg ctc tgc act gac gtt agc cat aaa gtc ctt cga              991
Glu Asn Ser Ile Met Leu Cys Thr Asp Val Ser His Lys Val Leu Arg
260                 265                 270                 275 agt gag act gtt ttg gat ttc atg ttc aac ttt tat cat cag aca gaa             1039
Ser Glu Thr Val Leu Asp Phe Met Phe Asn Phe Tyr His Gln Thr Glu
                280                 285                 290 gaa cat aaa ttt caa gaa caa gtt tcc aaa gaa nta ata ggt tta gtt             1087
Glu His Lys Phe Gln Glu Gln Val Ser Lys Glu Xaa Ile Gly Leu Val
            295                 300                 305 gtt ctt acc aag tat aac att aag aca tac aga gtg gat gat att gac             1135
Val Leu Thr Lys Tyr Asn Ile Lys Thr Tyr Arg Val Asp Asp Ile Asp
            310                 315                 320 tgg gac cag aat ccc aag agc acc ttt aag aaa gcc gac ggc tct ggg             1183
Trp Asp Gln Asn Pro Lys Ser Thr Phe Lys Lys Ala Asp Gly Ser Gly
325                 330                 335 gtc agc ttc tta gaa tac tac agg aag caa tac aac caa gag atc acc             1231
Val Ser Phe Leu Glu Tyr Tyr Arg Lys Gln Tyr Asn Gln Glu Ile Thr
340                 345                 350                 355 gac ttg aag cag cct gtc ttg gtc agc cag ccc aag aga agg cgg ggc             1279
Asp Leu Lys Gln Pro Val Leu Val Ser Gln Pro Lys Arg Arg Arg Gly
                360                 365                 370 cct ggg ggg aca ctg cca ggg cct gcc atg ctc att cct gag ctc tgc             1327
Pro Gly Gly Thr Leu Pro Gly Pro Ala Met Leu Ile Pro Glu Leu Cys
            375                 380                 385 tat ctt aca ggt cta act gat aaa atg cgt aat gat ttt aac gtg atg             1375
Tyr Leu Thr Gly Leu Thr Asp Lys Met Arg Asn Asp Phe Asn Val Met
            390                 395                 400 aaa gac tta gcc gtt cat aca aga cta act cca gag caa agg cag cgt             1423
Lys Asp Leu Ala Val His Thr Arg Leu Thr Pro Glu Gln Arg Gln Arg
405                 410                 415 gaa gtg gga cga ctc att gat tac att cat aaa aac gat aat gtt caa             1471
Glu Val Gly Arg Leu Ile Asp Tyr Ile His Lys Asn Asp Asn Val Gln
420                 425                 430                 435
```

```
agg gag ctt cga gac tgg ggt ttg agc ttt gat tcc aac tta ctg tcc    1519
Arg Glu Leu Arg Asp Trp Gly Leu Ser Phe Asp Ser Asn Leu Leu Ser
                440                 445                 450 ttc tca gga aga att ttg caa aca gaa aag att cac caa ggt gga aaa    1567
Phe Ser Gly Arg Ile Leu Gln Thr Glu Lys Ile His Gln Gly Gly Lys
            455                 460                 465 aca ttt gat tac aat cca caa ttt gca gat tgg tcc aaa gaa aca aga    1615
Thr Phe Asp Tyr Asn Pro Gln Phe Ala Asp Trp Ser Lys Glu Thr Arg
        470                 475                 480 ggt gca cca tta att agt gtt aag cca cta gat aac tgg ctg ttg atc    1663
Gly Ala Pro Leu Ile Ser Val Lys Pro Leu Asp Asn Trp Leu Leu Ile
    485                 490                 495 tat acg cga aga aat tat gaa gca gcc aat tca ttg ata caa aat cta    1711
Tyr Thr Arg Arg Asn Tyr Glu Ala Ala Asn Ser Leu Ile Gln Asn Leu
500                 505                 510                 515 ttt aaa gtt aca cca gcc atg ggc atg caa atg aga aaa gca ata atg    1759
Phe Lys Val Thr Pro Ala Met Gly Met Gln Met Arg Lys Ala Ile Met
            520                 525                 530 att gaa gtg gat gac aga act gaa gcc tac tta aga gtc tta cag caa    1807
Ile Glu Val Asp Asp Arg Thr Glu Ala Tyr Leu Arg Val Leu Gln Gln
        535                 540                 545 aag gtc aca gca gac acc cag ata gtt gtc tgt ctg ttg tca agt aat    1855
Lys Val Thr Ala Asp Thr Gln Ile Val Val Cys Leu Leu Ser Ser Asn
    550                 555                 560 cgg aag gac aaa tac gat gct att aaa aaa tac ctg tgt aca gat tgc    1903
Arg Lys Asp Lys Tyr Asp Ala Ile Lys Lys Tyr Leu Cys Thr Asp Cys
565                 570                 575 cct acc cca agt cag tgt gtg gtg gcc cga acc tta ggc aaa cag caa    1951
Pro Thr Pro Ser Gln Cys Val Val Ala Arg Thr Leu Gly Lys Gln Gln
580                 585                 590                 595 act gtc atg gcc att gct aca aag att gcc cta cag atg aac tgc aag    1999
Thr Val Met Ala Ile Ala Thr Lys Ile Ala Leu Gln Met Asn Cys Lys
            600                 605                 610 atg gga gga gag ctc tgg agg gtg gac atc ccc ctg aag ctc gtg atg    2047
Met Gly Gly Glu Leu Trp Arg Val Asp Ile Pro Leu Lys Leu Val Met
        615                 620                 625 atc gtt ggc atc gat tgt tac cat gac atg aca gct ggg cgg agg tca    2095
Ile Val Gly Ile Asp Cys Tyr His Asp Met Thr Ala Gly Arg Arg Ser
    630                 635                 640 atc gca gga ttt gtt gcc agc atc aat gaa ggg atg acc cgc tgg ttc    2143
Ile Ala Gly Phe Val Ala Ser Ile Asn Glu Gly Met Thr Arg Trp Phe
645                 650                 655 tca cgc tgc ata ttt cag gat aga gga cag gag ctg gta gat ggg ctc    2191
Ser Arg Cys Ile Phe Gln Asp Arg Gly Gln Glu Leu Val Asp Gly Leu
660                 665                 670                 675 aaa gtc tgc ctg caa gcg gct ctg agg gct tgg aat agc tgc aat gag    2239
Lys Val Cys Leu Gln Ala Ala Leu Arg Ala Trp Asn Ser Cys Asn Glu
            680                 685                 690 tac atg ccc agc cgg atc atc gtg tac cgc gat ggc gta gga gac ggc    2287
Tyr Met Pro Ser Arg Ile Ile Val Tyr Arg Asp Gly Val Gly Asp Gly
        695                 700                 705 cag ctg aaa aca ctg gtg aac tac gaa gtc cca cag ttt ttg gat tgt    2335
Gln Leu Lys Thr Leu Val Asn Tyr Glu Val Pro Gln Phe Leu Asp Cys
    710                 715                 720 cta aaa tcc att ggt aga ggt tac aac cct aga nta acg gta att gtg    2383
Leu Lys Ser Ile Gly Arg Gly Tyr Asn Pro Arg Xaa Thr Val Ile Val
725                 730                 735 gtg aag aaa aga gtg aac acc aga ttt ttt gct cag tct gga gga aga    2431
Val Lys Lys Arg Val Asn Thr Arg Phe Phe Ala Gln Ser Gly Gly Arg
740                 745                 750                 755
```

-continued

| | | |
|---|---|---|
| ctt cag aat cca ctt cct gga aca gtt att gat gta gag gtt acc aga<br>Leu Gln Asn Pro Leu Pro Gly Thr Val Ile Asp Val Glu Val Thr Arg<br>                760                      765                    770 | 2479 |
| cca gaa tgg tat gac ttt ttt atc gtg agc cag gct gtg aga agt ggt<br>Pro Glu Trp Tyr Asp Phe Phe Ile Val Ser Gln Ala Val Arg Ser Gly<br>   775                        780                        785 | 2527 |
| agt gtt tct ccc aca cat tac aat gtc atc tat gac aac agc ggc ctg<br>Ser Val Ser Pro Thr His Tyr Asn Val Ile Tyr Asp Asn Ser Gly Leu<br>        790                        795                      800 | 2575 |
| aag cca gac cac ata cag cgc ttg acc tac aag ctg tgc cac atc tat<br>Lys Pro Asp His Ile Gln Arg Leu Thr Tyr Lys Leu Cys His Ile Tyr<br>805                        810                      815 | 2623 |
| tac aac tgg cca ggt gtc att cgt gtt cct gct cct tgc cag tac gcc<br>Tyr Asn Trp Pro Gly Val Ile Arg Val Pro Ala Pro Cys Gln Tyr Ala<br>820                        825                      830                      835 | 2671 |
| cac aag ctg gct ttt ctt gtt ggc cag agt att cac aga gag cca aat<br>His Lys Leu Ala Phe Leu Val Gly Gln Ser Ile His Arg Glu Pro Asn<br>                840                      845                      850 | 2719 |
| ctg tca ctg tca aac cgc ctt tac tac ctc taacctgcag aagacgatgc<br>Leu Ser Leu Ser Asn Arg Leu Tyr Tyr Leu<br>                855                      860 | 2769 |
| agccgctttt cttttgaaa tgactttggg atttttttaa gcttttattt acttttttt | 2829 |
| taactgttat ctttctggat gaaacttggg aaggggatta ggagatctag cattttattt | 2889 |
| ctagcattgc tattcaccgg cttccttatt ttatatgtaa aaattaagat tttatatttt | 2949 |
| atcttcttgt ttctcataga tattttgtga gcatttttt gtttattttg aagaaatgtg | 3009 |
| gataagatac ttggtagtat aaaacagact ctctgagagt atttgaaatg tgtttggaga | 3069 |
| tttacttaaa cgtactttca ggagtgagca agtcctactt ataaacctat attaacttta | 3129 |
| tttttgagat acctgttttg aatttaaagg agataagagg cgtaaagtag gatgctcact | 3189 |
| acaaccatag gtgggtttc agctcatatc ttaaagataa aaggtactat tatataacct | 3249 |
| atacacaaga tacaggagaa aatatgcttg atttttattt ggcagggggg ctaggttgta | 3309 |
| tgggagtaaa aaaaacattg aaaattttta aattgtccaa agaaacattt taagactctt | 3369 |
| taacaaaaaa ggccatgagt aaatctctat attaacatca ctatttattt tgttttggaa | 3429 |
| ctgggacatg attctatttg ttataaaata aaattgatgt ccc | 3472 |

<210> SEQ ID NO 6
<211> LENGTH: 861
<212> TYPE: PRT
<213> ORGANISM: Homo sapiens
<220> FEATURE:
<221> NAME/KEY: misc_feature
<222> LOCATION: (76)
<223> OTHER INFORMATION: Xaa=Leu or Ile
<221> NAME/KEY: misc_feature
<222> LOCATION: (303)
<223> OTHER INFORMATION: Xaa=Leu or Ile
<221> NAME/KEY: misc_feature
<222> LOCATION: (735)
<223> OTHER INFORMATION: Xaa=Leu or Ile

<400> SEQUENCE: 6

Met Thr Gly Arg Ala Arg Ala Arg Ala Arg Gly Arg Ala Arg Gly Gln
1               5                   10                  15

Glu Thr Ala Gln Leu Val Gly Ser Thr Ala Ser Gln Gln Pro Gly Tyr
            20                  25                  30

Ile Gln Pro Arg Pro Gln Pro Pro Ala Glu Gly Glu Leu Phe Gly
        35                  40                  45

```
Arg Gly Arg Gln Arg Gly Thr Ala Gly Thr Ala Lys Ser Gln Gly
     50                  55                  60

Leu Gln Ile Ser Ala Gly Phe Gln Glu Leu Ser Xaa Ala Glu Arg Gly
 65                  70                  75                  80

Gly Arg Arg Arg Asp Phe His Asp Leu Gly Val Asn Thr Arg Gln Asn
                 85                  90                  95

Leu Asp His Val Lys Glu Ser Lys Thr Gly Ser Ser Gly Ile Ile Val
                100                 105                 110

Arg Leu Ser Thr Asn His Phe Arg Leu Thr Ser Arg Pro Gln Trp Ala
            115                 120                 125

Leu Tyr Gln Tyr His Ile Asp Tyr Asn Pro Leu Met Glu Ala Arg Arg
        130                 135                 140

Leu Arg Ser Ala Leu Leu Phe Gln His Glu Asp Leu Ile Gly Lys Cys
145                 150                 155                 160

His Ala Phe Asp Gly Thr Ile Leu Phe Leu Pro Lys Arg Leu Gln Gln
                165                 170                 175

Lys Val Thr Glu Val Phe Ser Lys Thr Arg Asn Gly Glu Asp Val Arg
                180                 185                 190

Ile Thr Ile Thr Leu Thr Asn Glu Leu Pro Pro Thr Ser Pro Thr Cys
            195                 200                 205

Leu Gln Phe Tyr Asn Ile Ile Phe Arg Arg Leu Leu Lys Ile Met Asn
        210                 215                 220

Leu Gln Gln Ile Gly Arg Asn Tyr Tyr Asn Pro Asn Asp Pro Ile Asp
225                 230                 235                 240

Ile Pro Ser His Arg Leu Val Ile Trp Pro Gly Phe Thr Thr Ser Ile
                245                 250                 255

Leu Gln Tyr Glu Asn Ser Ile Met Leu Cys Thr Asp Val Ser His Lys
                260                 265                 270

Val Leu Arg Ser Glu Thr Val Leu Asp Phe Met Phe Asn Phe Tyr His
            275                 280                 285

Gln Thr Glu Glu His Lys Phe Gln Glu Gln Val Ser Lys Glu Xaa Ile
        290                 295                 300

Gly Leu Val Val Leu Thr Lys Tyr Asn Ile Lys Thr Tyr Arg Val Asp
305                 310                 315                 320

Asp Ile Asp Trp Asp Gln Asn Pro Lys Ser Thr Phe Lys Lys Ala Asp
                325                 330                 335

Gly Ser Gly Val Ser Phe Leu Glu Tyr Tyr Arg Lys Gln Tyr Asn Gln
                340                 345                 350

Glu Ile Thr Asp Leu Lys Gln Pro Val Leu Val Ser Gln Pro Lys Arg
            355                 360                 365

Arg Arg Gly Pro Gly Gly Thr Leu Pro Gly Pro Ala Met Leu Ile Pro
        370                 375                 380

Glu Leu Cys Tyr Leu Thr Gly Leu Thr Asp Lys Met Arg Asn Asp Phe
385                 390                 395                 400

Asn Val Met Lys Asp Leu Ala Val His Thr Arg Leu Thr Pro Glu Gln
                405                 410                 415

Arg Gln Arg Glu Val Gly Arg Leu Ile Asp Tyr Ile His Lys Asn Asp
                420                 425                 430

Asn Val Gln Arg Glu Leu Arg Asp Trp Gly Leu Ser Phe Asp Ser Asn
            435                 440                 445

Leu Leu Ser Phe Ser Gly Arg Ile Leu Gln Thr Glu Lys Ile His Gln
450                 455                 460
```

Gly Gly Lys Thr Phe Asp Tyr Asn Pro Gln Phe Ala Asp Trp Ser Lys
465                 470                 475                 480

Glu Thr Arg Gly Ala Pro Leu Ile Ser Val Lys Pro Leu Asp Asn Trp
            485                 490                 495

Leu Leu Ile Tyr Thr Arg Arg Asn Tyr Glu Ala Ala Asn Ser Leu Ile
                500                 505                 510

Gln Asn Leu Phe Lys Val Thr Pro Ala Met Gly Met Gln Met Arg Lys
            515                 520                 525

Ala Ile Met Ile Glu Val Asp Asp Arg Thr Glu Ala Tyr Leu Arg Val
530                 535                 540

Leu Gln Gln Lys Val Thr Ala Asp Thr Gln Ile Val Val Cys Leu Leu
545                 550                 555                 560

Ser Ser Asn Arg Lys Asp Lys Tyr Asp Ala Ile Lys Lys Tyr Leu Cys
            565                 570                 575

Thr Asp Cys Pro Thr Pro Ser Gln Cys Val Val Ala Arg Thr Leu Gly
            580                 585                 590

Lys Gln Gln Thr Val Met Ala Ile Ala Thr Lys Ile Ala Leu Gln Met
            595                 600                 605

Asn Cys Lys Met Gly Gly Glu Leu Trp Arg Val Asp Ile Pro Leu Lys
610                 615                 620

Leu Val Met Ile Val Gly Ile Asp Cys Tyr His Asp Met Thr Ala Gly
625                 630                 635                 640

Arg Arg Ser Ile Ala Gly Phe Val Ala Ser Ile Asn Glu Gly Met Thr
            645                 650                 655

Arg Trp Phe Ser Arg Cys Ile Phe Gln Asp Arg Gly Gln Glu Leu Val
            660                 665                 670

Asp Gly Leu Lys Val Cys Leu Gln Ala Ala Leu Arg Ala Trp Asn Ser
            675                 680                 685

Cys Asn Glu Tyr Met Pro Ser Arg Ile Ile Val Tyr Arg Asp Gly Val
690                 695                 700

Gly Asp Gly Gln Leu Lys Thr Leu Val Asn Tyr Glu Val Pro Gln Phe
705                 710                 715                 720

Leu Asp Cys Leu Lys Ser Ile Gly Arg Gly Tyr Asn Pro Arg Xaa Thr
            725                 730                 735

Val Ile Val Val Lys Lys Arg Val Asn Thr Arg Phe Phe Ala Gln Ser
            740                 745                 750

Gly Gly Arg Leu Gln Asn Pro Leu Pro Gly Thr Val Ile Asp Val Glu
            755                 760                 765

Val Thr Arg Pro Glu Trp Tyr Asp Phe Phe Ile Val Ser Gln Ala Val
770                 775                 780

Arg Ser Gly Ser Val Ser Pro Thr His Tyr Asn Val Ile Tyr Asp Asn
785                 790                 795                 800

Ser Gly Leu Lys Pro Asp His Ile Gln Arg Leu Thr Tyr Lys Leu Cys
            805                 810                 815

His Ile Tyr Tyr Asn Trp Pro Gly Val Ile Arg Val Pro Ala Pro Cys
            820                 825                 830

Gln Tyr Ala His Lys Leu Ala Phe Leu Val Gly Gln Ser Ile His Arg
            835                 840                 845

Glu Pro Asn Leu Ser Leu Ser Asn Arg Leu Tyr Tyr Leu
            850                 855                 860

<210> SEQ ID NO 7
<211> LENGTH: 42
<212> TYPE: DNA

```
<213> ORGANISM: Artificial Sequence
<220> FEATURE:
<223> OTHER INFORMATION: Description of Artificial Sequence: Synthesized
      Oligonucleotide Primer

<400> SEQUENCE: 7
gatcatatgg agcaaaagct tattagcgag gaagatctga at                         42

<210> SEQ ID NO 8
<211> LENGTH: 42
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 8
gatcattcag atcttcctcg ctaataagct tttgctccat at                         42

<210> SEQ ID NO 9
<211> LENGTH: 45
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 9
ctagcatatg agcaaaagct tattagcgag gaagatctga ataag                      45

<210> SEQ ID NO 10
<211> LENGTH: 45
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 10
ctagcttatt cagatcttcc tcgctaataa gcttttgctc atatg                      45

<210> SEQ ID NO 11
<211> LENGTH: 17
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 11
acgataagtt ctgttat                                                     17

<210> SEQ ID NO 12
<211> LENGTH: 23
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 12
tgcactgcca ggtccttcat cac                                              23

<210> SEQ ID NO 13
<211> LENGTH: 29
<212> TYPE: DNA
<213> ORGANISM: Artificial Sequence
```

```
<220> FEATURE:
<223> OTHER INFORMATION: Description of Artificial Sequence: Synthesized
      Oligonucleotide Primer

<400> SEQUENCE: 13
ggccagtcat tttccagtca gctcaggtg                                         29

<210> SEQ ID NO 14
<211> LENGTH: 20
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 14
atggggtctt ttcttgctca                                                   20

<210> SEQ ID NO 15
<211> LENGTH: 20
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 15
tgcccattaa catcaccatc                                                   20

<210> SEQ ID NO 16
<211> LENGTH: 24
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 16
tgatttgggg acttatttta gagc                                              24

<210> SEQ ID NO 17
<211> LENGTH: 23
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 17
acttaccttg tgacttggat gtg                                               23

<210> SEQ ID NO 18
<211> LENGTH: 24
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 18
ttgaaaagca ttgaacacca taag                                              24

<210> SEQ ID NO 19
<211> LENGTH: 24
<212> TYPE: DNA
<213> ORGANISM: Artificial Sequence
<220> FEATURE:
```

-continued

```
<223> OTHER INFORMATION: Description of Artificial Sequence: Synthesized
      Oligonucleotide Primer

<400> SEQUENCE: 19
gataaccacc gccctgcctt tcac                                              24

<210> SEQ ID NO 20
<211> LENGTH: 20
<212> TYPE: DNA
<213> ORGANISM: Artificial Sequence
<220> FEATURE:
<223> OTHER INFORMATION: Description of Artificial Sequence: Synthesized
      Oligonucleotide Primer

<400> SEQUENCE: 20
tgcccattaa catcaccatc                                                   20

<210> SEQ ID NO 21
<211> LENGTH: 4
<212> TYPE: PRT
<213> ORGANISM: Artificial Sequence
<220> FEATURE:
<223> OTHER INFORMATION: Description of Artificial Sequence: linker
      peptide

<400> SEQUENCE: 21

Pro Pro Arg Gln
1
```